US012584163B2

(12) United States Patent
Otto et al.

(10) Patent No.: US 12,584,163 B2
(45) Date of Patent: Mar. 24, 2026

(54) COMPOSITIONS AND METHODS FOR EVALUATING GENOMIC ALTERATIONS

(71) Applicant: FOUNDATION MEDICINE, INC., Cambridge, MA (US)

(72) Inventors: Geoffrey Alan Otto, Cambridge, MA (US); Travis Clark, Winchester, MA (US); Doron Lipson, Cambridge, MA (US); Daniel Lieber, Needham, MA (US); David Fabrizio, Cambridge, MA (US)

(73) Assignee: Foundation Medicine, Inc., Boston, MA (US)

( * ) Notice: Subject to any disclaimer, the term of this patent is extended or adjusted under 35 U.S.C. 154(b) by 0 days.

(21) Appl. No.: 16/437,974

(22) Filed: Jun. 11, 2019

(65) Prior Publication Data

US 2020/0149097 A1     May 14, 2020

Related U.S. Application Data

(60) Provisional application No. 62/683,469, filed on Jun. 11, 2018.

(51) Int. Cl.
| | |
|---|---|
| *C12Q 1/6848* | (2018.01) |
| *C12N 15/10* | (2006.01) |
| *C12Q 1/6827* | (2018.01) |
| *C12Q 1/6853* | (2018.01) |
| *C12Q 1/6886* | (2018.01) |

(52) U.S. Cl.
CPC ....... *C12Q 1/6848* (2013.01); *C12N 15/1093* (2013.01); *C12Q 1/6827* (2013.01); *C12Q 1/6853* (2013.01); *C12Q 1/6886* (2013.01); *C12Q 2600/156* (2013.01); *C12Q 2600/158* (2013.01)

(58) Field of Classification Search
CPC C12N 15/1093; C12Q 1/6848; C12Q 1/6827; C12Q 1/6853; C12Q 2600/156
See application file for complete search history.

(56) References Cited

U.S. PATENT DOCUMENTS

| | | | |
|---|---|---|---|
| 7,244,567 | B2 | 7/2007 | Chen et al. |
| 7,381,526 | B2 | 6/2008 | Polansky |
| 7,807,352 | B2 | 10/2010 | Rabbani et al. |
| 9,340,830 | B2 | 5/2016 | Lipson et al. |
| 9,598,731 | B2 | 3/2017 | Talasaz |
| 9,792,403 | B2 | 10/2017 | Sun et al. |
| 9,834,822 | B2 | 12/2017 | Talasaz |
| 9,840,743 | B2 | 12/2017 | Talasaz |
| 9,850,523 | B1 | 12/2017 | Chudova et al. |
| 9,902,992 | B2 | 2/2018 | Talasaz et al. |
| 9,920,366 | B2 | 3/2018 | Eltoukhy et al. |
| 10,041,127 | B2 | 8/2018 | Talasaz |
| 11,118,213 | B2 | 9/2021 | Lipson et al. |
| 11,136,619 | B2 | 10/2021 | Lipson et al. |

| | | | | |
|---|---|---|---|---|
| 11,421,265 | B2 | 8/2022 | Lipson et al. | |
| 11,959,141 | B2 | 4/2024 | Otto et al. | |
| 12,180,540 | B2 | 12/2024 | Lipson et al. | |
| 2003/0134274 | A1* | 7/2003 | Wood | C12Q 1/682 |
| | | | | 435/6.12 |
| 2005/0209787 | A1 | 9/2005 | Waggener et al. | |
| 2006/0246497 | A1 | 11/2006 | Huang et al. | |
| 2006/0275779 | A1 | 12/2006 | Li et al. | |
| 2007/0087362 | A1 | 4/2007 | Church et al. | |
| 2007/0194225 | A1 | 8/2007 | Zorn | |
| 2008/0131887 | A1 | 6/2008 | Stephan et al. | |
| 2009/0047674 | A1* | 2/2009 | Dapprich | C12P 19/34 |
| | | | | 435/6.12 |
| 2009/0111094 | A1 | 4/2009 | Storhoff et al. | |
| 2009/0221438 | A1 | 9/2009 | Kitzman et al. | |
| 2010/0029498 | A1* | 2/2010 | Gnirke | C12Q 1/6811 |
| | | | | 506/9 |
| 2010/0105052 | A1 | 4/2010 | Drmanac et al. | |
| 2010/0216648 | A1 | 8/2010 | Staehler et al. | |
| 2010/0286143 | A1 | 11/2010 | Dias-Santagata et al. | |
| 2011/0236903 | A1 | 9/2011 | McClelland et al. | |
| 2012/0208706 | A1 | 8/2012 | Lipson et al. | |
| 2013/0136799 | A1 | 5/2013 | Faham et al. | |
| 2013/0338933 | A1 | 12/2013 | Deciu et al. | |
| 2014/0272976 | A1* | 9/2014 | Lee | C12Q 1/6816 |
| | | | | 435/6.11 |
| 2014/0315725 | A1 | 10/2014 | Faham et al. | |
| 2014/0336996 | A1 | 11/2014 | Sun et al. | |
| 2016/0032396 | A1 | 2/2016 | Diehn et al. | |
| 2017/0356053 | A1 | 12/2017 | Otto et al. | |
| 2019/0032118 | A1 | 1/2019 | Lipson et al. | |
| 2019/0119733 | A1 | 4/2019 | Lipson et al. | |
| 2019/0136301 | A1 | 5/2019 | Lipson et al. | |

(Continued)

FOREIGN PATENT DOCUMENTS

| | | |
|---|---|---|
| CN | 101619350 A | 1/2010 |
| CN | 107002128 A | 8/2017 |

(Continued)

OTHER PUBLICATIONS

International Search Report and Written Opinion issued in PCT/US2019/036555, mailed Aug. 28, 2019.
Albers et al., (2011). "Dindel: accurate indel calls from short-read data," Genome Res., 21(6):961-73.
Albert et al., (2007). "Direct selection of human genomic loci by microarray hybridization," Nat. Methods, 4(11):903-5.
Browning et al., (2009). "Simultaneous genotype calling and haplotype phasing improves genotype accuracy and reduces false-positive associations for genome-wide association studies," Am. J. Hum. Genet., 85(6):847-61.
Butler et al., (2008). "ALLPATHS: De novo assembly of whole-genome shotgun microreads," Genome Res., 18:810-820.

(Continued)

*Primary Examiner* — Heather Calamita
*Assistant Examiner* — Jessica D Parisi
(74) *Attorney, Agent, or Firm* — MORRISON & FOERSTER LLP

(57) ABSTRACT

Compositions and methods of evaluating genomic alterations in a sample are disclosed.

23 Claims, 3 Drawing Sheets

Specification includes a Sequence Listing.

(56) References Cited

U.S. PATENT DOCUMENTS

| | | | |
|---|---|---|---|
| 2023/0148412 | A1 | 5/2023 | Lipson et al. |
| 2024/0327926 | A1 | 10/2024 | Otto et al. |
| 2025/0154563 | A1 | 5/2025 | Lipson et al. |
| 2025/0171836 | A1 | 5/2025 | Otto et al. |

FOREIGN PATENT DOCUMENTS

| | | | | | |
|---|---|---|---|---|---|
| JP | 2008017853 | A | 1/2008 | | |
| JP | 2013524849 | A | 6/2013 | | |
| JP | 2014507133 | A | 3/2014 | | |
| JP | 2018502563 | A | 2/2018 | | |
| WO | 2009099602 | A1 | 8/2009 | | |
| WO | WO-2010028098 | A2 | 3/2010 | | |
| WO | WO-2010141955 | A2 | 12/2010 | | |
| WO | WO-2011139371 | A1 | 11/2011 | | |
| WO | WO-2012092426 | A1 | 7/2012 | | |
| WO | WO-2013028817 | A1 | 2/2013 | | |
| WO | WO-2013190441 | A2 | 12/2013 | | |
| WO | WO-2014008447 | A1 | 1/2014 | | |
| WO | WO-2014130975 | A1 | 8/2014 | | |
| WO | WO-2014164486 | A1 | 10/2014 | | |
| WO | WO-2014165785 | A2 | 10/2014 | | |
| WO | WO-2014183078 | A1 | 11/2014 | | |
| WO | WO-2015002908 | A1 | 1/2015 | | |
| WO | WO-2015021080 | A2 | 2/2015 | | |
| WO | WO-2016069939 | A1 | 5/2016 | | |
| WO | WO-2016090273 | A1 * | 6/2016 | .......... | C12Q 1/6806 |
| WO | WO-2017151524 | A1 | 9/2017 | | |
| WO | WO-2017201073 | A1 * | 11/2017 | .......... | C12Q 1/6816 |

OTHER PUBLICATIONS

Carr et al., (2016). "Defining actionable mutations for oncology therapeutic development," Nature Reviews Cancer, 16(5) 319-29.

Cronin et al., (2004). "Measurement of gene expression in archival paraffin-embedded tissues: development and performance of a 92-gene reverse transcriptase-polymerase chain reaction assay," Am J Pathol., 164(1):35-42.

Egholm et al., (1993). "PNA hybridizes to complementary oligo-nucleotides obeying the Watson-Crick hydrogen-bonding rules," Nature, 365(6446):566-8.

Forbes et al., (2015). "COSMIC: exploring the world's knowledge of somatic mutations in human cancer," Nucl. Acids Res., 43(D1):D805-D811.

Gnirke et al., (2009). "Solution hybrid selection with ultra-long oligonucleotides for massively parallel targeted sequencing," Nat Biotechnol., 27(2):182-189, 24 pages.

Goya et al., (2010). "SNVMix: predicting single nucleotide variants from next-generation sequencing of tumors," Bioinformatics, 26(6):730-736.

Gubin et al., (2015). "CANCER. The odds of immunotherapy success," Science, 350:158-9.

Hodges et al., (2007). "Genome-wide in situ exon capture for selective resequencing," Nat. Genet., 39(12):1522-7.

Kaur et al., (2006). "Thermodynamic, Counterion, and Hydration Effects for the Incorporation of Locked Nucleic Acid Nucleotides into DNA Duplexes," Biochemistry, 45(23):7347-55.

Le et al., (2011). "SNP detection and genotyping from low-coverage sequencing data on multiple diploid samples," Genome Res., 21(6):952-60.

Lek et al., (2016). "Analysis of protein-coding genetic variation in 60,706 humans," Nature 536(7616):285-291, 33 pages.

Li et al., (2009). "Genotype imputation," Annu. Rev. Genomics Hum. Genet., 10:387-406, 23 pages.

Li et al., (2009). "The Sequence Alignment/Map format and SAMtools," Bioinformatics, 25(16):2078-9.

Li et al., (2010). "Fast and accurate long-read alignment with Burrows-Wheeler transform," Bioinformatics, 26(5):589-95.

Life Technologies Corporation. (2011). "RecoverAll Total Nucleic Acid Isolation Protocol," Ambion, Cat. No. 10 AM 1975, 29 pages.

Lunter et al., (2011). "Stampy: a statistical algorithm for sensitive and fast mapping of Illumina sequence reads," Genome Res., 21(6):936-9.

Masuda et al., (1999). "Analysis of chemical modification of RNA from formalin-fixed samples and optimization of molecular biology applications for such samples," Nucleic Acids Res., 27(22):4436-4443.

McKenna et al., (2010). "The Genome Analysis Toolkit: a MapReduce framework for analyzing next-generation DNA sequencing data," Genome Res., 20(9):1297-303.

Metzker, (2010). "Sequencing technologies—the next generation," Nature Biotechnology Reviews, 11:31-46.

Okou et al., (2007). "Microarray-based genomic selection for high-throughput resequencing," Nat. Methods, 4(11):907-9.

Omega Bio-tek, (2019). "E.Z.N.A.® FPPE DNA Kit Product Manual," Product Nos. D3399-00, D3399-01, and D3399-02, 20 pages.

Promega, (2009, Revised 2015). "Maxwell® 16 Cell LEV Total RNA Purification Kit Technical Bulletin," Promega Literature #TB351, 18 pages.

Promega, (2017). "Maxwell® 16 FFPE Plus LEV DNA Purification Kit Technical Manual," Promega Literature #TM349, 13 pages.

Promega, (2017). "Maxwell® 16 LEV Blood DNA Kit and Max-well® 16 Buccal Swab LEV DNA Purification Kit Technical Manual," Promega Literature #TM333, 11 pages.

Qiagen, (2020). "QIAamp® DNA FFPE Tissue Handbook," Qiagen, Cat. No. 37625, 28 pages.

Sherry et al., (2001). "dbSNP: the NCBI database of genetic variation," Nucleic Acids Res., 29(1):308-311.

Specht et al., (2001). "Quantitative Gene Expression Analysis in Microdissected Archival Formalin-Fixed and Paraffin-Embedded Tumor Tissue," Am J Pathol., 158(2):419-429.

Sun et al., (2014). "Abstract 1893: A computational method for somatic versus germline variant status determination from targeted next-generation sequencing of clinical cancer specimens without a matched normal control," Cancer Research, 74(19S):1893.

Sun et al., (2018). "A computational approach to distinguish somatic vs. germline origin of genomic alterations from deep sequencing of cancer specimens without a matched normal," PLoS Comput Biol., 14(2):e1005965, 13 pages.

The 1000 Genomes Project Consortium, (2012). "An integrated map of genetic variation from 1,092 human genomes," Nature, 491:56-65.

Trapnell et al., (2009). "How to map billions of short reads onto genomes," Nature Biotech., 27:455-457, 9 pages.

Warren et al., (2007). "Assembling millions of short DNA sequences using SSAKE," Bioinformatics, 23:500-501.

Ye et al., (2009). "Pindel: a pattern growth approach to detect break points of large deletions and medium sized insertions from paired-end short reads," Bioinformatics, 25(21):2865-71.

Zerbino et al., (2008). "Velvet: Algorithms for de novo short read assembly using de Bruijn graphs," Genome Res., 18:821-829.

[No Author Listed] College of American Pathologists Molecular Pathology Checklist, draft dated Jun. 15, 2010, 64 pages.

[No Author Listed] Illumina Technical Note, Improved Accuracy for ELAND and Variant Calling, published Oct. 18, 2011, 8 pages.

Affidavit of S. Wang in Support of Patent Owner's Motion For Pro Hac Vice Admission submitted before the USPTO Patent Trial and Appeal Board case IPR2017-01170, U.S. Pat. No. 9,340,830, dated Dec. 1, 2017, 7 pages.

Affidavit of S. Wang in Support of Patent Owner's Motion For Pro Hac Vice Admission submitted before the USPTO Patent Trial and Appeal Board case IPR2017-01447, U.S. Pat. No. 9,340,830, dated Dec. 1, 2017, 7 pages.

Affidavit of S. Wang in Support of Patent Owner's Motion For Pro Hac Vice Admission submitted before the USPTO Patent Trial and Appeal Board case IPR2017-01448, U.S. Pat. No. 9,340,830, dated Dec. 1, 2017, 7 pages.

Agilent Technologies, Inc. (2009). "SureSelect Target Enrichment System: Illumina Single-End Sequencing Platform Library Prep—Protocol," Agilent Technologies, Inc. Protocols, 54 pages.

Agilent Technologies, Inc. (2011). "Sure Select Target Enrichment System From Sample to Analysis," 8 pages.

(56) References Cited

OTHER PUBLICATIONS

Agilent Technologies, Inc. (2011). "Sure Select Target Enrichment System, Sure Select Catalogue," 13 pages (English translation p. 1, Original copy p. 2-13).

Agreed Claim Constructions U.S. Pat. No. 9,340,830 in *Foundation Medicine, Inc.* v. *Guardant Health, Inc.*, C.A. No. 2:16-cv-00523-JRG-RSP, filed Mar. 2, 2017, 2 pages.

Ali et al., (2015). "Prospective Comprehensive Genomic Profiling of Advanced Gastric Carcinoma Cases Reveals Frequent Clinically Relevant Genomic Alterations and New Routes for Targeted Therapies," The Oncologist, 20:499-507.

Ali et al., (2016). "Comprehensive Genomic Profiling Identifies a Subset of Crizotinib-Responsive ALK-Rearranged Non-Small Cell Lung Cancer Not Detected by Fluorescence In Situ Hybridization," The Oncologist, 21:762-770.

Amended Scheduling Order submitted before the USPTO Patent Trial and Appeal Board case IPR2017-01447, U.S. Pat. No. 9,340,830, filed Dec. 5, 2017, 3 pages.

Amended Scheduling Order submitted before the USPTO Patent Trial and Appeal Board case IPR2017-01448, U.S. Pat. No. 9,340,830, filed Dec. 5, 2017, 3 pages.

Amended Scheduling Order, submitted before the USPTO Patent Trial and Appeal Board case IPR2017-01170, U.S. Pat. No. 9,340,830, filed Dec. 5, 2017, 8 pages.

ASLANIDIS and de JONG, "Ligation-Independent Cloning of PCR Products (LIC-PCR)," Nucleic Acids Res. 18:6069-6074 (1990).

AstraZeneca, (2011). "AstraZeneca updates on olaparib and TC-5214 development programmes," available online at <https://www.astrazeneca.com/media-centre/press-releases/2011/AstraZeneca-updates-on-olaparib-and-TC-5214-development-programmes-20122010.html#!>, accessed on Feb. 13, 2018, 5 pages.

Barlesi et al., (2016). "Routine molecular profiling of patients with advanced non-small-cell lung cancer: results of a 1-year nationwide programme of the French Cooperative Thoracic Intergroup (IFCT)," Lancet, 387:1415-26.

Barve et al., (2017). "Case Report: Immune Checkpoint Inhibitor Elicited Complete Response in a Heavily Pretreated Patient with Metastatic Endometrial Carcinoma with a High Tumor Mutation Burden (TMB)," Mol. Med: Current Aspects, 1(1):1-4.

Bashford-Rogers et al., (2014). "Capturing needles in haystacks: a comparison of B-cell receptor sequencing methods," BMC Immunology, 15:29, 9 pages.

Baum, (2013). "11 health companies make the World Economic Group tech pioneer list," available online at <https://medcitynews.com/2013/08/what-does-a-technology-pioneer-in-medtech-look-like-here-are-11/>, accessed on Feb. 8, 2018, 9 pages.

Bazan, et al., "Specific Condon 13 K-ras Mutations are Predictive of Clinical Outcome in Colorectal Cancer Patients, whereas Codon 12 K-ras Mutations are Associated with Mucinous Histotype", Annals. Oncol., 13(1438-1446, Especially p. 1440, col. 2 para. Sep. 1-2, 2002.

Berger, et al., "Integrative Analysis of the Melanoma Transcriptome," Genome Res., 20(4):413-427 (2010) (PMID 20179022).

Bezak et al., (2017). "Comprehensive Genomic Profiling of Central Giant Cell Lesions Identifies Clinically Relevant Genomic Alterations," J. Oral Maxillofac. Surg., 75:955-961.

Blumenstiel, B., et al., "Targeted Exon Sequencing by In-Solution Hybrid Selection," Curr. Protoc. Hum. Genet., Chapter 18.4, 24 pages. (2010).

Braggio et al. "Lessons from next-generation sequencing analysis in hematological malignancies" Blood Cancer Research (2013) vol. 3, e127, pp. 1-10.

Branton, D., et al., "The Potential and Challenges of Nanopore Sequencing," Nat. Biotechnol. 26(10):1146-1153 (2008).

Bridge, J. A. (2008). "Advantages and Limitations of Cytogenetic, Molecular Cytogenetic, and Molecular Diagnostic Testing in Mesenchymal Neoplasms," J. Orthop. Sci., 13:273-282.

Budowle et al., (2008). "Forensically relevant SNP classes," BioTechniques, 44(5):603-610.

Business Wire, (2017). "FDA Approves Foundation Medicine's FoundationOne CDx, the First and Only Comprehensive Genomic Profiling Test for All Solid Tumors Incorporating Multiple Companion Diagnostics," available online at <https://www.foundationmedicine.com/press-releases/f2b20698-10bd-4ac9-a5e5-c80c398a57b5>, 5 pages.

Business Wire, (2018). "Foundation Medicine Reports Preliminary 2017 Results," available online at <https://www.businesswire.com/news/home/20180108005713/en/Foundation-Medicine-Reports-Preliminary-2017-Results>, 4 pages.

Business Wire, (2018). "Foundation Medicine's New Liquid Biopsy Assay Granted Breakthrough Device Designation by U.S. Food and Drug Administration," available online at <https://www.foundationmedicine.com/press-releases/991ce685-7dbf-400a-aa33-eb4f9d411ed3>, 3 pages.

Campbell, P. J. et al. (2008). "Subclonal phylogenetic structures in cancer Revealed by Ultra-deep Sequencing," PNAS, 105(35):12 pages.

Canada's Michael Smith Genome Sciences Centre. (2009). "Slider II Results of SNPs concordance comparison to Maq," Available online at <http://www.bcgsc.ca/platform/bioinfo/software/SliderII>, 9 pages.

Center for Devices and Radiological Health, (2015). "Expedited Access for Premarket Approval and De Novo Medical Devices Intended for Unmet Medical Need for Life Threatening or Irreversibly Debilitating Diseases or Conditions," 45 pages.

CenterWatch, "FDA Approved Drugs for Oncology," available online at <https://www.centerwatch.com/drug-information/fda-approved-drugs/therapy>, accessed on Feb. 15, 2018, 19 pages.

Chalmers et al., (2017). "Analysis of 100,000 human cancer genomes reveals the landscape of tumor mutational burden," Genome Medicine, 9(34):1-14.

Chin et al., (2011). "Making sense of cancer genomic data," Genes & Development, 25:534-555.

Chiu et al. (2008). "Noninvasive prenatal diagnosis of fetal chromosomal aneuploidy by massively parallel genomic sequencing of DNA in maternal plasma," PNAS, 105(51):20458-20463.

Chmielecki et al., (2017). "Genomic Profiling of a Large Set f Diverse Pediatric Cancers Identifies Known and Novel Mutations across Tumor Spectra," Cancer Res., 77(2):509-519.

Chmielecki, J. et al. (2010). "Targeted Next-Generation Sequencing of DNA Regions Proximal to a Conserved GXGXXG Signaling Motif Enables Systematic Discovery of Tyrosine Kinase Fusions in Cancer," Nucleic Acids Research, 38(20): 6985-6996.

Claim Construction Memorandum Opinion and Order for *Foundation Medicine, Inc.* v. *Guardant Health, Inc.*, Civil Action No. 2:16-CV-00523-JRG-RSP, filed May 19, 2017, 27 pages.

Clean Version of the Modified Default Protective Order by Foundation Medicine, Inc., submitted before the USPTO Patent Trial and Appeal Board for Case Nos. IPR2017- 01170, IPR2017-01447, and IPR2017-01448, U.S. Pat. No. 9,340,830, filed Feb. 16, 2018, 8 pages.

ClinicalTrials.gov, (2016). "Pbi-shRNA WS/FLI1 Type 1 LPX in Subjects with Advanced Ewing's Sarcoma, NCT02736565," available online at <https://clinicaltrials.gov/ct2/show/NCT02736565>, accessed on Feb. 9, 2018. 7 pages.

Cloonan et al., "RNA-mate: a recursive mapping strategy for high-throughput RNA-sequencing data," Bioinformatics (2009) vol. 25, No. 19, pp. 2615-2616.

Complaint for Patent Infringement by Plaintiff in *Foundation Medicine, Inc.* v. *Guardant Health, Inc.*, Case 1:17-cv-00607-LPS-CJB, filed May 25, 2017, 10 pages.

Complaint for Patent Infringement by Plaintiff in *Foundation Medicine, Inc.* v. *Guardant Health, Inc.*, Civil Action No. 2:16-CV-00523, filed May 17, 2016, 11pages.

Confidential Videotaped Deposition of John Quackenbush, Ph.D. in *Foundation Medicine, Inc.* v. *Guardant Health, Inc.*, C.A. No. 2:16-cv-00523-JRG-RSP, filed Apr. 6, 2017, 6 pages.

Craig et al., (2008). "Identification of Genetic Variants Using Bar-Coded Multiplexed Sequencing", Nature Methods, 5(10):887-893, and Supplementary Information, 17 pages.

(56) References Cited

OTHER PUBLICATIONS

Cummings, N. et al. (2010). "Combining Target Enrichment with Barcode Multiplexing for High Throughput SNP Discovery," BMC Genomics, 11: 8 pages.

Curriculum Vitae of Dr. J. Quackenbush, dated Mar. 27, 2017, submitted before the USPTO Patent Trial and Appeal Board for U.S. Pat. No. 9,340,830, 45 pages.

Dahl, Fredrik et al., "Multigene Amplification and Massively Parallel Sequencing for Cancer Mutation Discovery", Proceedings of the National Academy of Sciences, 104(22), May 29, 2007, pp. 9387-9392.

Day et al., (2014). "Targeted Sequencing of Large Genomic Regions with CATCH-Seq," PLOS ONE, 9(10):1-11.

Decision—Denying Patent Owner's Motion for Protective Order, submitted before the USPTO Patent Trial and Appeal Board cases IPR2017-01170, IPR2017-01447, and IPR2017-01448, U.S. Pat. No. 9,340,830, filed Apr. 4, 2018, 5 pages.

Decision—Denying Patent Owner's Request for Rehearing, submitted before the USPTO Patent Trial and Appeal Board case IPR2017-01170, U.S. Pat. No. 9,340,830, filed Nov. 8, 2017, 7 pages.

Decision—Granting Joint Motion for Entry of a Modified Protective Order 37 C.F.R. sec 42.14, submitted before the USPTO Patent Trial and Appeal Board cases IPR2017-01170, IPR2017-01447, and IPR2017-01448, U.S. Pat. No. 9,340,830, filed Apr. 27, 2018, 3 pages.

Decision—Granting Patent Owner's Unopposed Renewed Motion to Seal 37 C.F.R. sec 42.14, submitted before the USPTO Patent Trial and Appeal Board cases IPR2017-01170, IPR2017-01447, and IPR2017-01448, U.S. Pat. No. 9,340,830, filed Apr. 27, 2018, 5 pages.

Decision—Granting-in-Part Patent Owner's Motion to Seal, submitted before the USPTO Patent Trial and Appeal Board cases IPR2017-01170, IPR2017-01447, and IPR2017-01448, U.S. Pat. No. 9,340,830, filed Apr. 4, 2018, 6 pages.

Decision—Institution of Inter Partes Review submitted before the USPTO Patent Trial and Appeal Board case IPR2017-01448, U.S. Pat. No. 9,340,830, filed Nov. 28, 2017, 31 pages.

Decision—Institution of Inter Partes Review, submitted before the USPTO Patent Trial and Appeal Board case IPR2017-01170, U.S. Pat. No. 9,340,830, filed Oct. 11, 2017, 27 pages.

Decision Granting Patent Owner's Unopposed Motion to Seal 37 C.F.R. § 42.14, submitted before the USPTO Patent Trial and Appeal Board cases IPR2017-01170, IPR2017-01447, and IPR2017-01448, U.S. Pat. No. 9,340,830, filed Jun. 5, 2018, 4 pages.

Decision Granting Patent Owner's Motion to Submit Supplemental Information Pursuant to 37 C.F.R. § 42.123(b), submitted before the USPTO Patent Trial and Appeal Board cases IPR2017-01170, IPR2017-01447, and IPR2017-01448, U.S. Pat. No. 9,340,830, filed May 29, 2018, 4 pages.

Decision submitted before the USPTO Patent Trial and Appeal Board case IPR2017-01447, U.S. Pat. No. 9,340,830, filed Nov. 28, 2017, 28 pages.

Declaration by Dr. J. Nemunaitis submitted before the USPTO Patent Trial and Appeal Board for cases IPR2017-01170, U.S. Pat. No. 9,340,830, filed Feb. 16, 2018, 107 pages.

Declaration by Dr. J. Nemunaitis submitted before the USPTO Patent Trial and Appeal Board for cases IPR2017-01447, U.S. Pat. No. 9,340,830, filed Feb. 16, 2018, 107 pages.

Declaration by Dr. J. Nemunaitis submitted before the USPTO Patent Trial and Appeal Board for cases IPR2017-01448, U.S. Pat. No. 9,340,830, filed Feb. 16, 2018, 107 pages.

Declaration of Dr. J. Quackenbush submitted before the USPTO Patent Trial and Appeal Board for U.S. Pat. No. 9,340,830, filed Mar. 30, 2017, 106 pages.

Declaration of E. Reines in Support of Petitioner Guardant Health, Inc.'s Motion for Pro Hac Vice Admission submitted before USPTO Patent Trial and Appeal Board for case IPR2017-01170, U.S. Pat. No. 9,340,830, dated Mar. 16, 2018, 7 pages.

Declaration of E. Reines in Support of Petitioner Guardant Health, Inc.'s Motion for Pro Hac Vice Admission submitted before USPTO Patent Trial and Appeal Board for case IPR2017-01447, U.S. Pat. No. 9,340,830, dated Mar. 16, 2018, 7 pages.

Declaration of E. Reines in Support of Petitioner Guardant Health, Inc.'s Motion for Pro Hac Vice Admission submitted before USPTO Patent Trial and Appeal Board for case IPR2017-01448, U.S. Pat. No. 9,340,830, dated Mar. 16, 2018, 7 pages.

Demichelis et al., (2008). "SNP panel identification assay (SPIA): a genetic-based assay for the identification of cell lines," Nucleic Acids Research, 36(7):2446-2456.

Deposition of Dr. J. Quackenbush, (Jan. 31, 2018) in *Guardant Health, Inc. v. Foundation Medicine, Inc.*: Case Nos. IPR2017-01170, IPR2017-01447, and IPR2017-01448, 342 pages.

Deposition of Dr. S. Gabriel, (Mar. 24, 2017) for *Foundation Medicine, Inc. v. Guardant Health, Inc.*, Civil Action No. 2:16-CV-00523-JRG-RSP, 146 pages.

Deposition of Stacey Gabriel Ph.D. on Mar. 24, 2017 in *Foundation Medicine, Inc. v. Guardant Health, Inc.*, C.A. No. 2:16-cv-00523-JRG-RSP, filed Apr. 20, 2017, 54 pages.

DePristo et al., (2011). "A framework for variation discovery and genotyping using next-generation DNA sequencing data," Nature Genetics, 43(5):491-500.

Ding, L., et al., "Analysis of Next-Generation Genomic Data in Cancer: Accomplishments and Challenges", Human Molecular Genetics, 19(R2), Sep. 15, 2010, pp. R188-R196.

Disputed Claim Constructions U.S. Pat. No. 9,340,830 in *Foundation Medicine, Inc. v. Guardant Health, Inc.*, C.A. No. 2:16-cv-00523-JRG-RSP, filed May 4, 2017, 10 pages.

Dowsett, M. et al. (2008). "Emerging Biomarkers and New Understanding of Traditional Markers in Personalized Therapy for Breast Cancer," Clin. Cancer. Res., 14(24):8019-8026.

Drilon et al. "Broad, Hybrid Capture-Based Next-Generation Sequencing Identifies Actionable Genomic Alternations in Lung Adenocarcinomas Otherwise Negative for Such Alterations by Other Genomic Testing Approaches" Clinical Cancer Research (2015) vol. 21 No. 16 pp. 3631-3639.

Drilon et al., (2013). "Response to Cabozantinib in Patients with RET Fusion-Positive Lung Adenocarcinomas," Cancer Discovery, 3(6):1-7.

Edwards, J.R., et al., "Mass-Spectrometry DNA Sequencing," Mut. Res. 573(1-2):3-12 (2005).

Evidentiary Declaration of P. Medley, submitted before the USPTO Patent Trial and Appeal Board for U.S. Pat. No. 9,340,830, filed Mar. 30, 2017, 6 pages.

Expert Declaration of John Quackenbush, Ph.D. in *Foundation Medicine, Inc. v. Guardant Health, Inc.*, C.A. No. 2:16-cv-00523-JRG-RSP, filed Apr. 6, 2017, 41 pages.

Extended European Search Report received for European Patent Application No. 15866246.0, mailed Sep. 28, 2018, 11 pages.

Extended European Search Report received for European Patent Application No. 19157180.1, mailed Sep. 24, 2019, 13 pages.

Extended European Search Report received for European Patent Application No. 19820152.7, mailed Feb. 15, 2022, 13 pages.

FDA, (2017). "FDA announces approval, CMS proposes coverage of first breakthrough-designated test to detect extensive number of cancer biomarkers," available online at <https://www.fda.gov/NewsEvents/Newsroom/PressAnnouncements/ucm587273.htm>, accessed on Feb. 8, 2018, 4 pages.

FDA, (2017). "FDA approves first cancer treatment for any solid tumor with a specific genetic feature," available online at <https://www.fda.gov/newsevents/newsroom/pressannouncements/ucm560167.htm>, accessed on Jan. 29, 2018, 3 pages.

Forbes et al., (2011). "COSMIC: mining complete cancer genomes in the Catalogue of Somatic Mutations in Cancer," Nucleic Acids Research, 39:D945-D950, 6 pages.

Foundation Medicine, Inc., "Foundation Medicine and Collaborators to Present New Clinical Data on FoundationOne® and FoundationOne Heme at the 2014 ASCO Annual Meeting" Press Release dated May 14, 2014, 5 pages.

(56) References Cited

OTHER PUBLICATIONS

Foundation Medicine, Inc., "Foundation Medicine and Memorial Sloan-Kettering Cancer Center Announce Partnership to Advance Patient Care in Hematologic Cancers" Press Release dated May 2, 2013, 2 pages.

Foundation Medicine, Inc., "Foundation Medicine Launches FoundationOne™ Heme, Developed in Collaboration with Memorial Sloan-Kettering Cancer Center" Press Release dated Dec. 7, 2013, 3 pages.

Foundation Medicine, Inc., "FoundationOne CDx Technical Information," submitted before the USPTO Patent Trial and Appeal Board for Case Nos. IPR2017-01170, IPR2017-01447, and IPR2017-01448, U.S. Pat. No. 9,340,830, filed Feb. 16, 2018, 36 pages.

Foundation Medicine, Inc., "FoundationOne™ Heme Enables Identification of Genomic Alterations Not Identified By Conventional Methods Across Hematologic Malignancies" Press Release dated Dec. 9, 2013, 2 pages.

Foundation Medicine, Inc., "Novel And Previously Reported Genomic Alterations Identified in Clinical Multiple Myeloma Cases Using FoundationOne™ Heme" Press Release dated Dec. 10, 2013, 2 pages.

Foundation Medicine, Inc., (2017). "FDA Approves Foundation Medicine's FoundationOne CDx™, the First and Only Comprehensive Genomic Profiling Test for All Solid Tumors Incorporating Multiple Companion Diagnostics," available online at <https://www.businesswire.com/news/home/20171130006320/en/>, accessed on Feb. 8, 2018, 6 pages.

Foundation Medicine, Inc.'s Opening Claim Constructions Brief in *Foundation Medicine, Inc.* v. *Guardant Health, Inc.*, C.A. No. 2:16-cv-00523-JRG-RSP, filed Apr. 6, 2017, 27 pages.

Foundation Medicine, "Bait Set Design Summary," Exhibit 1 of Redacted Deposition of Dr. S. Gabriel in *Guardant Health, Inc.* v. *Foundation Medicine, Inc.* Case Nos. IPR2017-01170, IPR2017-01447, and IPR2017-01448, U.S. Pat. No. 9,340,830, filed May 8, 2018, 5 pages.

Foundation Medicine's Power of Attorney Under 37 C.F.R. §42.10 submitted before the USPTO Patent Trial and Appeal Board case IPR2017-01447, U.S. Pat. No. 9,340,830, filed Jun. 6, 2017, 2 pages.

Foundation Medicine's Power of Attorney Under 37 C.F.R. §42.10, submitted before the USPTO Patent Trial and Appeal Board case IPR2017-01170, U.S. Pat. No. 9,340,830, filed Apr. 21, 2017, 2 pages.

Foundation Smart Trials, "An End-to-End Partner for Clinical Trials," submitted before the USPTO Patent Trial and Appeal Board for Case Nos. IPR2017-01170, IPR2017-01447, and IPR2017-01448, U.S. Pat. No. 9,340,830, filed Feb. 16, 2018, 8 pages.

Frampton et al., (2013). "Development and validation of a clinical cancer genomic profiling test based on massively parallel DNA sequencing," Nature Biotechnology, and Online Methods Supplementary Information, 31(11):1023-1033.

Garber, et al., "Computational Methods for Transcriptome Annotation and Quantification Using RNA-seq," Nat. Methods. 8(6):469-477 (2011). Abstract Only.

Garber, K., (2008). "Fixing the Front End," Nature Biotechnology, 26(10):1101-1104.

Gazzola et al. "The evolution of clonality testing in the diagnosis and monitoring of hematological malignancies" Therapeutic Advances in Hematology (2014) vol. 5, No. 2, pp. 35-47.

Georgiou et al "The promise and challenge of high-throughput sequencing of the antibody repertoire" Nature Biotechnology (2014) vol. 32, No. 2, pp. 158-168.

Granting Petitioner's Motion for Pro Hac Vice Admission of Edward R. Reines 37 C.F.R. 42.10, submitted before the USPTO Patent Trial and Appeal Board cases IPR2017-01170, IPR2017-01447, and IPR2017-01448, U.S. Pat. No. 9,340,830, filed Mar. 22, 2018, 3 pages.

Griffith et al., (2015). "Optimizing cancer genome sequencing and analysis," Cell Syst., 1(3):210-223.

Groisberg et al., (2017). "Clinical genomic profiling to identify actionable alterations for investigational therapies in patients with diverse sarcomas," Oncotarget, 14 pages.

Guardant Health, Inc.'s Responsive Claim Construction Brief for *Foundation Medicine, Inc.* v *Guardant Health, Inc.*: Case Nos. 2:16-CV-00523-JRG, dated Feb. 2, 2017, 172 pages.

Guardant Health, Inc.'s Responsive Claim Construction Brief in *Foundation Medicine, Inc.* v. *Guardant Health, Inc.*, C.A. No. 2:16-cv-00523-JRG-RSP, filed Apr. 20, 2017, 31 pages.

Guardant's Notice of Deposition of Dr. J. Nemunaitis submitted before the USPTO Patent Trial and Appeal Board case IPR2017-01447, U.S. Pat. No. 9,340,830, filed Mar. 23, 2018, 3 pages.

Guardant's Notice of Deposition of Dr. John Nemunaitis, M.D. submitted before the USPTO Patent Trial and Appeal Board case IPR2017-01448, U.S. Pat. No. 9,340,830, filed Mar. 23, 2018, 3 pages.

Guardant's Notice of Deposition of Dr. John Nemunaitis, M.D., submitted before the USPTO Patent Trial and Appeal Board case IPR2017-01170, U.S. Pat. No. 9,340,830, filed Mar. 23, 2018, 3 pages.

Guardant's Notice of Deposition of Dr. S. Gabriel submitted before the USPTO Patent Trial and Appeal Board case IPR2017-01447, U.S. Pat. No. 9,340,830, filed Mar. 23, 2018, 3 pages.

Guardant's Notice of Deposition of Dr. Stacey Gabriel, Ph.D. submitted before the USPTO Patent Trial and Appeal Board case IPR2017-01448, U.S. Pat. No. 9,340,830, filed Mar. 23, 2018, 3 pages.

Guardant's Notice of Deposition of Dr. Stacey Gabriel, Ph.D., submitted before the USPTO Patent Trial and Appeal Board case IPR2017-01170, U.S. Pat. No. 9,340,830, filed Mar. 23, 2018, 3 pages.

Hanna, G.J., et al., "Comparison of Sequencing by Hybridization and Cycle Sequencing for Genotype of Human Immunodeficiency Virus Type 1 Reverse Transcriptase," J. Clin. Microbiol., 38(7):2715-21, 14 pages. (2000).

He et al. "Integrated genomic DNA/RNA profiling of hematologic malignancies in the clinical setting" Blood (2016) vol. 127, No. 24, pp. 3004-3014.

Hui et al., (2015). "Differences in attitudes and beliefs toward end-of-life care between hematologic and solid tumor oncology specialists," Annals of Oncology, 26:1440-1446.

Hutchinson et al. "BRAF Fusions Define a Distinct Molecular Subset of Melanomas with Potential Sensitivity to MEK Inhibition" Clinical Cancer Research (2013) vol. 19 No. 24, 12 pages.

Imielinski et al., "Mapping the Hallmarks of Lung Adenocarcinoma with Massively Parallel Sequencing" Cell (2012) vol. 150 pp. 1107-1120.

In Re E. Reines for US Court of Appeals for the Federal Circuit Case 14-MA004, filed Nov. 5, 2014, 19 pages.

Initial Declaration of Stacey Gabriel, Ph.D. in Support of Foundation Medicine, Inc.'s Proposed Claim Constructions in *Foundation Medicine, Inc.* v. *Guardant Health, Inc.*, C.A. No. 2:16-cv-00523-JRG-RSP, filed Apr. 6, 2017, 26 pages.

International Search Report received for PCT Patent Application No. PCT/US2011/67725, mailed on Apr. 27, 2012, 4 pages.

International Search Report and Written Opinion for International Application No. PCT/US2015/064044 dated Apr. 8, 2016, 22 pages.

Jemal et al., (2011). "Global Cancer Statistics," CA Cancer J. Clin., 61:69-90.

Jiang et al., (2014). "Deep sequencing reveals clonal evolution patterns and mutation events associated with relapse in B-cell lymphomas," Genome Biology, 15:432, 17 pages.

Johnson et al., (2017). "Comprehensive Genomic Profiling of 282 Pediatric Low- and High-Grade Gliomas Reveals Genomic Drivers, Tumor Mutational Burden, and Hypermutation Signatures," The Oncologist, 22:1478-1490.

Joint Claim Construction Chart Pursuant To Patent Local Rule 4-5 in *Foundation Medicine, Inc.* v. *Guardant Health, Inc.*, C.A. No. 2:16-cv-00523-JRG-RSP, filed May 4, 2017, 3 pages.

Joint Motion for Entry of a Modified Protective Order submitted before the USPTO Patent Trial and Appeal Board case IPR2017-01447, U.S. Pat. No. 9,340,830, filed Apr. 23, 2018, 4 pages.

(56) References Cited

OTHER PUBLICATIONS

Joint Motion for Entry of a Modified Protective Order submitted before the USPTO Patent Trial and Appeal Board case IPR2017-01448, U.S. Pat. No. 9,340,830, filed Apr. 23, 2018, 4 pages.

Joint Motion for Entry of a Modified Protective Order, submitted before the USPTO Patent Trial and Appeal Board case IPR2017-01170, U.S. Pat. No. 9,340,830, filed Apr. 23, 2018, 4 pages.

Joint Motion to Keep Confidential and Separate Under 35 U.S.C. § 317(b) and 37 C.F.R. § 42.74( c), submitted before the USPTO Patent Trial and Appeal Board cases IPR2017-01170, IPR2017-01447, and IPR2017-01448, U.S. Pat. No. 9,340,830, filed Jul. 2, 2018, 3 pages.

Joint Motion to Terminate Under 35 U.S.C. § 317(a), submitted before the USPTO Patent Trial and Appeal Board cases IPR2017-01170, IPR2017-01447, and IPR2017-01448, U.S. Pat. No. 9,340,830, filed Jul. 2, 2018, 6 pages.

Joint Stipulation to Modify the Scheduling Order submitted before the USPTO Patent Trial and Appeal Board case IPR2017-01447, U.S. Pat. No. 9,340,830, filed Apr. 20, 2018, 4 pages.

Joint Stipulation to Modify the Scheduling Order submitted before the USPTO Patent Trial and Appeal Board case IPR2017-01448, U.S. Pat. No. 9,340,830, filed Apr. 20, 2018, 4 pages.

Joint Stipulation to Modify the Scheduling Order, submitted before the USPTO Patent Trial and Appeal Board case IPR2017-01170, U.S. Pat. No. 9,340,830, filed Apr. 20, 2018, 4 pages.

Kenny, E. M. et al. (2011). "Multiplex Target Enrichment Using DNA Indexing for Ultra-High Throughput SNP Detection," DNA Research, 18:31-38.

Kidd et al., "A Human Genome Structural Variation Sequencing Resource Reveals Insights into Mutational Mechanisms," Cell (2010) vol. 143, pp. 837-847.

Koboldt, et al. (2010). "Challenges of Sequencing Human Genomes," Briefings in Bioinformatics, 11(5):484-498.

Lavinder et al. "Next-generation sequencing and protein mass spectrometry for the comprehensive analysis of human cellular and serum antibody repertoires" Current Opinion in Chemical Biology (2015) vol. 24, pp. 112-120.

Leary et al. (2010). "Development of Personalized Tumor Biomarkers Using Massively Parallel Sequencing," Sci Transl Med, 2(20):20ra14.

Leary et al. (2012). "Detection of Chromosomal Alterations in the Circulation of Cancer Patients with Whole-Genome Sequencing," Sci Transl Med, 4(162):162ra154.

LeBlanc et al., (2015). "What Is Different About Patients With Hematologic Malignancies? A Retrospective Cohort Study of Cancer Patients Referred to a Hospice Research Network," Journal of Pain and Symptom Management, 49(3):505-512.

Ledermann (2014). "Olaparib maintenance therapy in patients with platinum-sensitive relapsed serous ovarian cancer: a preplanned retrospective analysis of outcomes by BRCA status in a randomised phase 2 trial," Lancet Oncol., 15:852-861.

Levin et al., (2009) "Targeted Next-Generation Sequencing of a Cancer Transcriptome Enhances Detection of Sequence Variants and Novel Fusion Transcripts," Genome Biol., 10(10):R115, and Supplementary Information, 485 pages.

Ley et al., (2008). "DNA Sequencing of a Cytogenetically Normal Acute Myeloid Leukaemia Genome," Nature, 456:66-72, and Supplementary Information, 39 pages.

Li et al., "A survey of sequence alignment algorithms for next-generation sequencing," Briefings in Bioinformatics (2010) vol. 2, No. 5, pp. 473-483.

Li, et al. (2009). "Fast and Accurate Short Read Alignment with Burrows-Wheeler Transform," Bioinformatics, 25(14):1754-1760.

Liang et al., (2014). "Short intronic repeat sequences facilitate circular RNA production," Genes & Development, 28:2233-2247.

Lindeman et al., (2013). "Molecular Testing Guideline for Selection of Lung Cancer Patients for EGFR and ALK Tyrosine Kinase Inhibitors," J. Thorac. Oncol., 8(7):823-859.

Lipson et al., (2012). "Identification of new ALK and RET gene fusions from colorectal and lung cancer biopsies," Nat. Med., 18(3):382-384.

Logan et al. "High-throughput VDJ sequencing for quantification of minimal residual disease in chronic lymphocytic leukemia and immune reconstitution assessment" PNAS (2011) vol. 108, No. 52, pp. 21194-21199.

Lozano et al., (2012). "Global and regional mortality from 235 causes of death for 20 age groups in 1990 and 2010: a systematic analysis for the Global Burden of Disease Study 2010," Lancet, 380:2095-128.

Magi et al., (2010). "Bioinformatics for Next Generation Sequencing Data," Genes, 1:294-307.

Malhis, et al. (2010). "High Quality SNP Calling Using Illumina Data at Shallow Coverage," Bioinformatics, 26(8):1029-1035.

Mamanova, L. et al. (2010). "Target-Enrichment Strategies for Next Generation Sequencing," Nature Methods, 7(2):111-118.

Mardis, (2008). "Next-Generation DNA Sequencing Methods," Annu. Rev. Genomics Hum. Genet., 9:387-402.

Mardis, et al. (2009). "Recurring Mutations Found by Sequencing an Acute Myeloid Leukemia Genome," The New England Journal of Medicine, 361:1058-1066.

Marsh, S. et al. (2007). "Pharmacogenetic Analysis of Paclitaxel Transport and Metabolism Genes in Breast Cancer," The Pharmacogenomics Journal, 7:362-365.

McBride et al. (2010). "Use of Cancer-Specific Genomic Rearrangements to Quantify Disease Burden in Plasma from Patients with Solid Tumors," Genes Chromosomes Cancer, 49(11):1062-1069.

Meldrum et al., (2011). "Next-Generation Sequencing for Cancer Diagnostics: a Practical Perspective," Clin. Biochem Rev., 32:177-195.

Mertes et al., (2011). "Targeted enrichment of genomic DNA regions for next-generation sequencing," Briefings in Functional Genomics, 10(6):374-386.

Meyerson et al., (2010). "Advances in understanding cancer genomes through second-generation sequencing," Nature Reviews Genetics, 11(10):685-696.

Miklos, (2005). "The Human Cancer Genome Project-one more misstep in the war on cancer," Nature Biotechnology, 23(5):535-537.

Morlan, J. et al. (2009). "Mutation Detection by Real-Time PCR: A Simple, Robust and Highly Selective Method," PLoS ONE, 4(2):e4584, 11 pages.

Motion for Protective Order submitted before the USPTO Patent Trial and Appeal Board case IPR2017-01447, U.S. Pat. No. 9,340,830, filed Feb. 16, 2018, 8 pages.

Motion for Protective Order submitted before the USPTO Patent Trial and Appeal Board case IPR2017-01448, U.S. Pat. No. 9,340,830, filed Feb. 16, 2018, 8 pages.

Motion for Protective Order, submitted before the USPTO Patent Trial and Appeal Board case IPR2017-01170, U.S. Pat. No. 9,340,830, filed Feb. 16, 2018, 8 pages.

Mullighan et al. "Genome sequencing of lymphoid malignancies" Blood (2013) vol. 122, No. 24, pp. 3899-3907.

National Human Genome Research Institute, "The Cost of Sequencing a Human Genome," available online at <https://www.genome.gov/sequencingcosts/>, accessed on Jul. 7, 2017, 4 pages.

Negrini, S. et al. (2010). "Genomic Instability—an Evolving Hallmark of Cancer," Nature Reviews Molecular Cell Biology, 11:220-228.

New England Biolabs. "Master Mixes," available online at <http://www.neb.sg/products/pcr ..qpcr-and-amplification-technologies/master-mixes/master-mixes>, accessed on Jul. 6, 2017, 3 pages.

Ngeow, J. et al. (2016). "Precision Medicine in Heritable Cancer: When Somatic Tumour Testing and Germline Mutations Meet," Genomic Medicine, 3 pages.

NGS Alignment Programs. (2009). Available online at <http://lh3lh3.users.sourceforge.net/NGSalign.shtml>, 4 pages.

Nord, A. S. et al., (2011). "Accurate and Exact CNV Identification from Targeted High-throughput Sequence Data," BMC Genomics, 12:184, 10 pages.

(56) References Cited

OTHER PUBLICATIONS

Notice of Deposition of Dr. J. Quackenbush submitted before the USPTO Patent Trial and Appeal Board case IPR2017-01447, U.S. Pat. No. 9,340,830, filed Jan. 5, 2018, 3 pages.

Notice of Deposition of Dr. John Quackenbush submitted before the USPTO Patent Trial and Appeal Board case IPR2017-01447, U.S. Pat. No. 9,340,830, filed Apr. 27, 2018, 4 pages.

Notice of Deposition of Dr. John Quackenbush submitted before the USPTO Patent Trial and Appeal Board case IPR2017-01448, U.S. Pat. No. 9,340,830, filed Apr. 27, 2018, 4 pages.

Notice of Deposition of Dr. John Quackenbush submitted before the USPTO Patent Trial and Appeal Board case IPR2017-01448, U.S. Pat. No. 9,340,830, filed Jan. 5, 2018, 3 pages.

Notice of Deposition of Dr. John Quackenbush, submitted before the USPTO Patent Trial and Appeal Board case IPR2017-01170, U.S. Pat. No. 9,340,830, filed Apr. 27, 2018, 4 pages.

Notice of Deposition of Dr. John Quackenbush, submitted before the USPTO Patent Trial and Appeal Board case IPR2017-01170, U.S. Pat. No. 9,340,830, filed Jan. 5, 2018, 3 pages.

Notice of Deposition of Dr. John Quackenbush, submitted before the USPTO Patent Trial and Appeal Board case IPR2017-01170, U.S. Pat. No. 9,340,830, filed Nov. 16, 2017, 3 pages.

Notice of Filing Date Accorded to Petition and Time For Filing Patent Owner Preliminary Response submitted before the USPTO Patent Trial and Appeal Board case IPR2017-01447, U.S. Pat. No. 9,340,830, filed Jun. 6, 2017, 5 pages.

Notice of Filing Date Accorded to Petition and Time for Filing Patent Owner Preliminary Response submitted before the USPTO Patent Trial and Appeal Board case IPR2017-01448, U.S. Pat. No. 9,340,830, filed Jun. 6, 2017, 5 pages.

Notice of Filing Date Accorded to Petition and Time For Filing Patent Owner Preliminary Response, submitted before the USPTO Patent Trial and Appeal Board case IPR2017-01170, U.S. Pat. No. 9,340,830, filed Apr. 12, 2017, 4 pages.

Notice of Joint Stipulation to Revised Schedule submitted before the USPTO Patent Trial and Appeal Board case IPR2017-01447, U.S. Pat. No. 9,340,830, filed Jan. 9, 2018, 3 pages.

Notice of Joint Stipulation to Revised Schedule submitted before the USPTO Patent Trial and Appeal Board case IPR2017-01448, U.S. Pat. No. 9,340,830, filed Jan. 9, 2018, 3 pages.

Notice of Joint Stipulation to Revised Schedule, submitted before the USPTO Patent Trial and Appeal Board case IPR2017-01170, U.S. Pat. No. 9,340,830, filed Jan. 9, 2018, 3 pages.

Order—Patent Owner's Motion for Pro Hac Vice Admission of Sophie F. Wang—37 CFR 42.10 submitted before the USPTO Patent Trial and Appeal Board case IPR2017-01448, U.S. Pat. No. 9,340,830, filed Dec. 5, 2017, 3 pages.

Order—Patent Owner's Motion for Pro Hac Vice Admission of Sophie F. Wang—37 CFR 42.10, submitted before the USPTO Patent Trial and Appeal Board case IPR2017-01170, U.S. Pat. No. 9,340,830, filed Dec. 5, 2017, 3 pages.

Order Granting Guardant Health, Inc.'s Motion To Dismiss Foundation Medicine, Inc.'s Complaint in *Foundation Medicine, Inc. v. Guardant Health, Inc.*, C.A. No. 2:16-cv-00523-JRG-RSP, filed Jun. 12, 2017, 1 page.

Order Granting Patent Owner's Unopposed Motion to Expunge, 37 C.F.R. § 42.56, submitted before the USPTO Patent Trial and Appeal Board cases IPR2017-01170, IPR2017-01447, and IPR2017-01448, U.S. Pat. No. 9,340,830, filed Aug. 10, 2018, 3 pages.

Order Patent Owner's Motion for Pro Hac Vice Admission of Sophie F. Wang 37 CFR 42.10 submitted before the USPTO Patent Trial and Appeal Board case IPR2017-01447, U.S. Pat. No. 9,340,830, filed Dec. 5, 2017, 3 pages.

Order Trial Hearing 37 C.F.R. § 42.70, submitted before the USPTO Patent Trial and Appeal Board cases IPR2017-01170, IPR2017-01447, and IPR2017-01448, U.S. Pat. No. 9,340,830, filed May 25, 2018, 4 pages.

P.R. 4-3 Joint Claim Construction and Prehearing Statement in *Foundation Medicine, Inc. v. Guardant Health, Inc.*, C.A. No. 2:16-cv-00523-JRG-RSP, filed Mar. 2, 2017, 4 pages.

Pao transcript of "Emerging new targets and new drugs in non-small cell lung cancer: Discussion: Inhibition of immune checkpoint programmed death protein—1 (PD-1) in NSCLC," American Society of Clinical Oncology (Jun. 2, 2012), video available at <http://meetinglibrary.asco.org/record/71618/video>, submitted before the USPTO Patent Trial and Appeal Board for Case Nos. IPR2017-01170, IPR2017-01447, and IPR2017-01448, U.S. Pat. No. 9,340,830, filed Feb. 16, 2018, 14 pages.

Parties' Proposed Preliminary Claim Constructions U.S. Pat. No. 9,340,830 in *Foundation Medicine, Inc. v. Guardant Health, Inc.*, C.A. No. 2:16-cv-00523-JRG-RSP, filed Mar. 2, 2017, 19 pages.

Patent Owner's Unopposed Motion for Pro Hac Vice Admission Under 37 C.F.R. § 42.10( c ), submitted before the USPTO Patent Trial and Appeal Board case IPR2017-01170, U.S. Pat. No. 9,340,830, filed Nov. 22, 2017, 4 pages.

Patent Owner's Unopposed Motion for Pro Hac Vice Admission Under 37 C.F.R. § 42.10(c) submitted before the USPTO Patent Trial and Appeal Board case IPR2017-01448, U.S. Pat. No. 9,340,830, filed Dec. 1, 2017, 4 pages.

Patent Owner's First Amended Mandatory Notices Under 37 C.F.R. §42.8 submitted before the USPTO Patent Trial and Appeal Board case IPR2017-01447, U.S. Pat. No. 9,340,830, filed Dec. 12, 2017, 8 pages.

Patent Owner's First Amended Mandatory Notices Under 37 C.F.R. §42.8, submitted before the USPTO Patent Trial and Appeal Board case IPR2017-01170, U.S. Pat. No. 9,340,830, filed Jun. 21, 2017, 8 pages.

Patent Owner's First Amended Mandatory Notices Under 37 C.F.R. sec. 42.8 submitted before the USPTO Patent Trial and Appeal Board case IPR2017-01448, U.S. Pat. No. 9,340,830, filed Dec. 12, 2017, 8 pages.

Patent Owner's Mandatory Notices Under 37 C.F.R. §42.8 submitted before the USPTO Patent Trial and Appeal Board case IPR2017-01447, U.S. Pat. No. 9,340,830, filed Jun. 6, 2017, 8 pages.

Patent Owner's Mandatory Notices Under 37 C.F.R. §42.8, submitted before the USPTO Patent Trial and Appeal Board case IPR2017-01170, U.S. Pat. No. 9,340,830, filed Apr. 21, 2017, 8 pages.

Patent Owner's Mandatory Notices Under 37 C.F.R. sec. 42.8 submitted before the USPTO Patent Trial and Appeal Board case IPR2017-01448, U.S. Pat. No. 9,340,830, filed Jun. 6, 2017, 8 pages.

Patent Owner's Motion to Seal submitted before the USPTO Patent Trial and Appeal Board case IPR2017-01447, U.S. Pat. No. 9,340,830, filed Feb. 16, 2018, 5 pages.

Patent Owner's Motion to Seal submitted before the USPTO Patent Trial and Appeal Board case IPR2017-01448, U.S. Pat. No. 9,340,830, filed Feb. 16, 2018, 5 pages.

Patent Owner's Motion to Seal, submitted before the USPTO Patent Trial and Appeal Board case IPR2017-01170, U.S. Pat. No. 9,340,830, filed Feb. 16, 2018, 5 pages.

Patent Owner's Motion to Submit Supplemental Information Pursuant to 37 C.F.R. § 42.123(b), submitted before the USPTO Patent Trial and Appeal Board case IPR2017-01170, U.S. Pat. No. 9,340,830, filed May 7, 2018, 11 pages.

Patent Owner's Motion to Submit Supplemental Information Pursuant to 37 C.F.R. § 42.123(b) submitted before the USPTO Patent Trial and Appeal Board case IPR2017-01447, U.S. Pat. No. 9,340,830, filed May 7, 2018, 10 pages.

Patent Owner's Motion to Submit Supplemental Information Pursuant to 37 C.F. R. sec. 42.123(b) submitted before the USPTO Patent Trial and Appeal Board case IPR2017-01448, U.S. Pat. No. 9,340,830, filed May 7, 2018, 10 pages.

Patent Owner's Objections to Evidence Pursuant to 37 C.F.R. § 42.64 submitted before the USPTO Patent Trial and Appeal Board case IPR2017-01447, U.S. Pat. No. 9,340,830, filed Dec. 12, 2017, 4 pages.

Patent Owner's Objections to Evidence Pursuant to 37 C.F.R. § 42.64, submitted before the USPTO Patent Trial and Appeal Board case IPR2017-01170, U.S. Pat. No. 9,340,830, filed Oct. 25, 2017, 4 pages.

(56) References Cited

OTHER PUBLICATIONS

Patent Owner's Objections to Evidence Pursuant to 37 C.F.R. sec. 42.64 submitted before the USPTO Patent Trial and Appeal Board case IPR2017-01448, U.S. Pat. No. 9,340,830, filed Dec. 12, 2017, 4 pages.

Patent Owner's Objections to Petitioner's Oral Hearing Demonstratives, submitted before the USPTO Patent Trial and Appeal Board cases IPR2017-01170, IPR2017-01447, and IPR2017-01448, U.S. Pat. No. 9,340,830, filed Jun. 8, 2018, 3 pages.

Patent Owner's Power of Attorney submitted before the USPTO Patent Trial and Appeal Board case IPR2017-01447, U.S. Pat. No. 9,340,830, filed Dec. 12, 2017, 2 pages.

Patent Owner's Power of Attorney submitted before the USPTO Patent Trial and Appeal Board case IPR2017-01448, U.S. Pat. No. 9,340,830, filed Dec. 1, 2017, 2 pages.

Patent Owner's Power of Attorney Under 37 C.F.R. sec. 42.10 submitted before the USPTO Patent Trial and Appeal Board case IPR2017-01448, U.S. Pat. No. 9,340,830, filed Jun. 6, 2017, 2 pages.

Patent Owner's Power of Attorney, submitted before the USPTO Patent Trial and Appeal Board case IPR2017-01170, U.S. Pat. No. 9,340,830, filed Dec. 12, 2017, 2 pages.

Patent Owner's Preliminary Response submitted before the USPTO Patent Trial and Appeal Board case IPR2017-01447, U.S. Pat. No. 9,340,830, filed Sep. 6, 2017, 72 pages.

Patent Owner's Preliminary Response submitted before the USPTO Patent Trial and Appeal Board case IPR2017-01448, U.S. Pat. No. 9,340,830, filed Sep. 6, 2017, 71 pages.

Patent Owner's Preliminary Response, submitted before the USPTO Patent Trial and Appeal Board case IPR2017-01170, U.S. Pat. No. 9,340,830, filed Jul. 12, 2017, 70 pages.

Patent Owner's Request for Oral Argument submitted before the USPTO Patent Trial and Appeal Board case IPR2017-01447, U.S. Pat. No. 9,340,830, filed May 22, 2018, 4 pages.

Patent Owner's Request for Oral Argument submitted before the USPTO Patent Trial and Appeal Board case IPR2017-01448, U.S. Pat. No. 9,340,830, filed May 22, 2018, 4 pages.

Patent Owner's Request for Oral Hearing, submitted before the USPTO Patent Trial and Appeal Board case IPR2017-01170, U.S. Pat. No. 9,340,830, filed May 22, 2018, 4 pages.

Patent Owner's Request for Rehearing Pursuant to 37 C.F.R. § 42.71(d), submitted before the USPTO Patent Trial and Appeal Board case IPR2017-01170, U.S. Pat. No. 9,340,830, filed Oct. 25, 2017, 14 pages.

Patent Owner's Response submitted before the USPTO Patent Trial and Appeal Board case IPR2017-01447, U.S. Pat. No. 9,340,830, filed Feb. 16, 2018, 80 pages.

Patent Owner's Response submitted before the USPTO Patent Trial and Appeal Board case IPR2017-01448, U.S. Pat. No. 9,340,830, filed Feb. 16, 2018, 80 pages.

Patent Owner's Response, submitted before the USPTO Patent Trial and Appeal Board case IPR2017-01170, U.S. Pat. No. 9,340,830, filed Feb. 16, 2018, 80 pages.

Patent Owner's Revocation of Power of Attorney With New Power of Attorney Under 37 C.F.R. §42.10, submitted before the USPTO Patent Trial and Appeal Board case IPR2017-01170, U.S. Pat. No. 9,340,830, filed Jun. 21, 2017, 2 pages.

Patent Owner's Second Amended Mandatory Notices Under 37 C.F.R. §42.8, submitted before the USPTO Patent Trial and Appeal Board case IPR2017-01170, U.S. Pat. No. 9,340,830, filed Dec. 12, 2017, 8 pages.

Patent Owner's Unopposed Motion for Pro Hac Vice Admission Under 37 C.F.R. § 42.10( c ) submitted before the USPTO Patent Trial and Appeal Board case IPR2017-01447, U.S. Pat. No. 9,340,830, filed Dec. 1, 2017, 4 pages.

Patent Owner's Unopposed Motion to Expunge Unredacted Versions of Exhibits 2077, 2026, 1052, 1053, and 1054 and Petitioner's Reply, submitted before the USPTO Patent Trial and Appeal Board cases IPR2017-01170, IPR2017-01447, and IPR2017-01448, U.S. Pat. No. 9,340,830, filed Aug. 8, 2018, 6 pages.

Patent Owner's Unopposed Motion to Seal, submitted before the USPTO Patent Trial and Appeal Board cases IPR2017-01170, IPR2017-01447, and IPR2017-01448, U.S. Pat. No. 9,340,830, filed May 31, 2018, 9 pages.

Patent Owner's Unopposed Renewed Motion to Seal submitted before the USPTO Patent Trial and Appeal Board case IPR2017-01447, U.S. Pat. No. 9,340,830, filed Apr. 23, 2018, 7 pages.

Patent Owner's Unopposed Renewed Motion to Seal submitted before the USPTO Patent Trial and Appeal Board case IPR2017-01448, U.S. Pat. No. 9,340,830, filed Apr. 23, 2018, 7 pages.

Patent Owner's Unopposed Renewed Motion to Seal, submitted before the USPTO Patent Trial and Appeal Board case IPR2017-01170, U.S. Pat. No. 9,340,830, filed Apr. 23, 2018, 7 pages.

Patent Owner's Updated Exhibit List submitted before the USPTO Patent Trial and Appeal Board case IPR2017-01447, U.S. Pat. No. 9,340,830, filed Apr. 17, 2018, 11 pages.

Patent Owner's Updated Exhibit List submitted before the USPTO Patent Trial and Appeal Board case IPR2017-01447, U.S. Pat. No. 9,340,830, filed Apr. 23, 2018, 11 pages.

Patent Owner's Updated Exhibit List submitted before the USPTO Patent Trial and Appeal Board case IPR2017-01448, U.S. Pat. No. 9,340,830, filed Apr. 17, 2018, 11 pages.

Patent Owner's Updated Exhibit List submitted before the USPTO Patent Trial and Appeal Board case IPR2017-01448, U.S. Pat. No. 9,340,830, filed Apr. 23, 2018, 11 pages.

Patent Owner's Updated Exhibit List, submitted before the USPTO Patent Trial and Appeal Board case IPR2017-01170, U.S. Pat. No. 9,340,830, filed Apr. 17, 2018, 11 pages.

Patent Owner's Updated Exhibit List, submitted before the USPTO Patent Trial and Appeal Board case IPR2017-01170, U.S. Pat. No. 9,340,830, filed Apr. 23, 2018, 11 pages.

Payseur et al., (2010). "A Genomic Portrait of Human Microsatellite Variation," Mol. Biol. Evol., 28(1):303-312.

Peled et al., (2012). "Next Generation Sequencing Identifies and Immunohistochemistry Confirms a Novel Crizotinib Sensitive ALK Rearrangement in a Patient with Metastatic Non-small Cell Lung Cancer," J. Thorac. Oncol., 7(9):1-5.

Pengelly et al., (2013). "A Snp profiling panel for sample tracking in whole-exome sequencing studies," Genome Medicine, 5(89):1-7.

Personal Statement of E. Reines for US Court of Appeals for the Federal Circuit Case 14-MA004, filed Jul. 7, 2014, 2 pages.

Petition For Inter Partes Review of U.S. Pat. No. 9,340,830 submitted before the USPTO Patent Trial and Appeal Board case IPR2017-01447, U.S. Pat. No. 9,340,830, filed May 17, 2017, 75 pages.

Petition for Inter Partes Review of U.S. Pat. No. 9,340,830 submitted before the USPTO Patent Trial and Appeal Board case IPR2017-01448, U.S. Pat. No. 9,340,830, filed May 17, 2017, 77 pages.

Petition For Inter Partes Review of U.S. Pat. No. 9,340,830, submitted before the USPTO Patent Trial and Appeal Board case IPR2017-01170, U.S. Pat. No. 9,340,830, filed Mar. 30, 2017, 73 pages.

Petitioner Guardant Health Inc.'s Updated Exhibit List submitted before the USPTO Patent Trial and Appeal Board case IPR2017-01448, U.S. Pat. No. 9,340,830, filed May 31, 2018, 8 pages.

Petitioner Guardant Health, Inc.'s Motion for Pro Hac Vice Admission Under 37 C.F.R. § 42.10( c ) submitted before the USPTO Patent Trial and Appeal Board case IPR2017-01447, U.S. Pat. No. 9,340,830, filed Motion for Pro Hac Vice Admission, filed Mar. 16, 2018, 13 pages.

Petitioner Guardant Health, Inc.'s Motion For Pro Hac Vice Admission Under 37 C.F.R. § 42.10( c) submitted before the USPTO Patent Trial and Appeal Board case IPR2017-01448, U.S. Pat. No. 9,340,830, filed Mar. 16, 2018, 14 pages.

Petitioner Guardant Health, Inc.'s Motion for Pro Hac Vice Admission Under 37 C.F.R. § 42.10( c), submitted before the USPTO Patent Trial and Appeal Board case IPR2017-01170, U.S. Pat. No. 9,340,830, filed Mar. 16, 2018, 14 pages.

Petitioner Guardant Health, Inc.'s Power of attorney submitted before the USPTO Patent Trial and Appeal Board case IPR2017-01447, U.S. Pat. No. 9,340,830, filed May 17, 2017, 2 pages.

(56)                References Cited

OTHER PUBLICATIONS

Petitioner Guardant Health, Inc.'s Power of attorney submitted before the USPTO Patent Trial and Appeal Board case IPR2017-01448, U.S. Pat. No. 9,340,830, filed May 17, 2017, 2 pages.

Petitioner Guardant Health, Inc.'s Power of attorney, submitted before the USPTO Patent Trial and Appeal Board case IPR2017-01170, U.S. Pat. No. 9,340,830, filed Mar. 30, 2017, 2 pages.

Petitioner Guardant Health, Inc.'s Reply to Patent Owner Response submitted before the USPTO Patent Trial and Appeal Board case IPR2017-01447, U.S. Pat. No. 9,340,830, filed May 8, 2018, 36 pages.

Petitioner Guardant Health, Inc.'s Reply to Patent Owner Response submitted before the USPTO Patent Trial and Appeal Board case IPR2017-01448, U.S. Pat. No. 9,340,830, filed May 8, 2018, 37 pages.

Petitioner Guardant Health, Inc.'s Reply to Patent Owner Response, submitted before the USPTO Patent Trial and Appeal Board case IPR2017-01170, U.S. Pat. No. 9,340,830, filed May 8, 2018, 36 pages.

Petitioner Guardant Health, Inc.'s Updated Exhibit List submitted before the USPTO Patent Trial and Appeal Board case IPR2017-01447, U.S. Pat. No. 9,340,830, filed May 31, 2018, 8 pages.

Petitioner Guardant Health, Inc.'s Updated Exhibit List, submitted before the USPTO Patent Trial and Appeal Board case IPR2017-01170, U.S. Pat. No. 9,340,830, filed May 31, 2018, 8 pages.

Petitioner's List of Proposed Motions submitted before the USPTO Patent Trial and Appeal Board case IPR2017-01447, U.S. Pat. No. 9,340,830, filed Dec. 4, 2017, 4 pages.

Petitioner's List of Proposed Motions submitted before the USPTO Patent Trial and Appeal Board case IPR2017-01448, U.S. Pat. No. 9,340,830, filed Dec. 4, 2017, 4 pages.

Petitioner's List of Proposed Motions, submitted before the USPTO Patent Trial and Appeal Board case IPR2017-01170, U.S. Pat. No. 9,340,830, filed Oct. 23, 2017, 4 pages.

Petitioner's Notice of Objection to Evidence submitted before the USPTO Patent Trial and Appeal Board case IPR2017-01447, U.S. Pat. No. 9,340,830, filed Feb. 26, 2018, 6 pages.

Petitioner's Notice of Objection to Evidence submitted before the USPTO Patent Trial and Appeal Board case IPR2017-01448, U.S. Pat. No. 9,340,830, filed Feb. 26, 2018, 6 pages.

Petitioner's Notice of Objection to Evidence, submitted before the USPTO Patent Trial and Appeal Board case IPR2017-01170, U.S. Pat. No. 9,340,830, filed Feb. 26, 2018, 6 pages.

Petitioner's Notice of Objection to Evidence, submitted before the USPTO Patent Trial and Appeal Board cases IPR2017-01170, IPR2017-01447, and IPR2017-01448, U.S. Pat. No. 9,340,830, filed May 14, 2018, 4 pages.

Petitioner's Opposition to Patent Owner's Motion for Protective Order submitted before the USPTO Patent Trial and Appeal Board case IPR2017-01447, U.S. Pat. No. 9,340,830, filed Mar. 5, 2018, 9 pages.

Petitioner's Opposition to Patent Owner's Motion for Protective Order submitted before the USPTO Patent Trial and Appeal Board case IPR2017-01448, U.S. Pat. No. 9,340,830, filed Mar. 5, 2018, 9 pages.

Petitioner's Opposition to Patent Owner's Motion for Protective Order, submitted before the USPTO Patent Trial and Appeal Board case IPR2017-01170, U.S. Pat. No. 9,340,830, filed Mar. 5, 2018, 9 pages.

Petitioner's Opposition to Patent Owner's Motion to Seal submitted before the USPTO Patent Trial and Appeal Board case IPR2017-01447, U.S. Pat. No. 9,340,830, filed Mar. 5, 2018, 7 pages.

Petitioner's Opposition to Patent Owner's Motion to Seal submitted before the USPTO Patent Trial and Appeal Board case IPR2017-01448, U.S. Pat. No. 9,340,830, filed Mar. 5, 2018, 7 pages.

Petitioner's Opposition to Patent Owners Motion to Seal, submitted before the USPTO Patent Trial and Appeal Board case IPR2017-01170, U.S. Pat. No. 9,340,830, filed Mar. 5, 2018, 7 pages.

Petitioner's Opposition to Patent Owner's Motion to Submit Supplemental Information submitted before the USPTO Patent Trial and Appeal Board case IPR2017-01447, U.S. Pat. No. 9,340,830, filed May 21, 2018, 10 pages.

Petitioner's Opposition to Patent Owner's Motion to Submit Supplemental Information submitted before the USPTO Patent Trial and Appeal Board case IPR2017-01448, U.S. Pat. No. 9,340,830, filed May 21, 2018, 10 pages.

Petitioner's Opposition to Patent Owner's Motion to Submit Supplemental Information, submitted before the USPTO Patent Trial and Appeal Board case IPR2017-01170, U.S. Pat. No. 9,340,830, filed May 21, 2018, 10 pages.

Petitioner's Request for Oral Argument Pursuant to 37 C.F.R. § 42.70 submitted before the USPTO Patent Trial and Appeal Board case IPR2017-01447, U.S. Pat. No. 9,340,830, filed May 22, 2018, 3 pages.

Petitioner's Request for Oral Argument Pursuant to 37 C.F.R. § 42.70, submitted before the USPTO Patent Trial and Appeal Board case IPR2017-01170, U.S. Pat. No. 9,340,830, filed May 22, 2018, 3 pages.

Petitioner's Request for Oral Argument Pursuant to 37 C.F.R. sec. 42.70 submitted before the USPTO Patent Trial and Appeal Board case IPR2017-01448, U.S. Pat. No. 9,340,830, filed May 22, 2018, 3 pages.

Petitioner's Updated Exhibit List submitted before the USPTO Patent Trial and Appeal Board case IPR2017-01447, U.S. Pat. No. 9,340,830, filed Jun. 6, 2017, 7 pages.

Plaintiff Foundation Medicine, Inc.'s Opposition to Defendant's Motion To Dismiss Complaint Pursuant To FED. R. CIV. P. 12(B)(6), Civil Action No. 2:16-CV-00523-JRG-RSP, filed Aug. 25, 2016, 10 pages.

Plaintiff Foundation Medicine's First Preliminary Infringement Contentions in *Foundation Medicine, Inc.* v. *Guardant Health, Inc.*, C.A. No. 2:16-cv-00523-JRG-RSP, filed Aug. 25, 2016, 91 pages.

Plaintiff's P.R. 4-2 Preliminary Claim Constructions in *Foundation Medicine, Inc.* v. *Guardant Health, Inc.*, C.A. No. 2:16-cv-00523-JRG-RSP, filed Apr. 20, 2017, 8 pages.

Proposed Clean Version of the Modified Default Protective Order by Foundation Medicine, Inc., submitted before the USPTO Patent Trial and Appeal Board for Case Nos. IPR2017-01170, IPR2017-01447, and IPR2017-01448, U.S. Pat. No. 9,340,830, filed Apr. 23, 2018, 6 pages.

Proposed Redline Version of the Modified Default Protective Order by Foundation Medicine, Inc., submitted before the USPTO Patent Trial and Appeal Board for Case Nos. IPR2017-01170, IPR2017-01447, and IPR2017-01448, U.S. Pat. No. 9,340,830, filed Apr. 23, 2018, 6 pages.

Protective Order, submitted before the USPTO Patent Trial and Appeal Board cases IPR2017-01170, IPR2017-01447, and IPR2017-01448, U.S. Pat. No. 9,340,830, filed May 31, 2018, 9 pages.

Rebuttal Declaration of Dr. S. Gabriel in Support of Foundation Medicine, Inc.'s Proposed Claim Constructions for *Foundation Medicine, Inc.* v. *Guardant Health, Inc.*, Civil Action No. 2:16-CV-00523-JRG-RSP, dated Mar. 17, 2017, 11 pages.

Rebuttal Declaration of Stacey Gabriel, Ph. D. in Support of Foundation Medicine, Inc.'s Proposed Claim Constructions in *Foundation Medicine, Inc.* v. *Guardant Health, Inc.*, C.A. No. 2:16-cv-00523-JRG-RSP, filed Apr. 6, 2017, 12 pages.

Record of Oral Hearing held on Jun. 13, 2018, submitted before the USPTO Patent Trial and Appeal Board cases IPR2017-01170, IPR2017-01447, and IPR2017-01448, U.S. Pat. No. 9,340,830, filed Jun. 13, 2018, 88 pages.

Redacted Deposition of Dr. J. Nemunaitis (Apr. 5, 2018) in *Guardant Health, Inc.* v. *Foundation Medicine, Inc.* Case Nos. IPR2017-01170, IPR2017-01447, and IPR2017-01448, U.S. Pat. No. 9,340,830, 166 pages.

Redacted Deposition of Dr. S. Gabriel (Apr. 3, 2018) in *Guardant Health, Inc.* v. *Foundation Medicine, Inc.* Case Nos. IPR2017-01170, IPR2017-01447, and IPR2017-01448, U.S. Pat. No. 9,340,830, filed May 31, 2018, 287 pages.

(56)        References Cited

OTHER PUBLICATIONS

Redacted Deposition of Dr. S. Gabriel (Apr. 3, 2018) in *Guardant Health, Inc.* v. *Foundation Medicine, Inc.* Case Nos. IPR2017-01170, IPR2017-01447, and IPR2017-01448, U.S. Pat. No. 9,340,830, filed May 8, 2018, 287 pages.
Redacted Expert Declaration of Dr. S. Gabriel submitted before the USPTO Patent Trial and Appeal Board for case IPR2017-01170, U.S. Pat. No. 9,340,830, filed Apr. 23, 2018, 88 pages.
Redacted Expert Declaration of Dr. S. Gabriel submitted before the USPTO Patent Trial and Appeal Board for case IPR2017-01170, U.S. Pat. No. 9,340,830, filed Feb. 16, 2018, 88 pages.
Redacted Expert Declaration of Dr. S. Gabriel submitted before the USPTO Patent Trial and Appeal Board for case IPR2017-01447, U.S. Pat. No. 9,340,830, filed Apr. 23, 2018, 88 pages.
Redacted Expert Declaration of Dr. S. Gabriel submitted before the USPTO Patent Trial and Appeal Board for case IPR2017-01447, U.S. Pat. No. 9,340,830, filed Feb. 16, 2018, 88 pages.
Redacted Expert Declaration of Dr. S. Gabriel submitted before the USPTO Patent Trial and Appeal Board for case IPR2017-01448, U.S. Pat. No. 9,340,830, filed Apr. 23, 2018, 88 pages.
Redacted Expert Declaration of Dr. S. Gabriel submitted before the USPTO Patent Trial and Appeal Board for case IPR2017-01448, U.S. Pat. No. 9,340,830, filed Feb. 16, 2018, 88 pages.
Redline Version of the Modified Default Protective Order by Foundation Medicine, Inc., submitted before the USPTO Patent Trial and Appeal Board for Case Nos. IPR2017-01170, IPR2017-01447, and IPR2017-01448, U.S. Pat. No. 9,340,830, filed Feb. 16, 2018, 8 pages.
Reply in Support of Patent Owner's Motion for Protective Order submitted before the USPTO Patent Trial and Appeal Board case IPR2017-01447, U.S. Pat. No. 9,340,830, filed Mar. 12, 2018, 8 pages.
Reply in Support of Patent Owner's Motion for Protective Order submitted before the USPTO Patent Trial and Appeal Board case IPR2017-01448, U.S. Pat. No. 9,340,830, filed Mar. 12, 2018, 8 pages.
Reply in Support of Patent Owner's Motion for Protective Order, submitted before the USPTO Patent Trial and Appeal Board case IPR2017-01170, U.S. Pat. No. 9,340,830, filed Mar. 12, 2018, 8 pages.
Reply in Support of Patent Owner's Motion to Seal submitted before the USPTO Patent Trial and Appeal Board case IPR2017-01447, U.S. Pat. No. 9,340,830, filed Mar. 12, 2018, 8 pages.
Reply in Support of Patent Owner's Motion to Seal submitted before the USPTO Patent Trial and Appeal Board case IPR2017-01448, U.S. Pat. No. 9,340,830, filed Mar. 12, 2018, 8 pages.
Reply in Support of Patent Owner's Motion to Seal, submitted before the USPTO Patent Trial and Appeal Board case IPR2017-01170, U.S. Pat. No. 9,340,830, filed Mar. 12, 2018, 8 pages.
Reporter's Transcription of Teleconference Board Meeting, (Apr. 16, 2018) in *Guardant Health, Inc.* v. *Foundation Medicine, Inc* : Case Nos. IPR2017-01170, IPR2017-01447, and IPR2017-01448, 22 pages.
Rhei et al., (1997). "Mutation Analysis of the Putative Tumor Suppressor Gene PTEN/MMAC1 in Primary Breast Carcinomas," Cancer Res., 57(17):3657-3659.
Rosell et al., (2009). "Screening for Epidermal Growth Factor Receptor Mutations in Lung Cancer," N. Engl. J. Med, 361:958-67.
Ross et al., (2013). "Comprehensive genomic profiling of epithelial ovarian cancer by next generation sequencing-based diagnostic assay reveals new routes to targeted therapies," Gynecologic Oncology, 130:554-559.
Ross et al., (2017). "ALK Fusions in a Wide Variety of Tumor Types Respond to Anti-ALK Targeted Therapy," The Oncologist, 22:1444-1450.
Roy, et al. (2006). "Survival Advantage from Imatinib Compared with the Combination Interferon-alpha plus Cytarabine in Chronic-Phase Chronic Myelogenous Leukemia: Historical Comparison Between Two Phase 3 Trials," Blood, 108(5): 1478-1484.
Sakharkar et al., (2004). "Distributions of Exons and Introns in the Human Genome," In Silico Biology, 4:387-393.
Sambrook et al., (2001). "In Vitro Amplification of DNA by the Polymerase Chain Reaction," Molecular Cloning: A Laboratory Manual, 3rd edition, 2:6-28.
Scheduling Order submitted before the USPTO Patent Trial and Appeal Board case IPR2017-01447, U.S. Pat. No. 9,340,830, filed Nov. 28, 2017, 7 pages.
Scheduling Order submitted before the USPTO Patent Trial and Appeal Board case IPR2017-01448, U.S. Pat. No. 9,340,830, filed Nov. 28, 2017, 7 pages.
Scheduling Order, submitted before the USPTO Patent Trial and Appeal Board case IPR2017-01170, U.S. Pat. No. 9,340,830, filed Oct. 11, 2017, 7 pages.
Schuster, (2008). Next-generation sequencing transforms today's biology, Nature Methods, 5(1):16-18.
Second Amended Scheduling Order submitted before the USPTO Patent Trial and Appeal Board case IPR2017-01447, U.S. Pat. No. 9,340,830, filed Dec. 12, 2017, 3 pages.
Second Amended Scheduling Order submitted before the USPTO Patent Trial and Appeal Board case IPR2017-01448, U.S. Pat. No. 9,340,830, filed Dec. 12, 2017, 3 pages.
Second Amended Scheduling Order, submitted before the USPTO Patent Trial and Appeal Board case IPR2017-01170, U.S. Pat. No. 9,340,830, filed Dec. 12, 2017, 3 pages.
Shah et al., (2009). "Mutational Evolution in a Lobular Breast Tumour Profiled at Single Nucleotide Resolution," Nature, 461:809-813, and Supplementary Information, 1021 pages.
Shah et al., (2012). "The clonal and mutational evolution spectrum of primary triple-negative breast cancers," Nature, 486:395-399.
Shepherd et al., (2005). "Erlotinib in Previously Treated Non-Small-Cell Lung Cancer," N. Engl. J. Med, 353:123-32.
Shum, J. et al. (2009). "Chemically Modified Primers for Improved Multiplex PCR," Anal. Biochem., 388(2):15 pages.
Singapore Search Report for Singapore Application No. 201305122-2, mailed on Oct. 8, 2014, 7 pages.
Singapore Written Opinion for Singapore Application No. 201305122-2, mailed on Nov. 18, 2014, 9 pages.
Stephens, et al., (2009). "Complex Landscapes of Somatic Rearrangement in Human Breast Cancer Genomes," Nature, 462: 8 pages.
Stratton et al., (2009). "The cancer genome," Nature, 458: 6 pages.
Sucker et al., (2017). "Acquired IFNgamma resistance impairs anti-tumor immunity and gives rise to T-cell-resistant melanoma lesions," Nature Communications, 8(154):1-15.
Summerer et al., "Microarray-based multicycle-enrichment of genomic subsets for targeted next generation sequencing," Genome Research (2009) vol. 19, pp. 1616-1621.
Summerer et al., (2010). "Supplementary Information Targeted High Throughput Sequencing of a Cancer-related Exome Subset by Specific Sequence Capture with a Fully Automated Microarray Platform," Genomics, 95(4), Apr. 1, 2010, 9 pages.
Summerer et al., (2010). "Targeted high Throughput Sequencing of a Cancer-Related Exome Subset by specific Sequence Capture with a Fully Automated Microarray Platform", Genomics, 95(4):241-246.
Summerer, (2009). "Enabling technologies of genomic-scale sequence enrichment for targeted high-throughput sequencing," Genomics, 94:363-368.
Supplemental European Search Report for European Application No. 11853462, mailed on Apr. 24, 2014, 8 pages.
Taylor et al., (2011). "Clinical cancer genomics: how soon is now?" The Journal of Pathology, 223(2):319-327.
Taylor, (2017). "Foundation Medicine gets FDA, CMS nods for pan-cancer genomic test," available online at <https://www.fiercebiotech.com/medtech/foundation-medicine-gets-fda-cms-nods-for-pan-cancer-genomic-test>, accessed on Feb. 16, 2018, 3 pages.
Teer et al., (2010). "Systematic Comparison of Three Genomic Enrichment Methods for Massively Parallel DNA Sequencing", Genome Research, 20(10):1420-1431.
Termination, Terminating the Proceeding 37 C.F.R. sec. 42.72, submitted before the USPTO Patent Trial and Appeal Board cases

(56) References Cited

OTHER PUBLICATIONS

IPR2017-01170, IPR2017-01447, and IPR2017-01448, U.S. Pat. No. 9,340,830, filed Jul. 10, 2018, 3 pages.

Tewhey et al., (2009). "Enrichment of Sequencing Targets from the Human Genome by solution Hybridization," Genome Biology, 10:R116, 13 pages.

The Cancer Genome Atlas Network, (2015). "Genome Classification of Cutaneous Melanoma" Cell Press, 161:1681-1696.

Third Party Observations Filed in Australian Patent Application No. 2011352070, Jan. 30, 2017, 4 pages.

Timmermann et al., "Somatic Mutation Profiles of MSI and MSS Colorectal Cancer Identified by Whole Exome Next Generation Sequencing and Bioinformatics Analysis," PLOS One (2010) vol. 5, Issue 12, Article e15661, 10 pages.

Walker, et al., (2013). "Characterization of IGH Locus Breakpoints in Multiple Myeloma Indicates a Subset of Translocations Appear to Occur in Pregerminal Center B Cells," Blood, 121(17):3413-3419.

Wang et al., (2012). "A quick and simple FISH protocol with hybridization-sensitive fluorescent linear oligodeoxynucleotide probes," RNA, 18:166-175.

Wilkerson et al., (2014). "Integrated RNA and DNA sequencing improves mutation detection in low purity tumors," Nucleic Acids Research, e107, 12 pages.

Wong, K.K., et al., "Use of Tagged Random Hexamer Amplification (TRHA) to Clone and Sequence Minute Quantities of DNA-Application to a 180 kb Plasmid Isolated from Sphingomonas F199," Nucleic Acids Res. 24(19):3778-3783 (1996).

World Health Organization, (2014). "World Cancer Report 2014," WHO Press, World Health Organization, 19 pages.

Written Opinion of the International Searching Authority for PCT/US11/67725 mailed Apr. 27, 2012, 12 pages.

Wu, D. et al. (1989). "Allele-Specific Enzymatic Amplification of β-Globin Genomic DNA for Diagnosis of Sickle Cell Anemia," Proc. Natl. Acad. Sci. USA, 86:2757-2760.

Yassour, M. et al. (2009). "Ab Initio Construction of a Eukaryotic Transcriptome by Massively Parallel mRNA Sequencing," PNAS, 106(9):13 pages.

Coronella et al., (2002). "Antigen-Driven Oligoclonal Expansion of Tumor-Infiltrating B Cells in Infiltrating Ductal Carcinoma of the Breast," J. Immunol., 169(4):1829-1836.

Thor Straten et al., (2004). "T-cell clonotypes in cancer," Journal of Translational Medicine, 2:11, 10 pages.

Woodsworth et al., (2013). "Sequence analysis of T-cell repertoires in health and disease," Genome Medicine, 5:98, 13 pages.

File history for U.S. Appl. No. 13/339,986, filed Dec. 29, 2011, 1,385 pages.

Clement et al., (2010). "The GNUMAP algorithm: unbiased probabilistic mapping of oligonucleotides from next-generation sequencing," Bioinformatics, 26(1):38-45.

De Bona et al., (2008). "Optimal spliced alignments of short sequence reads," Bioinformatics, 24(16):i174-i180.

Eaves et al., (2009). "MOM: maximum oligonucleotide mapping," Bioinformatics, 25(7):969-70.

Extended European Search Report received for European Patent Application No. 22168503.5, mailed Nov. 14, 2022, 7 pages.

Fahlgren et al., (2009). "Computational and analytical framework for small RNA profiling by high-throughput sequencing," RNA, 15:992-1002.

Homer et al., (2009). "BFAST: An Alignment Tool for Large Scale Genome Resequencing," PLoS One, 4(11):e7767, 12 pages.

Jiang et al., (2008). "SeqMap: mapping massive amount of oligonucleotides to the genome," Bioinformatics, 24:2395-2396.

Kent, (2002). "BLAT—the BLAST-like alignment tool," Genome Res., 12(4):656-64.

Kim et al., (2009). "ProbeMatch: rapid alignment of oligonucleotides to genome allowing both gaps and mismatches," Bioinformatics, 25(11):1424-5.

Krishnakumar et al., (2008). "A comprehensive assay for targeted multiplex amplification of human DNA sequences," Proc. Natl. Acad. Sci. USA, 105:9296-9310.

Langmead et al., (2009). "Ultrafast and memory-efficient alignment of short DNA sequences to the human genome," Genome Biol., 10(3):R25, 10 pages.

Lasken, (2007). "Single-cell genomic sequencing using Multiple Displacement Amplification," Curr Opin Microbiol., 10(5):510-6.

Li et al., (2008). "Mapping short DNA sequencing reads and calling variants using mapping quality scores," Genome Res., 18(11):1851-8.

Li et al., (2008). "SOAP: short oligonucleotide alignment program," Bioinformatics, 24(5):713-4.

Li et al., (2009). "SOAP2: an improved ultrafast tool for short read alignment," Bioinformatics, 25(15):1966-7.

Malhis et al., (2009). "Slider—maximum use of probability information for alignment of short sequence reads and SNP detection," Bioinformatics, 25(1):6-13.

Muller et al., (2001). "Non-symmetric score matrices and the detection of homologous transmembrane proteins," Bioinformatics, 17 Suppl 1:S182-9.

Ning et al., (2001). "SSAHA: a fast search method for large DNA databases," Genome Res., 11(10):1725-9.

Ondov et al., (2008). "Efficient mapping of Applied Biosystems SOLiD sequence data to a reference genome for functional genomic applications," Bioinformatics, 24(23):2776-7.

Porreca et al., (2007). "Multiplex amplification of large sets of human exons," Nature Methods, 4:931-936.

Prufer et al., (2008). "PatMaN: rapid alignment of short sequences to large databases," Bioinformatics, 24(13):1530-1.

Rumble et al., (2009). "SHRiMP: Accurate Mapping of Short Color-space Reads," PLoS Comput. Biol., 5(5):e1000386, 11 pages.

Salmela, (2010). "Correction of sequencing errors in a mixed set of reads," Bioinformatics, 26(10):1284-90.

Schatz, (2009). "CloudBurst: highly sensitive read mapping with MapReduce," Bioinformatics, 25(11):1363-9.

Shi et al., (2010). "A parallel algorithm for error correction in high-throughput short-read data on CUDA-enabled graphics hardware," J Comput Biol., 17(4):603-15, 20 pages.

Smith et al., (2009). "Updates to the RMAP short-read mapping software," Bioinformatics, 25(21):2841-2.

Tewhey et al., (2009). "Microdroplet-based PCR enrichment for large-scale targeted sequencing," Nature Biotech., 27:1025-1031, 24 pages.

Turner et al., (2009). "Massively parallel exon capture and library-free resequencing across 16 genomes," Nature Methods, 6:315-316, 5 pages.

Weese et al., (2009). "RazerS—fast read mapping with sensitivity control," Genome Research, 19:1646-1654.

Wong et al., (1996). "Use of tagged random hexamer amplification (TRHA) to clone and sequence minute quantities of DNA—application to a 180 kb plasmid isolated from Sphingomonas F199," Nucleic Acids Res., 24(19):3778-83.

Wu et al., (2005). "GMAP: a genomic mapping and alignment program for mRNA and EST sequences," Bioinformatics, 21(9):1859-75.

Wu et al., (2010). "Fast and SNP-tolerant detection of complex variants and splicing in short reads," Bioinformatics, 26(7):873-81.

* cited by examiner

Expected APC median coverage by
target capture reagent:anti-target capture reagent ratio

SEQUENCE LISTING

<160> NUMBER OF SEQ ID NOS: 1

<210> SEQ ID NO 1
<211> LENGTH: 150
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: modified_base
<222> LOCATION: (16)..(135)
<223> OTHER INFORMATION: a, c, t, g, unknown or other

<400> SEQUENCE: 1
atcgcaccag cgtgtnnnnn nnnnnnnnnn nnnnnnnnnn nnnnnnnnnn nnnnnnnnnn       60
nnnnnnnnnn nnnnnnnnnn nnnnnnnnnn nnnnnnnnnn nnnnnnnnnn nnnnnnnnnn      120
nnnnnnnnnn nnnnncactg cggctcctca                                     150

1

COMPOSITIONS AND METHODS FOR EVALUATING GENOMIC ALTERATIONS

CROSS REFERENCE TO RELATED APPLICATIONS

This application claims the benefit of U.S. Provisional Application No. 62/683,469, filed Jun. 11, 2018. The contents of the aforementioned application are hereby incorporated by reference in their entirety.

SEQUENCE LISTING

The instant application contains a Sequence Listing which has been submitted electronically in ASCII format and is hereby incorporated by reference in its entirety. Said ASCII copy, created on Jun. 6, 2019, is named F2036-707210_SL.txt and is 840 bytes in size.

FIELD OF THE INVENTION

The invention relates to compositions and methods for evaluating genomic alterations.

BACKGROUND OF THE INVENTION

Cancer cells accumulate mutations during cancer development and progression. These mutations may be the consequence of intrinsic malfunction of DNA repair, replication, or modification, or exposures to external mutagens. Certain mutations have conferred growth advantages on cancer cells and are positively selected in the microenvironment of the tissue in which the cancer arises. While the selection of advantageous mutations contributes to tumorigenesis, the likelihood of generating tumor neoantigens and subsequent immune recognition may also increase as mutations develop (Gubin and Schreiber. *Science* 350:158-9, 2015). Therefore, total mutational burden, as measured by whole exome sequencing (WES), can be used to guide patient treatment decisions, for example, to predict a durable response to a cancer immunotherapy. However, translating genomic studies to routine clinical practice remains problematic as whole exome sequencing is not widely available and is expensive, time intensive, and technically challenging.

Therefore, the need still exists for novel approaches, including genomic profiling targeting a subset of the genome or exome from patient samples.

SUMMARY OF THE INVENTION

In one aspect, the invention features a plurality of target capture reagents, comprising first target capture reagents (R1s) and second target capture reagents (R2s), wherein:

R1s comprise R1s that comprise a functional first member of a binding pair (e.g., a binding pair described herein), and optionally, R1s that lack a functional first member of the binding pair; and R2s comprise R2s that comprise a functional first member of the binding pair and R2s that lack a functional first member of the binding pair;

wherein the first member of the binding pair is capable of binding to a second member of the binding pair disposed on substrate, and wherein the proportion of R1s that comprises a functional first member of the binding pair is greater than the proportion of R2s that comprise a functional first member of the binding pair.

In some embodiments of the plurality of target capture reagents, the proportion of R1s that comprise a functional first member of the binding pair is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the proportion of R2s that comprise a functional first member of the binding pair.

In some embodiments of the plurality of target capture reagents, each of the R1s is capable of forming a first fragment/first target capture reagent (F1/R1) hybrid, and each of the R2s is capable of forming a second fragment/second target capture reagent (F2/R2) hybrid, and wherein F1, F2, or both, comprises a subject interval from a gene described in Tables 1A-5A.

In some embodiments, F1 comprises a high sequencing depth event.

In some embodiments, F2 comprises a low sequencing depth event. In other embodiments, the level of the low sequencing depth event is associated with determination of one or more biomarkers, e.g., tumor mutational burden (TMB), or microsatellite instability (MSI).

In some embodiments, the plurality of target capture reagents further comprises third target capture reagents (R3s), wherein R3s comprise R3s that comprise a functional first member of the binding pair and R3s that lack a functional first member of the binding pair;

wherein the first member of the binding pair is capable of binding to a second member of the binding pair disposed on substrate, and wherein the proportion of R2s that comprises a functional first member of the binding pair is greater (e.g., at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold) than the proportion of R3s that comprise a functional first member of the binding pair.

In some embodiments of the plurality of target capture reagents, each of the R3s is capable of forming a third fragment/first target capture reagent (F3/R3) hybrid, and wherein F3 comprises a subject interval from a gene described in Tables 1A-5A.

In some embodiments of the plurality of target capture reagents, the ratio of R1s that comprise a functional first member of a binding pair (e.g., a binding pair described herein) to R1s that lack a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R1s that lack a functional first member of a binding pair (e.g., a binding pair described herein) to R1s that comprise a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R2s that comprise a functional first member of a binding pair (e.g., a binding pair described herein) to R2s that lack a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R2s that lack a functional first member of a binding pair (e.g., a binding pair described herein) to R2s that comprise a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R3s that comprise a functional first member of a binding pair (e.g., a binding pair described herein) to R3s that lack a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R3s that lack a functional first member of a binding pair (e.g., a binding pair described herein) to R3s that comprise a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In an embodiment of the plurality of target capture reagents, the ratio of A to B is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%, wherein:

A comprises R1s (e.g., that comprise a functional first member of the binding pair), and R2s that lack a functional first member of a binding pair (e.g., a binding pair described herein); and B comprises R1s (e.g., that comprise a functional first member of a binding pair), and R2s that comprise a functional first member of a binding pair.

In an embodiment of the plurality of target capture reagents, the ratio of A to B is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%, wherein:

A comprises R1s that comprise a functional first member of the binding pair; and R2s that lack a functional first member of a binding pair (e.g., a binding pair described herein); and B comprises R1s that comprise a functional first member of a binding pair and R2s that comprise a functional first member of a binding pair.

In an embodiment, the ratio of the plurality of target capture reagents is determined by an assay described in Example 1. In an embodiment, the ratio is determined based on a first sequencing depth, e.g., the sequencing depth of one or more subgenomic intervals comprising a high sequencing depth event, e.g., as described herein. In an embodiment, the ratio is determined based on a second sequencing depth, e.g., the sequencing depth of a different subgenomic interval, e.g., one or more subgenomic intervals comprising a low sequencing depth event. In an embodiment, the ratio is determined based on a first sequencing depth, e.g., the sequencing depth of one or more subgenomic intervals comprising a high sequencing depth event, e.g., as described herein; and a second sequencing depth, e.g., the sequencing depth of a different subgenomic interval, e.g., one or more subgenomic intervals comprising a low sequencing depth event. In an embodiment, the ratio is determined based on the sequencing depth of a first fragment (F1), e.g., an F1 comprising a high sequencing depth event. In an embodiment, the ratio is determined based on the sequencing depth of a second fragment (F2), e.g., an F2 comprising a low sequencing depth event. In an embodiment, the ratio is determined based on the sequencing depth of F1, e.g., an F1 comprising a high sequencing depth event; and the sequencing depth of F2, e.g., an F2 comprising a low sequencing depth event.

In an embodiment, the ratio is determined based on the sequencing depth of one or more genes, e.g., pre-selected genes. In an embodiment, the ratio is chosen by determining the sequencing depth of one or more genes or subgenomic intervals, e.g., pre-selected genes or pre-selected subgenomic intervals. In an embodiment, the ratio is altered, e.g., increased or decreased, based on the sequencing depth of one or more genes, e.g., pre-selected genes or pre-selected subgenomic intervals. In an embodiment, the ratio is altered, e.g., increased or decreased, to obtain a pre-selected sequencing depth of one or more genes or subgenomic intervals.

In an embodiment, the plurality of target capture reagents has a ratio of target capture reagents that comprise a functional first member of a binding pair to target capture reagents that lack a functional first member of a binding pair that allows for a first sequencing depth. In an embodiment, the plurality of target capture reagents has a ratio of target capture reagents that comprise a functional first member of a binding pair to target capture reagents that lack a functional first member of a binding pair that allows for a second sequencing depth. In an embodiment, the second sequencing depth is other than a first sequencing depth. In an embodiment, the first sequencing depth is greater than the second sequencing depth, e.g., at least 1.1, 2, 3, 4, 5, 6, 7, 8, 9 or 10-fold greater than the second sequencing depth. In an embodiment, the first sequencing depth is about 1.1 to 10-fold, about 1.1 to 9-fold, about 1.1 to 8 fold, about 1.1 to 7-fold, about 1.1 to 6-fold, about 1.1 to 5-fold, about 1.1 to 4-fold, about 1.1 to 3-fold, about 1.1 to 2-fold, about 2 to 10-fold, about 3 to 10-fold, about 4 to 10-fold, about 5 to 10-fold, about 6 to 10-fold, about 7 to 10-fold, about 8 to 10-fold, or about 9 to 10-fold greater than the second sequencing depth. In an embodiment, the first sequencing depth is about 1.1-fold, about 2-fold, about 3-fold, about 4-fold, about 5-fold, about 6-fold, about 7-fold, about 8-fold, about 9-fold, about 10-fold greater than the second sequencing depth.

In an embodiment, the second sequencing depth is greater than the first sequencing depth, e.g., at least 1.1, 2, 3, 4, 5, 6, 7, 8, 9 or 10-fold greater than the first sequencing depth. In an embodiment, the second sequencing depth is about 1.1 to 10-fold, about 1.1 to 9-fold, about 1.1 to 8 fold, about 1.1 to 7-fold, about 1.1 to 6-fold, about 1.1 to 5-fold, about 1.1 to 4-fold, about 1.1 to 3-fold, about 1.1 to 2-fold, about 2 to 10-fold, about 3 to 10-fold, about 4 to 10-fold, about 5 to 10-fold, about 6 to 10-fold, about 7 to 10-fold, about 8 to 10-fold, or about 9 to 10-fold greater than the first sequencing depth. In an embodiment, the second sequencing depth is about 1.1-fold, about 2-fold, about 3-fold, about 4-fold, about 5-fold, about 6-fold, about 7-fold, about 8-fold, about 9-fold, about 10-fold greater than the first sequencing depth.

In an embodiment, a first sequencing depth, e.g., F1 sequencing depth, is a narrow high sequencing depth, e.g., as described in Example 1.

In an embodiment, a second sequencing depth, e.g., F2 sequencing depth, is a wide moderate sequencing depth, e.g., as described in Example 1.

In an embodiment, a first sequencing depth, e.g., F2 sequencing depth, is a narrow high sequencing depth, e.g., as described in Example 1.

In an embodiment, a second sequencing depth, e.g., F1 sequencing depth, is a wide moderate sequencing depth, e.g., as described in Example 1.

In an embodiment, F1 comprises a high sequencing depth event. In an embodiment, the high sequencing depth event comprises an actionable event, e.g., an actionable event described herein. In an embodiment, the high sequencing depth event comprises a sequence (e.g., a subgenomic interval sequence) that is sequenced to a high sequencing depth, e.g., a depth which is at least 1, 2, 3, 4, 5, 6, 7, 8, 9, or 10-fold greater, than a low sequencing depth event.

In an embodiment, F1 does not comprise a low sequencing depth event.

In an embodiment, F2 comprises a low sequencing depth event. In an embodiment, the low sequencing depth event comprises an event. In an embodiment, the level of the low sequencing depth event is associated with determination of one or more biomarkers, e.g., tumor mutational burden (TMB), microsatellite instability (MSI), or both. In an embodiment, the low sequencing depth event comprises an actionable event, e.g., an actionable event described herein. In an embodiment, the low sequencing depth event does not comprise an actionable event, e.g., not an actionable event described herein. In an embodiment, the low sequencing depth event comprises a sequence (e.g., a subgenomic interval sequence) that is sequenced to a low sequencing depth, e.g., a depth which is less than 1, 2, 3, 4, 5, 6, 7, 8, 9, or 10-fold lower, than a high sequencing depth event.

In an embodiment, F2 does not comprise a high sequencing depth event.

In an embodiment, the plurality of target capture reagents, e.g., R1s, R2s and/or R3s, is not limiting, e.g., is at an excess e.g., a molar excess, of about 100-2000X. In an embodiment, the plurality of target capture reagents is at an excess, e.g., a molar excess, of about 100X, 200X, 300X, 400X, 500X, 600X, 700X, 800X, 900X, 1000X, 1100X, 1200X, 1300X 1400X, 1500X, 1600×1700X, 1800X, 1900X, or 2000X. In an embodiment, the plurality of target capture reagents is at an excess, e.g., a molar excess, of about 100-1900X, 100-1800X, 100-1700X, 100-1600X, 100-1500X, 100-1400X, 100-1300X, 100-1200X, 100-1100X, 100-1000X, 100-900X, 100-800X, 100-700X, 100-600X, 100-500X, 100-400X, 100-300X, 100-200X, 200-2000X, 300-2000X, 400-2000X, 500-2000X, 600-2000X, 700-2000X, 800-2000X, 900-2000X, 1000-2000X, 1100-2000X, 1200-2000X, 1300-2000X, 1400-2000X, 1500-2000X, 1600-2000X, 1700-2000X, 1800-2000X, or 1900-2000X.

In an embodiment of the plurality of target capture reagents, the concentrations of: (i) R2s comprising a first member; (ii) R2s not comprising a first member; and (iii) F2; are such that the proportion of R2s not comprising a first member to R2s comprising a first member affects the number of complexes of F2-R2s comprising a first member.

In an embodiment of the plurality of target capture reagents, the concentrations of: (i) R1s comprising a first member; (ii) R1s not comprising a first member; and (iii) F1; are such that the proportion of R1s not comprising a first member to R1s comprising a first member affects the number of complexes of F1-R1s comprising a first member.

In another aspect, disclosed herein is a method of analyzing a sample, comprising:

contacting a plurality of first fragment/first target capture reagent (F1/R1) hybrids with substrate to form F1/R1 hybrid/substrate complexes; and contacting a plurality of second fragment/second target capture reagent (F2/R2) hybrids with substrate to form F2/R2 hybrid/substrate complexes, wherein the proportion of F1/R1 hybrids which bind to substrate is greater than the proportion of F2/R2 hybrids which bind to substrate, thereby analyzing the sample.

In some embodiments, a portion of the R1s and a portion of the R2s comprise a functional first member of a binding pair. In some embodiments, the first member of the binding pair is capable of binding to a second member of the binding pair disposed on substrate.

In some embodiments, a portion of the R1s, a portion of the R2s, or both, lack a functional first member of a binding pair, e.g., an altered or blocked first member that is not capable of binding, or has reduced binding affinity, to a second member of the binding pair disposed on substrate.

In some embodiments, the R1s comprise R1s that comprise a functional first member of a binding pair and R1s that lack a functional first member of the binding pair; and the R2s comprise R2s that comprise a functional first member of a binding pair and R2s that lack a functional first member of the binding pair.

In some embodiments, the proportion of R1s that comprise a functional first member of the binding pair is greater than the proportion of R2s that comprise a functional first member of the binding pair.

In some embodiments, the proportion of R1s that comprise a functional first member of the binding pair is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the proportion of R2s that comprise a functional first member of the binding pair.

In some embodiments, F1 comprises a high sequencing depth event.

In some embodiments, F2 comprises a low sequencing depth event. In other embodiments, the level of the low sequencing depth event is associated with determination of one or more biomarkers, e.g., tumor mutational burden (TMB), or microsatellite instability (MSI).

In some embodiments, the proportion of R1s that comprise a functional first member of the binding pair and the proportion of R2s that comprise a functional first member of the binding pair are such that, upon formation of the F1/R1 hybrid/substrate complexes and the F2/R2 hybrid/substrate complexes, the number of F1s in the F1/R1 hybrid/substrate complexes and the number of F2s in the F2/R2 hybrid/substrate complexes have one or both of the following relationships:

(i) the number of F1s is greater than, or is substantially the same as, the number of F2s; and/or (ii) the number of F1s comprising an alteration in a first subject interval is greater than, or is substantially the same as, the number of F2s comprising an alteration in a second subject interval.

In some embodiments, the number of F1s is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F2s In some embodiments, the number of F1s comprising an alteration in a first subject interval is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F2s comprising an alteration in a second subject interval.

In some embodiments, the first subject interval, the second subject interval, or both, is from a gene described in Tables 1A-5A.

In some embodiments, the alteration in the first subject interval is present at a mutant allele frequency (MAF) of about 0.01-20%, e.g., about 0.02-19%, 0.03-18%, 0.04-17%, 0.05-16%, 0.06-15%, 0.07-14%, 0.08-13%, 0.09-12%, 0.1-10%, 0.2-9%, 0.3-8%, 0.4-7%, 0.5-6%, 0.6-5%, 0.7-4%, 0.8-3%, 0.9-2%, 1-1.9%, 1.1-1.8%, 1.2-1.7%, 1.3-1.6%, or 1.4-1.5%, in the sample. In some embodiments, the first subject interval is present at a mutant allele frequency (MAF) of equal to or greater than about 0.1% (e.g., equal to or greater than about 0.2%, 0.3%, 0.4%, 0.5%, 0.6%, 0.7%, 0.8%, or 0.9%, e.g., about 0.1% to 0.9%, 0.2% to 0.8%, 0.3% to 0.7%, or 0.4% to 0.6%) in the sample. In some embodiments, the first subject interval is present at a mutant allele frequency (MAF), of equal to or greater than about 1% (e.g., equal to or greater than about 2%, 3%, 4%, 5%, 6%, 7%, 8%, or 9%, e.g., about 1% to 9%, 2% to 8%, 3% to 7%, or 4% to 6%) in the sample.

In some embodiments, F1, F2, or both, comprises a subject interval from a gene described in Tables 1A-5A.

In some embodiments, the subject interval in F1 is sequenced to a first depth, and the subject interval in F2 is sequenced to a second depth, wherein the first depth is at least 1, 2, 3, 4, 5, 6, 7, 8, 9, 10-fold greater than the second depth.

In some embodiments, F1 comprises a subject interval from a gene described in Tables 1A-5A, and wherein the subject interval comprises an alteration, e.g., a somatic alteration, e.g., a functional alteration in cancer.

In some embodiments, the subject interval is sequenced to at least about 5,000X depth.

In some embodiments, F2 comprises a subject interval from a gene described in Tables 1A-5A, and wherein the subject interval comprises an alteration, e.g., a somatic alteration, wherein the determination of the alteration is used for evaluating one or more genomic signatures, e.g., continuous/complex biomarkers, e.g., tumor mutational burden (TMB), e.g., blood tumor mutational burden (bTMB).

In some embodiments, the subject interval is sequenced to at least about 800X but less than about 5,000X, e.g., for evaluating one or more genomic signatures, e.g., continuous/complex biomarkers, e.g., tumor mutational burden (TMB), e.g., blood tumor mutational burden (bTMB).

In some embodiments, any of the methods disclosed herein further comprise contacting a plurality of third fragment/third target capture reagent (F3/R3) hybrids with substrate to form F3/R3 hybrid/substrate complexes.

In some embodiments, R3s comprise R3s that comprise a functional first member of the binding pair and R3s that lack a functional first member of the binding pair.

In some embodiments, the proportion of R2s that comprise a functional first member of the binding pair is greater than the proportion of R3s that comprise a functional first member of the binding pair.

In some embodiments, the proportion of R2s that comprise a functional first member of the binding pair is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the proportion of R3s that comprise a functional first member of the binding pair.

In some embodiments of the plurality of target capture reagents, the ratio of R1s that comprise a functional first member of a binding pair (e.g., a binding pair described herein) to R1s that lack a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R1s that lack a functional first member of a binding pair (e.g., a binding pair described herein) to R1s that comprise a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R2s that comprise a functional first member of a binding pair (e.g., a binding pair described herein) to R2s that lack a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R2s that lack a functional first member of a binding pair (e.g., a binding pair described herein) to R2s that comprise a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R3s that comprise a functional first member of a binding pair (e.g., a binding pair described herein) to R3s that lack a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In some embodiments of the plurality of target capture reagents, the ratio of R3s that lack a functional first member of a binding pair (e.g., a binding pair described herein) to R3s that comprise a functional first member of the binding pair is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%.

In an embodiment of the plurality of target capture reagents, the ratio of A to B is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%, wherein:

A comprises R1s (e.g., that comprise a functional first member of the binding pair), and R2s that lack a functional first member of a binding pair (e.g., a binding pair described herein); and B comprises R1s (e.g., that comprise a functional first member of a binding pair), and R2s that comprise a functional first member of a binding pair.

In an embodiment of the plurality of target capture reagents, the ratio of A to B is about 2% to about 50%, e.g., about 3% to about 40%, about 4% to about 30%, about 5% to about 25%, about 8% to about 20%, about 10% to about 15%, e.g., about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39%, about 40%, about 41%, about 42%, about 43%, about 44%, about 45%, about 46%, about 47%, about 48%, about 49%, or about 50%, wherein:

A comprises R1s that comprise a functional first member of the binding pair; and R2s that lack a functional first member of a binding pair (e.g., a binding pair described herein); and B comprises R1s that comprise a functional first member of a binding pair and R2s that comprise a functional first member of a binding pair.

In an embodiment, the ratio of the plurality of target capture reagents is determined by an assay described in Example 1. In an embodiment, the ratio is determined based on a first sequencing depth, e.g., the sequencing depth of one or more subgenomic intervals comprising a high sequencing depth event, e.g., as described herein. In an embodiment, the ratio is determined based on a second sequencing depth, e.g., the sequencing depth of a different subgenomic interval, e.g., one or more subgenomic intervals comprising a low sequencing depth event. In an embodiment, the ratio is determined based on a first sequencing depth, e.g., the sequencing depth of one or more subgenomic intervals comprising a high sequencing depth event, e.g., as described herein; and a second sequencing depth, e.g., the sequencing depth of a different subgenomic interval, e.g., one or more subgenomic intervals comprising a low sequencing depth event. In an embodiment, the ratio is determined based on the sequencing depth of a first fragment (F1), e.g., an F1 comprising a high sequencing depth event. In an embodiment, the ratio is determined based on the sequencing depth of a second fragment (F2), e.g., an F2 comprising a low sequencing depth event. In an embodiment, the ratio is determined based on the sequencing depth of F1, e.g., an F1 comprising a high sequencing depth event; and the sequencing depth of F2, e.g., an F2 comprising a low sequencing depth event.

In an embodiment, the ratio is determined based on the sequencing depth of one or more genes, e.g., pre-selected genes. In an embodiment, the ratio is chosen by determining the sequencing depth of one or more genes or subgenomic intervals, e.g., pre-selected genes or pre-selected subgenomic intervals. In an embodiment, the ratio is altered, e.g., increased or decreased, based on the sequencing depth of one or more genes, e.g., pre-selected genes or pre-selected subgenomic intervals. In an embodiment, the ratio is altered, e.g., increased or decreased, to obtain a pre-selected sequencing depth of one or more genes or subgenomic intervals.

In an embodiment, the plurality of target capture reagents has a ratio of target capture reagents that comprise a functional first member of a binding pair to target capture reagents that lack a functional first member of a binding pair that allows for a first sequencing depth. In an embodiment, the plurality of target capture reagents has a ratio of target capture reagents that comprise a functional first member of a binding pair to target capture reagents that lack a functional first member of a binding pair that allows for a second sequencing depth. In an embodiment, the second sequencing depth is other than a first sequencing depth. In an embodiment, the first sequencing depth is greater than the second sequencing depth, e.g., at least 1.1, 2, 3, 4, 5, 6, 7, 8, 9 or 10-fold greater than the second sequencing depth. In an embodiment, the first sequencing depth is about 1.1 to 10-fold, about 1.1 to 9-fold, about 1.1 to 8 fold, about 1.1 to 7-fold, about 1.1 to 6-fold, about 1.1 to 5-fold, about 1.1 to 4-fold, about 1.1 to 3-fold, about 1.1 to 2-fold, about 2 to 10-fold, about 3 to 10-fold, about 4 to 10-fold, about 5 to 10-fold, about 6 to 10-fold, about 7 to 10-fold, about 8 to 10-fold, or about 9 to 10-fold greater than the second sequencing depth. In an embodiment, the first sequencing depth is about 1.1-fold, about 2-fold, about 3-fold, about 4-fold, about 5-fold, about 6-fold, about 7-fold, about 8-fold, about 9-fold, about 10-fold greater than the second sequencing depth.

In an embodiment, the second sequencing depth is greater than the first sequencing depth, e.g., at least 1.1, 2, 3, 4, 5, 6, 7, 8, 9 or 10-fold greater than the first sequencing depth. In an embodiment, the second sequencing depth is about 1.1 to 10-fold, about 1.1 to 9-fold, about 1.1 to 8 fold, about 1.1 to 7-fold, about 1.1 to 6-fold, about 1.1 to 5-fold, about 1.1 to 4-fold, about 1.1 to 3-fold, about 1.1 to 2-fold, about 2 to 10-fold, about 3 to 10-fold, about 4 to 10-fold, about 5 to 10-fold, about 6 to 10-fold, about 7 to 10-fold, about 8 to 10-fold, or about 9 to 10-fold greater than the first sequencing depth. In an embodiment, the second sequencing depth is about 1.1-fold, about 2-fold, about 3-fold, about 4-fold, about 5-fold, about 6-fold, about 7-fold, about 8-fold, about 9-fold, about 10-fold greater than the first sequencing depth.

In an embodiment, a first sequencing depth, e.g., F1 sequencing depth, is a narrow high sequencing depth, e.g., as described in Example 1.

In an embodiment, a second sequencing depth, e.g., F2 sequencing depth, is a wide moderate sequencing depth, e.g., as described in Example 1.

In an embodiment, a first sequencing depth, e.g., F2 sequencing depth, is a narrow high sequencing depth, e.g., as described in Example 1.

In an embodiment, a second sequencing depth, e.g., F1 sequencing depth, is a wide moderate sequencing depth, e.g., as described in Example 1.

In an embodiment, the plurality of target capture reagents, e.g., R1s, R2s and/or R3s, is not limiting, e.g., is at an excess e.g., a molar excess, of about 100-2000X. In an embodiment, the plurality of target capture reagents is at an excess, e.g., a molar excess, of about 100X, 200X, 300X, 400X, 500X, 600X, 700X, 800X, 900X, 1000X, 1100X, 1200X, 1300X 1400X, 1500X, 1600×1700X, 1800X, 1900X, or 2000X. In an embodiment, the plurality of target capture reagents is at an excess, e.g., a molar excess, of about 100-1900X, 100-1800X, 100-1700X, 100-1600X, 100-1500X, 100-1400X, 100-1300X, 100-1200X, 100-1100X, 100-1000X, 100-900X, 100-800X, 100-700X, 100-600X, 100-500X, 100-400X, 100-300X, 100-200X, 200-2000X, 300-2000X, 400-2000X, 500-2000X, 600-2000X, 700-2000X, 800-2000X, 900-2000X, 1000-2000X, 1100-2000X, 1200-2000X, 1300-2000X, 1400-2000X, 1500-2000X, 1600-2000X, 1700-2000X, 1800-2000X, or 1900-2000X.

In an embodiment of the plurality of target capture reagents, the concentrations of: (i) R2s comprising a first member; (ii) R2s not comprising a first member; and (iii) F2; are such that the proportion of R2s not comprising a first member to R2s comprising a first member affects the number of complexes of F2-R2s comprising a first member.

In an embodiment of the plurality of target capture reagents, the concentrations of: (i) R1s comprising a first member; (ii) R1s not comprising a first member; and (iii) F1; are such that the proportion of R1s not comprising a first member to R1s comprising a first member affects the number of complexes of F1-R1s comprising a first member.

In some embodiments, the proportion of R2s that comprise a functional first member of the binding pair and the proportion of R3s that comprise a functional first member of the binding pair are such that, upon formation of the F2/R2 hybrid/substrate complexes and the F3/R3 hybrid/substrate complexes, the number of F2s in the F2/R2 hybrid/substrate complexes and the number of F3s in the F3/R3 hybrid/substrate complexes have one or both of the following relationships:

(i) the number of F2s is greater than the number of F3s; and/or (ii) the number of F2s comprising an alteration in a second subject interval is greater than the number of F3s comprising an alteration in a third subject interval.

In some embodiments, the number of F2s is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F3s.

In some embodiments, the number of F2s comprising an alteration in a second subject interval is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F3s comprising an alteration in a third subject interval.

In some embodiments, the second subject interval, the third subject interval, or both, is from a gene described in Tables 1A-5A.

In some embodiments, one, two or all of F1, F2, or F3 comprises a subject interval from a gene described in Tables 1A-5A.

In some embodiments, the subject interval in F2 is sequenced to a second depth, and the subject interval in F3 is sequenced to a third depth, wherein the second depth is at least 1, 2, 3, 4, 5, 6, 7, 8, 9, 10-fold greater than the third depth.

In some embodiments, F3 comprises a subject interval from a gene described in Tables 1A-5A, and wherein the subject interval comprises a germline alteration, e.g., a germline single nucleotide polymorphism (SNP).

In some embodiments, the subject interval is sequenced to at least about 100X depth but less than about 800X.

In some embodiments, any of the methods disclosed herein further comprises providing the sample from a subject. In some embodiments, the sample comprises DNA, e.g., genomic DNA, e.g., cell-free DNA (cfDNA) or circulating tumor DNA (ctDNA). In some embodiments, the sample comprises RNA, e.g., mRNA. In some embodiments, the method further comprises providing cDNA from RNA.

In some embodiments, any of the methods disclosed herein further comprises obtaining, e.g., isolating, nucleic acids from the sample.

In some embodiments, any of the methods disclosed herein further comprises fragmenting nucleic acids in the sample to provide F1 and F2.

In some embodiments, any of the methods disclosed herein further comprises amplifying F1 to provide a plurality of F1s, and amplifying F2 to provide a plurality of F2s.

In some embodiments, any of the methods disclosed herein further comprises attaching adapter sequences to F1 and F2 to provide adapterized F1 (AF1) and adapterized F2 (AF2).

In some embodiments, any of the methods disclosed herein further comprises amplifying AF1 to provide a plurality of AF1s, and amplifying AF2 to provide a plurality of AF2s.

In some embodiments, any of the methods disclosed herein further comprises contacting a plurality of F1s to R1 to provide a plurality of F1/R1 hybrids, and contacting a plurality of F2s to R2 to provide a plurality of F2/R2 hybrids.

In some embodiments, any of the methods disclosed herein further comprises contacting a plurality of AF1s to R1 to provide a plurality of AF1/R1 hybrids, and contacting a plurality of AF2s to R2 to provide a plurality of AF2/R2 hybrids.

In some embodiments, a method disclosed herein comprises contacting a plurality of F1/R1 hybrids with substrate to form F1/R1 hybrid/substrate complexes comprises contacting a plurality of AF1/R1 hybrids with substrate to form AF1/R1 hybrid/substrate complexes; and contacting a plurality of F2/R2 hybrids with substrate to form F2/R2 hybrid/substrate complexes comprises contacting a plurality of AF2/R2 hybrids with substrate to form AF2/R2 hybrid/substrate complexes.

In some embodiments, the contacting occurs in solution or on a solid surface.

In some embodiments of any of the methods disclosed herein, the first member of the binding pair comprises a biotin moiety, and wherein the second member of the binding pair comprises a streptavidin or avidin (or a modified version, e.g., NeutrAvidin or CaptAvidin) moiety.

In some embodiments of any of the methods disclosed herein, the first member of the binding pair comprises a digoxigenin moiety, and wherein the second member of the binding pair comprises an anti-digoxigenin antibody moiety.

In some embodiments of any of the methods disclosed herein, the first member of the binding pair comprises an FITC moiety, and wherein the second member of the binding pair comprises an anti-FITC antibody moiety.

In some embodiments of any of the methods disclosed herein, the first member of the binding pair in R1 is coupled to a moiety (e.g., a nucleotide sequence) in R1 that captures (e.g., hybridizes to) F1 via a linker. In some embodiments, the first member of the binding pair in R2 is coupled to a moiety (e.g., a nucleotide sequence) in R2 that captures (e.g., hybridizes to) F2 via a linker. In some embodiments, the linker is a cleavable linker.

In some embodiments, any of the methods disclosed herein further comprises sequencing F1 from the plurality of F1/R1 hybrid/substrate complexes, and sequencing F2 from the plurality of F2/R2 hybrid/substrate complexes. In some embodiments, F1 is sequenced to a greater depth than F2, e.g., at least 1, 2, 3, 4, 5, 6, 7, 8, 9, or 10-fold greater.

In yet another aspect, the disclosure provides a method of analyzing a sample, comprising:

a) providing a plurality of first fragment/first target capture reagent (F1/R1) hybrids and a plurality of second fragment/second target capture reagent (F2/R2) hybrids, wherein the proportion of R1s that comprise a functional first member of the binding pair is greater than the proportion of R2s that comprise a functional first member of the binding pair, and wherein the first member of the binding pair is capable of binding to a second member of the binding pair disposed on substrate;

b) contacting the plurality of F1/R1 hybrids with substrate to form F1/R1 hybrid/substrate complexes, and contacting the plurality of F2/R2 hybrids with substrate to form F2/R2 hybrid/substrate complexes, wherein the proportion of F1/R1 hybrids which bind to the substrate is greater than the proportion of F2/R2 hybrids which bind to the substrate; and c) sequencing F1 from the plurality of F1/R1 hybrid/substrate complexes, and sequencing F2 from the plurality of F2/R2 hybrid/substrate complexes, wherein F1 is sequenced to a greater depth than F2, thereby analyzing the sample.

In an aspect, disclosed herein is a method of analyzing a sample, comprising:

1) providing a sample, e.g., a sample comprising genomic DNA, e.g., cell-free DNA (cfDNA) or circulating tumor DNA (ctDNA), from a subject;

2) obtaining, e.g., isolating, nucleic acids from the sample;

3) fragmenting the nucleic acids to provide a plurality of fragments (Fs);

4) attaching adapter sequences to the plurality of fragments (Fs) to provide a plurality of adapterized fragments (AFs);

5) amplifying a first AF (AF1) to provide a plurality of AF1, and amplifying a second AF (AF2) to provide a plurality of AF2;

6) contacting a plurality of AF1 with first target capture reagents (R1s), each comprising a nucleotide sequence that hybridizes to AF1, to provide a plurality of AF1/R1 hybrids, and contacting a plurality of AF2 with second target capture reagents (R2s), each comprising a nucleotide sequence that hybridizes to AF2, to provide a plurality of AF2/R2 hybrids, wherein a portion of the R1s and a portion of the R2s comprise a functional first member of a binding pair, and wherein the first member of the binding pair is capable of binding to a second member of the binding pair disposed on substrate, and wherein a portion of the R1s, a portion of the R2s, or both, lack a functional first member of a binding pair;

7) contacting the plurality of AF1/R1 hybrids with substrate to form AF1/R1 hybrid/substrate complexes, and contacting the plurality of AF2/R2 hybrids with substrate to form AF2/R2 hybrid/substrate complexes, wherein the proportion of AF1/R1 hybrids which bind to the substrate is greater than the proportion of AF2/R2 hybrids which bind to the substrate; and 8) sequencing AF1 from the plurality of AF1/R1 hybrid/substrate complexes, and sequencing AF2 from the plurality of AF2/R2 hybrid/substrate complexes, optionally, wherein AF1 is sequenced to a greater depth than AF2, e.g., at least 1, 2, 3, 4, 5, 6, 7, 8, 9, or 10-fold greater;

thereby analyzing the sample.

In some embodiments, any of the methods disclosed herein further comprises acquiring a library comprising a plurality of nucleic acid molecules from the sample.

In some embodiments, any of the methods disclosed herein further comprises contacting the library with target capture reagents to provide selected nucleic acid molecules, wherein said target capture reagents hybridize with the nucleic acid molecule, thereby providing a library catch.

In some embodiments, any of the methods disclosed herein further comprises acquiring a read for a subject interval comprising an alteration (e.g., a somatic alteration) from a nucleic acid molecule from said library or library catch, thereby acquiring a read for the subject interval, e.g., by a next-generation sequencing method.

In some embodiments, the method comprises acquiring reads for subject intervals in a plurality of genes.

In some embodiments, the plurality of genes comprises genes in mutant form, e.g., the mutant genes are associated with an effect on cell division, growth or survival, or are associated with cancer.

In some embodiments, the plurality of genes comprises at least about 50 or more, about 100 or more, about 150 or more, about 200 or more, about 250 or more, about 300 or more, about 350 or more, about 400 or more, about 450 or more, about 500 or more genes, or about 1,000 or more genes, or all genes for whole exon sequencing (WES).

In some embodiments, the plurality of genes comprises at least about 50 or more, about 100 or more, about 150 or more, about 200 or more, about 250 or more, about 300 or more, or all of the genes described in Tables 1A-5A.

In some embodiments, acquiring reads for subject intervals comprises sequencing subject intervals from at least about 50 or more, about 100 or more, about 150 or more, about 200 or more, about 250 or more, about 300 or more, or all of the genes described in Tables 1A-5A.

In some embodiments, subject intervals are sequenced to greater than about 100X, greater than about 250X, greater than about 500X, greater than about 800X, greater than about 1,000X, greater than about 2,000X, greater than about 3,000X, greater than about 4,000X, or greater than about 5,000X, average depth.

In some embodiments, subject intervals are sequenced to greater than about 100X, greater than about 250X, greater than about 500X, greater than about 800X, greater than about 1,000X, greater than about 2,000X, greater than about 3,000X, greater than about 4,000X, or greater than about 5,000X, average depth, at greater than about 95%, greater than about 97%, or greater than about 99%, of the genes (e.g., exons) sequenced.

In some embodiments, any of the methods disclosed herein further comprises aligning said read by an alignment method.

In some embodiments, any of the methods disclosed herein further comprises assigning a nucleotide value from said read for a nucleotide position.

In some embodiments of any of the methods disclosed herein, evaluating one or more genomic signatures, e.g., continuous/complex biomarkers in the sample, e.g., tumor mutational burden (TMB), e.g., blood TMB (bTMB).

In some embodiments, the sample is a blood sample and bTMB is evaluated.

In some embodiments, any of the methods disclosed herein further comprises characterizing an alteration in the sample as a somatic or germline alteration.

In some embodiments, any of the methods disclosed herein further comprises determining the zygosity of an alteration in the sample.

In some embodiments, any of the methods disclosed herein further comprises classifying the sample or a subject from which the sample was obtained responsive to the analysis of the sample.

In some embodiments, any of the methods disclosed herein further comprises providing a report, e.g., an electronic, web-based, or paper report, to the subject from which the sample is obtained or to another person or entity, a caregiver, a physician, an oncologist, a hospital, clinic, third-party payor, insurance company or government office.

Any of the compositions and methods disclosed herein can be combined with one or more of the embodiments below.

Multigene Analysis

The methods and compositions described herein can be used to evaluate a set of subject intervals, e.g., from a set of genes or gene products described herein.

In certain embodiments, the set of genes comprises a plurality of genes, which in mutant form, are associated with an effect on cell division, growth or survival, or are associated with a cancer, e.g., a cancer described herein.

In certain embodiments, the set of genes comprises at least about 50 or more, about 100 or more, about 150 or more, about 200 or more, about 250 or more, about 300 or more, about 350 or more, about 400 or more, about 450 or more, about 500 or more, about 550 or more, about 600 or more, about 650 or more, about 700 or more, about 750 or more, or about 800 or more genes, e.g., as described herein. In some embodiments, the set of genes comprises at least about 50 or more, about 100 or more, about 150 or more, about 200 or more, about 250 or more, about 300 or more, or all of the genes chosen described in Tables 1A-5A.

In certain embodiments, the method comprises acquiring a library comprising a plurality of tumor nucleic acid molecules from the sample. In certain embodiments, the method further comprises contacting a library with target capture reagents to provide selected tumor nucleic acid molecules, wherein said target capture reagents hybridize with a tumor nucleic acid molecule from the library, thereby providing a library catch. In certain embodiments, the method further comprises acquiring a read for a subject interval comprising an alteration (e.g., somatic alteration) from a tumor nucleic acid molecule from a library or library catch, thereby acquiring a read for the subject interval, e.g., by a next-generation sequencing method. In certain embodiments, the method further comprises aligning a read for the subject interval by an alignment method, e.g., an alignment method described herein. In certain embodiments, the method further comprises assigning a nucleotide value for a nucleotide position from a read for the subject interval, e.g., by a mutation calling method described herein.

In certain embodiments, the method comprises one, two, three, four, or all of:

(a) acquiring a library comprising a plurality of tumor nucleic acid molecules from a sample;

(b) contacting the library with a plurality of target capture reagents to provide selected tumor nucleic acid molecules, wherein said plurality of target capture reagents hybridize with the tumor nucleic acid molecules, thereby providing a library catch;

(c) acquiring a read for a subject interval comprising the alteration (e.g., somatic alteration) from a tumor nucleic acid molecule from said library catch, thereby acquiring a read for the subject interval, e.g., by a next-generation sequencing method;

(d) aligning said read by an alignment method, e.g., an alignment method described herein; or (e) assigning a nucleotide value from said read for a nucleotide position, e.g., by a mutation calling method described herein.

In certain embodiments, acquiring a read for the subject interval comprises sequencing a subject interval from at least about 50 or more, about 100 or more, about 150 or more, about 200 or more, about 250 or more, about 300 or more, about 350 or more, about 400 or more, about 450 or more, about 500 or more, about 550 or more, about 600 or more, about 650 or more, about 700 or more, about 750 or more, or about 800 or more genes. In certain embodiments, acquiring a read for the subject interval comprises sequencing a subject interval from at least about 50 or more, about 100 or more, about 150 or more, about 200 or more, about 250 or more, about 300 or more, or all of the genes described in Tables 1A-5A.

In certain embodiments, acquiring a read for the subject interval comprises sequencing with 100X or more average depth. In certain embodiments, acquiring a read for the subject interval comprises sequencing with about 250X or more average depth. In other embodiments, acquiring a read for the subject interval comprises sequencing with about 500X or more average depth. In certain embodiments, acquiring a read for the subject interval comprises sequencing with about 800X or more average depth. In other embodiments, acquiring a read for the subject interval comprises sequencing with about 1,000X or more average depth. In other embodiments, acquiring a read for the subject interval comprises sequencing with about 1,500X or more average depth. In other embodiments, acquiring a read for the subject interval comprises sequencing with about 2,000X or more average depth. In other embodiments, acquiring a read for the subject interval comprises sequencing with about 2,500X or more average depth. In certain embodiments, acquiring a read for the subject interval comprises sequencing with about 3,000X or more average depth. In certain embodiments, acquiring a read for the subject interval comprises sequencing with about 3,500X or more average depth. In certain embodiments, acquiring a read for the subject interval comprises sequencing with about 4,000X or more average depth. In certain embodiments, acquiring a read for the subject interval comprises sequencing with about 4,500X or more average depth. In certain embodiments, acquiring a read for the subject interval comprises sequencing with about 5,000X or more average depth. In certain embodiments, acquiring a read for the subject interval comprises sequencing with about 5,500X or more average depth. In certain embodiments, acquiring a read for the subject interval comprises sequencing with about 6,000X or more average depth.

In certain embodiments, acquiring a read for the subject interval comprises sequencing with about 100X or more average depth, at greater than about 99% of genes (e.g., exons) sequenced. In certain embodiments, acquiring a read for the subject interval comprises sequencing with about 250X or more average depth, at greater than about 99% of genes (e.g., exons) sequenced. In other embodiments, acquiring a read for the subject interval comprises sequencing with about 500X or more average depth, at greater than about 95% of genes (e.g., exons) sequenced. In other embodiments, acquiring a read for the subject interval comprises sequencing with about 800X or more average depth, at greater than about 95% of genes (e.g., exons) sequenced. In other embodiments, acquiring a read for the subject interval comprises sequencing with greater than about 1,000X average depth, at greater than about 90% of genes (e.g., exons) sequenced. In other embodiments, acquiring a read for the subject interval comprises sequencing with about 2,000X or more average depth, at greater than about 90% of genes (e.g., exons) sequenced. In other embodiments, acquiring a read for the subject interval comprises sequencing with about 3,000X or more average depth, at greater than about 90% of genes (e.g., exons) sequenced. In other embodiments, acquiring a read for the subject interval comprises sequencing with about 3,500X or more average depth, at greater than about 90% of genes (e.g., exons) sequenced. In other embodiments, acquiring a read for the subject interval comprises sequencing with about 4,000X or more average depth, at greater than about 90% of genes (e.g., exons) sequenced. In other embodiments, acquiring a read for the subject interval comprises sequencing with about 4,500X or more average depth, at greater than about 90% of genes (e.g., exons) sequenced. In other embodiments, acquiring a read for the subject interval comprises sequencing with about 5,000X or more average depth, at greater than about 90% of genes (e.g., exons) sequenced. In other embodiments, acquiring a read for the subject interval comprises sequencing with about 5,500X or more average depth, at greater than about 90% of genes (e.g., exons) sequenced. In other embodiments, acquiring a read for the subject interval comprises sequencing with about 6,000X or more average depth, at greater than about 90% of genes (e.g., exons) sequenced. In certain embodiments, acquiring a read for the subject interval comprises sequencing with about 100X or more, about 250X or more, about 500X or more, about 1,000X or more, about 1,500X or more, about 2,000X or more, about 2,500X or more, about 3,000X or more, about 3,500X or more, about 4,000X or more, about 4,500X or more, about 5,000X or more, about 5,500X or more, or about 6,000X or more average depth, at greater than about 99% of genes (e.g., exons) sequenced.

In certain embodiments, the sequence, e.g., a nucleotide sequence, of a set of subject intervals (e.g., coding subject intervals), described herein, is provided by a method described herein. In certain embodiments, the sequence is provided without using a method that includes a matched normal control (e.g., a wild-type control), a matched tumor control (e.g., primary versus. metastatic), or both.

Samples

The methods and compositions described herein can be used to evaluate subject intervals in various types of samples from a number of different sources.

In some embodiments, the sample comprises a nucleic acid, e.g., DNA, RNA, or both. In certain embodiments, the sample comprises one or more nucleic acids from a tumor. In certain embodiments, the sample further comprises one or more non-nucleic acid components from the tumor, e.g., a cell, protein, carbohydrate, or lipid. In certain embodiments, the sample further comprises one or more nucleic acids from a non-tumor cell or tissue. In certain embodiments, the sample is acquired from a solid tumor, a hematological cancer, or a metastatic form thereof. In certain embodiments, the sample is obtained from a subject having a cancer, or a subject who has not received a therapy to treat a cancer, is receiving a therapy to treat a cancer or has received a therapy to treat a cancer, as described herein.

In some embodiments, the sample comprises one or more of: premalignant or malignant cells; cells from a solid tumor, a soft tissue tumor or a metastatic lesion; tissue or cells from a surgical margin; a histologically normal tissue; one or more circulating tumor cells (CTCs); a normal adjacent tissue (NAT); a blood sample; or a formaldehyde- or paraformaldehyde-fixed paraffin-embedded (FFPE) sample. In certain embodiments, the sample is a blood sample. In certain embodiments, the sample is a plasma sample. In certain embodiments, the sample comprises cell-free DNA (cfDNA).

In certain embodiments, the sample comprises circulating tumor DNA (ctDNA). In certain embodiments, the sample comprises cerebral spinal fluid (CSF). In certain embodiments, the sample comprises urine. In certain embodiments, the sample comprises pleural effusion. In certain embodiments, the sample comprises ascites. In certain embodiments, the sample is a FFPE sample. In certain embodiments, the sample comprises a resection, a needle biopsy, a fine needle aspirate, or a cytology smear.

Target Capture Reagents

Compositions and methods described herein provide for optimized sequencing of a large number of genes and gene products from samples, e.g., from a cancer described herein, from one or more subjects by the appropriate selection of target capture reagents, e.g., target capture reagents for use in solution hybridization, for the selection of target nucleic acid molecules to be sequenced. Target nucleic acid molecules captured by target capture reagents are typically recovered by substrate. In some embodiments, a target nucleic acid molecule captured by a target capture reagent is recovered by, e.g., bound to, a substrate. In some embodiments, two or more pluralities of target capture reagents, each capturing different target nucleic acid molecules, are used.

In some embodiments, a recovery efficiency is the ratio of target nucleic acid molecules captured by a target capture reagent which is recovered by (e.g., bound to), a substrate, to total target nucleic acid molecules. In some embodiments, at least two pluralities of target capture reagents have different recovery efficiencies. In some embodiments, the recovery efficiency correlates to the sequencing depth as it is adjusted according to a target subject interval. In some embodiments, the recovery efficiency correlates to the sequencing depth with respect to a target subject interval. In some embodiments, the recovery efficiency of a target capture reagent is corelated with the proportion of target capture reagent comprising a functional binding pair.

Thus, in some embodiments, a method described herein comprises contacting a library with two, three, or more pluralities of target capture reagents having different recovery efficiencies to identify or isolate selected nucleic acid molecules (e.g., a library catch). In some embodiments, the library is contacted with the two, three, or more pluralities of target capture reagents having different recovery efficiencies at essentially the same time and/or in the same sample container (e.g., a tube). In some embodiments, target nucleic acid molecules are captured by the two, three, or more pluralities of target capture reagents having different recovery efficiencies at essentially the same time and/or in the same sample container (e.g., a tube). In some embodiments, target nucleic acid molecules captured by the two, three, or more pluralities of target capture reagents having different recovery efficiencies are recovered by substrate at essentially the same time and/or in the same sample container (e.g., a tube).

In some embodiments, the first plurality of target capture reagents comprise target capture reagents that comprise a functional first member of a binding pair and target capture reagents that lack a functional first member of the binding pair, and the second plurality of target capture reagents comprise target capture reagents that comprise a functional first member of a binding pair and target capture reagents that lack a functional first member of the binding pair, wherein a functional first member of the binding pair is capable of binding to a second member of the binding pair disposed on substrate. In some embodiments, the proportion of target capture reagents that comprise a functional first member of the binding pair in the first plurality is greater than the proportion of target capture reagents that comprise a functional first member of the binding pair in the second plurality, such that the recovery efficiency for the first plurality of target capture reagents is greater than the recovery efficiency for the second plurality of target capture reagents.

Any combination of two, three, four, five, or more pluralities of target capture reagents can be used, for example, a combination of first and second pluralities of target capture reagents; first and third pluralities of target capture reagents; first and fourth pluralities of target capture reagents; first and fifth pluralities of target capture reagents; second and third pluralities of target capture reagents; second and fourth pluralities of target capture reagents; second and fifth pluralities of target capture reagents; third and fourth pluralities of target capture reagents; third and fifth pluralities of target capture reagents; fourth and fifth pluralities of target capture reagents; first, second and third pluralities of target capture reagents; first, second and fourth pluralities of target capture reagents; first, second and fifth pluralities of target capture reagents; first, second, third, and fourth pluralities of target capture reagents; first, second, third, fourth and fifth pluralities of target capture reagents, and so on.

In some embodiments, the method comprises:

(a) acquiring a library comprising a plurality of nucleic acid molecules (e.g., target nucleic acid molecules) from a sample, e.g., a plurality of tumor nucleic acid molecules from a sample, e.g., a sample described herein;

(b) contacting the library with two, three, or more pluralities of target capture reagents to provide selected nucleic acid molecules (e.g., a library catch);

(c) acquiring a read for a subject interval from a nucleic acid molecule, e.g., a tumor nucleic acid molecule from said library or library catch, e.g., by a method comprising sequencing, e.g., with a next-generation sequencing method;

(d) aligning said read by an alignment method, e.g., an alignment method described herein; and (e) assigning a nucleotide value (e.g., calling a mutation, e.g., with a Bayesian method or a method described herein) from said read for a nucleotide position.

In some embodiments, the method comprises contacting the library with at least two or three pluralities of target capture reagents, wherein each plurality has a unique (as opposed to the other target capture reagents in the plurality), recovery efficiency. For example, each unique plurality of target capture reagents results in, or is correlated with, a unique depth of sequencing.

In an embodiment, the method comprises acquiring a library from which a nucleic acid molecule corresponding to a subgenomic interval and a nucleic acid molecule corresponding to an expressed subgenomic interval, are each obtained. In an embodiment, the method comprises acquiring a first library from which a nucleic acid molecule corresponding to a subgenomic interval is obtained and acquiring a second library from which a nucleic acid molecule corresponding to an expressed subgenomic interval is obtained. In an embodiment, target capture reagents are used to provide nucleic acid molecules or a library catch comprising both a subgenomic interval and an expressed subgenomic interval. In an embodiment, a first target capture reagent is used to provide nucleic acid molecules or a library catch comprising a subgenomic interval and a second target capture reagent is used to provide nucleic acid molecules or a library catch comprising an expressed subgenomic interval.

In an embodiment, the recovery efficiency of a first plurality of target capture reagents differs from the recovery efficiency of a second plurality of target capture reagents by at least 2, 5, 10, 25, 50, 100, 200, 300, 400, 500, 600, 700, 800, 900, or 1,000 fold. In an embodiment, the first and second pluralities of target capture reagents provide for a depth of sequencing that differs by at least 2, 5, 10, 25, 50, 100, 200, 300, 400, 500, 600, 700, 800, 900, or 1,000 fold.

In some embodiments, the level of sequencing depth as used herein (e.g., X-fold level of sequencing depth) refers to the number of reads (e.g., unique reads), after detection and removal of duplicate reads, e.g., PCR duplicate reads. In other embodiments, duplicate reads are evaluated, e.g., to support detection of copy number alteration (CNAs).

In one embodiment, the target capture reagent selects a subject interval containing one or more rearrangements, e.g., an intron containing a genomic rearrangement. In such embodiments, the target capture reagent is designed such that repetitive sequences are masked to increase the selection efficiency. In those embodiments where the rearrangement has a known juncture sequence, complementary target capture reagents can be designed to the juncture sequence to increase the selection efficiency.

In some embodiments, the method comprises the use of target capture reagents designed to capture two or more different target categories, each category having a different design strategy. In some embodiments, the method (e.g., hybrid capture method) and composition disclosed herein capture a subset of target sequences (e.g., target nucleic acid molecules) and provide homogenous coverage of the target sequence, while minimizing coverage outside of that subset. In one embodiment, the target sequences include the entire exome out of genomic DNA, or a selected subset thereof. In another embodiment, the target sequences include a large chromosomal region, e.g., a whole chromosome arm. The methods and compositions disclosed herein provide different target capture reagents for achieving different sequencing depths and patterns of coverage for complex target nucleic acid sequences (e.g., nucleic acid libraries).

In an embodiment, the method comprises providing selected nucleic acid molecules of one or a plurality of nucleic acid libraries (e.g., a library catch). For example, the method comprises:

providing one or a plurality of libraries (e.g., one or a plurality of nucleic acid libraries) comprising a plurality of nucleic acid molecules, e.g., target nucleic acid nucleic acid molecules (e.g., including a plurality of tumor nucleic acid molecules and/or reference nucleic acid molecules);

contacting the one or a plurality of libraries, e.g., in a solution-based reaction, with two, three, or more pluralities of target capture reagents (e.g., oligonucleotide target capture reagents) to form a hybridization mixture comprising a plurality of target capture reagent/nucleic acid molecule hybrids;

separating the plurality of target capture reagent/nucleic acid molecule hybrids from said hybridization mixture, e.g., by contacting said hybridization mixture with a binding entity that allows for separation of said plurality of target capture reagent/nucleic acid molecule hybrids from the hybridization mixture, thereby providing a library catch (e.g., a selected or enriched subgroup of nucleic acid molecules from the one or a plurality of libraries).

In one embodiment, each of the first, second, or third pluralities of target capture reagents has a unique recovery efficiency. In some embodiments, at least two, or all three pluralities of target capture reagents have recovery efficiency values that differ. For example, a value for recovery efficiency chosen from one of more of:

(i) the first recovery efficiency has a value that is at least about 5,000X or higher sequencing depth e.g., has a value for recovery efficiency that is greater than the value for the second or third recovery efficiency (e.g., about 5-10 fold (e.g., 6-7 fold) greater than the value for the second recovery efficiency; or about 40-60 fold (e.g., 45-50 fold) greater than the value for the third recovery efficiency);

(ii) the second recovery efficiency has a value that is at least about 800X or higher sequencing depth, e.g., has a value for recovery efficiency that is greater than the value for the third recovery efficiency (e.g., about 5-10 fold (e.g., 7-9 fold) greater than the value for the third recovery efficiency); or (iii) the third recovery efficiency has a value that is at least about 100X or higher sequencing depth.

In certain embodiments, the value for recovery efficiency is modified by one or more of: differential representation of different target capture reagents, differential overlap of target capture reagent subsets, differential target capture reagent parameters, mixing of different target capture reagents, and/or using different types of target capture reagents. For example, a variation in recovery efficiency (e.g., relative sequence coverage of each target capture reagent/target category) can be adjusted, e.g., within a plurality of target capture reagents and/or among different pluralities of target capture reagents, by altering one or more of:

(i) Differential representation of different target capture reagents—The target capture reagent design to capture a given target (e.g., a target nucleic acid molecule) can be included in more/fewer number of copies to enhance/reduce relative target sequencing depths;

(ii) Differential overlap of target capture reagent subsets—The target capture reagent design to capture a given target (e.g., a target nucleic acid molecule) can include a longer or shorter overlap between neighboring target capture reagents to enhance/reduce relative target sequencing depths;

(iii) Differential target capture reagent parameters—The target capture reagent design to capture a given target (e.g., a target nucleic acid molecule) can include sequence modifications/shorter length to reduce capture efficiency and lower the relative target sequencing depths;

(iv) Mixing of different target capture reagents—Target capture reagents that are designed to capture different target sets can be mixed at different molar ratios to enhance/reduce relative target sequencing depths;

(v) Mixing of differently modified target capture reagents—Target capture reagents modified to have different substrate binding properties can be mixed at different molar ratios to enhance/reduce relative target sequencing depths;

(vi) Using different types of oligonucleotide target capture reagents—In certain embodiments, the target capture reagent can include:

(a) one or more chemically (e.g., non-enzymatically) synthesized (e.g., individually synthesized) target capture reagents, (b) one or more target capture reagents synthesized in an array, (c) one or more enzymatically prepared, e.g., in vitro transcribed, target capture reagents;

(d) any combination of (a), (b) and/or (c), (e) one or more DNA oligonucleotides (e.g., a naturally or non-naturally occurring DNA oligonucleotide), (f) one or more RNA oligonucleotides (e.g., a naturally or non-naturally occurring RNA oligonucleotide), (g) a combination of (e) and (f), or (h) a combination of any of the above.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized target capture reagent to array-generated target capture reagent is chosen from 1:5, 1:10, or 1:20. The DNA or RNA oligonucleotides can be naturally- or non-naturally-occurring. In certain embodiments, the target capture reagents include one or more non-naturally-occurring nucleotides to, e.g., increase melting temperature. Exemplary non-naturally occurring oligonucleotides include modified DNA or RNA nucleotides. Exemplary modified nucleotides (e.g., modified RNA or DNA nucleotides) include, but are not limited to, a locked nucleic acid (LNA), wherein the ribose moiety of an LNA nucleotide is modified with an extra bridge connecting the 2' oxygen and 4' carbon; peptide nucleic acid (PNA), e.g., a PNA composed of repeating N-(2-aminoethyl)-glycine units linked by peptide bonds; a DNA or RNA oligonucleotide modified to capture low GC regions; a bicyclic nucleic acid (BNA); a crosslinked oligonucleotide; a modified 5-methyl deoxycytidine; and 2,6-diaminopurine. Other modified DNA and RNA nucleotides are known in the art.

In certain embodiments, a substantially uniform or homogeneous coverage of a target sequence (e.g., a target nucleic acid molecule) is obtained. For example, within each target capture reagent/target category, uniformity of coverage can be optimized by modifying target capture reagent parameters, for example, by one or more of:

(i) Increasing/decreasing target capture reagent representation or overlap can be used to enhance/reduce coverage of targets (e.g., target nucleic acid molecules), which are under/over-covered relative to other targets in the same category;

(ii) For low coverage, hard to capture target sequences (e.g., high GC content sequences), expand the region being targeted with the target capture reagents to cover, e.g., adjacent sequences (e.g., less GC-rich adjacent sequences);

(iii) Modifying a target capture reagent sequence can be used to reduce secondary structure of the target capture reagent and enhance its recovery efficiency;

(iv) Modifying a target capture reagent length can be used to equalize melting hybridization kinetics of different target capture reagents within the same category. Target capture reagent length can be modified directly (by producing target capture reagents with varying lengths) or indirectly (by producing target capture reagents of consistent length, and replacing the target capture reagent ends with arbitrary sequence);

(v) Modifying target capture reagents of different orientation for the same target region (i.e. forward and reverse strand) may have different binding efficiencies. The target capture reagent with either orientation providing optimal coverage for each target may be selected;

(vi) Modifying the amount of a binding entity, e.g., a capture tag (e.g. biotin), present on each target capture reagent may affect its binding efficiency. Increasing/decreasing the tag level of target capture reagents targeting a specific target may be used to enhance/reduce the relative target coverage;

(vii) Modifying the type of nucleotide used for different target capture reagents can be used to affect binding affinity to the target, and enhance/reduce the relative target coverage; or (viii) Using modified oligonucleotide target capture reagents, e.g., having more stable base pairing can be used to equalize melting hybridization kinetics between areas of low or normal GC content relative to high GC content.

In other embodiments, the recovery efficiency is adjusted by adjusting the relative abundance of the target capture reagents comprising a functional first member of a binding pair and the target capture reagents lacking a functional first member of the binding pair. In some embodiments, the first member of the binding pair is capable of binding to a second member of the binding pair disposed on substrate, such that the target nucleic acid molecules captured by the target capture reagents comprising a first member of the binding pair are recovered by the substrate comprising a second member of the binding pair.

In an embodiment, the method comprises the use of a plurality of target capture reagents that includes a target capture reagent that selects a tumor nucleic acid molecule, e.g., a nucleic acid molecule comprising a subject interval from a tumor cell. The tumor nucleic acid molecule can be any nucleotide sequence present in a tumor cell, e.g., a mutated, a wild-type, a reference or an intron nucleotide sequence, as described herein, that is present in a tumor or cancer cell. In one embodiment, the tumor nucleic acid molecule includes an alteration (e.g., one or more mutations) that appears at a low frequency, e.g., about 5% or less of the cells from the sample harbor the alteration in their genome. In other embodiments, the tumor nucleic acid molecule includes an alteration (e.g., one or more mutations) that appears at a frequency of about 10% of the cells from the sample. In other embodiments, the tumor nucleic acid molecule includes a subgenomic interval from an intron sequence, e.g., an intron sequence as described herein, a reference sequence that is present in a tumor cell.

In other embodiments, the method comprises amplifying the library catch (e.g., by PCR). In other embodiments, the library catch is not amplified.

In another aspect, the invention features target capture reagents described herein and combinations of individual plurality of target capture reagents described herein. The target capture reagents can be part of a kit which can optionally comprise instructions, standards, buffers or enzymes or other reagents.

Alignment Methods disclosed herein can integrate the use of multiple, individually tuned, alignment methods or algorithms to optimize performance in sequencing methods, particularly in methods that rely on massively parallel sequencing of a large number of diverse genetic events in a large number of diverse genes, e.g., methods of analyzing samples, e.g., from a cancer described herein.

In some embodiments, the alignment method used to analyze reads is not individually customized or tuned to each of a number of variants in different genes. In some embodiments, a multiple alignment method that is individually customized or tuned to at least a subset of a number of variants in different genes is used to analyze reads. In some embodiments, a multiple alignment method that is individually customized or tuned to each of a number of variants in different genes is used to analyze reads. In some embodiments, tuning can be a function of (one or more of) the gene (or other subject interval) being sequenced, the tumor type in the sample, the variant being sequenced, or a characteristic of the sample or the subject. The selection or use of alignment conditions that are individually tuned to a number of subject intervals to be sequenced allows optimization of speed, sensitivity and specificity. The method is particularly effective when the alignments of reads for a relatively large number of diverse subject intervals are optimized.

In some embodiments, a read from each of X unique subject intervals is aligned with a unique alignment method, wherein unique subject interval (e.g., subject interval or expressed subject interval) means different from the other X−1 subject intervals, and wherein the unique alignment method means different from the other X−1 alignment methods, and X is at least 2.

In an embodiment, subject intervals from at least X genes, e.g. at least X genes from Tables 1A-5A, are aligned with a unique alignment method, and X is equal to 2, 3, 4, 5, 10, 15, 20, 30, 40, 50, 60, 70, 80, 90, 100, 200, 300, 400, 500, or greater.

In an embodiment, a method comprises selecting or using an alignment method for analyzing, e.g., aligning, a read, wherein said alignment method is a function of, is selected responsive to, or is optimized for, one or more or all of:

(i) tumor type, e.g., the tumor type in said sample;

(ii) the gene, or type of gene, in which said subject interval (e.g., subject interval or expressed subject interval) being sequenced is located, e.g., a gene or type of gene characterized by a variant or type of variant, e.g., a mutation, or by a mutation of a frequency;

(iii) the site (e.g., nucleotide position) being analyzed;

(iv) the type of variant, e.g., a substitution, within the subject interval (e.g., subject interval or expressed subject interval) being evaluated;

(v) the type of sample, e.g., a sample described herein; and (vi) sequence in or near said subject interval being evaluated, e.g., the expected propensity for misalignment for said subject interval (e.g., subject interval or expressed subject interval), e.g., the presence of repeated sequences in or near said subject interval (e.g., subject interval or expressed subject interval).

As referred to elsewhere herein, in some embodiments, a method is particularly effective when the alignment of reads for a relatively large number of subject intervals is optimized. Thus, in an embodiment, at least X unique alignment methods are used to analyze reads for at least X unique subject intervals, wherein unique means different from the other X−1, and X is equal to 2, 3, 4, 5, 10, 15, 20, 30, 50, 100, 200, 300, 400, 500, 600, 700, 800, 900, 1,000, or greater.

In an embodiment, subject intervals from at least X genes from Tables 1A-5A, are analyzed, and X is equal to 2, 3, 4, 5, 10, 15, 20, 30, 40, 50, 60, 70, 80, 90, 100, 200, 300, 400, 500, or greater.

In an embodiment, a unique alignment method is applied to subject intervals in each of at least 3, 5, 10, 20, 30, 40, 50, 60, 70, 80, 90, 100, 200, 300, 400, or 500 different genes.

In an embodiment, a nucleotide position in at least 20, 30, 40, 60, 80, 100, 120, 140, 160 or 180, 200, 300, 400, or 500 genes, e.g., genes from Tables 1A-5A, is assigned a nucleotide value. In an embodiment, a unique alignment method is applied to subject intervals in each of at least 10%, 20%, 30%, 40%, or 50% of said genes analyzed.

Methods disclosed herein allow for the rapid and efficient alignment of troublesome reads, e.g., a read having a rearrangement. Thus, in an embodiment where a read for a subject interval (e.g., a subject interval or an expressed subject interval) comprises a nucleotide position with a rearrangement, e.g., a translocation, the method can comprise using an alignment method that is appropriately tuned and that includes:

selecting a rearrangement reference sequence for alignment with a read, wherein said rearrangement reference sequence aligns with a rearrangement (in some embodiments, the reference sequence is not identical to the genomic rearrangement); and comparing, e.g., aligning, a read with said rearrangement reference sequence.

In some embodiments, a different method, e.g., another method is used to align troublesome reads. These methods are particularly effective when the alignment of reads for a relatively large number of diverse subject intervals is optimized. By way of example, a method of analyzing a sample can comprise:

performing a comparison, e.g., an alignment comparison, of a read under a first set of parameters (e.g., a first mapping algorithm or with a first reference sequence), and determining if said read meets a first alignment criterion (e.g., the read can be aligned with said first reference sequence, e.g., with less than a number of mismatches);

if said read fails to meet the first alignment criterion, performing a second alignment comparison under a second set of parameters, (e.g., a second mapping algorithm or with a second reference sequence); and, optionally, determining if said read meets said second criterion (e.g., the read can be aligned with said second reference sequence with less than a predefined number of mismatches), wherein said second set of parameters comprises use of a set of parameters, e.g., said second reference sequence, which, compared with said first set of parameters, is more likely to result in an alignment with a read for a variant, e.g., a rearrangement, e.g., an insertion, deletion, or translocation.

These and other alignment methods are discussed in more detail elsewhere herein, e.g., in the section entitled "Alignment" in the Detailed Description. Elements of that module can be included in methods of analyzing a tumor. In embodiments, an alignment method from the section entitled "Alignment" (in the Summary and/or Detailed Description) is combined with a mutation calling method from the section entitled "Mutation Calling" (in the Summary and/or Detailed Description) and/or a target capture reagent from the section entitled "Target Capture Reagents" (in the Summary) and/or the sections entitled "Design and Construction of Target Capture Reagents" and "Competition of Target Capture Reagents" in the Detailed Description). The method can be applied to a set of subject intervals from the section entitled "Gene Selection" (in the Summary and/or Detailed Description).

Mutation Calling

Methods disclosed herein can integrate the use of customized or tuned mutation calling parameters to optimize performance in sequencing methods, particularly in methods that rely on massively parallel sequencing of a large number of diverse genetic events in a large number of diverse genes, e.g., from samples, e.g., from a cancer described herein.

Without wishing to be bound by the theory, it is believed that in some embodiments, mutation calling determines the expected probability for an observing non-reference alteration, e.g., an alteration described herein. Mutation calling is typically based on a threshold value established to provide sufficient confidence that a called alteration is real and not the result of noise or other artifact of the sequencing or analysis process.

In some embodiments, mutation calling for each of a number of subject intervals is not individually customized or fine-tuned. In some embodiments, mutation calling for at least a subset of a number of subject intervals is, individually, customized or fine-tuned. In some embodiments, mutation calling for each of a number of subject intervals is, individually, customized or fine-tuned. The customization or tuning can be based on one or more of the factors described herein, e.g., the type of cancer in a sample, the gene in which the subject interval to be sequenced is located, or the variant to be sequenced. This selection or use of alignment conditions finely tuned to a number of subject intervals to be sequenced allows optimization of speed, sensitivity and specificity. The method is particularly effective when the alignment of reads for a relatively large number of diverse subject intervals is optimized.

In some embodiments, a nucleotide value is assigned for a nucleotide position in each of X unique subject intervals by a unique calling method, wherein unique subject interval (means different from the other X−1 subject intervals (e.g., subgenomic intervals, expressed subgenomic intervals, or both)), and wherein the unique calling method means different from the other X−1 calling methods, and X is at least 2. The calling methods can differ, and thereby be unique, e.g., by relying on different Bayesian prior values.

In an embodiment, assigning said nucleotide value is a function of a value which is or represents the prior (e.g., literature) expectation of observing a read showing a variant, e.g., a mutation, at said nucleotide position in a tumor of type.

In an embodiment, the method comprises assigning a nucleotide value (e.g., calling a mutation) for at least 10, 20, 30, 40, 50, 60, 70, 80, 90, 100, 200, 300, 400, 500, 600, 700, 800, 900, or 1,000 nucleotide positions, wherein each assignment is a function of a unique (as opposed to the value for the other assignments) value which is or represents the prior (e.g., literature) expectation of observing a read showing a variant, e.g., a mutation, at said nucleotide position in a tumor of type.

In an embodiment, assigning said nucleotide value is a function of a set of values which represent the probabilities of observing a read showing said variant at said nucleotide position if the variant is present in the sample at a frequency (e.g., 1%, 5%, 10%, etc.) and/or if the variant is absent (e.g., observed in the reads due to base-calling error alone).

In an embodiment, the mutation calling method described herein can include the following: acquiring, for a nucleotide position in each of said X subject intervals:

(i) a first value which is or represents the prior (e.g., literature) expectation of observing a read showing a variant, e.g., a mutation, at said nucleotide position in a tumor of type X; and (ii) a second set of values which represent the probabilities of observing a read showing said variant at said nucleotide position if the variant is present in the sample at a frequency (e.g., 1%, 5%, 10%, etc.) and/or if the variant is absent (e.g., observed in the reads due to base-calling error alone);

responsive to said values, assigning a nucleotide value (e.g., calling a mutation) from said reads for each of said nucleotide positions by weighing, e.g., by a Bayesian method described herein, the comparison among the values in the second set using the first value (e.g., computing the posterior probability of the presence of a mutation), thereby analyzing said sample.

In an embodiment, the method comprises one or more or all of:

(i) assigning a nucleotide value (e.g., calling a mutation) for at least 10, 20, 30, 40, 50, 60, 70, 80, 90, 100, 200, 300, 400, 500, 600, 700, 800, 900, or 1,000 nucleotide positions, wherein each assignment is based on a unique (as opposed to the other assignments) first and/or second values;

(ii) the assignment of method of (i), wherein at least 10, 20, 30, 40, 50, 60, 70, 80, 90, 100, 200, 300, 400, or 500 of the assignments are made with first values which are a function of a probability of a variant being present in less than 5%, 10%, or 20%, e.g., of the cells in a tumor type;

(iii) assigning a nucleotide value (e.g., calling a mutation) for at least X nucleotide positions, each of which of which being associated with a variant having a unique (as opposed to the other X–1 assignments) probability of being present in a tumor of type, e.g., the tumor type of said sample, wherein, optionally, each of said of X assignments is based on a unique (as opposed to the other X–1 assignments) first and/or second value (wherein X=2, 3, 5, 10, 20, 30, 40, 50, 60, 70, 80, 90, 100, 200, 300, 400, or 500);

(iv) assigning a nucleotide value (e.g., calling a mutation) at a first and a second nucleotide position, wherein the likelihood of a first variant at said first nucleotide position being present in a tumor of type (e.g., the tumor type of said sample) is at least 2, 5, 10, 20, 30, or 40 times greater than the likelihood of a second variant at said second nucleotide position being present, wherein, optionally, each assignment is based on a unique (as opposed to the other assignments) first and/or second value;

(v) assigning a nucleotide value to a plurality of nucleotide positions (e.g., calling mutations), wherein said plurality comprises an assignment for variants falling into one or more, e.g., at least 3, 4, 5, 6, 7, or all, of the following probability percentage ranges: less than or equal to 0.01%; greater than 0.01% and less than or equal to 0.02%; greater than 0.02% and less than or equal to 0.03%; greater than 0.03% and less than or equal to 0.04%; greater than 0.04% and less than or equal to 0.05%; greater than 0.05% and less than or equal to 0.1%; greater than 0.1% and less than or equal to 0.2%; greater than 0.2% and less than or equal to 0.5%; greater than 0.5% and less than or equal to 1.0%; greater than 1.0% and less than or equal to 2.0%; greater than 2.0% and less than or equal to 5.0%; greater than 5.0% and less than or equal to 10.0%; greater than 10.0% and less than or equal to 20.0%; greater than 20.0% and less than or equal to 50.0%; and greater than 50% and less than or equal to 100.0%, wherein, a probability range is the range of probabilities that a variant at a nucleotide position will be present in a tumor type (e.g., the tumor type of said sample) or the probability that a variant at a nucleotide position will be present in the recited percentage (%) of the cells in a sample, a library from the sample, or library catch from that library, for a preselected type (e.g., the tumor type of said sample), and wherein, optionally, each assignment is based on a unique first and/or second value (e.g., unique as opposed to the other assignments in a recited probability range or unique as opposed to the first and/or second values for one or more or all of the other listed probability ranges).

(vi) assigning a nucleotide value (e.g., calling a mutation) for at least 1, 2, 3, 5, 10, 20, 30, 40, 50, 60, 70, 80, 90, 100, 200, 300, 400, 500, 600, 700, 800, 900, or 1,000 nucleotide positions each, independently, having a variant present in less than 50%, 40%, 25%, 20%, 15%, 10%, 5%, 4%, 3%, 2%, 1%, 0.5%, 0.4%, 0.3%, 0.2%, or 0.1% of the DNA in said sample, wherein, optionally, each assignment is based on a unique (as opposed to the other assignments) first and/or second value;

(vii) assigning a nucleotide value (e.g., calling a mutation) at a first and a second nucleotide position, wherein the likelihood of a variant at the first position in the DNA of said sample is at least 2, 5, 10, 20, 30, or 40 times greater than the likelihood of a variant at said second nucleotide position in the DNA of said sample, wherein, optionally, each assignment is based on a unique (as opposed to the other assignments) first and/or second value;

(viii) assigning a nucleotide value (e.g., calling a mutation) in one or more or all of the following:

(1) at least 1, 2, 3, 4 or 5 nucleotide positions having a variant present in less than 1% of the cells in said sample, of the nucleic acids in a library from said sample, or the nucleic acid in a library catch from that library;

(2) at least 1, 2, 3, 4 or 5 nucleotide positions having a variant present in 1-2% of the cells in said sample, of the nucleic acid in a library from said sample, or the nucleic acid in a library catch from that library;

(3) at least 1, 2, 3, 4 or 5 nucleotide positions having a variant present in greater than 2% and less than or equal to 3% of the cells in said sample, of the nucleic acid in a library from said sample, or the nucleic acid in a library catch from that library;

(4) at least 1, 2, 3, 4 or 5 nucleotide positions having a variant present in greater than 3% and less than or equal to 4% of the cells in said sample, of the nucleic acid in a library from said sample, or the nucleic acid in a library catch from that library;

(5) at least 1, 2, 3, 4 or 5 nucleotide positions having a variant present in greater than 4% and less than or equal to 5% of the cells in said sample, of the nucleic acid in a library from said sample, or the nucleic acid in a library catch from that library;

(6) at least 1, 2, 3, 4 or 5 nucleotide positions having a variant present in greater than 5% and less than or equal to 10% of the cells in said sample, of the nucleic acid in a library from said sample, or the nucleic acid in a library catch from that library;

(7) at least 1, 2, 3, 4 or 5 nucleotide positions having a variant present in greater than 10% and less than or equal to 20% of the cells in said sample, of the nucleic acid in a library from said sample, or the nucleic acid in a library catch from that library;

(8) at least 1, 2 3, 4 or 5 nucleotide positions having a variant present in greater than 20% and less than or equal to 40% of the cells in said sample, of the nucleic acid in a library from said sample, or the nucleic acid in a library catch from that library;

(9) at least 1, 2 3, 4 or 5 nucleotide positions having a variant present at greater than 40% and less than or equal to 50% of the cells in said sample, of the nucleic acid in a library from said sample, or the nucleic acid in a library catch from that library; or

(10) at least 1, 2 3, 4 or 5 nucleotide positions having a variant present in greater than 50% and less than or equal to 100% of the cells in said sample, of the nucleic acid in a library from said sample, or the nucleic acid in a library catch from that library;

wherein, optionally, each assignment is based on a unique first and/or second value (e.g., unique as opposed to the other assignments in the recited range (e.g., the range in (1) of less than 1%) or unique as opposed to a first and/or second values for a determination in one or more or all of the other listed ranges); or (ix) assigning a nucleotide value (e.g., calling a mutation) at each of X nucleotide positions, each nucleotide position, independently, having a likelihood (of a variant being present in the DNA of said sample) that is unique as compared with the likelihood for a variant at the other X–1 nucleotide positions, wherein X is equal to or greater than 1, 2, 3, 5, 10, 20, 30, 40, 50, 60, 70, 80, 90, 100, 200, 300, 400, 500, 600, 700, 800, 900, or 1,000, and wherein each assignment is based on a unique (as opposed to the other assignments) first and/or second value.

In some embodiments, a "threshold value" is used to evaluate reads, and select from the reads a value for a nucleotide position, e.g., calling a mutation at a specific position in a gene. In some embodiments, a threshold value for each of a number of subject intervals is customized or fine-tuned. The customization or tuning can be based on one or more of the factors described herein, e.g., the type of cancer in a sample, the gene in which the subject interval (subgenomic interval or expressed subgenomic interval) to be sequenced is located, or the variant to be sequenced. This provides for calling that is finely tuned to each of a number of subject intervals to be sequenced. In some embodiments, the method is particularly effective when a relatively large number of diverse subgenomic intervals are analyzed.

Thus, in another embodiment, the method comprises the following mutation calling method:

acquiring, for each of said X subject intervals, a threshold value, wherein each of said acquired X threshold values is unique as compared with the other X−1 threshold values, thereby providing X unique threshold values;

for each of said X subject intervals, comparing an observed value which is a function of the number of reads having a nucleotide value at a nucleotide position with its unique threshold value, thereby applying to each of said X subject intervals its unique threshold value; and optionally, responsive to the result of said comparison, assigning a nucleotide value to a nucleotide position, wherein X is equal to or greater than 2.

In an embodiment, the method includes assigning a nucleotide value to at least 2, 3, 5, 10, 20, 30, 40, 50, 60, 70, 80, 90, 100, 200, 300, 400, 500, 600, 700, 800, 900, or 1,000 nucleotide positions, each having, independently, a first value that is a function of a probability that is less than 0.5, 0.4, 0.25, 0.15, 0.10, 0.05, 0.04, 0.03, 0.02, or 0.01.

In an embodiment, the method includes assigning a nucleotide value to at each of at least X nucleotide positions, each independently having a first value that is unique as compared with the other X−1 first values, and wherein each of said X first values is a function of a probability that is less than 0.5, 0.4, 0.25, 0.15, 0.10, 0.05, 0.04, 0.03, 0.02, or 0.01, wherein X is equal to or greater than 1, 2, 3, 5, 10, 20, 30, 40, 50, 60, 70, 80, 90, 100, 200, 300, 400, 500, 600, 700, 800, 900, or 1,000.

In an embodiment, a nucleotide position in at least 20, 30, 40, 60, 80, 100, 120, 140, 160 or 180, 200, 300, 400, or 500 genes, e.g., genes from Tables 1A-5A, is assigned a nucleotide value. In an embodiment unique first and/or second values are applied to subject intervals in each of at least 10%, 20%, 30%, 40%, or 50% of said genes analyzed.

Embodiments of the method can be applied where threshold values for a relatively large number of subject intervals are optimized, as is seen, e.g., from the following embodiments.

In an embodiment, a unique threshold value is applied to subject intervals, e.g., subgenomic intervals or expressed subgenomic intervals, in each of at least 3, 5, 10, 20, 30, 40, 50, 60, 70, 80, 90, 100, 200, 300, 400, 500, 600, 700, 800, 900, or 1,000 different genes.

In an embodiment, a nucleotide position in at least 20, 30, 40, 60, 80, 100, 120, 140, 160 or 180, 200, 300, 400, or 500 genes, e.g., genes from Tables 1A-5A, is assigned a nucleotide value. In an embodiment a unique threshold value is applied to a subgenomic interval in each of at least 10%, 20%, 30%, 40%, or 50% of said genes analyzed.

In an embodiment, a nucleotide position in at least 5, 10, 20, 30, or 40 genes from Tables 1A-5A is assigned a nucleotide value. In an embodiment a unique threshold value is applied to a subject interval (e.g., a subgenomic interval or an expressed subgenomic interval) in each of at least 10%, 20%, 30%, 40%, or 50% of said genes analyzed.

These and other mutation calling methods are discussed in more detail elsewhere herein, e.g., in the section entitled "Mutation Calling." Elements of that module can be included in methods of analyzing a tumor. In embodiments, an alignment method from the section entitled "Mutation Calling" is combined with an alignment method from the section entitled "Alignment" (in the Summary and/or Detailed Description) and/or target capture reagents from the section entitled "Target Capture Reagents" (in the Summary) and/or the sections entitled "Design and Construction of Target Capture Reagents" and "Competition of Target Capture Reagents" (in the Detailed Description). The method can be applied to a set of subject intervals from the section entitled "Gene Selection" (in the Summary and/or Detailed Description).

SGZ Analysis

In certain embodiments, the alteration evaluated in accordance with a method described herein is a germline alteration. In certain embodiments, the germline alteration is identified by an SGZ algorithm (e.g., as described in Sun et al. *PLoS Comput Biol.* 2018; 14(2):e1005965, and U.S. Pat. No. 9,792,403). For example, when tumor mutational burden is evaluated, a germline alteration can be excluded by a method or system comprising the use of an SGZ algorithm.

In certain embodiments, the method further comprises characterizing a variant in a sample from a subject as being a somatic or germline event, the method comprising:

a) sequencing each of a plurality of selected subject intervals, each of a plurality of selected germline SNPs, and a variant;

b) acquiring:

i) a sequence coverage input (SCI), which comprises, for each of the plurality of selected subject intervals, a value for normalized sequence coverage at the selected subject intervals, wherein SCI comprises a comparison of the number of reads for a subject interval with the number of reads for a process-matched control;

ii) an SNP allele frequency input (SAFI), which comprises, for each of the plurality of selected germline SNPs, a value for a minor allele frequency in the sample; and iii) for said variant being characterized, a variant allele frequency input (VAFI), which comprises the allele frequency for said variant in the sample;

c) acquiring values, as a function of SCI and SAFI, for:

a genomic segment total copy number (C) for each of a plurality of genomic segments;

a genomic segment minor allele copy number (M) for each of the plurality of genomic segments; and sample purity (p), wherein SCI, SAFI, C, M, and p are related to one another by the following:

$$r_{ij} \sim N\left(\log_2 \frac{p * C_i + (1-p) * 2}{p * (\Sigma_i l_i C_i)/\Sigma_i l_i + (1-p) * 2}, \sigma_{ri}\right), \text{ and}$$

-continued $$fik \sim N\left(\frac{p*Mi + (1-p)*1}{p*Ci + (1-p)*2}, \sigma fi\right),$$

when SCI and SAFI are notated as $r_{ij}$ and $f_{ik}$, respectively; and where $r_{ij}$ is the log ratio (LR) of subject interval j within a genomic segment ($S_i$), $C_i$ is the total copy number (C) of $S_i$, $l_i$ is the length of $S_i$, fik is the minor allele frequency of SNP k within $S_i$, $M_i$ is the copy number of a minor allele (M) at $S_i$, and $\sigma_{ri}$, and $\sigma_{fi}$ are noise parameters; and d) acquiring a value for mutation type, g, for which is indicative of the variant, being somatic, a subclonal somatic variant, germline, or not-distinguishable, wherein g, VAFI, p, C, and M are related to one another by the following:

$$VAFI = \frac{pM + g(1-p)}{pC + 2(1-p)}.$$

In some embodiments, a value of g that is 0, or close to 0, indicates that the variant is a somatic variant; a value of g that is 1, or close to 1, indicates that the variant is a germline variant;

a value of g that is less than 1 but more than 0, indicates an indistinguishable result; and a value of g that is significantly less than 0, indicates that the variant is a subclonal somatic variant.

In some embodiments, the sample purity (p) is a global purity value.

In some embodiments, a value of M equal to 0 and not equal to C is indicative of absence of the variant; a non-zero value of M equal to C is indicative of homozygosity of the variant; a value of M equal to 0 and equal to C is indicative of homozygous deletion of the variant; and a non-zero value of M not equal to C is indicative of heterozygosity of the variant.

In some embodiments, the plurality of selected subject intervals comprises an exon. In some embodiments, the variant is positively associated with the type of tumor present in the subject. In some embodiments, the method further comprises acquiring an indication of the zygosity of the variant in the sample. In some embodiments, the value for mutation type, g, is acquired without the use of a subject-matched normal control. In some embodiments, the average sequencing depth prior to normalization is at least about 100X, 250X, 500X, 800X, 1,000X, 1,500X, 2,000X, 2,500X, 3,000X, 3,500X, 4,000X, 4.500X, 5,000X, 5,500X, 6,000X, 6,500X, 7,000X, 7,500X, or 8,000X.

Tumor Mutational Burden

The methods and compositions described herein can be used to evaluate tumor mutational burden.

In certain embodiments, the method comprises providing a sequence of a set of subgenomic intervals from a sample (e.g., a sample described herein); and determining a value for the mutational burden, wherein the value is a function of the number of alterations in the set of subgenomic intervals. In certain embodiments, the set of subgenomic intervals are from a set of genes, for example, a set of genes that does not include the entire genome or exome. In certain embodiments, the set of subgenomic intervals is a set of coding subgenomic intervals. In other embodiments, the set of subgenomic intervals contains one or more coding subgenomic intervals and one or more non-coding subgenomic intervals. In certain embodiments, the value for the mutational burden is a function of the number of alterations (e.g., somatic alterations) in the set of subgenomic intervals. In certain embodiments, the number of alterations excludes the number of functional alterations, germline alterations, or both.

The methods described herein can also include, e.g., one or more of: acquiring a library comprising a plurality of tumor nucleic acid molecules from the sample; contacting the library with target capture reagents to provide selected tumor nucleic acid molecules by hybridization, thereby providing a library catch; acquiring a read for a subgenomic interval comprising an alteration from the tumor nucleic acid molecule from the library catch; aligning the read by an alignment method; assigning a nucleotide value from the read for a nucleotide position; and selecting a set of subgenomic intervals from a set of the assigned nucleotide positions, wherein the set of subgenomic intervals are from a set of genes.

In certain embodiments, the mutational burden is measured in a sample from a subject, e.g., a subject described herein. In certain embodiments, the mutational burden is expressed as a percentile, e.g., among the mutational burdens in samples from a reference population. In certain embodiments, the reference population includes patients having the same type of cancer as the subject. In other embodiments, the reference population includes patients who are receiving, or have received, the same type of therapy, as the subject. In certain embodiments, the mutational burden obtained by a method described herein, e.g., by evaluating the level of an alteration (e.g., a somatic alteration) in a set of genes set forth in Tables 1A-5A, correlates with the whole genome or exome mutational burden.

Type of Alterations

Various types of alterations (e.g., somatic alterations) can be evaluated and used for the analysis of genomic alterations, in a method or system as described herein. For example, genomic alterations associated with cancer and/or tumor mutational burden can be analyzed. Without wishing to be bound by theory, it is believed that in some embodiments, the methods described herein are useful for analyzing samples with low tumor content and/or low amounts of tumor nucleic acids.

Somatic Alterations

In certain embodiments, the alteration evaluated in accordance with a method described herein is a somatic alteration.

In certain embodiments, the alteration (e.g., somatic alteration) is a coding short variant, e.g., a base substitution or an indel (insertion or deletion). In certain embodiments, the alteration (e.g., somatic alteration) is a point mutation. In other embodiments, the alteration (e.g., somatic alteration) is other than a rearrangement, e.g., other than a translocation. In certain embodiments, the alteration (e.g., somatic alteration) is a splice variant.

In certain embodiments, the alteration (e.g., somatic alteration) is a silent mutation, e.g., a synonymous alteration. In other embodiments, the alteration (e.g., somatic alteration) is a non-synonymous single nucleotide variant (SNV). In other embodiments, the alteration (e.g., somatic alteration) is a passenger mutation, e.g., an alteration that has no detectable effect on the fitness of a clone of cells. In certain embodiments, the alteration (e.g., somatic alteration) is a variant of unknown significance (VUS), e.g., an alteration, the pathogenicity of which can neither be confirmed nor ruled out. In certain embodiments, the alteration (e.g., somatic alteration) has not been identified as being associated with a cancer phenotype.

In certain embodiments, the alteration (e.g., somatic alteration) is not associated with, or is not known to be associated with, an effect on cell division, growth or survival. In other embodiments, the alteration (e.g., somatic alteration) is associated with an effect on cell division, growth or survival.

In certain embodiments, an increased level of a somatic alteration is an increased level of one or more classes or types of a somatic alteration (e.g., a rearrangement, a point mutation, an indel, or any combination thereof). In certain embodiments, an increased level of a somatic alteration is an increased level of one class or type of a somatic alteration (e.g., a rearrangement only, a point mutation only, or an indel only). In certain embodiments, an increased level of a somatic alteration is an increased level of a somatic alteration at a position (e.g., a nucleotide positions, e.g., at one or more nucleotide positions), or at a region, (e.g., at a nucleotide region, e.g., at one or more nucleotide regions). In certain embodiments, an increased level of a somatic alteration is an increased level of a somatic alteration (e.g., a somatic alteration described herein).

Functional Alterations

In certain embodiments, the alteration (e.g., a somatic alteration) is a functional alteration in a subgenomic interval. In other embodiments, the alteration (e.g., a somatic alteration) is not a known functional alteration in a subgenomic interval. For example, when tumor mutational burden is evaluated, the number of alterations (e.g., somatic alterations) can exclude one or more functional alterations.

In some embodiments, the functional alteration is an alteration that, compared with a reference sequence, e.g., a wild-type or unmutated sequence, has an effect on cell division, growth or survival, e.g., promotes cell division, growth or survival. In certain embodiments, the functional alteration is identified as such by inclusion in a database of functional alterations, e.g., the COSMIC database (cancer-.sanger.ac.uk/cosmic; Forbes et al. *Nucl. Acids Res.* 2015; 43 (D1): D805-D811). In other embodiments, the functional alteration is an alteration with known functional status, e.g., occurring as a known somatic alteration in the COSMIC database. In certain embodiments, the functional alteration is an alteration with a likely functional status, e.g., a truncation in a tumor suppressor gene. In certain embodiments, the functional alteration is a driver mutation, e.g., an alteration that gives a selective advantage to a clone in its microenvironment, e.g., by increasing cell survival or reproduction. In other embodiments, the functional alteration is an alteration capable of causing clonal expansions. In certain embodiments, the functional alteration is an alteration capable of causing one, two, three, four, five, or all of the following: (a) self-sufficiency in a growth signal; (b) decreased, e.g., insensitivity, to an antigrowth signal; (c) decreased apoptosis; (d) increased replicative potential; (e) sustained angiogenesis; or (f) tissue invasion or metastasis.

In certain embodiments, the functional alteration is not a passenger mutation, e.g., is not an alteration that has no detectable effect on the fitness of a clone of cells. In certain embodiments, the functional alteration is not a variant of unknown significance (VUS), e.g., is not an alteration, the pathogenicity of which can neither be confirmed nor ruled out.

In certain embodiments, a plurality (e.g., about 10%, 20%, 30%, 40%, 50%, 60%, 70%, 80%, 90%, or more) of functional alterations in a gene described in Tables 1A-5A are excluded. In certain embodiments, all functional alterations in a gene described in Tables 1A-5A are excluded. In certain embodiments, a plurality of functional alterations in a plurality of genes described in Tables 1A-5A is excluded. In certain embodiments, all functional alterations in all genes described in Tables 1A-5A are excluded.

Germline Alterations

In certain embodiments, the alteration is a germline alteration. In other embodiments, the alteration is not a germline alteration. In certain embodiments, the alteration is not identical or similar to, e.g., is distinguishable from, a germline alteration. For example, when tumor mutational burden is evaluated, the number of alterations can exclude the number of germline alterations.

In certain embodiments, the germline alteration is a single nucleotide polymorphism (SNP), a base substitution, an indel (e.g., an insertion or a deletion), or a silent alteration (e.g., synonymous alteration).

In certain embodiments, the germline alteration is identified by use of a method that does not use a comparison with a matched normal sequence. In other embodiments, the germline alteration is identified by a method comprising the use of an SGZ algorithm. In certain embodiments, the germline alteration is identified as such by inclusion in a database of germline alterations, e.g., the dbSNP database (www.ncbi.nlm.nih.gov/SNP/index.html; Sherry et al. *Nucleic Acids Res.* 2001; 29(1): 308-311). In other embodiments, the germline alteration is identified as such by inclusion in two or more counts of the ExAC database (exac.broadinstitute.org; Exome Aggregation Consortium et al. "Analysis of protein-coding genetic variation in 60,706 humans," bioRxiv preprint. Oct. 30, 2015). In some embodiments, the germline alteration is identified as such by inclusion in the 1000 Genome Project database (www.1000genomes.org; McVean et al. *Nature.* 2012; 491, 56-65). In some embodiments, the germline alteration is identified as such by inclusion in the ESP database (Exome Variant Server, NHLBI GO Exome Sequencing Project (ESP), Seattle, WA (evs.gs.washington.edu/EVS/).

Gene Selection

Subject intervals, e.g., subgenomic intervals, expressed subgenomic intervals, or both, for analysis, e.g., a group or set of subgenomic intervals for sets or groups of genes and other regions, are described herein.

In some embodiments, the method comprises sequencing, e.g., by a next-generation sequencing method, a subject interval from at least 5, 6, 7, 8, 9, 10, 15, 20, 25, 30, 40, 50, 60, 70, 80, 90, 100, 200, 300, 400, 500, or more genes or gene products from the acquired nucleic acid sample, wherein the genes are chosen from Tables 1A-5A.

In some embodiments, the method comprises sequencing, e.g., by a next-generation sequencing method, a subject interval from at least 5, 6, 7, 8, 9, 10, 15, 20, 25, 30, 40, 50, 60, 70, 80, 90, 100, 200, 300, 400, 500, or more genes or gene products from the sample, wherein the genes are chosen from Tables 1A-5A.

In another embodiment, subject intervals of one of the following sets or groups are analyzed. E.g., subject intervals associated with a tumor or cancer gene or gene product and a reference (e.g., a wild-type) gene or gene product can provide a group or set of subgenomic intervals from the sample.

In an embodiment, the method acquires a read, e.g., sequences, a set of subject intervals from the sample, wherein the subject intervals are chosen from at least 1, 2, 3, 4, 5, 6, 7 or all of the following:

A) at least 5, 6, 7, 8, 9, 10, 15, 20, 25, 30, 40, 50, 60, 70, 80, 90, 100, 200, 300, 400, 500, or more subject intervals, e.g., subgenomic intervals, or expressed subgenomic intervals, or both, from a mutated or wild-type gene according to Tables 1A-5A;

B) at least 5, 6, 7, 8, 9, 10, 15, 20, 25, 30, 40, 50, 60, 70, 80, 90, 100, 200, 300, 400, 500, or more subject intervals from a gene or gene product that is associated with a tumor or cancer (e.g., is a positive or negative treatment response predictor, is a positive or negative prognostic factor for, or enables differential diagnosis of a tumor or cancer, e.g., a gene according to Tables 1A-5A);

C) at least 5, 6, 7, 8, 9, 10, 15, 20, 25, 30, 40, 50, 60, 70, 80, 90, 100, 200, 300, 400, 500, or more of subject intervals from a mutated or wild-type gene or gene product (e.g., single nucleotide polymorphism (SNP)) of a subgenomic interval that is present in a gene chosen from Tables 1A-5A;

D) at least 5, 6, 7, 8, 9, 10, 15, 20, 25, 30, 40, 50, 60, 70, 80, 90, 100, 200, 300, 400, 500, or more of subject intervals from a mutated or wild-type gene (e.g., single nucleotide polymorphism (SNP)) of a subject interval that is present in a gene chosen from Tables 1A-5A associated with one or more of: (i) better survival of a cancer patient treated with a drug (e.g., better survival of a breast cancer patient treated with paclitaxel); (ii) paclitaxel metabolism; (iii) toxicity to a drug; or (iv) a side effect to a drug;

E) a plurality of translocation alterations involving at least 5, 6, 7, 8, 9, 10, 15, 20, 25, 30, 40, 50, 60, 70, 80, 90, 100, 200, 300, 400, 500, or more genes or gene products according to Tables 1A-5A;

F) at least five genes selected from Tables 1A-5A, wherein an allelic variation, e.g., at a position, is associated with a type of tumor and wherein said allelic variation is present in less than 5% of the cells in said tumor type;

G) at least five genes selected from Tables 1A-5A, which are embedded in a GC-rich region; or H) at least five genes indicative of a genetic (e.g., a germline risk) factor for developing cancer (e.g., the gene or gene product is chosen from Tables 1A-5A).

In yet another embodiment, the method acquires reads, e.g., sequences, for a set of subject intervals from the sample, wherein the subject intervals are chosen from 5, 6, 7, 8, 9, 10, 15, 20, 25, 30, 40, 50, 60, 70, 80, 90, 100, 200, 300, 400, or all of the genes described in Tables 1A-IC.

In yet another embodiment, the method acquires reads, e.g., sequences, for a set of subject intervals from the sample, wherein the subject intervals are chosen from 5, 6, 7, 8, 9, 10, 15, 20, 25, 30, or all of the genes described in Tables 2A-2B.

In yet another embodiment, the method acquires reads, e.g., sequences, for a set of subject intervals from the sample, wherein the subject intervals are chosen from 5, 6, 7, 8, 9, 10, 15, 20, 25, 30, 40, 50, 60, 70, 80, 90, 100, 200, 300, or all of the genes described in Tables 3A-3C.

In yet another embodiment, the method acquires reads, e.g., sequences, for a set of subject intervals from the sample, wherein the subject intervals are chosen from 5, 6, 7, 8, 9, 10, 15, 20, 25, 30, 40, 50, 60, 70, 80, or all of the genes described in Tables 4A-4B.

These and other sets and groups of subgenomic intervals are discussed in more detail elsewhere herein, e.g., in the section entitled "Gene Selection" (in the Summary and/or Detailed Description).

Applications

Methods disclosed herein allow integration of a number of optimized elements including optimized target capture reagent (e.g., bait)-based selection, optimized alignment, and optimized mutation calling, as applied, e.g., to cancer related segments of the genome. Methods described herein provide for NGS-based analysis of tumors that can be optimized on a cancer-by-cancer, gene-by-gene and site-by-site basis. This can be applied e.g., to the genes/sites and tumor types described herein. The methods optimize levels of sensitivity and specificity for mutation detection with a given sequencing technology. Cancer by cancer, gene by gene, and site by site optimization provides very high levels of sensitivity/specificity (e.g., >99% for both) that are essential for a clinical product.

Without wishing to be bound by theory, it is believed that in some embodiments, the methods described herein can be applied to general sequencing applications which would benefit from increased sensitivity in detection of selected genomic regions. For example, those applications include, but are not limited to, hereditary cancer panels with increased coverage based upon prevalence, other whole exome sequencing (WES) tests targeted to specific disease pathways, and prenatal testing with enrichment for candidate actionable focal events.

In some embodiments, the methods and compositions described herein can be used to modulate (e.g., adjust or optimize) the sequencing depth for one or more subgenomic intervals, e.g., based on the type of alteration or the purpose of analysis. For example, high-sensitivity somatic mutation calling may require a high sequencing depth and evaluation of tumor mutational burden (TMB) may need a moderate sequencing depth. In some embodiments, a small number of subgenomic intervals are sequenced to a higher sequencing depth (e.g., for analyzing somatic mutations) and a large number of subgenomic intervals are sequenced to a lower sequencing depth (e.g., for evaluating TMB).

In some embodiments, the methods and compositions described herein can be used for combined germline and somatic mutation calling. For example, high sequencing depth may be needed for calling somatic mutations (e.g., to increase the sensitivity of calling) but not for calling germline mutations. In some embodiments, the target capture reagents (e.g., baits) described herein can be modulated to increase the recovery of subject intervals associated with somatic mutations and lower the recovery of subject intervals associated with germline mutations, e.g., at the same time or in a single capturing step. In some embodiments, modulating the target capture reagents (e.g., baits) comprises altering the ratio of one or more (e.g., all) of the target capture reagents (e.g., baits). The methods and compositions described herein can be useful, e.g., for analyzing germline mutations with clinical significance (e.g., BRCA1/2). The methods and compositions described herein can also be useful, e.g., for combined somatic mutation calling with human leukocyte antigen (HLA) typing, e.g., for determining background mutation rate (pCV).

In some embodiments, the methods and compositions described herein can be used for optimization of large dynamic-range gene expression profiling. For example, high sequencing depth may be needed for analyzing high-expressed genes but not for analyzing low-expressed genes. In some embodiments, high sequencing depth may be needed for analyzing low-expressed genes. In some embodiments, high sequencing depth may be needed for analyzing low-expressed genes but not for high-expressed genes. In some embodiments, the target capture reagents (e.g., baits)

described herein can be modulated to lower the recovery of subject intervals associated with high-expressed genes and increase the recovery of subject intervals associated with low-expressed genes, e.g., at the same time or in a single capturing step.

In some embodiments, the methods and compositions described herein can be used for combined copy number alteration (CNA) calling and somatic mutation calling. For example, high sequencing depth may be needed for calling somatic mutations (e.g., to increase the sensitivity of calling) but not for calling CNAs. In some embodiments, the target capture reagents (e.g., baits) described herein can be modulated to increase the recovery of subject intervals associated with somatic mutations and lower the recovery of subject intervals that have been amplified, e.g., at the same time or in a single capturing step.

In some embodiments, the method further comprises selecting a treatment responsive to the evaluation of a genomic alteration, e.g., a somatic alteration. In some embodiments, the method can further comprise selecting a treatment responsive to the evaluation of mutational burden, e.g., an increased or decreased level of mutational burden. In some embodiments, the method further comprises administering a treatment responsive to the evaluation of a genomic alteration. In some embodiments, the method further comprises classifying the sample or the subject from which the sample was derived responsive to the evaluation of a genomic alteration. In some embodiments, the method further comprises determining clinical trial eligibility for a subject from which a sample is obtained. In some embodiments, the method further comprises generating and delivering a report, e.g., an electronic, web-based, or paper report, to the patient or to another person or entity, a caregiver, a physician, an oncologist, a hospital, clinic, third-party payor, insurance company or government office. In some embodiments, the report comprises output from the method described herein.

Methods described herein provide for clinical and regulatory grade comprehensive analysis and interpretation of genomic aberrations for a comprehensive set of plausibly actionable genes (which may typically range from 50 to 500 genes) using next-generation sequencing technologies from routine, real-world samples in order to inform optimal treatment and disease management decisions.

Methods described herein provide one-stop-shopping for oncologists/pathologists to send a sample and receive a comprehensive analysis and description of the genomic and other molecular changes for a tumor, in order to inform optimal treatment and disease management decisions.

Methods described herein provide a robust, real-world clinical oncology diagnostic tool that takes standard available samples and in one test provides a comprehensive genomic and other molecular aberration analysis to provide the oncologist with a comprehensive description of what aberrations may be driving the tumor and could be useful for informing the oncologists treatment decisions.

Methods described herein provide for a comprehensive analysis of a patient's cancer genome, e.g., by next-generation sequencing (NGS), with clinical grade quality. Methods include the most relevant genes and potential alterations and include one or more of the analysis of mutations (e.g., indels or base substitutions), copy number, rearrangements, e.g., translocations, expression, and epigenetic markers. The output of the genetic analysis can be contextualized with descriptive reporting of actionable results. Methods connect the use with an up to date set of relevant scientific and medical knowledge.

In some embodiments, the method analyzes a sample derived from a human body for the purpose of providing information for the diagnosis, prevention or treatment of any disease (e.g., cancer) or impairment of, or the assessment of the health of, human beings. In some embodiments, the method is performed in accordance with the guidelines provided by Clinical Laboratory Improvement Amendment (CLIA) and/or the College of American Pathologists (CAP). In some embodiments, the method is performed in a CLIA and/or CAP certified facility. In some embodiments, the method is performed in accordance with the guidelines provided by the Food and Drug Administration (FDA), the European Medicines Agency (EMA), Quality System Regulation (QSR), European Commission (CE), e.g., CE in vitro diagnostics (CE-IVD), Chinese Food and Drug Administration (CFDA) or other regulatory agency. In some embodiments, the method is performed in a FDA, QSR, CE or CFDA certified facility. In some embodiments, the method is performed in a QSR certified facility. In some embodiments, the method analyzes a clinical grade sample, e.g., a sample suitable for clinical practice, trials, or management of patient care. In some embodiments, the sample comprises a retrospective sample and/or a prospective sample. In some embodiments, a retrospective sample comprises a sample analyzed before or after a treatment has been administered, or is a research sample. In some embodiments, a prospective sample comprises a sample from a subject that has not been treated with a treatment. In some embodiments, use of a method described herein to analyze a prospective sample can result in a prediction of the outcome of a therapy on the subject from which the sample was obtained, e.g., derived.

In some embodiments, the method is used as a diagnostic, e.g., as described herein. In some embodiments, the method is used in or with a companion diagnostic. In some embodiments, the method is used as a complementary diagnostic.

In some embodiments, the validity of the method is established (e.g., under CLIA regulations) by determination of one or more (e.g., two, three, four, five, or all) of accuracy, precision, sensitivity, specificity, reportable range, or reference interval. In certain embodiments, accuracy is determined by the coverage and quality (e.g., Phred scores), e.g., for known variants (e.g., SNP, indel) in targeted regions. In certain embodiments, precision is determined by the sequence replication and coverage distribution between different operators and instruments, e.g., for known variants. In certain embodiments, specificity is determined by the false positive rate, degree with which a false variant is identified at a specific coverage threshold, e.g., in several samples with well characterized targets. In certain embodiments, sensitivity is determined by the likelihood test that detects known variant, e.g., in several samples with well characterized targets. In certain embodiments, reportable range is determined by the intron buffer and exon region of one or more genes, e.g., with repeat regions, indels, or allele drop outs. In certain embodiments, reference interval is determined by sequence variation background measurement, e.g., in an unaffected population.

In some embodiments, the method is performed in a setting (e.g., under CAP regulations) that includes consideration for one or more (e.g., two, three, four, five, or all) of validated sample extraction, library preparation, barcoding, pooling, target enrichment, or bioinformatics (e.g., how precise and sensitive variants are called).

Methods described herein provide for increasing both the quality and efficiency of patient care. This includes applications where a tumor is of a rare or poorly studied type such that there is no standard of care or the patient is refractory to established lines of therapy and a rational basis for selection of further therapy or for clinical trial participation could be useful. E.g., the methods allow, at any point of therapy, selection where the oncologist would benefit by having the full "molecular image" and/or "molecular sub-diagnosis" available to inform decision making. The results can be used to determine whether a patient may be eligible to enroll in a clinical trial.

Methods described herein can comprise providing a report, e.g., in electronic, web-based, or paper form, to the patient or to another person or entity, e.g., a caregiver, e.g., a physician, e.g., an oncologist, a hospital, clinic, third-party payor, insurance company or government office. The report can comprise output from the method, e.g., the identification of nucleotide values, the indication of the presence or absence of an alteration, mutation, or wild-type sequence, e.g., for subject intervals associated with a tumor of the type of the sample. The report can also comprise information on the level of tumor mutational burden. The report can also comprise information on one or more other genomic signatures, e.g., continuous/complex biomarkers, e.g., the level of microsatellite instability, or the presence or absence of heterozygosity (LOH). The report can also comprise information on the role of a sequence, e.g., an alteration, mutation, or wild-type sequence, in disease. Such information can include information on prognosis, resistance, or potential or suggested therapeutic options. The report can comprise information on the likely effectiveness of a therapeutic option, the acceptability of a therapeutic option, or the advisability of applying the therapeutic option to a patient, e.g., a patient having a sequence, alteration identified in the test, and in embodiments, identified in the report. E.g., the report can include information, or a recommendation on, the administration of a drug, e.g., the administration at a dosage or in a treatment regimen, e.g., in combination with other drugs, to the patient. In an embodiment, not all mutations identified in the method are identified in the report. E.g., the report can be limited to mutations in genes having a level of correlation with the occurrence, prognosis, stage, or suscep-tibility of the cancer to treatment, e.g., with a therapeutic option. Methods featured herein allow for delivery of the report, e.g., to an entity described herein, within 7, 14, or 21 days from receipt of the sample by the entity practicing the method. Thus, methods featured in the invention allow a quick turnaround time, e.g., within 7, 14 or 21 days of receipt of sample.

Methods described herein can also be used to evaluate a histologically normal sample, e.g., samples from surgical margins. If one or more alterations as described herein is detected, the tissue can be re-classified, e.g., as malignant or premalignant, and/or the course of treatment can be modi-fied.

In some embodiments, the methods described herein are useful in non-cancer applications, e.g., in forensic applica-tions (e.g., identification as alternative to, or in addition to, use of dental records), paternity testing, and disease diag-nosis and prognosis, e.g., for an infectious disease, an autoimmune disorder, cystic fibrosis, Huntington's Disease, Alzheimer's Disease, among others. For example, identifi-cation of genetic alterations by the methods described herein can indicate the presence or risk of an individual for devel-oping a particular disorder.

Systems

In another aspect, the invention features a system for evaluating genomic alterations in a sample. The system includes at least one processor operatively connected to a memory, the at least one processor when executing is configured to perform a method of analyzing a sample as described herein.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

Figure 1:
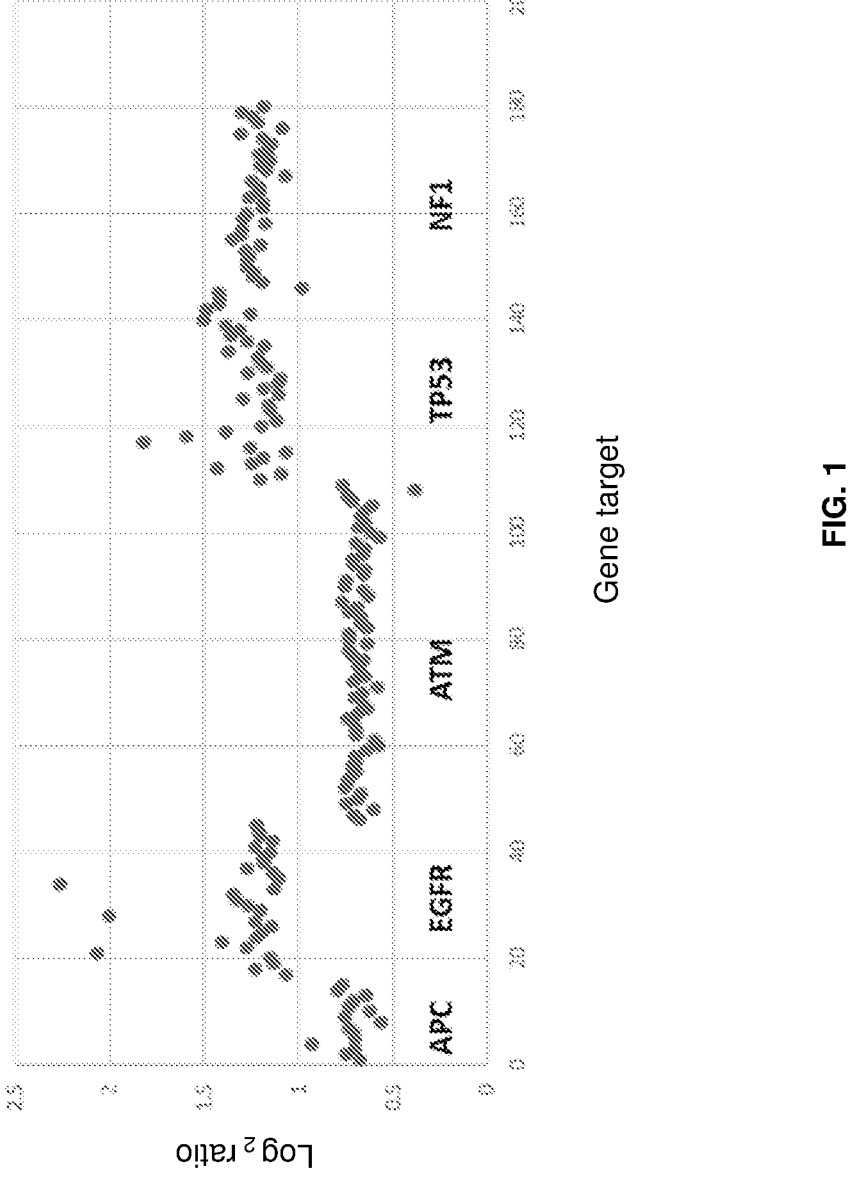
FIG. 1 is a plot showing target coverage of ATM and APC relative to three genes (EGFR, NF1 and TP53) without blockers. The y-axis depicts log 2 ratios and the x-axis depicts the gene target.

The methods described herein are based, at least in part, on the observation that differential sequencing depth of targets can be achieved in a controlled manner by optimizing the level of modification (e.g., biotinylation) on target cap-ture reagents for different targets. In certain embodiments, the method provides higher sensitivity for specific genomic regions, exons, or RNA transcripts, which are likely to contain subclonal mutations or are of higher clinical impor-tance. In other embodiments, the method provides higher sequencing depth on targets in which somatic mutations are evaluated versus ones which are used to assess germline SNP allele balance.

Without wishing to be bound by theory, it is believed that in some embodiments, the methods described herein can achieve a similar performance for evaluating genomic alterations with a lower cost.

The methods described herein allow for providing target capture reagents that can measure somatic mutations from tissue, blood, CTCs, cfDNA, or ctDNA at high sequencing depth in a smaller set of genes and simultaneously measure genomic signatures, e.g., continuous/complex biomarkers (e.g., tumor mutational burden, e.g., blood tumor mutational burden) on a larger genomic region at a lower sequencing depth. In certain embodiments, the methods described herein allow for measuring somatic alterations at high sequencing depth and germline alteration calling at low sequencing depth. In certain embodiments, the methods described herein allow for measuring somatic alterations at high sequencing depth and measuring copy number or structural variants (e.g., about 1 Kb to 3 Mb in length) at low sequencing depth. In other embodiments, this method can be used to control the sequencing depth of specific genes in an RNA-sequencing or cDNA-sequencing application or other applications where the abundance of different genes or sequences is differential in the source sample. In this situation there may be an advantage in reducing the sequence coverage of high abundance genes in order to improve the efficiency in measuring lower-abundance genes. Without wishing to be bound by theory, it is believed that in some embodiments, the methods described herein can be used to normalize sequencing coverage across different targets, where some targets are more efficiently and/or specifically captured by target capture reagents, whereas other targets are less efficiently and/or specifically captured by target capture reagents (e.g., due to high or low GC content in the target, or similarities between two different targets). Other utilities of the methods described herein include, but are not limited to, gene expression profiling, identification of SNPs, and determination of copy number alterations (CNA).

One of the challenges in obtaining differential sequencing depth with a hybrid capture approach is that the target capture reagents are typically in high molar excess with respect to the target DNA, which is needed for an efficient capture (e.g., to ensure saturation of target capture) and to allow quantitative measurement of the number of copies of target DNA (e.g., if the majority of target DNA is captured, the depth will be approximately linearly proportional to the number of copies of the target). In this situation, increasing or decreasing the relative amount of specific target capture reagents has a relatively minor effect on the obtained sequencing depth.

The methods described herein provide differential sequencing depth, e.g., by controlling the level of modification (e.g., biotinylation) on target capture reagents for different targets. Assuming that the majority of target DNA is captured (since the target capture reagents are in excess), the relative amount of target capture reagent for a specific target that is modified (e.g., biotinylated) can have a direct effect on the amount of the specific target DNA that is retained by the hybrid capture reaction. For example, if target capture reagents for target A are 25% biotinylated and target capture reagents for target B are 50% biotinylated, it would be expected that the relative amount of target A DNA versus the amount of target B DNA to be approximately 1:2. Since it is easy to reduce the level of modification (e.g., biotinylation) of a specific type of target capture reagent by mixing in non-modified (e.g., non-biotinylated) target capture reagent at a given proportion, and it is easy to determine the output sequencing depth ratios of different targets by sequencing, it would be desirable to titrate the reaction to achieve specific differential sequencing depths of specific targets.

In some embodiments, increasing the level of modification (e.g., biotinylation) on a specific type of target capture reagent can be achieved by different modifications, purification methods, or substrates for capture (e.g., in solution versus on surface). In other embodiments, the uniformity of sequencing depth of different targets is increased by reducing the level of modification (e.g., biotinylation) on better-performing target capture reagents and/or increasing the level of modification (e.g., biotinylation) of lower-performing target capture reagents to tighten the distribution of measured target sequencing depths.

Definitions

Certain terms are first defined. Additional terms are defined throughout the specification.

As used herein, the articles "a" and "an" refer to one or to more than one (e.g., to at least one) of the grammatical object of the article.

"About" and "approximately" shall generally mean an acceptable degree of error for the quantity measured given the nature or precision of the measurements. Exemplary degrees of error are within 20 percent (%), typically, within 10%, and more typically, within 5% of a given value or range of values.

A "high sequencing depth event" as the term is used herein refers to a sequence (e.g., a subgenomic interval sequence) which is sequenced to a high sequencing depth, e.g., at least 2000X, 2500X, 3000X, 3500X, 4000X, 4500X, 5000X, 5500X, 6000X, 6500X, 7000X, 7500X, 8000X, 8500X, 9000X, 9500X, 10000X, or higher. In an embodiment, the high sequencing depth event is associated with a phenotype (e.g., a cancer phenotype, an effect on cell division, growth or survival).

In an embodiment, the high sequencing depth event has a correlation with an outcome (e.g., a treatment outcome, a diagnosis or a prognosis). In an embodiment, the high sequencing depth event is a genetic event which has a correlation (e.g., a positive correlation or a negative correlation) with an unwanted phenotype, a disorder or likelihood of response to a therapy. In an embodiment, the high sequencing depth event comprises an alteration, e.g., a mutation, which leads to or drives tumorigenesis, or which is correlated with responsiveness or non-responsiveness to a therapeutic modality. In an embodiment, the high sequencing depth event comprises a genetic event in a gene described in any one of Tables 1A-5A. In an embodiment, the high sequencing depth event comprises a genetic event in a gene described in Tables 3C, 3D, 3E or 5A. In an embodiment, a first fragment (F1) is associated with a high sequencing depth event. In an embodiment, a high sequencing depth event is present in or within F1. In an embodiment, F1 comprises a high sequencing depth event. In an embodiment, a second fragment (F2) is not associated with a high sequencing depth event. In an embodiment, the high sequencing depth event is not present in or within F2. In an embodiment, F2 does not comprise a high sequencing depth event. In an embodiment, the high sequencing depth event is not an event, the level of which is associated with determination of one or more biomarkers, e.g., tumor mutational burden (TMB), microsatellite instability (MSI), or both. In an embodiment, the high sequencing depth event comprises an actionable event, e.g., an actionable event described herein. In an embodiment, the high sequencing depth event comprises a sequence (e.g., a subgenomic interval sequence) that is sequenced to a high sequencing depth, e.g., a depth which is at least 1, 2, 3, 4, 5, 6, 7, 8, 9, or 10-fold greater, than a low sequencing depth event.

A "low sequencing depth event" as the term is used herein refers to a sequence (e.g., a subgenomic interval sequence) which is sequenced to a low sequencing depth, e.g., less than 2000X, 1500X, 1000X, 900X, 800X, 700X, 600X, 500X, 400X, 300X, 200X, or lower. In an embodiment, the low sequencing depth event is not associated with a phenotype (e.g., a cancer phenotype, an effect on cell division, growth or survival). In an embodiment, the low sequencing depth event has, or does not have, a correlation with an outcome (e.g., a treatment outcome, a diagnosis or a prognosis). In an embodiment, the low sequencing depth event is a genetic event which has, or does not have, a correlation (e.g., a positive correlation or a negative correlation) with an unwanted phenotype, a disorder or likelihood of response to a therapy. In an embodiment, the low sequencing depth event is an alteration with no phenotype, e.g., a silent mutation or a SNP. In an embodiment, the low sequencing depth event is a genetic event in a gene described in any one of Tables 1A-5A. In an embodiment, the low sequencing depth event is not a genetic event in a gene described in Tables 3C, 3D, 3E or 5A. In an embodiment, a second fragment (F2) is associated with a low sequencing depth event. In an embodiment, a low sequencing depth event is present in or within F2. In an embodiment, F2 comprises a low sequencing depth event. In an embodiment, a first fragment (F1) is not associated with a low sequencing depth event. In an embodiment, the low sequencing depth event is not present in or within F1. In an embodiment, F1 does not comprise a low sequencing depth event. In an embodiment, the low sequencing depth event comprises an event, the level of which is associated with determination of one or more biomarkers, e.g., tumor mutational burden (TMB), microsatellite instability (MSI), or both. In an embodiment, the low sequencing depth event comprises an actionable event, e.g., an actionable event described herein. In an embodiment, the low sequencing depth event does not comprise an actionable event, e.g., not an actionable event described herein. In an embodiment, the low sequencing depth event comprises a sequence (e.g., a subgenomic interval sequence) that is sequenced to a low sequencing depth, e.g., a depth which is less than 1, 2, 3, 4, 5, 6, 7, 8, 9, or 10-fold lower, than a high sequencing depth event.

An "actionable event" or "actionability" as the terms are used herein refer to a sequence (e.g., a subgenomic interval sequence) which is associated with a phenotype (e.g., a cancer phenotype, an effect on cell division, growth or survival). In an embodiment, an actionable event has a correlation with an outcome (e.g., a treatment outcome, a diagnosis or a prognosis). In an embodiment, an actionable event is a genetic event which has a correlation (e.g., a positive correlation or a negative correlation) with an unwanted phenotype, a disorder or likelihood of response to a therapy. In an embodiment, an actionable event is an alteration, e.g., a mutation, which leads to or drives tumorigenesis, or which is correlated with responsiveness or non-responsiveness to a therapeutic modality. In an embodiment, an actionable event is a genetic event in a gene described in any one of Tables 1A-5A. In an embodiment, the level of TMB or MSI can be associated with an actionable event, but one or more alterations identified when determining the level of TMB or MSI may or may not be actionable.

In an embodiment, an actionable event can be determined based on a method described in Hedley et al., (2016) *Nature Reviews* 16(5) 319-29, the entire contents of which are hereby incorporated by reference. In an embodiment, an actionable event comprises a well-characterized recurrent mutation. In an embodiment, an actionable event comprises a mutation which can result in transformation in a cellular assay. In an embodiment, an actionable event comprises a mutation which can alter, e.g., enhance, the sensitivity of a cell to a compound. In an embodiment, an actionable event comprises a mutation which is pathogenic.

"Acquire" or "acquiring" as the terms are used herein, refer to obtaining possession of a physical entity, or a value, e.g., a numerical value, by "directly acquiring" or "indirectly acquiring" the physical entity or value. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non-covalent bond, between a first and a second atom of the analyte; or by changing the structure of a reagent, or a fragment or other derivative thereof, e.g., by breaking or forming a covalent or non-covalent bond, between a first and a second atom of the reagent.

"Acquiring a sequence" or "acquiring a read" as the term is used herein, refers to obtaining possession of a nucleotide sequence or amino acid sequence, by "directly acquiring" or "indirectly acquiring" the sequence or read. "Directly acquiring" a sequence or read means performing a process (e.g., performing a synthetic or analytical method) to obtain the sequence, such as performing a sequencing method (e.g., a Next-generation Sequencing (NGS) method). "Indirectly acquiring" a sequence or read refers to receiving information or knowledge of, or receiving, the sequence from another party or source (e.g., a third party laboratory that directly acquired the sequence). The sequence or read acquired need not be a full sequence, e.g., sequencing of at least one nucleotide, or obtaining information or knowledge, that identifies one or more of the alterations disclosed herein as being present in a subject constitutes acquiring a sequence.

Directly acquiring a sequence or read includes performing a process that includes a physical change in a physical substance, e.g., a starting material, such as a sample described herein. Exemplary changes include making a physical entity from two or more starting materials, shearing or fragmenting a substance, such as a genomic DNA fragment; separating or purifying a substance (e.g., isolating a nucleic acid sample from a tissue); combining two or more separate entities into a mixture, performing a chemical reaction that includes breaking or forming a covalent or non-covalent bond. Directly acquiring a value includes performing a process that includes a physical change in a sample or another substance as described above. The size of the fragment (e.g., the average size of the fragments) can be 2500 bp or less, 2000 bp or less, 1500 bp or less, 1000 bp or less, 800 bp or less, 600 bp or less, 400 bp or less, or 200 bp or less. In some embodiments, the size of the fragment (e.g., cfDNA) is between about 150 bp and about 200 bp (e.g., between about 160 bp and about 170 bp). In some embodiments, the size of the fragment (e.g., DNA fragments from FFPE samples) is between about 150 bp and about 250 bp. In some embodiments, the size of the fragment (e.g., cDNA fragments obtained from RNA in FFPE samples) is between about 100 bp and about 150 bp.

"Acquiring a sample" as the term is used herein, refers to obtaining possession of a sample, e.g., a sample described herein, by "directly acquiring" or "indirectly acquiring" the sample. "Directly acquiring a sample" means performing a process (e.g., performing a physical method such as a surgery or extraction) to obtain the sample. "Indirectly acquiring a sample" refers to receiving the sample from another party or source (e.g., a third party laboratory that directly acquired the sample). Directly acquiring a sample includes performing a process that includes a physical change in a physical substance, e.g., a starting material, such as a tissue, e.g., a tissue in a human patient or a tissue that has was previously isolated from a patient. Exemplary changes include making a physical entity from a starting material, dissecting or scraping a tissue; separating or purifying a substance (e.g., a sample tissue or a nucleic acid sample); combining two or more separate entities into a mixture; performing a chemical reaction that includes breaking or forming a covalent or non-covalent bond. Directly acquiring a sample includes performing a process that includes a physical change in a sample or another substance, e.g., as described above.

"Alteration" or "altered structure" as used herein, of a gene or gene product (e.g., a marker gene or gene product) refers to the presence of a mutation or mutations within the gene or gene product, e.g., a mutation, which affects integrity, sequence, structure, amount or activity of the gene or gene product, as compared to the normal or wild-type gene. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, an alteration which is associated with cancer, or predictive of responsiveness to anti-cancer therapeutics, can have an altered nucleotide sequence (e.g., a mutation), amino acid sequence, chromosomal transloca- tion, intra-chromosomal inversion, copy number, expression level, protein level, protein activity, epigenetic modification (e.g., methylation or acetylation status, or post-translational modification, in a cancer tissue or cancer cell, as compared to a normal, healthy tissue or cell. Exemplary mutations include, but are not limited to, point mutations (e.g., silent, missense, or nonsense), deletions, insertions, inversions, duplications, amplification, translocations, inter- and intra- chromosomal rearrangements. Mutations can be present in the coding or non-coding region of the gene. In certain embodiments, the alteration(s) is detected as a rearrange- ment, e.g., a genomic rearrangement comprising one or more introns or fragments thereof (e.g., one or more rear- rangements in the 5'- and/or 3'-UTR). In certain embodi- ments, the alterations are associated (or not associated) with a phenotype, e.g., a cancerous phenotype (e.g., one or more of cancer risk, cancer progression, cancer treatment or resistance to cancer treatment). In one embodiment, the alteration (or tumor mutational burden) is associated with one or more of: a genetic risk factor for cancer, a positive treatment response predictor, a negative treatment response predictor, a positive prognostic factor, a negative prognostic factor, or a diagnostic factor.

As used herein, the term "indel" refers to an insertion, a deletion, or both, of one or more nucleotides in a nucleic acid of a cell. In certain embodiments, an indel includes both an insertion and a deletion of one or more nucleotides, where both the insertion and the deletion are nearby on the nucleic acid. In certain embodiments, the indel results in a net change in the total number of nucleotides. In certain embodi- ments, the indel results in a net change of about 1 to about 50 nucleotides.

"Clonal profile", as that term is used herein, refers to the occurrence, identity, variability, distribution, expression (the occurrence or level of transcribed copies of a subgenomic signature), or abundance, e.g., the relative abundance, of one or more sequences, e.g., an allele or signature, of a subject interval (or of a cell comprising the same). In an embodi- ment, the clonal profile is a value for the relative abundance for one sequence, allele, or signature, for a subject interval (or of a cell comprising the same) when a plurality of sequences, alleles, or signatures for that subject interval are present in a sample. E.g., in an embodiment, a clonal profile comprises a value for the relative abundance, of one or more of a plurality of VDJ or VJ combinations for a subject interval. In an embodiment, a clonal profile comprises a value for the relative abundance of a selected V segment for a subject interval. In an embodiment, a clonal profile com- prises a value for the diversity, e.g., as arises from somatic hypermutation, within the sequences of a subject interval. In an embodiment, a clonal profile comprises a value for the occurrence or level of expression of a sequence, allele, or signature, e.g., as evidenced by the occurrence or level of an expressed subgenomic interval comprising the sequence, allele or signature.

"Expressed subgenomic interval", as that term is used herein, refers to the transcribed sequence of a subgenomic interval. In an embodiment, the sequence of the expressed subgenomic interval will differ from the subgenomic inter- val from which it is transcribed, e.g., as some sequence may not be transcribed.

"Mutant allele frequency" (MAF) as that term is used herein, refers to the relative frequency of a mutant allele at a particular locus, e.g., in a sample. In some embodiments, a mutant allele frequency is expressed as a fraction or percentage.

"Signature", as that term is used herein, refers to a sequence of a subject interval. A signature can be diagnostic of the occurrence of one of a plurality of possibilities at a subject interval, e.g., a signature can be diagnostic of: the occurrence of a selected V segment in a rearranged heavy or light chain variable region gene; the occurrence of a selected VJ junction, e.g., the occurrence of a selected V and a selected J segment in a rearranged heavy chain variable region gene. In an embodiment, a signature comprises a plurality of a specific nucleic acid sequences. Thus, a signature is not limited to a specific nucleic acid sequence, but rather is sufficiently unique that it can distinguish between a first group of sequences or possibilities at a subject interval and a second group of possibilities at a subject interval, e.g., it can distinguish between a first V segment and a second V segment, allowing e.g., evaluation of the usage of various V segments. The term signature comprises the term specific signature, which is a specific nucleic acid sequence. In an embodiment the signature is indicative of, or is the product of, a specific event, e.g., a rearrangement event.

"Subgenomic interval" as that term is used herein, refers to a portion of genomic sequence. In an embodiment, a subgenomic interval can be a single nucleotide position, e.g., a variant at the position is associated (positively or nega- tively) with a tumor phenotype. In an embodiment, a sub- genomic interval comprises more than one nucleotide posi- tion. Such embodiments include sequences of at least 2, 5, 10, 50, 100, 150, or 250 nucleotide positions in length. Subgenomic intervals can comprise an entire gene, or a portion thereof, e.g., the coding region (or portions thereof), an intron (or portion thereof) or exon (or portion thereof). A subgenomic interval can comprise all or a part of a fragment of a naturally occurring, e.g., genomic DNA, nucleic acid. E.g., a subgenomic interval can correspond to a fragment of genomic DNA which is subjected to a sequencing reaction.

In embodiments, a subgenomic interval is continuous sequence from a genomic source. In embodiments, a subgenomic interval includes sequences that are not contiguous in the genome, e.g., subgenomic intervals in cDNA can include exon-exon junctions formed as a result of splicing.

In an embodiment, a subgenomic interval corresponds to a rearranged sequence, e.g., a sequence in a B or T cell that arises as a result of the joining of, a V segment to a D segment, a D segment to a J segment, a V segment to a J segment, or a J segment to a class segment.

In an embodiment, the subgenomic interval is represented by one sequence. In an embodiment, the subgenomic interval is represented by more than one sequence, e.g., the subgenomic interval that covers a VD sequence can be represented by more than one signature.

In an embodiment, a subgenomic interval comprises or consists of: a single nucleotide position; an intragenic region or an intergenic region; an exon or an intron, or a fragment thereof, typically an exon sequence or a fragment thereof; a coding region or a non-coding region, e.g., a promoter, an enhancer, a 5' untranslated region (5' UTR), or a 3' untranslated region (3' UTR), or a fragment thereof; a cDNA or a fragment thereof; an SNP; a somatic mutation, a germline mutation or both; an alteration, e.g., a point or a single mutation; a deletion mutation (e.g., an in-frame deletion, an intragenic deletion, a full gene deletion); an insertion mutation (e.g., intragenic insertion); an inversion mutation (e.g., an intra-chromosomal inversion); an inverted duplication mutation; a tandem duplication (e.g., an intrachromosomal tandem duplication); a translocation (e.g., a chromosomal translocation, a non-reciprocal translocation); a rearrangement (e.g., a genomic rearrangement (e.g., a rearrangement of one or more introns, a rearrangement of one or more exons, or a combination and/or a fragment thereof; a rearranged intron can include a 5'- and/or 3'-UTR)); a change in gene copy number; a change in gene expression; a change in RNA levels; or a combination thereof. The "copy number of a gene" refers to the number of DNA sequences in a cell encoding a particular gene product. Generally, for a given gene, a mammal has two copies of each gene. The copy number can be increased, e.g., by gene amplification or duplication, or reduced by deletion.

"Subject interval", as that term is used herein, refers to a subgenomic interval or an expressed subgenomic interval. In an embodiment, a subgenomic interval and an expressed subgenomic interval correspond, meaning that the expressed subgenomic interval comprises sequence expressed from the corresponding subgenomic interval. In an embodiment, a subgenomic interval and an expressed subgenomic interval are non-corresponding, meaning that the expressed subgenomic interval does not comprise sequence expressed from the non-corresponding subgenomic interval, but rather corresponds to a different subgenomic interval. In an embodiment, a subgenomic interval and an expressed subgenomic interval partially correspond, meaning that the expressed subgenomic interval comprises sequence expressed from the corresponding subgenomic interval and sequence expressed from a different corresponding subgenomic interval.

As used herein, the term "library" refers to a collection of nucleic acid molecules. In one embodiment, the library includes a collection of nucleic acid nucleic acid molecules, e.g., a collection of whole genomic, subgenomic fragments, cDNA, cDNA fragments, RNA, e.g., mRNA, RNA fragments, or a combination thereof. Typically, a nucleic acid molecule is a DNA molecule, e.g., genomic DNA or cDNA. A nucleic acid molecule can be fragmented, e.g., sheared or enzymatically prepared, genomic DNA. Nucleic acid molecules comprise sequence from a subject and can also comprise sequence not derived from the subject, e.g., an adapter sequence, a primer sequence, or other sequences that allow for identification, e.g., "barcode" sequences. In one embodiment, a portion or all of the library nucleic acid molecules comprises an adapter sequence. The adapter sequence can be located at one or both ends. The adapter sequence can be useful, e.g., for a sequencing method (e.g., an NGS method), for amplification, for reverse transcription, or for cloning into a vector. The library can comprise a collection of nucleic acid molecules, e.g., a target nucleic acid molecule (e.g., a tumor nucleic acid molecule, a reference nucleic acid molecule, or a combination thereof). The nucleic acid molecules of the library can be from a single individual. In embodiments, a library can comprise nucleic acid molecules from more than one subject (e.g., 2, 3, 4, 5, 6, 7, 8, 9, 10, 20, 30 or more subjects), e.g., two or more libraries from different subjects can be combined to form a library comprising nucleic acid molecules from more than one subject. In one embodiment, the subject is a human having, or at risk of having, a cancer or tumor.

"Library catch" refers to a subset of a library, e.g., a subset enriched for subject intervals, e.g., product captured by hybridization with target capture reagents.

"Target Capture Reagent," as used herein, refers to a molecule capable of capturing a target. A target capture reagent (e.g., a bait or a target capture oligonucleotide) can comprise a nucleic acid molecule, e.g., a DNA or RNA molecule, which can hybridize to (e.g., be complementary to), and thereby allow capture of a target nucleic acid. In one embodiment, a target capture reagent comprises a DNA molecule (e.g., a naturally-occurring or modified DNA molecule), an RNA molecule (e.g., a naturally-occurring or modified RNA molecule), or a combination thereof. In some embodiments, the target capture reagent further comprises a functional first member of a binding pair, which is capable of binding to a second member of the binding pair, e.g., disposed on substrate. In other embodiments, the target capture reagent lacks a functional first member of the binding pair, e.g., the first member of the binding pair is altered or blocked, such that the affinity between the first and second members of the binding pair is reduced or eliminated. In one embodiment, a target capture reagent is suitable for solution phase hybridization. Target capture reagents that comprise a functional first member of a binding pair can be mixed with target capture reagents that lack a functional first member of a binding pair, e.g., at different ratios, to achieve different efficiencies of recovery by substrate, which may correlate to different sequencing depths. In some embodiments, the target capture reagent is modified, e.g., by including a first member of a binding pair, e.g., a functional first member of a binding pair. In some embodiments, the target capture reagent is unmodified, e.g., not including a functional first member of a binding pair, or the first member of a binding pair is altered or blocked.

The first member of a binding pair can be any molecular tag that can be directly or indirectly attached to a target capture reagent that is, when functional, capable of specifically binding to a substrate. The first member of a binding pair can be an affinity tag on a target capture reagent sequence. In certain embodiments, the first member of a binding pair allows for separation of the target capture reagent/nucleic acid molecule hybrids from the hybridization mixture by binding to a second member of the binding pair, such as an avidin molecule, or an antibody that binds to the hapten or an antigen-binding fragment thereof. Exemplary first members of binding pairs include, but are not limited to, a biotin molecule, a hapten, an antibody, an antibody binding fragment, a peptide, and a protein. In some embodiments, the substrate comprises a bead.

"Complementary" refers to sequence complementarity between regions of two nucleic acid strands or between two regions of the same nucleic acid strand. It is known that an adenine residue of a first nucleic acid region is capable of forming specific hydrogen bonds ("base pairing") with a residue of a second nucleic acid region which is antiparallel to the first region if the residue is thymine or uracil. Similarly, it is known that a cytosine residue of a first nucleic acid strand is capable of base pairing with a residue of a second nucleic acid strand which is antiparallel to the first strand if the residue is guanine. A first region of a nucleic acid is complementary to a second region of the same or a different nucleic acid if, when the two regions are arranged in an antiparallel fashion, at least one nucleotide residue of the first region is capable of base pairing with a residue of the second region. In certain embodiments, the first region comprises a first portion and the second region comprises a second portion, whereby, when the first and second portions are arranged in an antiparallel fashion, at least about 50%, at least about 75%, at least about 90%, or at least about 95% of the nucleotide residues of the first portion are capable of base pairing with nucleotide residues in the second portion. In other embodiments, all nucleotide residues of the first portion are capable of base pairing with nucleotide residues in the second portion.

The terms "cancer" and "tumor" are used interchangeably herein. These terms refer to the presence of cells possessing characteristics typical of cancer-causing cells, such as uncontrolled proliferation, immortality, metastatic potential, rapid growth and proliferation rate, and certain characteristic morphological features. Cancer cells are often in the form of a tumor, but such cells can exist alone within an animal, or can be a non-tumorigenic cancer cell, such as a leukemia cell. These terms include a solid tumor, a soft tissue tumor, or a metastatic lesion. As used herein, the term "cancer" includes premalignant, as well as malignant cancers.

"Likely to" or "increased likelihood," as used herein, refers to an increased probability that an item, object, thing or person will occur. Thus, in one example, a subject that is likely to respond to treatment has an increased probability of responding to treatment relative to a reference subject or group of subjects.

"Unlikely to" refers to a decreased probability that an event, item, object, thing or person will occur with respect to a reference. Thus, a subject that is unlikely to respond to treatment has a decreased probability of responding to treatment relative to a reference subject or group of subjects.

"Control nucleic acid molecule" refers to a nucleic acid molecule having sequence from a non-tumor cell.

"Next-generation sequencing" or "NGS" or "NG sequencing" as used herein, refers to any sequencing method that determines the nucleotide sequence of either individual nucleic acid molecules (e.g., in single molecule sequencing) or clonally expanded proxies for individual nucleic acid molecules in a high throughput fashion (e.g., greater than $10^3$, $10^4$, $10^5$ or more molecules are sequenced simultaneously). In one embodiment, the relative abundance of the nucleic acid species in the library can be estimated by counting the relative number of occurrences of their cognate sequences in the data generated by the sequencing experiment. Next-generation sequencing methods are known in the art, and are described, e.g., in Metzker, M. (2010) *Nature Biotechnology Reviews* 11:31-46, incorporated herein by reference. Next-generation sequencing can detect a variant present in less than 5% or less than 1% of the nucleic acids in a sample.

"Nucleotide value" as referred herein, represents the identity of the nucleotide(s) occupying or assigned to a nucleotide position. Typical nucleotide values include: missing (e.g., deleted); additional (e.g., an insertion of one or more nucleotides, the identity of which may or may not be included); or present (occupied); A; T; C; or G. Other values can be, e.g., not Y, wherein Y is A, T, G, or C; A or X, wherein X is one or two of T, G, or C; T or X, wherein X is one or two of A, G, or C; G or X, wherein X is one or two of T, A, or C; C or X, wherein X is one or two of T, G, or A; a pyrimidine nucleotide; or a purine nucleotide. A nucleotide value can be a frequency for 1 or more, e.g., 2, 3, or 4, bases (or other value described herein, e.g., missing or additional) at a nucleotide position. E.g., a nucleotide value can comprise a frequency for A, and a frequency for G, at a nucleotide position.

"Or" is used herein to mean, and is used interchangeably with, the term "and/or", unless context clearly indicates otherwise. The use of the term "and/or" in some places herein does not mean that uses of the term "or" are not interchangeable with the term "and/or" unless the context clearly indicates otherwise.

"Primary control" refers to a non-tumor tissue other than a normal adjacent tissue (NAT) tissue in a sample. Blood is a typical primary control.

"Sample," as used herein, refers to a biological sample obtained or derived from a source of interest, as described herein. In some embodiments, a source of interest comprises an organism, such as an animal or human. The source of the sample can be solid tissue as from a fresh, frozen and/or preserved organ, tissue sample, biopsy, resection, smear, or aspirate; blood or any blood constituents; bodily fluids such as cerebral spinal fluid, amniotic fluid, peritoneal fluid or interstitial fluid; or cells from any time in gestation or development of the subject. In some embodiments, the source of the sample is blood or blood constituents.

In some embodiments, the sample is or comprises biological tissue or fluid. The sample can contain compounds that are not naturally intermixed with the tissue in nature such as preservatives, anticoagulants, buffers, fixatives, nutrients, antibiotics or the like. In one embodiment, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. In another embodiment, the sample is a blood or blood constituent sample. In yet another embodiment, the sample is a bone marrow aspirate sample. In another embodiment, the sample comprises cell-free DNA (cfDNA). Without wishing to be bound by theory, it is believed that in some embodiments, cfDNA is DNA from apoptosed or necrotic cells. Typically, cfDNA is bound by protein (e.g., histone) and protected by nucleases. CfDNA can be used as a biomarker for non-invasive prenatal testing (NIPT), organ transplant, cardiomyopathy, microbiome, and cancer. In another embodiment, the sample comprises circulating tumor DNA (ctDNA). Without wishing to be bound by theory, it is believed that in some embodiments, ctDNA is cfDNA with a genetic or epigenetic alteration (e.g., a somatic alteration or a methylation signature) that can discriminate it originating from a tumor cell versus a non-tumor cell. In another embodiment, the sample comprises circulating tumor cells (CTCs). Without wishing to be bound by theory, it is believed that in some embodiments, CTCs are cells shed from a primary or metastatic tumor into the circulation. In some embodiments, CTCs apoptose and are a source of ctDNA in the blood/lymph.

In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; oral swabs; nasal swabs; washings or lavages such as a ductal lavages or bronchoalveolar lavages; aspirates; scrapings; bone marrow specimens; tissue biopsy specimens; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained.

In some embodiments, a sample is a "primary sample" obtained directly from a source of interest by any appropriate means. For example, in some embodiments, a primary biological sample is obtained by a method chosen from biopsy (e.g., fine needle aspiration or tissue biopsy), surgery, collection of body fluid (e.g., blood, lymph, or feces), etc. In some embodiments, as will be clear from context, the term "sample" refers to a preparation that is obtained by processing (e.g., by removing one or more components of and/or by adding one or more agents to) a primary sample, e.g., filtering using a semi-permeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

In an embodiment, the sample is a cell associated with a tumor, e.g., a tumor cell or a tumor-infiltrating lymphocyte (TIL). In one embodiment, the sample includes one or more premalignant or malignant cells. In an embodiment, the sample is acquired from a hematologic malignancy (or premaligancy), e.g., a hematologic malignancy (or premaligancy) described herein. In certain embodiments, the sample is acquired from a solid tumor, a soft tissue tumor or a metastatic lesion. In other embodiments, the sample includes tissue or cells from a surgical margin. In another embodiment, the sample includes one or more circulating tumor cells (CTCs) (e.g., a CTC acquired from a blood sample). In an embodiment, the sample is a cell not associated with a tumor, e.g., a non-tumor cell or a peripheral blood lymphocyte.

"Sensitivity," as used herein, is a measure of the ability of a method to detect a sequence variant in a heterogeneous population of sequences. A method has a sensitivity of S % for variants of F % if, given a sample in which the sequence variant is present as at least F % of the sequences in the sample, the method can detect the sequence at a confidence of C %. S % of the time. By way of example, a method has a sensitivity of 90% for variants of 5% if, given a sample in which the variant sequence is present as at least 5% of the sequences in the sample, the method can detect the sequence at a confidence of 99%, 9 out of 10 times (F=5%; C=99%; S=90%). Exemplary sensitivities include those of S=90%, 95%, 99% for sequence variants at F=1%, 5%, 10%, 20%, 50%, 100% at confidence levels of C=90%, 95%, 99%, and 99.9%.

"Specificity," as used herein, is a measure of the ability of a method to distinguish a truly occurring sequence variant from sequencing artifacts or other closely related sequences. It is the ability to avoid false positive detections. False positive detections can arise from errors introduced into the sequence of interest during sample preparation, sequencing error, or inadvertent sequencing of closely related sequences like pseudo-genes or nucleic acid molecules of a gene family. A method has a specificity of X % if, when applied to a sample set of $N_{Total}$ sequences, in which $X_{True}$ sequences are truly variant and $X_{Not\ true}$ are not truly variant, the method selects at least X % of the not truly variant as not variant. E.g., a method has a specificity of 90% if, when applied to a sample set of 1,000 sequences, in which 500 sequences are truly variant and 500 are not truly variant, the method selects 90% of the 500 not truly variant sequences as not variant. Exemplary specificities include 90, 95, 98, and 99%.

A "tumor nucleic acid" as used herein, refers to nucleic acid molecules from a tumor or cancer. Typically, it is DNA, e.g., genomic DNA, or cDNA derived from RNA, from a tumor or cancer sample. In certain embodiments, the tumor nucleic acid sample is purified or isolated (e.g., it is removed from its natural state). In some embodiments, the tumor nucleic acid is a cfDNA. In some embodiments, the tumor nucleic acid is a ctDNA. In some embodiments, the tumor nucleic acid is DNA from a CTC.

A "control nucleic acid" or "reference nucleic acid" as used herein, refers to nucleic acid molecules from a control or reference sample. Typically, it is DNA, e.g., genomic DNA, or cDNA derived from RNA, not containing the alteration or variation in the gene or gene product. In certain embodiments, the reference or control nucleic acid sample is a wild-type or a non-mutated sequence. In certain embodiments, the reference nucleic acid sample is purified or isolated (e.g., it is removed from its natural state). In other embodiments, the reference nucleic acid sample is from a blood control, a normal adjacent tissue (NAT), or any other non-cancerous sample from the same or a different subject. In some embodiments, the reference nucleic acid sample comprises normal DNA mixtures. In some embodiments, the normal DNA mixture is a process matched control. In some embodiments, the reference nucleic acid sample has germline variants. In some embodiments, the reference nucleic acid sample does not have somatic alterations, e.g., serves as a negative control.

"Sequencing" a nucleic acid molecule requires determining the identity of at least 1 nucleotide in the molecule (e.g., a DNA molecule, an RNA molecule, or a cDNA molecule derived from an RNA molecule). In embodiments the identity of less than all of the nucleotides in a molecule are determined. In other embodiments, the identity of a majority or all of the nucleotides in the molecule is determined.

"Threshold value," as used herein, is a value that is a function of the number of reads required to be present to assign a nucleotide value to a subject interval (e.g., a subgenomic interval or an expressed subgenomic interval). E.g., it is a function of the number of reads having a specific nucleotide value, e.g., "A," at a nucleotide position, required to assign that nucleotide value to that nucleotide position in the subgenomic interval. The threshold value can, e.g., be expressed as (or as a function of) a number of reads, e.g., an integer, or as a proportion of reads having the value. By way of example, if the threshold value is X, and X+1 reads having the nucleotide value of "A" are present, then the value of "A" is assigned to the position in the subject interval (e.g., subgenomic interval or expressed subgenomic interval). The threshold value can also be expressed as a function of a mutation or variant expectation, mutation frequency, or of Bayesian prior. In an embodiment, a mutation frequency would require a number or proportion of reads having a nucleotide value, e.g., A or G, at a position, to call that nucleotide value. In embodiments the threshold value can be a function of mutation expectation, e.g., mutation frequency, and tumor type. E.g., a variant at a nucleotide position could have a first threshold value if the patient has a first tumor type and a second threshold value if the patient has a second tumor type.

As used herein, "target nucleic acid molecule" refers to a nucleic acid molecule that one desires to isolate from the nucleic acid library. In one embodiment, the target nucleic acid molecules can be a tumor nucleic acid molecule, a reference nucleic acid molecule, or a control nucleic acid molecule, as described herein.

"Tumor nucleic acid molecule," or other similar term (e.g., a "tumor or cancer-associated nucleic acid molecule"), as used herein refers to a nucleic acid molecule having sequence from a tumor cell. In one embodiment, the tumor nucleic acid molecule includes a subject interval having a sequence (e.g., a nucleotide sequence) that has an alteration (e.g., a mutation) associated with a cancerous phenotype. In other embodiments, the tumor nucleic acid molecule includes a subject interval having a wild-type sequence (e.g., a wild-type nucleotide sequence). For example, a subject interval from a heterozygous or homozygous wild-type allele present in a cancer cell. A tumor nucleic acid molecule can include a reference nucleic acid molecule.

"Reference nucleic acid molecule," or other similar term (e.g., a "control nucleic acid molecule"), as used herein, refers to a nucleic acid molecule that comprises a subject interval having a sequence (e.g., a nucleotide sequence) that is not associated with the cancerous phenotype. In one embodiment, the reference nucleic acid molecule includes a wild-type or a non-mutated nucleotide sequence of a gene or gene product that when mutated is associated with the cancerous phenotype. The reference nucleic acid molecule can be present in a cancer cell or non-cancer cell.

"Variant," as used herein, refers to a structure that can be present at a subgenomic interval that can have more than one structure, e.g., an allele at a polymorphic locus.

An "isolated" nucleic acid molecule is one which is separated from other nucleic acid molecules which are present in the natural source of the nucleic acid molecule. In certain embodiments, an "isolated" nucleic acid molecule is free of sequences (such as protein-encoding sequences) which naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kB, less than about 4 kB, less than about 3 kB, less than about 2 kB, less than about 1 kB, less than about 0.5 kB or less than about 0.1 kB of nucleotide sequences which naturally flank the nucleic acid molecule in genomic DNA of the cell from which the nucleic acid is derived. Moreover, an "isolated" nucleic acid molecule, such as an RNA molecule or a cDNA molecule, can be substantially free of other cellular material or culture medium, e.g., when produced by recombinant techniques, or substantially free of chemical precursors or other chemicals, e.g., when chemically synthesized.

The language "substantially free of other cellular material or culture medium" includes preparations of nucleic acid molecule in which the molecule is separated from cellular components of the cells from which it is isolated or recombinantly produced. Thus, nucleic acid molecule that is substantially free of cellular material includes preparations of nucleic acid molecule having less than about 30%, less than about 20%, less than about 10%, or less than about 5% (by dry weight) of other cellular material or culture medium.

As used herein, "X is a function of Y" means, e.g., one variable X is associated with another variable Y. In one embodiment, if X is a function of Y, a causal relationship between X and Y may be implied, but does not necessarily exist.

Headings, e.g., (a), (b), (i) etc., are presented merely for ease of reading the specification and claims. The use of headings in the specification or claims does not require the steps or elements to be performed in alphabetical or numerical order or the order in which they are presented. The use of headings in the specification or claims also does not require performance of all of the steps or elements.

Competition of Target Capture Reagents

Hybrid capture (e.g., in solution or solid phase) can be used to enrich genes of interest from a whole genome or transcriptome library. For example, the hybridization reaction can use 5'biotinylated target capture reagents (e.g., single stranded DNA (ssDNA) or double stranded DNA (dsRNA)) to hybridize to the target region, subsequent affinity capture of the dsDNA capture complex to streptavidin coated paramagnetic beads, stringent washes with buffers to remove off-target sequences, and a post-enrichment PCR to amplify the target molecules. In some embodiments, although the goal is to have even coverage across the target regions, variation in coverage across targets in a set of target capture reagents can be target sequence specific, and high GC or AT content and repetitive sequences can lead to over or under capture efficiencies. To drive efficient capture of unique target in the input whole genome library, excess of redundant (e.g., >50X), tiling target capture reagent (e.g., bait) is typically used in the capture reaction. With excess of target capture reagents and differences in capture efficiency across targets, coverage per target is generally predictable and reproducible across sample types but cannot be tuned to high and low coverage simply by adjusting the amount of target capture reagents.

In certain applications (e.g., liquid biopsy assay) there is a need to have high unique coverage for regions that have alterations of interest that could exist in the genomic library at low frequency. Other informative regions (e.g., gender SNPs, sample identification SNPs, haplotyping SNPs for chromosomal copy number calling, or tumor mutational burden or other genomic signatures, e.g., continuous/complex biomarkers) may not require high coverage and are often either captured as a component in a set of target capture reagents and over-sequenced or sequenced in a separate reaction and sequenced at a lower depth. In certain embodiments, processing multiple reactions of the same sample library is inefficient in use of the limited library material, and can add complexity to the assay workflow, and higher sequencing cost.

The methods described herein use, for example, a combination of unmodified target capture reagents and modified (e.g., 5' biotinylated) target capture reagents to modulate target coverage on a specific, per-target basis. In certain embodiments, the modification (e.g., 5' biotin) on the target capture reagent is only used to separate on-target from non-target in the genome library, and by using non-modified target capture reagents, the same reaction conditions can proceed but the amount of target pulled from the genome library and also subsequently sequenced can be by the ratio of modified to unmodified target capture reagents. The methods described herein allow the use of a single target capture reagent reaction and have a single capture library with low, high, and intermediate target coverages.

Samples

A variety of tissue can be the source of the samples used in the present methods. Genomic or subgenomic nucleic acid (e.g., DNA or RNA) can be isolated from a subject's sample (e.g., a sample comprising tumor cells, a blood sample, a blood constituent sample, a sample comprising cell-free DNA (cfDNA), a sample comprising circulating tumor DNA (ctDNA), a sample comprising circulating tumor cells (CTCs), or any normal control (e.g., a normal adjacent tissue (NAT)).

In some embodiments, the sample comprises a nucleic acid, e.g., DNA, RNA, or both, e.g., from a tumor. The nucleic acid can be a DNA or RNA. In certain embodiments, the sample further comprises a non-nucleic acid component, e.g., a cell, protein, carbohydrate, or lipid, e.g., from the tumor. In certain embodiments, the sample further comprises a nucleic acid from a normal cell or tissue.

In certain embodiments, the sample is preserved as a frozen sample or as formaldehyde- or paraformaldehyde-fixed paraffin-embedded (FFPE) tissue preparation. For example, the sample can be embedded in a matrix, e.g., an FFPE block or a frozen sample. In certain embodiments, the sample is a blood sample. In certain embodiments, the tissue sample is a blood constituent sample. In certain embodiments, the sample is a plasma sample. In certain embodiments, the sample is a serum sample. In certain embodiments, the sample is a cfDNA sample. In certain embodiments, the sample is a ctDNA sample. In certain embodiments, the sample is a CTC sample. In other embodiments, the tissue sample is a bone marrow aspirate (BMA) sample. In certain embodiments, the sample is a urine sample. The isolating step can include flow-sorting of individual chromosomes; and/or microdissecting a subject's sample (e.g., a sample described herein).

In other embodiments, the sample comprises one or more premalignant or malignant cells. In certain embodiments, the sample is acquired from a solid tumor, a soft tissue tumor, or a metastatic lesion. In certain embodiments, the sample is acquired from a hematologic malignancy or premaligancy. In other embodiments, the sample comprises a tissue or cells from a surgical margin. In certain embodiments, the sample comprises tumor-infiltrating lymphocytes. The sample can be histologically normal tissue. In an embodiment, the sample comprises one or more non-malignant cells.

In certain embodiments, the FFPE sample has one, two or all of the following properties: (a) has a surface area of about 10 mm$^2$ or greater, about 25 mm$^2$ or greater, or about 50 mm$^2$ or greater; (b) has a sample volume of about 0.1 mm$^3$ or greater, about 0.2 mm$^3$ or greater, about 0.3 mm$^3$ or greater, about 0.4 mm$^3$ or greater, about 0.5 mm$^3$ or greater, about 0.6 mm$^3$ or greater, about 0.7 mm$^3$ or greater, about 0.8 mm$^3$ or greater, about 0.9 mm$^3$ or greater, about 1 mm$^3$ or greater, about 2 mm$^3$ or greater, about 3 mm$^3$ or greater, about 4 mm$^3$ or greater, or about 5 mm$^3$ or greater; (c) has a cellularity of about 50% or more, about 60% or more, about 70% or more, about 80% or more, or about 90% or more; and/or (d) has a count of nucleated cells of about 10,000 cells or more, about 20,000 cells or more, about 30,000 cells or more, about 40,000 cells or more, or about 50,000 cells or more.

In one embodiment, the method further includes acquiring a sample, e.g., a sample described herein. The sample can be acquired directly or indirectly. In an embodiment, the sample is acquired, e.g., by isolation or purification, from a sample that comprises cfDNA. In an embodiment, the sample is acquired, e.g., by isolation or purification, from a sample that comprises ctDNA. In an embodiment, the sample is acquired, e.g., by isolation or purification, from a sample that comprises both a malignant cell and a non-malignant cell (e.g., tumor-infiltrating lymphocyte). In an embodiment, the sample is acquired, e.g., by isolation or purification, from a sample that comprises CTCs.

In other embodiments, the method includes evaluating a sample, e.g., a histologically normal sample, e.g., from a surgical margin, using the methods described herein. Without wishing to be bound by theory, it is believed that in some embodiments, samples obtained from histologically normal tissues (e.g., otherwise histologically normal tissue margins) may still have an alteration as described herein. The methods may thus further include re-classifying a sample based on the presence of the detected alteration. In an embodiment, multiple samples, e.g., from different subjects, are processed simultaneously.

In an embodiment, the method includes isolating nucleic acids from a sample to provide an isolated nucleic acid sample. In an embodiment, the method includes isolating nucleic acids from a control to provide an isolated control nucleic acid sample. In an embodiment, a method further comprises rejecting a sample with no detectable nucleic acid.

In an embodiment, the method further comprises determining if a primary control is available and if so isolating a control nucleic acid (e.g., DNA) from said primary control. In an embodiment, the method further comprises determining if NAT is present in said sample (e.g., where no primary control sample is available). In an embodiment, a method further comprises acquiring a sub-sample enriched for non-tumor cells, e.g., by macrodissecting non-tumor tissue from said NAT in a sample not accompanied by a primary control. In an embodiment, a method further comprises determining that no primary control and no NAT is available and marking said sample for analysis without a matched control.

In an embodiment, a method further comprises acquiring a value for nucleic acid yield in said sample and comparing the acquired value to a reference criterion, e.g., wherein if said acquired value is less than said reference criterion, then amplifying the nucleic acid prior to library construction. In an embodiment, a method further comprises acquiring a value for the size of nucleic acid fragments in said sample and comparing the acquired value to a reference criterion, e.g., a size, e.g., average size, of at least 300, 600, or 900 bps. A parameter described herein can be adjusted or selected in response to this determination.

In certain embodiments, the method includes isolating nucleic acids from an aged sample, e.g., an aged FFPE sample. The aged sample, can be, for example, years old, e.g., 1 year, 2 years, 3 years, 4 years, 5 years, 10 years, 15 years, 20 years, 25 years, 50 years, 75 years, or 100 years old or older.

Nucleic acids can be obtained from samples of various sizes. For example, nucleic acids can be isolated from a sample from 5 to 200 μm, or larger. For example, the sample can measure 5 μm, 10 μm, 20 μm, 30 μm, 40 μm, 50 μm, 70 μm, 100 μm, 110 μm, 120 μm, 150 μm or 200 μm or larger.

Protocols for DNA isolation from a sample are known in the art, e.g., as provided in Example 1 of International Patent Application Publication No. WO 2012/092426. Additional methods to isolate nucleic acids (e.g., DNA) from formaldehyde- or paraformaldehyde-fixed, paraffin-embedded (FFPE) tissues are disclosed, e.g., in Cronin M. et al., (2004) *Am J Pathol.* 164(1):35-42; Masuda N. et al., (1999) *Nucleic Acids Res.* 27(22):4436-4443; Specht K. et al., (2001) *Am J Pathol.* 158(2):419-429, Ambion RecoverAll™ Total Nucleic Acid Isolation Protocol (Ambion, Cat. No.

AM1975, September 2008), Maxwell® 16 FFPE Plus LEV DNA Purification Kit Technical Manual (Promega Literature # TM349, February 2011), E.Z.N.A.® FFPE DNA Kit Handbook (OMEGA bio-tek, Norcross, GA, product numbers D3399-00, D3399-01, and D3399-02; June 2009), and QIAamp® DNA FFPE Tissue Handbook (Qiagen, Cat. No. 37625, October 2007). RecoverAll™ Total Nucleic Acid Isolation Kit uses xylene at elevated temperatures to solubilize paraffin-embedded samples and a glass-fiber filter to capture nucleic acids. Maxwell® 16 FFPE Plus LEV DNA Purification Kit is used with the Maxwell® 16 Instrument for purification of genomic DNA from 1 to 10 μm sections of FFPE tissue. DNA is purified using silica-clad paramagnetic particles (PMPs), and eluted in low elution volume. The E.Z.N.A.® FFPE DNA Kit uses a spin column and buffer system for isolation of genomic DNA. QIAamp® DNA FFPE Tissue Kit uses QIAamp® DNA Micro technology for purification of genomic and mitochondrial DNA. Protocols for DNA isolation from blood are disclosed, e.g., in the Maxwell® 16 LEV Blood DNA Kit and Maxwell 16 Buccal Swab LEV DNA Purification Kit Technical Manual (Promega Literature # TM333, Jan. 1, 2011).

Protocols for RNA isolation are disclosed, e.g., in the Maxwell® 16 Total RNA Purification Kit Technical Bulletin (Promega Literature # TB351, August 2009).

The isolated nucleic acids (e.g., genomic DNA) can be fragmented or sheared by practicing routine techniques. For example, genomic DNA can be fragmented by physical shearing methods, enzymatic cleavage methods, chemical cleavage methods, and other methods well known to those skilled in the art. The nucleic acid library can contain all or substantially all of the complexity of the genome. The term "substantially all" in this context refers to the possibility that there can in practice be some unwanted loss of genome complexity during the initial steps of the procedure. The methods described herein also are useful in cases where the nucleic acid library is a portion of the genome, e.g., where the complexity of the genome is reduced by design. In some embodiments, any selected portion of the genome can be used with a method described herein. In certain embodiments, the entire exome or a subset thereof is isolated.

In certain embodiments, the method further includes isolating nucleic acids from the sample to provide a library (e.g., a nucleic acid library as described herein). In certain embodiments, the sample includes whole genomic, subgenomic fragments, or both. The isolated nucleic acids can be used to prepare nucleic acid libraries. Protocols for isolating and preparing libraries from whole genomic or subgenomic fragments are known in the art (e.g., Illumina's genomic DNA sample preparation kit). In certain embodiments, the genomic or subgenomic DNA fragment is isolated from a subject's sample (e.g., a sample described herein). In one embodiment, the sample is a preserved specimen, e.g., embedded in a matrix, e.g., an FFPE block or a frozen sample. In certain embodiments, the isolating step includes flow-sorting of individual chromosomes; and/or microdissecting the sample. In certain embodiments, the amount of nucleic acid used to generate the nucleic acid library is less than 5 micrograms, less than 1 microgram, or less than 500 ng, less than 200 ng, less than 100 ng, less than 50 ng, less than 10 ng, less than 5 ng, or less than 1 ng.

In still other embodiments, the nucleic acids used to generate the library include RNA or cDNA derived from RNA. In some embodiments, the RNA includes total cellular RNA. In other embodiments, certain abundant RNA sequences (e.g., ribosomal RNAs) have been depleted. In some embodiments, the poly(A)-tailed mRNA fraction in the total RNA preparation has been enriched. In some embodiments, the cDNA is produced by random-primed cDNA synthesis methods. In other embodiments, the cDNA synthesis is initiated at the poly(A) tail of mature mRNAs by priming by oligo(dT)-containing oligonucleotides. Methods for depletion, poly(A) enrichment, and cDNA synthesis are well known to those skilled in the art.

In other embodiments, the nucleic acids are fragmented or sheared by a physical or enzymatic method, and optionally, ligated to synthetic adapters, size-selected (e.g., by preparative gel electrophoresis) and amplified (e.g., by PCR). Alternative methods for DNA shearing are known in the art, e.g., as described in Example 4 in International Patent Application Publication No. WO 2012/092426. For example, alternative DNA shearing methods can be more automatable and/or more efficient (e.g., with degraded FFPE samples). Alternatives to DNA shearing methods can also be used to avoid a ligation step during library preparation.

In other embodiments, the isolated DNA (e.g., the genomic DNA) is fragmented or sheared. In some embodiments, the library includes less than 50% of genomic DNA, such as a subfraction of genomic DNA that is a reduced representation or a defined portion of a genome, e.g., that has been subfractionated by other means. In other embodiments, the library includes all or substantially all genomic DNA.

In other embodiments, the fragmented and adapter-ligated group of nucleic acids is used without explicit size selection or amplification prior to hybrid selection. In some embodiments, the nucleic acid is amplified by a specific or non-specific nucleic acid amplification method that is well known to those skilled in the art. In some embodiments, the nucleic acid is amplified, e.g., by a whole-genome amplification method such as random-primed strand-displacement amplification.

The methods described herein can be performed using a small amount of nucleic acids, e.g., when the amount of source DNA or RNA is limiting (e.g., even after whole-genome amplification). In one embodiment, the nucleic acid comprises less than about 5 μg, 4 μg, 3 μg, 2 μg, 1 μg, 0.8 μg, 0.7 μg, 0.6 μg, 0.5 μg, or 400 ng, 300 ng, 200 ng, 100 ng, 50 ng, 10 ng, 5 ng, 1 ng, or less of nucleic acid sample. For example, one can typically begin with 50-100 ng of genomic DNA. One can start with less, however, if one amplifies the genomic DNA (e.g., using PCR) before the hybridization step, e.g., solution hybridization. Thus it is possible, but not essential, to amplify the genomic DNA before hybridization, e.g., solution hybridization.

In an embodiment, the sample comprises DNA, RNA (or cDNA derived from RNA), or both, from a non-cancer cell or a non-malignant cell, e.g., a tumor-infiltrating lymphocyte. In an embodiment, the sample comprises DNA, RNA (or cDNA derived from RNA), or both, from a non-cancer cell or a non-malignant cell, e.g., a tumor-infiltrating lymphocyte, and does not comprise, or is essentially free of, DNA, RNA (or cDNA derived from RNA), or both, from a cancer cell or a malignant cell.

In an embodiment, the sample comprises DNA, RNA (or cDNA derived from RNA) from a cancer cell or a malignant cell. In an embodiment, the sample comprises DNA, RNA (or cDNA derived from RNA) from a cancer cell or a malignant cell, and does not comprise, or is essentially free of, DNA, RNA (or cDNA derived from RNA), or both, from a non-cancer cell or a non-malignant cell, e.g., a tumor-infiltrating lymphocyte.

In an embodiment, the sample comprises DNA, RNA (or cDNA derived from RNA), or both, from a non-cancer cell or a non-malignant cell, e.g., a tumor-infiltrating lymphocyte, and DNA, RNA (or cDNA derived from RNA), or both, from a cancer cell or a malignant cell.

In certain embodiments, the sample is acquired from a subject having a cancer. Exemplary cancers include, but are not limited to, B cell cancer, e.g., multiple myeloma, melanomas, breast cancer, lung cancer (such as non-small cell lung carcinoma or NSCLC), bronchus cancer, colorectal cancer, prostate cancer, pancreatic cancer, stomach cancer, ovarian cancer, urinary bladder cancer, brain or central nervous system cancer, peripheral nervous system cancer, esophageal cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, adenocarcinomas, inflammatory myofibroblastic tumors, gastrointestinal stromal tumor (GIST), colon cancer, multiple myeloma (MM), myelodysplastic syndrome (MDS), myeloproliferative disorder (MPD), acute lymphocytic leukemia (ALL), acute myelocytic leukemia (AML), chronic myelocytic leukemia (CML), chronic lymphocytic leukemia (CLL), polycythemia Vera, Hodgkin lymphoma, non-Hodgkin lymphoma (NHL), soft-tissue sarcoma, fibrosarcoma, myxosarcoma, liposarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, seminoma, embryonal carcinoma, Wilms' tumor, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, neuroblastoma, retinoblastoma, follicular lymphoma, diffuse large B-cell lymphoma, mantle cell lymphoma, hepatocellular carcinoma, thyroid cancer, gastric cancer, head and neck cancer, small cell cancers, essential thrombocythemia, agnogenic myeloid metaplasia, hypereosinophilic syndrome, systemic mastocytosis, familiar hypereosinophilia, chronic eosinophilic leukemia, neuroendocrine cancers, carcinoid tumors, and the like.

In an embodiment, the cancer is a hematologic malignancy (or premaligancy). As used herein, a hematologic malignancy refers to a tumor of the hematopoietic or lymphoid tissues, e.g., a tumor that affects blood, bone marrow, or lymph nodes. Exemplary hematologic malignancies include, but are not limited to, leukemia (e.g., acute lymphoblastic leukemia (ALL), acute myeloid leukemia (AML), chronic lymphocytic leukemia (CLL), chronic myelogenous leukemia (CML), hairy cell leukemia, acute monocytic leukemia (AMoL), chronic myelomonocytic leukemia (CMML), juvenile myelomonocytic leukemia (JMML), or large granular lymphocytic leukemia), lymphoma (e.g., AIDS-related lymphoma, cutaneous T-cell lymphoma, Hodgkin lymphoma (e.g., classical Hodgkin lymphoma or nodular lymphocyte-predominant Hodgkin lymphoma), mycosis fungoides, non-Hodgkin lymphoma (e.g., B-cell non-Hodgkin lymphoma (e.g., Burkitt lymphoma, small lymphocytic lymphoma (CLL/SLL), diffuse large B-cell lymphoma, follicular lymphoma, immunoblastic large cell lymphoma, precursor B-lymphoblastic lymphoma, or mantle cell lymphoma) or T-cell non-Hodgkin lymphoma (mycosis fungoides, anaplastic large cell lymphoma, or precursor T-lymphoblastic lymphoma)), primary central nervous system lymphoma, Sézary syndrome, Waldenström macroglobulinemia), chronic myeloproliferative neoplasm, Langerhans cell histiocytosis, multiple myeloma/plasma cell neoplasm, myelodysplastic syndrome, or myelodysplastic/myeloproliferative neoplasm. Premaligancy, as used herein, refers to a tissue that is not yet malignant but is poised to become malignant.

In some embodiments, a sample described herein is also referred to as a specimen.

In some embodiments, the sample is a tissue sample, blood sample or bone marrow sample. In some embodiments, the blood sample comprises cell-free DNA (cfDNA). In some embodiments, cfDNA comprises DNA from healthy tissue, e.g., non-diseased cells, or tumor tissue, e.g., tumor cells. In some embodiments cfDNA from tumor tissue comprises circulating tumor DNA (ctDNA). In some embodiments, ctDNA samples are obtained, e.g., collected, from a patient with a solid tumor, e.g., lung cancer, breast cancer or colon cancer.

In some embodiments, the sample, e.g., specimen, is a formalin-fixed paraffin embedded (FFPE) specimen. In some embodiments, the FPPE specimen includes, but is not limited to specimens chosen from: core-needle biopsies, fine-needle aspirates, or effusion cytologies. In some embodiments, the sample comprises an FPPE block and one original hematoxylin and eosin (H&E) stained slide. In some embodiments, the sample comprises unstained slides (e.g., positively charged, unbaked and 4-5 microns thick; e.g., 1, 2, 3, 4, 5, 6, 7, 8, 9, 10 or more such slides) and one or more H&E stained slides.

In some embodiments, the sample comprises an FPPE block or unstained slides, e.g., 1, 2, 3, 4, 5, 6, 7, 8, 9, 10, 11, 12, 13, 14, 15, 16 or more unstained slides and one or more H&E slide. In some embodiments, the sample comprises tissue that is formalin-fixed and embedded into a paraffin block, e.g., using a standard fixation method, e.g. as described herein.

In some embodiments, the sample comprises a surface area of at least 1-30 mm$^2$, e.g., about 5-25 mm$^2$. In some embodiments, the sample comprises a surface area of at least 1, 2, 3, 4, 5, 6, 7, 8, 9, or 10 mm$^2$, e.g., 5 mm$^2$. In some embodiments, the sample comprises a surface area of at least 5 mm$^2$.

In some embodiments, the sample comprises a surface area of about 20, 21, 22, 23, 24, 25, 26, 27, 28, 29 or 30 mm$^2$, e.g., 25 mm$^2$. In some embodiments, the sample comprises a surface area of 25 mm$^2$.

In some embodiments, the sample comprises a surface volume of at least 1-5 mm$^3$, e.g., about 2 mm$^3$. In some embodiments, a surface volume of about 2 mm$^3$ comprises a sample having a surface area of about 25 mm$^2$ at a depth of about 80 microns, e.g., at least or more than 80 microns.

In some embodiments, the sample comprises a tumor content, e.g., comprising tumor nuclei. In some embodiments, the sample comprises a tumor content with at least 5-50%, 10-40%, 15-25%, or 20-30% tumor nuclei. In some embodiments, the sample comprises a tumor content of at least 20% tumor nuclei. In some embodiments, the sample comprises a tumor content of about 30% tumor nuclei. In some embodiments, percent tumor nuclei is determined, e.g., calculated, by dividing the number of tumor cells by the total number of all cells with nuclei. In some embodiments, when the sample is a liver sample, e.g., comprising hepatocytes, higher tumor content may be required. In some embodiments, hepatocytes have nuclei with twice, e.g., double, the DNA content of other, e.g., non-hepatocyte, somatic nuclei. In some embodiments, sensitivity of detection of an alteration, e.g., as described herein, depends on tumor content of the sample, e.g., a lower tumor content can result in lower sensitivity of detection.

In some embodiments, DNA is extracted from nucleated cells from the sample. In some embodiments, a sample has a low nucleated cellularity, e.g., when the sample is comprised mainly of erythrocytes, lesional cells that contain excessive cytoplasm, or tissue with fibrosis. In some embodiments, a sample with low nucleated cellularity may require more, e.g., greater, tissue volume, e.g., more than 2 mm³, for DNA extraction.

In some embodiments, the FPPE sample, e.g., specimen, is prepared using a standard fixation method to preserve nucleic acid integrity. In some embodiments, the standard fixation method comprises using 10% neutral-buffered formalin, e.g., for 6-72 hours. In some embodiments, the method does not include fixatives such as Bouins, B5, AZF of Holland's. In some embodiments, the method dose not comprise decalcification. In some embodiments, the method includes decalcification. In embodiments, decalcification is performed with EDTA. In some embodiments, strong acids, e.g., hydrochloric acid, sulfuric acid or picric acid, are not used for decalcification.

In some embodiments, the sample comprises an FPPE block or unstained slides, e.g., 1, 2, 3, 4, 5, 6, 7, 8, 9, 10, 11, 12, 13, 14, 15, 16 or more unstained slides and one or more H&E slides. In some embodiments, the sample comprises tissue that is formalin-fixed and embedded into a paraffin block, e.g., using a standard fixation method, e.g. as described herein.

In some embodiments, the sample comprises peripheral whole blood or bone marrow aspirate. In some embodiments, the sample, e.g., lesion tissue, comprises at least 20% nucleated elements. In some embodiments, the peripheral whole blood sample or bone marrow aspirate sample is collected at a volume of about 2.5 ml. In some embodiments, the blood sample is shipped, e.g., at ambient temperature, e.g., 43-99° F. or 6-37° C., on the same day as collection. In some embodiments, the blood sample is not frozen or refrigerated.

In some embodiments, the sample comprises isolated, e.g., extracted, nucleic acid, e.g., DNA or RNA. In some embodiments, the isolated nucleic acid comprises DNA or RNA, e.g., in nuclease-free water.

In some embodiments, the sample comprises a blood sample, e.g., peripheral whole blood sample. In some embodiments, the peripheral whole blood sample is collected in, e.g., two tubes, e.g., with about 8.5 ml blood per tube. In some embodiments, the peripheral whole blood sample is collected by venipuncture, e.g., according to CLSI H3-A6. In some embodiments, the blood is immediately mixed, e.g., by gentle inversion, for, e.g., about 8-10 times. In some embodiments, inversion is performed by a complete, e.g., full, 180° turn, e.g., of the wrist. In some embodiments, the blood sample is shipped, e.g., at ambient temperature, e.g., 43-99° F. or 6-37° C. on the same day as collection. In some embodiments, the blood sample is not frozen or refrigerated. In some embodiments, the collected blood sample is kept, e.g., stored, at 43-99° F. or 6-37° C.

Subject Selection

In some embodiments, the sample is obtained, e.g., collected, from a subject, e.g., patient, with a condition or disease, e.g., a hyperproliferative disease (e.g., as described herein) or a non-cancer indication. In some embodiments, the disease is a hyperproliferative disease. In some embodiments, the hyperproliferative disease is a cancer, e.g., a solid tumor or a hematological cancer. In some embodiments, the cancer is a solid tumor. In some embodiments, the cancer is a hematological cancer, e.g. a leukemia or lymphoma.

In some embodiments, the patient has been previously treated with a targeted therapy, e.g., one or more targeted therapies. In some embodiments, for a patient who has been previously treated with a targeted therapy, a post-targeted therapy sample, e.g., specimen is obtained, e.g., collected. In some embodiments, the post-targeted therapy sample is a sample obtained, e.g., collected, after the completion of the targeted therapy.

In some embodiments, the patient has not been previously treated with a targeted therapy. In some embodiments, for a patient who has not been previously treated with a targeted therapy, the sample comprises a resection, e.g., an original resection, or a recurrence, e.g., disease recurrence post-therapy, e.g., non-targeted therapy. In some embodiments, the sample is or is part of a primary tumor or a metastasis, e.g., metastasis biopsy. In some embodiments, the sample is obtained from a site, e.g., tumor site, with the highest percent of tumor, e.g., tumor cells, as compared to adjacent sites, e.g., adjacent sites with tumor cells. In some embodiments, the sample is obtained from a site, e.g., tumor site, with the largest tumor focus as compared to adjacent sites, e.g., adjacent sites with tumor cells.

In some embodiments, the disease is chosen from: non-small cell lung cancer (NSCLC), melanoma, breast cancer, colorectal cancer (CRC), or ovarian cancer. In some embodiments, an NSCLC described herein includes NSCLC having, e.g., an EGFR alteration (e.g., exon 19 deletion or exon 21 L858R alteration), ALK rearrangement, or BRAF V600E. In some embodiments, a melanoma described herein includes melanoma having a BRAF alteration, e.g., V600E and/or V600K. In some embodiments, a breast cancer described herein includes breast cancer having an ERBB2 (HER2) amplification. In some embodiments, a colorectal cancer described herein includes a colorectal cancer having wild-type KRAS, e.g., absence of mutations in codon 12 and/or 13, or absence of mutations in codons 2, 3, and/or 4. In some embodiments, a colorectal cancer described herein includes a colorectal cancer having wild-type NRAS, e.g., absence of mutations in codons 2, 3, and/or 4. In some embodiments, a colorectal cancer described herein includes a colorectal cancer having a wild-type KRAS, e.g., as described herein, and a wild-type NRAS, e.g., as described herein. In some embodiments, an ovarian cancer described herein includes an ovarian cancer having a BRCA1 and/or BRCA2 alteration.

Design and Construction of Target Capture Reagents

In some embodiments, a target capture reagent is a molecule, which can bind to and thereby allow capture of a target molecule. For example, a target capture reagent can be a bait, e.g., a nucleic acid molecule, e.g., a DNA or RNA molecule, which can hybridize to (e.g., be complementary to), and thereby allow capture of a target nucleic acid. In some embodiments, the target capture reagent, e.g., bait, is a capture oligonucleotide. In certain embodiments, the target nucleic acid is a genomic DNA molecule. In other embodiments, the target nucleic acid is an RNA molecule or a cDNA molecule derived from an RNA molecule. In one embodiment, the target capture reagent is a DNA molecule. In one embodiment, the target capture reagent is an RNA molecule. In other embodiments, the target capture reagent includes a first member of a binding pair that allows binding and separation of a hybrid formed by a target capture reagent and a nucleic acid molecule hybridized to the target capture reagent. In one embodiment, the target capture reagent is suitable for solution phase hybridization. In one embodiment, the target capture reagent is suitable for solid phase hybridization. In one embodiment, the target capture reagent is suitable for both solution phase and solid phase hybridization.

Typically, DNA molecules are used as target capture reagent sequences, although RNA molecules can also be used. In some embodiments, a DNA molecule target capture reagent can be single stranded DNA (ssDNA) or double-stranded DNA (dsDNA).

In some embodiments, a RNA-DNA duplex is more stable than a DNA-DNA duplex, and therefore provides for potentially better capture of nucleic acids. RNA target capture reagents can be made as described elsewhere herein, using methods known in the art including, but not limited to, de novo chemical synthesis and transcription of DNA molecules using a DNA-dependent RNA polymerase. In one embodiment, the target capture reagent sequence is produced using a known nucleic acid amplification method, such as PCR, e.g., using human DNA or pooled human DNA samples as the template. The oligonucleotides can then be converted to RNA target capture reagents.

In one embodiment, in vitro transcription is used, for example, based on adding an RNA polymerase promoter sequence to one end of the oligonucleotide. In one embodiment, the RNA polymerase promoter sequence is added at the end of the target capture reagent by amplifying or re-amplifying the target capture reagent sequence, e.g., using PCR or another nucleic acid amplification method, e.g., by tailing one primer of each target-specific primer pairs with an RNA promoter sequence. In one embodiment, the RNA polymerase is a T7 polymerase, a SP6 polymerase, or a T3 polymerase. In one embodiment, RNA target capture reagent is labeled with a tag, e.g., an affinity tag. In one embodiment, RNA target capture reagent is made by in vitro transcription, e.g., using biotinylated UTP. In another embodiment, RNA target capture reagent is produced without biotin and then biotin is crosslinked to the RNA molecule using a method well known in the art, such as psoralen crosslinking. In one embodiment, the RNA target capture reagent is an RNase-resistant RNA molecule, which can be made, e.g., by using modified nucleotides during transcription to produce a RNA molecule that resists RNase degradation. In one embodiment, the RNA target capture reagent corresponds to only one strand of the double-stranded DNA target. Typically, such RNA target capture reagents are not self-complementary and are more effective as hybridization drivers.

The target capture reagents can be designed from reference sequences, such that the target capture reagents are optimal for selecting targets of the reference sequences. In some embodiments, target capture reagent sequences are designed using a mixed base (e.g., degeneracy). For example, the mixed base(s) can be included in the target capture reagent sequence at the position(s) of a common SNP or mutation, to optimize the target capture reagent sequences to catch both alleles (e.g., SNP and non-SNP; mutant and non-mutant). In some embodiments, all known sequence variations (or a subset thereof) can be targeted with multiple oligonucleotide target capture reagents, rather than by using mixed degenerate oligonucleotides.

In certain embodiments, the target capture reagent includes an oligonucleotide (or a plurality of oligonucleotides) between about 100 nucleotides and 300 nucleotides in length. Typically, the target capture reagent includes an oligonucleotide (or a plurality of oligonucleotides) between about 130 nucleotides and 230 nucleotides, or about 150 and 200 nucleotides, in length. In other embodiments, the target capture reagent includes an oligonucleotide (or a plurality of oligonucleotides) between about 300 nucleotides and 1000 nucleotides in length.

In some embodiments, the target nucleic acid molecule-specific sequences in the oligonucleotide are between about 40 and 1000 nucleotides, about 70 and 300 nucleotides, about 100 and 200 nucleotides in length, typically between about 120 and 170 nucleotides in length.

In some embodiments, the target capture reagent includes a first member of a binding pair. The first member of a binding pair can be an affinity tag on a target capture reagent. In some embodiments, the affinity tag is a biotin molecule or a hapten. In certain embodiments, the first member of a binding pair allows for separation of the target capture reagent/nucleic acid molecule hybrids from the hybridization mixture by binding to a second member of the binding pair, such as an avidin molecule, or an antibody that binds to the hapten or an antigen-binding fragment thereof.

In other embodiments, the oligonucleotides in the target capture reagent contain forward and reverse complement sequences for the same target nucleic acid molecule sequence whereby the oligonucleotides with reverse-complemented nucleic acid molecule-specific sequences also carry reverse complement universal tails. This can lead to RNA transcripts that are the same strand, i.e., not complementary to each other.

In other embodiments, the target capture reagent includes oligonucleotides that contain degenerate or mixed bases at one or more positions. In still other embodiments, the target capture reagent includes multiple or substantially all known sequence variants present in a population of a single species or community of organisms. In one embodiment, the target capture reagent includes multiple or substantially all known sequence variants present in a human population.

In other embodiments, the target capture reagent includes cDNA sequences or is derived from cDNA sequences. In other embodiments, the target capture reagent includes amplification products (e.g., PCR products) that are amplified from genomic DNA, cDNA or cloned DNA.

In other embodiments, the target capture reagent includes RNA molecules. In some embodiments, the set includes chemically, enzymatically modified, or in vitro transcribed RNA molecules, including but not limited to, those that are more stable and resistant to RNase.

In yet other embodiments, the target capture reagents are produced by a method described in US 2010/0029498 and Gnirke, A. et al. (2009) *Nat Biotechnol.* 27(2):182-189, incorporated herein by reference. For example, biotinylated RNA target capture reagents can be produced by obtaining a pool of synthetic long oligonucleotides, originally synthesized on a microarray, and amplifying the oligonucleotides to produce the target capture reagent sequences. In some embodiments, the target capture reagents are produced by adding an RNA polymerase promoter sequence at one end of the target capture reagent sequences, and synthesizing RNA sequences using RNA polymerase. In one embodiment, libraries of synthetic oligodeoxynucleotides can be obtained from commercial suppliers, such as Agilent Technologies, Inc., and amplified using a known nucleic acid amplification method.

Accordingly, a method of making the aforesaid target capture reagent is provided. The method includes, for example, selecting one or more target capture reagents, e.g., target-specific bait oligonucleotide sequences (e.g., one or more mutation capturing, reference or control oligonucleotide sequences as described herein); obtaining a pool of target capture reagents, e.g., target-specific bait oligonucleotide sequences (e.g., synthesizing the pool of target-specific bait oligonucleotide sequences, e.g., by microarray synthesis); and optionally, amplifying the target capture reagents, e.g., target-specific bait oligonucleotide sequences.

In other embodiments, the method further includes amplifying (e.g., by PCR) the oligonucleotides using one or more biotinylated primers. In some embodiments, the oligonucleotides include a universal sequence at the end of each oligonucleotide attached to the microarray. The methods can further include removing the universal sequences from the oligonucleotides. Such methods can also include removing the complementary strand of the oligonucleotides, annealing the oligonucleotides, and extending the oligonucleotides. In some of these embodiments, the method for amplifying (e.g., by PCR) the oligonucleotides uses one or more biotinylated primers. In some embodiments, the method further includes size selecting the amplified oligonucleotides.

In one embodiment, an RNA target capture reagent is made. The methods include producing a set of target capture reagent sequences according to the methods described herein, adding an RNA polymerase promoter sequence at one end of the target capture reagent sequences, and synthesizing RNA sequences using RNA polymerase. The RNA polymerase can be chosen from a T7 RNA polymerase, an SP6 RNA polymerase, or a T3 RNA polymerase. In other embodiments, the RNA polymerase promoter sequence is added at the ends of the target capture reagent sequences by amplifying (e.g., by PCR) the target capture reagent sequences. In embodiments where the target capture reagent sequences are amplified by PCR with specific primer pairs out of genomic DNA or cDNA, adding an RNA promoter sequence to the 5' end of one of the two specific primers in each pair will lead to a PCR product that can be transcribed into an RNA target capture reagent using a standard method.

In other embodiments, target capture reagents can be produced using human DNA or pooled human DNA samples as the template. In such embodiments, the oligonucleotides are amplified by polymerase chain reaction (PCR). In other embodiments, the amplified oligonucleotides are reamplified by rolling circle amplification or hyperbranched rolling circle amplification. The same methods also can be used to produce target capture reagent sequences using human DNA or pooled human DNA samples as the template. The same methods can also be used to produce target capture reagent sequences using subfractions of a genome obtained by other methods, including but not limited to restriction digestion, pulsed-field gel electrophoresis, flow-sorting, CsCl density gradient centrifugation, selective kinetic reassociation, microdissection of chromosome preparations, and other fractionation methods known to those skilled in the art.

In certain embodiments, the number of target capture reagents (e.g., baits) in the plurality of target capture reagents is less than 1,000. In other embodiments, the number of target capture reagents (e.g., baits) in the plurality target capture reagent is greater than 1,000, greater than 5,000, greater than 10,000, greater than 20,000, greater than 50,000, greater than 100,000, or greater than 500,000.

The length of the target capture reagent sequence can be between about 70 nucleotides and 1000 nucleotides. In one embodiment, the target capture reagent length is between about 100 and 300 nucleotides, 110 and 200 nucleotides, or 120 and 170 nucleotides, in length. In addition to those mentioned above, intermediate oligonucleotide lengths of about 70, 80, 90, 100, 110, 120, 130, 140, 150, 160, 170, 180, 190, 200, 210, 220, 230, 240, 250, 300, 400, 500, 600, 700, 800, and 900 nucleotides in length can be used in the methods described herein. In some embodiments, oligonucleotides of about 70, 80, 90, 100, 110, 120, 130, 140, 150, 160, 170, 180, 190, 200, 210, 220, or 230 bases can be used.

Each target capture reagent sequence can include a target-specific (e.g., a nucleic acid molecule-specific) target capture reagent sequence and universal tails on one or both ends. As used herein, the term "target capture reagent sequence" can refer to the target-specific target capture reagent sequence or the entire oligonucleotide including the target-specific "target capture reagent sequence" and other nucleotides of the oligonucleotide. The target-specific sequences in the target capture reagents are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length, typically 120 nucleotides in length. Intermediate lengths in addition to those mentioned above also can be used in the methods described herein, such as target-specific sequences of about 40, 50, 60, 70, 80, 90, 100, 110, 120, 130, 140, 150, 160, 170, 180, 190, 200, 210, 220, 230, 240, 250, 300, 400, 500, 600, 700, 800, and 900 nucleotides in length, as well as target-specific sequences of lengths between the above-mentioned lengths.

In one embodiment, the target capture reagent is an oligomer (e.g., comprised of RNA oligomers, DNA oligomers, or a combination thereof) about 50 to 200 nucleotides in length (e.g., about 50, 60, 80, 90, 100, 110, 120, 130, 140, 150, 160, 170, 190, or 200 nucleotides in length). In one embodiment, each target capture reagent oligomer includes about 120 to 170, or typically, about 120 nucleotides, which are a target-specific target capture reagent sequence. The target capture reagent can comprise additional non-target-specific nucleotide sequences at one or both ends. The additional nucleotide sequences can be used, e.g., for PCR amplification or as a target capture reagent identifier. In certain embodiments, the target capture reagent additionally comprises a first member of a binding pair as described herein (e.g., an affinity tag such as a biotin molecule). The first member of a binding pair, e.g., biotin molecule, can be attached to the target capture reagent, e.g., at the 5'-end, 3'-end, or internally (e.g., by incorporating a biotinylated nucleotide), of the target capture reagent. In one embodiment, the biotin molecule is attached at the 5'-end of the target capture reagent.

In one exemplary embodiment, the target capture reagent is an oligonucleotide about 150 nucleotides in length, of which 120 nucleotides are target-specific "target capture reagent sequence". The other 30 nucleotides (e.g., 15 nucleotides on each end) are universal arbitrary tails used for PCR amplification. The tails can be any sequence selected by the user. For example, the pool of synthetic oligonucleotides can include oligonucleotides of the sequence of 5'-ATCGCACCAGCGTGTN$_{120}$CACTGCGGCTCCTCA-3' (SEQ ID NO: 1) with N$_{120}$ indicating the target-specific target capture reagent sequences.

The target capture reagent sequences described herein can be used for selection of exons and short target sequences. In one embodiment, the target capture reagent is between about 100 nucleotides and 300 nucleotides in length. In another embodiment, the target capture reagent is between about 130 nucleotides and 230 nucleotides in length. In yet another embodiment, the target capture reagent is between about 150 nucleotides and 200 nucleotides in length. The target-specific sequences in the target capture reagents, e.g., for selection of exons and short target sequences, are between about 40 nucleotides and 1000 nucleotides in length. In one embodiment, the target-specific sequence is between about 70 nucleotides and 300 nucleotides in length. In another embodiment, the target-specific sequence is between about 100 nucleotides and 200 nucleotides in length. In yet another embodiment, the target-specific sequence is between about 120 nucleotides and 170 nucleotides in length.

In some embodiments, long oligonucleotides can minimize the number of oligonucleotides necessary to capture the target sequences. For example, one oligonucleotide can be used per exon. It is known in the art that the mean and median lengths of the protein-coding exons in the human genome are about 164 and 120 base pairs, respective. Longer target capture reagent sequences can be more specific and capture better than shorter ones. As a result, the success rate per oligonucleotide target capture reagent sequence is higher than with short oligonucleotides. In one embodiment, the minimum target capture reagent-covered sequence is the size of one target capture reagent (e.g., 120-170 bases), e.g., for capturing exon-sized targets. In determining the length of the target capture reagent sequences, one also can take into consideration that unnecessarily long target capture reagents catch more unwanted DNA directly adjacent to the target. Longer oligonucleotide target capture reagents can also be more tolerant to polymorphisms in the targeted region in the DNA samples than shorter ones. Typically, the target capture reagent sequences are derived from a reference genome sequence. If the target sequence in the actual DNA sample deviates from the reference sequence, for example if it contains a single nucleotide polymorphism (SNP), it can hybridize less efficiently to the target capture reagent and may therefore be under-represented or completely absent in the sequences hybridized to the target capture reagent sequences. Allelic drop-outs due to SNPs can be less likely with the longer synthetic target capture reagent molecules for the reason that a single mismatch in, e.g., 120 to 170 bases can have less of an effect on hybrid stability than a single mismatch in, 20 or 70 bases, which are the typical target capture reagent or primer lengths in multiplex amplification and microarray capture, respectively.

For selection of targets that are long compared to the length of the capture target capture reagents, such as genomic regions, target capture reagent sequence lengths are typically in the same size range as the target capture reagents for short targets mentioned above, except that there is no need to limit the maximum size of target capture reagent sequences for the sole purpose of minimizing targeting of adjacent sequences. Alternatively, oligonucleotides can be tiled across a much wider window (typically 600 bases). This method can be used to capture DNA fragments that are much larger (e.g., about 500 bases) than a typical exon. As a result, much more unwanted flanking non-target sequences are selected.

Synthesis of Target Capture Reagents

The target capture reagents can be, for example, any type of oligonucleotide, e.g., DNA or RNA. The DNA or RNA target capture reagents ("oligo target capture reagents") can be synthesized individually, or can be synthesized in an array, as a DNA or RNA target capture reagent (e.g., "array baits"). An oligo target capture reagent, whether provided in an array format, or as an isolated oligo, is typically single stranded. The target capture reagent can additionally comprise a first member of a binding pair as described herein (e.g., an affinity tag such as a biotin molecule). The first member of a binding pair, e.g., biotin molecule, can be attached to the target capture reagent, e.g., at the 5' or 3'-end of the target capture reagent, typically, at the 5'-end of the target capture reagent. Target capture reagents can be synthesized by a method described in the art, e.g., as described in International Patent Application Publication No. WO 2012/092426, or International Patent Application Publication No. WO 2015/021080, the entire contents of which are herein incorporated by reference.

Hybridization Conditions

The methods featured in the invention include the step of contacting the library (e.g., the nucleic acid library) with a plurality of target capture reagents to provide a selected library catch. The contacting step can be effected in solution hybridization. In certain embodiments, the method includes repeating the hybridization step by one or more additional rounds of solution hybridization. In some embodiments, the method further includes subjecting the library catch to one or more additional rounds of solution hybridization with the same or different collection of target capture reagents. Hybridization methods that can be adapted for use in the methods herein are described in the art, e.g., as described in International Patent Application Publication No. WO 2012/092426.

Additional embodiments or features of the present invention are as follows:

In certain embodiments, the method comprises determining the presence or absence of an alteration associated, e.g., positively or negatively, with a cancerous phenotype (e.g., at least 10, 20, 30, 50 or more of the alterations in the genes or gene products described herein) in the sample. In other embodiments, the method comprises determining genomic signatures, e.g., continuous/complex biomarkers (e.g., the level of tumor mutational burden). In other embodiments, the method comprises determining one or more genomic signatures, e.g., continuous/complex biomarkers, e.g., the level of microsatellite instability, or the presence or absence of heterozygosity (LOH). The method includes contacting the nucleic acids in the sample in a solution-based reaction according to any of the methods and target capture reagents described herein to obtain a library catch; and sequencing (e.g., by next-generation sequencing) all or a subset of the library catch, thereby determining the presence or absence of the alteration in the genes or gene products described herein.

In certain embodiments, the target capture reagent includes an oligonucleotide (or a plurality of oligonucleotides) between about 100 nucleotides and 300 nucleotides in length. Typically, the target capture reagent includes an oligonucleotide (or a plurality of oligonucleotides) between about 130 nucleotides and 230 nucleotides, or about 150 and 200 nucleotides, in length. In other embodiments, the target capture reagent includes an oligonucleotide (or a plurality of oligonucleotides) between about 300 nucleotides and 1000 nucleotides in length.

In other embodiments, the target capture reagents include cDNA sequences or are derived from cDNAs sequences. In one embodiment, the cDNA is prepared from an RNA sequence, e.g., a tumor- or cancer cell-derived RNA, e.g., an RNA obtained from a tumor-FFPE sample, a blood sample, or a bone marrow aspirate sample. In other embodiments, the target capture reagent includes amplification products (e.g., PCR products) that are amplified from genomic DNA, cDNA or cloned DNA.

In certain embodiments, a library (e.g., a nucleic acid library) includes a collection of nucleic acid molecules. As described herein, the nucleic acid molecules of the library can include a target nucleic acid molecule (e.g., a tumor nucleic acid molecule, a reference nucleic acid molecule and/or a control nucleic acid molecule; also referred to herein as a first, second and/or third nucleic acid molecule, respectively). The nucleic acid molecules of the library can be from a single individual. In some embodiments, a library can comprise nucleic acid molecules from more than one subject (e.g., 2, 3, 4, 5, 6, 7, 8, 9, 10, 20, 30 or more subjects), e.g., two or more libraries from different subjects can be combined to form a library having nucleic acid molecules from more than one subject. In one embodiment, the subject is a human having, or at risk of having, a cancer or tumor.

In some embodiments, the method comprises the step of contacting one or a plurality of libraries (e.g., one or a plurality of nucleic acid libraries) with a plurality of target capture reagents to provide a selected subgroup of nucleic acids, e.g., a library catch. In one embodiment, the contacting step is effected in a solid support, e.g., an array. Suitable solid supports for hybridization are described in, e.g., Albert, T J. et al. (2007) *Nat. Methods* 4(11):903-5; Hodges, E. et al. (2007) *Nat. Genet.* 39(12):1522-7; and Okou, D. T. et al. (2007) *Nat. Methods* 4(11):907-9, the contents of which are hereby incorporated by reference. In other embodiments, the contacting step is effected in solution hybridization. In certain embodiments, the method includes repeating the hybridization step by one or more additional rounds of hybridization. In some embodiments, the method further includes subjecting the library catch to one or more additional rounds of hybridization with the same or different collection of target capture reagents.

In yet other embodiments, the method further includes the step of subjecting the library catch to genotyping, thereby identifying the genotype of the selected nucleic acids.

In certain embodiments, the method further includes one or more of:

i) fingerprinting the sample;

ii) quantifying the abundance of a gene or gene product (e.g., a gene or gene product as described herein) in the sample (e.g., quantifying the relative abundance of a transcript in the sample);

iii) identifying the sample as belonging to a particular subject (e.g., a normal control or a cancer patient);

iv) identifying a genetic trait in the sample (e.g., one or more subject's genetic make-up (e.g., ethnicity, race, familial traits));

v) determining the ploidy in the nucleic acid sample; determining a loss of heterozygosity in the sample;

vi) determining the presence or absence of an alteration described herein, e.g., a nucleotide substitution, copy number alteration, indel, or rearrangement, in the sample;

vii) determining the level of tumor mutational burden and/or microsatellite instability (and/or other complex biomarker) in the sample; or viii) determining the level of tumor/normal cellular admixture in the sample.

The different oligonucleotide combinations can be mixed at different ratios, e.g., a ratio chosen from 1:1, 1:2, 1:3, 1:4, 1:5, 1:10, 1:20, 1:50; 1:100, 1:1000, or the like. In one embodiment, the ratio of chemically-synthesized target capture reagents (e.g., baits) to array-generated target capture reagents (e.g., baits) is chosen from 1:5, 1:10, or 1:20. The DNA or RNA oligonucleotides can be naturally- or non-naturally-occurring. In certain embodiments, the target capture reagents (e.g., baits) include one or more non-naturally-occurring nucleotides to, e.g., increase melting temperature.

Exemplary non-naturally occurring oligonucleotides include modified DNA or RNA nucleotides. An exemplary modified RNA nucleotide is a locked nucleic acid (LNA), wherein the ribose moiety of an LNA nucleotide is modified with an extra bridge connecting the 2' oxygen and 4' carbon (Kaur, H; Arora, A; Wengel, J; Maiti, S; Arora, A.; Wengel, J.; Maiti, S. (2006). "Thermodynamic, Counterion, and Hydration Effects for the Incorporation of Locked Nucleic Acid Nucleotides into DNA Duplexes". Biochemistry 45 (23): 7347-55). Other modified exemplary DNA and RNA nucleotides include, but are not limited to, peptide nucleic acid (PNA) composed of repeating N-(2-aminoethyl)-glycine units linked by peptide bonds (Egholm, M. et al. (1993) *Nature* 365 (6446): 566-8); a DNA or RNA oligonucleotide modified to capture low GC regions; a bicyclic nucleic acid (BNA) or a crosslinked oligonucleotide; a modified 5-methyl deoxycytidine; and 2,6-diaminopurine. Other modified DNA and RNA nucleotides are known in the art.

In an embodiment, a method further comprises acquiring a library wherein the size of said nucleic acid fragments in the library are less than or equal to a reference value, and said library is made without a fragmentation step between DNA isolation and making the library.

In an embodiment, a method further comprises acquiring nucleic acid fragments and if the size of said nucleic acid fragments are equal to or greater than a reference value and are fragmented and then such nucleic acid fragments are made into a library.

In an embodiment, a method further comprises labeling each of a plurality of library nucleic acid molecules, e.g., by addition of an identifiable distinct nucleic acid sequence (a barcode), to each of a plurality of nucleic acid molecules.

In an embodiment, a method further comprises attaching a primer to each of a plurality of library nucleic acid molecules.

In an embodiment, a method further comprises providing a plurality of target capture reagents and selecting a plurality of target capture reagents, said selection being responsive to: 1) a patient characteristic, e.g., age, stage of tumor, prior treatment, or resistance; 2) tumor type; 3) a characteristic of the sample; 4) a characteristic of a control sample; 5) presence or type of control; 6) a characteristic of the isolated tumor (or control) nucleic acid sample; 7) a library characteristic; 8) a mutation known to be associated with the type of tumor in the sample; 9) a mutation not known to be associated with the type of tumor in the sample; 10) the ability to sequence (or hybridize to or recover) a sequence or identify a mutation, e.g., the difficulty associated with sequence having a high GC region or a rearrangement; or 11) the genes being sequenced.

In an embodiment, a method further comprises responsive, e.g., to a determination of a low number of tumor cells in said sample, selecting a target capture reagent, or plurality of target capture reagents, giving relatively highly efficient capture of nucleic acid molecules of a first gene as compared with nucleic acid molecules of a second gene, e.g., wherein a mutation in the first gene is associated the tumor phenotype for the tumor type of the sample, optionally wherein a mutation in the second gene is not associated with the tumor phenotype for the tumor type of the sample.

In an embodiment, the method further comprises acquiring a value for a library catch characteristic, e.g., the nucleic acid concentration, and comparing the acquired value with a reference criterion for the characteristic.

In an embodiment, a method further comprises selecting a library with a value for a library characteristic that meets the reference criterion for library quantitation.

Sequencing

The invention also includes methods of sequencing nucleic acids. In these methods, nucleic acid molecules from a library are isolated by using the methods described herein, e.g., using solution hybridization, thereby providing a library catch. The library catch or a subgroup thereof can be sequenced. Accordingly, the methods featured in the invention further include analyzing the library catch. In one embodiment, the library catch is analyzed by a sequencing method, e.g., a next-generation sequencing method as described herein. The methods include isolating a library catch by solution hybridization, and subjecting the library catch by nucleic acid sequencing. In certain embodiments, the library catch can be re-sequenced.

Any method of sequencing known in the art can be used. Sequencing of nucleic acids isolated by selection methods are typically carried out using next-generation sequencing (NGS). Sequencing methods suitable for use herein are described in the art, e.g., as described in International Patent Application Publication No. WO 2012/092426.

In an embodiment, at least 10%, 20%, 30%, 40%, 50%, 60%, 70%, 80%, or 90% of the reads acquired or analyzed are for subject intervals from genes described herein, e.g., genes from Tables 1A-5A. In an embodiment, at least 0.01, 0.02, 0.03, 0.04, 0.05, 0.1, 0.2, 0.3, 0.4, 0.5, 0.6, 0.7, 0.8, 0.9, 1.0, 2.0, 5.0, 10, 15, or 30 megabases, e.g., genomic bases, are sequenced. In an embodiment, the method comprises acquiring a nucleotide sequence read obtained from a sample described herein. In an embodiment, the reads are provided by an NGS sequencing method.

The methods disclosed herein can be used to detect alterations present in the genome, whole exome or transcriptome of a subject, and can be applied to DNA and RNA sequencing, e.g., targeted DNA and/or RNA sequencing. In some embodiments, a transcript of a gene described herein is sequenced. In other embodiments, the method includes detection of a change (e.g., an increase or decrease) in the level of a gene or gene product, e.g., a change in expression of a gene or gene product described herein. The methods can, optionally, include a step of enriching a sample for a target RNA. In other embodiments, the methods include the step of depleting the sample of certain high abundance RNAs, e.g., ribosomal or globin RNAs. The RNA sequencing methods can be used, alone or in combination with the DNA sequencing methods described herein. In one embodiment, the method includes performing a DNA sequencing step and an RNA sequencing step. The methods can be performed in any order. For example, the method can include confirming by RNA sequencing the expression of an alteration described herein, e.g., confirming expression of a mutation or a fusion detected by the DNA sequencing methods of the invention. In other embodiments, the method includes performing an RNA sequencing step, followed by a DNA sequencing step.

Alignment

Alignment is the process of matching a read with a location, e.g., a genomic location. Misalignment (e.g., the placement of base-pairs from a short read on incorrect locations in the genome), e.g., misalignment due to sequence context (e.g., presence of repetitive sequence) of reads around an actual cancer mutation can lead to reduction in sensitivity of mutation detection, as reads of the alternate allele may be shifted off the main pile-up of alternate allele reads. If the problematic sequence context occurs where no actual mutation is present, misalignment may introduce artifactual reads of "mutated" alleles by placing actual reads of reference genome bases onto the wrong location. Because mutation-calling algorithms for multiplied multigene analysis should be sensitive to even low-abundance mutations, these misalignments may increase false positive discovery rates/reduce specificity.

As discussed herein, reduced sensitivity for actual mutations may be addressed by evaluating the quality of alignments (manually or in an automated fashion) around expected mutation sites in the genes being analyzed. The sites to be evaluated can be obtained from databases of cancer mutations (e.g. COSMIC). Regions that are identified as problematic can be remedied with the use of an algorithm selected to give better performance in the relevant sequence context, e.g., by alignment optimization (or re-alignment) using slower, but more accurate alignment algorithms such as Smith-Waterman alignment. In cases where general alignment algorithms cannot remedy the problem, customized alignment approaches may be created by, e.g., adjustment of maximum difference mismatch penalty parameters for genes with a high likelihood of containing substitutions; adjusting specific mismatch penalty parameters based on specific mutation types that are common in certain tumor types (e.g. C→T in melanoma); or adjusting specific mismatch penalty parameters based on specific mutation types that are common in certain sample types (e.g. substitutions that are common in FFPE).

Reduced specificity (increased false positive rate) in the evaluated gene regions due to misalignment can be assessed by manual or automated examination of all mutation calls in samples sequenced. Those regions found to be prone to spurious mutation calls due to misalignment can be subjected to same alignment remedies as above. In cases where no algorithmic remedy is found possible, "mutations" from the problem regions can be classified or screened out from the test panel.

Methods disclosed herein allow the use of multiple, individually tuned, alignment methods or algorithms to optimize performance in the sequencing of subject intervals associated with rearrangements, e.g., indels, particularly in methods that rely on massively parallel sequencing of a large number of diverse genetic events in a large number of diverse genes, e.g., from samples. In some embodiments, a multiple alignment method that is individually customized or tuned to each of a number of rearrangements in different genes is used to analyze reads. In embodiments tuning can be a function of (one or more of) the gene (or other subject interval) being sequenced, the tumor type in the sample, the variant being sequenced, or a characteristic of the sample or the subject. This selection or use of alignment conditions finely tuned to a number of subject intervals to be sequenced allows optimization of speed, sensitivity and specificity. The method is particularly effective when the alignment of reads for a relatively large number of diverse subject intervals is optimized. In embodiments, the method includes the use of an alignment method optimized for rearrangements and others optimized for subject intervals not associated with rearrangements.

In some embodiments, an alignment selector is used. "Alignment selector," as used herein, refers to a parameter that allows or directs the selection of an alignment method, e.g., an alignment algorithm or parameter, that can optimize the sequencing of a subject interval. An alignment selector can be specific to, or selected as a function, e.g., of one or more of the following:

1. The sequence context, e.g., sequence context, of a subject interval (e.g., the nucleotide position to be evaluated) that is associated with a propensity for misalignment of reads for said subject interval. E.g., the existence of a sequence element in or near the subject interval to be evaluated that is repeated elsewhere in the genome can cause misalignment and thereby reduce performance. Performance can be enhanced by selecting an algorithm or an algorithm parameter that minimizes misalignment. In this case the value for the alignment selector can be a function of the sequence context, e.g., the presence or absence of a sequence of length that is repeated at least a number of times in the genome (or in the portion of the genome being analyzed).

2. The tumor type being analyzed. E.g., a specific tumor type can be characterized by increased rate of deletions. Thus, performance can be enhanced by selecting an algorithm or algorithm parameter that is more sensitive to indels. In this case the value for the alignment selector can be a function of the tumor type, e.g., an identifier for the tumor type. In an embodiment the value is the identity of the tumor type, e.g., a solid tumor or a hematologic malignancy (or premaligancy).

3. The gene, or type of gene, being analyzed, e.g., a gene, or type of gene, can be analyzed. Oncogenes, by way of example, are often characterized by substitutions or in-frame indels. Thus, performance can be enhanced by selecting an algorithm or algorithm parameter that is particularly sensitive to these variants and specific against others. Tumor suppressors are often characterized by frame-shift indels. Thus, performance can be enhanced by selecting an algorithm or algorithm parameter that is particularly sensitive to these variants. Thus, performance can be enhanced by selecting an algorithm or algorithm parameter matched with the subject interval. In this case the value for the alignment selector can be a function of the gene or gene type, e.g., an identifier for gene or gene type. In an embodiment the value is the identity of the gene.

4. The site (e.g., nucleotide position) being analyzed. In this case the value for the alignment selector can be a function of the site or the type of site, e.g., an identifier for the site or site type. In an embodiment the value is the identity of the site. (E.g., if the gene containing the site is highly homologous with another gene, normal/fast short read alignment algorithms (e.g., BWA) may have difficulty distinguishing between the two genes, potentially necessitating more intensive alignment methods (Smith-Waterman) or even assembly (ARACHNE). Similarly, if the gene sequence contains low-complexity regions (e.g., AAAAAA), more intensive alignment methods may be necessary.

5. The variant, or type of variant, associated with the subject interval being evaluated. E.g., a substitution, insertion, deletion, translocation or other rearrangement. Thus, performance can be enhanced by selecting an algorithm or algorithm parameter that is more sensitive to the specific variant type. In this case the value for the alignment selector can be a function of the type of variant, e.g., an identifier for the type of variant. In an embodiment the value is the identity of the type of variant, e.g., a substitution.

6. The type of sample, e.g., a sample described herein. Sample type/quality can affect error (spurious observation of non-reference sequence) rate. Thus, performance can be enhanced by selecting an algorithm or algorithm parameter that accurately models the true error rate in the sample. In this case the value for the alignment selector can be a function of the type of sample, e.g., an identifier for the sample type. In an embodiment, the value is the identity of the sample type.

Generally, the accurate detection of indel mutations is an exercise in alignment, as the spurious indel rate on the sequencing platforms disabled herein is relatively low (thus, even a handful of observations of correctly aligned indels can be strong evidence of mutation). Accurate alignment in the presence of indels can be difficult however (especially as indel length increases). In addition to the general issues associated with alignment, e.g., of substitutions, the indel itself can cause problems with alignment. (For instance, a deletion of 2 bp of a dinucleotide repeat cannot be readily definitively placed.) Both sensitivity and specificity can be reduced by incorrect placement of shorter (<15 bp) apparent indel-containing reads. Larger indels (getting closer in magnitude to the length of individual reads, e.g., reads of 36 bp) can cause failure to align the read at all, making detection of the indel impossible in the standard set of aligned reads.

Databases of cancer mutations can be used to address these problems and improve performance. To reduce false positive indel discovery (improve specificity), regions around commonly expected indels can be examined for problematic alignments due to sequence context and addressed similarly to substitutions above. To improve sensitivity of indel detection, several different approaches of using information on the indels expected in cancer can be used. E.g., short-reads contained expected indels can be simulated and alignment attempted. The alignments can be studied and problematic indel regions can have alignment parameters adjusted, for instance by reducing gap open/extend penalties or by aligning partial reads (e.g. the first or second half of a read).

Alternatively, initial alignment can be attempted not just with the normal reference genome, but also with alternate versions of the genome, containing each of the known or likely cancer indel mutations. In this approach, reads of indels that initially failed to align or aligned incorrectly are placed successfully on the alternate (mutated) version of the genome.

In this way, indel alignment (and thus calling) can be optimized for the expected cancer genes/sites. As used herein, a sequence alignment algorithm embodies a computational method or approach used to identify from where in the genome a read sequence (e.g., a short-read sequence, e.g., from next-generation sequencing) most likely originated by assessing the similarity between the read sequence and a reference sequence. A variety of algorithms can be applied to the sequence alignment problem. Some algorithms are relatively slow but allow relatively high specificity. These include, e.g., dynamic programming-based algorithms. Dynamic programming is a method for solving complex problems by breaking them down into simpler steps. Other approaches are relatively more efficient but are typically not as thorough. These include, e.g., heuristic algorithms and probabilistic methods designed for large-scale database search.

Alignment parameters are used in alignment algorithms to adjust performance of an algorithm, e.g., to produce an optimal global or local alignment between a read sequence and a reference sequence. Alignment parameters can give weights for match, mismatch, and indels. For example, lower weights allow alignments with more mismatches and indels.

Sequence context, e.g., presence of repetitive sequences (e.g., tandem repeats, interspersed repeats), low-complexity regions, indels, pseudogenes, or paralogs can affect the alignment specificity (e.g., cause misalignment). As used herein, misalignment refers to the placement of base-pairs from the short read on incorrect locations in the genome.

The sensitivity of alignment can be increased when an alignment algorithm is selected or an alignment parameter is adjusted based on tumor type, e.g., a tumor type that tends to have a particular mutation or mutation type.

The sensitivity of alignment can be increased when an alignment algorithm is selected or an alignment parameter is adjusted based on a particular gene type (e.g., oncogene, tumor suppressor gene). Mutations in different types of cancer-associated genes can have different impacts on cancer phenotype. For example, mutant oncogene alleles are typically dominant. Mutant tumor suppressor alleles are typically recessive, which means that in most cases both alleles of a tumor suppressor genes must be affected before an effect is manifested.

The sensitivity of alignment can be adjusted (e.g., increased) when an alignment algorithm is selected or an alignment parameter is adjusted based on mutation type (e.g., single nucleotide polymorphism, indel (insertion or deletion), inversion, translocation, tandem repeat).

The sensitivity of alignment can be adjusted (e.g., increased) when an alignment algorithm is selected or an alignment parameter is adjusted based on mutation site (e.g., a mutation hotspot). A mutation hotspot refers to a site in the genome where mutations occur up to 100 times more frequently than the normal mutation rate.

The sensitivity/specificity of alignment can be adjusted (e.g., increased) when an alignment algorithm is selected or an alignment parameter is adjusted based on sample type (e.g., cfDNA sample, ctDNA sample, FFPE sample, or CTC sample).

In some embodiments, NGS reads can be aligned to a known reference sequence or assembled de novo. For example, the NGS reads can be aligned to a reference sequence (e.g., a wild-type sequence). Methods of sequence alignment for NGS are described e.g., in Trapnell C. and Salzberg S. L. *Nature Biotech.*, 2009, 27:455-457. Examples of de novo assemblies are described, e.g., in Warren R. et al., *Bioinformatics,* 2007, 23:500-501; Butler J. et al., *Genome Res.,* 2008, 18:810-820; and Zerbino D. R. and Birney E., *Genome Res.,* 2008, 18:821-829. Sequence alignment or assembly can be performed using read data from one or more NGS platforms, e.g., mixing Roche/454 and Illumina/ Solexa read data.

Optimization of alignment is described in the art, e.g., as set out in International Patent Application Publication No. WO 2012/092426.

Mutation Calling

Base calling refers to the raw output of a sequencing device. Mutation calling refers to the process of selecting a nucleotide value, e.g., A, G, T, or C, for a nucleotide position being sequenced. Typically, the sequencing reads (or base calling) for a position will provide more than one value, e.g., some reads will give a T and some will give a G. Mutation calling is the process of assigning a nucleotide value, e.g., one of those values to the sequence. Although it is referred to as "mutation" calling it can be applied to assign a nucleotide value to any nucleotide position, e.g., positions corresponding to mutant alleles, wild-type alleles, alleles that have not been characterized as either mutant or wild-type, or to positions not characterized by variability. Methods for mutation calling can include one or more of the following: making independent calls based on the information at each position in the reference sequence (e.g., examining the sequence reads; examining the base calls and quality scores; calculating the probability of observed bases and quality scores given a potential genotype; and assigning genotypes (e.g., using Bayes rule)); removing false positives (e.g., using depth thresholds to reject SNPs with read depth much lower or higher than expected; local realignment to remove false positives due to small indels); and performing linkage disequilibrium (LD)/imputation based analysis to refine the calls.

Equations to calculate the genotype likelihood associated with a specific genotype and position are described, e.g., in Li H. and Durbin R. *Bioinformatics,* 2010; 26(5): 589-95. The prior expectation for a particular mutation in a certain cancer type can be used when evaluating samples from that cancer type. Such likelihood can be derived from public databases of cancer mutations, e.g., Catalogue of Somatic Mutation in Cancer (COSMIC), HGMD (Human Gene Mutation Database), The SNP Consortium, Breast Cancer Mutation Data Base (BIC), and Breast Cancer Gene Database (BCGD).

Examples of LD/imputation based analysis are described, e.g., in Browning B. L. and Yu Z. *Am. J. Hum. Genet.* 2009, 85(6):847-61. Examples of low-coverage SNP calling methods are described, e.g., in Li Y. et al., *Annu. Rev. Genomics Hum. Genet.* 2009, 10:387-406.

After alignment, detection of substitutions can be performed using a calling method, e.g., Bayesian mutation calling method; which is applied to each base in each of the subject intervals, e.g., exons of the gene to be evaluated, where presence of alternate alleles is observed. This method will compare the probability of observing the read data in the presence of a mutation with the probability of observing the read data in the presence of base-calling error alone. Mutations can be called if this comparison is sufficiently strongly supportive of the presence of a mutation.

Methods have been developed that address limited deviations from frequencies of 50% or 100% for the analysis of cancer DNA. (e.g., SNVMix-Bioinformatics. 2010 Mar. 15; 26(6): 730-736.) Methods disclosed herein however allow consideration of the possibility of the presence of a mutant allele in anywhere between 1% and 100% of the sample DNA, and especially at levels lower than 50%. This approach is particularly important for the detection of mutations in low-purity FFPE samples of natural (multi-clonal) tumor DNA.

An advantage of a Bayesian mutation-detection approach is that the comparison of the probability of the presence of a mutation with the probability of base-calling error alone can be weighted by a prior expectation of the presence of a mutation at the site. If some reads of an alternate allele are observed at a frequently mutated site for the given cancer type, then presence of a mutation may be confidently called even if the amount of evidence of mutation does not meet the usual thresholds. This flexibility can then be used to increase detection sensitivity for even rarer mutations/lower purity samples, or to make the test more robust to decreases in read coverage. The likelihood of a random base-pair in the genome being mutated in cancer is ~1e-6. The likelihood of specific mutations at many sites in a typical multigenic cancer genome panel can be orders of magnitude higher. These likelihoods can be derived from public databases of cancer mutations (e.g., COSMIC). Indel calling is a process of finding bases in the sequencing data that differ from the reference sequence by insertion or deletion, typically including an associated confidence score or statistical evidence metric.

Methods of indel calling can include the steps of identifying candidate indels, calculating genotype likelihood through local re-alignment, and performing LD-based geno-type inference and calling. Typically, a Bayesian approach is used to obtain potential indel candidates, and then these candidates are tested together with the reference sequence in a Bayesian framework.

Algorithms to generate candidate indels are described, e.g., in McKenna A. et al., *Genome Res.* 2010; 20(9):1297-303; Ye K. et al., *Bioinformatics,* 2009; 25(21):2865-71; Lunter G. and Goodson M. *Genome Res.* 2011; 21(6):936-9; and Li H. et al., *Bioinformatics* 2009, Bioinformatics 25(16): 2078-9.

Methods for generating indel calls and individual-level genotype likelihoods include, e.g., the Dindel algorithm (Albers C. A. et al., *Genome Res.* 2011; 21(6):961-73). For example, the Bayesian EM algorithm can be used to analyze the reads, make initial indel calls, and generate genotype likelihoods for each candidate indel, followed by imputation of genotypes using, e.g., QCALL (Le S. Q. and Durbin R. *Genome Res.* 2011; 21(6):952-60). Parameters, such as prior expectations of observing the indel can be adjusted (e.g., increased or decreased), based on the size or location of the indels.

In an embodiment, at least 10%, 20%, 30%, 40%, 50%, 60%, 70%, 80%, or 90% of the mutation calls made in the method are for subject intervals from genes or gene products described herein, e.g., genes or gene products from Tables 1A-5A. In an embodiment, at least 10%, 20%, 30%, 40%, 50%, 60%, 70%, 80%, or 90% of the unique threshold values described herein are for subject intervals from genes or gene products described herein, e.g., genes or gene products from Tables 1A-5A. In an embodiment, at least 10%, 20%, 30%, 40%, 50%, 60%, 70%, 80%, or 90% of the mutation calls annotated, or reported to a third party, are for subject intervals from genes or gene products described herein, e.g., genes or gene products from Tables 1A-5A.

In an embodiment, the assigned value for a nucleotide position is transmitted to a third party, optionally, with explanatory annotation. In an embodiment, the assigned value for a nucleotide position is not transmitted to a third party. In an embodiment, the assigned value for a plurality of nucleotide position is transmitted to a third party, option-ally, with explanatory annotations, and the assigned value for a second plurality of nucleotide position is not transmit-ted to a third party.

In an embodiment, the method comprises assigning one or more reads to a subject, e.g., by barcode deconvolution. In an embodiment, the method comprises assigning one or more reads as a tumor read or a control read, e.g., by barcode deconvolution. In an embodiment, the method comprises mapping, e.g., by alignment with a reference sequence, each of said one or more reads. In an embodiment, the method comprises memorializing a called mutation.

In an embodiment, the method comprises annotating a called mutation, e.g., annotating a called mutation with an indication of mutation structure, e.g., a missense mutation, or function, e.g., a disease phenotype. In an embodiment, the method comprises acquiring nucleotide sequence reads for tumor and control nucleic acid. In an embodiment, the method comprises calling a nucleotide value, e.g., a variant, e.g., a mutation, for each of the subject intervals (e.g., subgenomic intervals, expressed subgenomic intervals, or both), e.g., with a Bayesian calling method or a non-Bayesian calling method. In an embodiment, the method comprises evaluating a plurality of reads that include at least one SNP. In an embodiment, the method comprises deter-mining an SNP allele ratio in the sample and/or control read.

In some embodiments, the method further comprises building a database of sequencing/alignment artifacts for the targeted subgenomic regions. In an embodiment, the data-base can be used to filter out spurious mutation calls and improve specificity. In an embodiment the database is built by sequencing unrelated samples or cell-lines and recording non-reference allele events that appear more frequently than expected due to random sequencing error alone in 1 or more of these normal samples. This approach may classify ger-mline variation as artifact, but that is acceptable in a method concerned with somatic mutations. This misclassification of germline variation as artifact may be ameliorated if desired by filtering this database for known germline variations (removing common variants) and for artifacts that appear in only 1 individual (removing rarer variations).

Optimization of mutation calling is described in the art, e.g., as set out in International Patent Application Publica-tion No. WO 2012/092426.

SGZ Algorithm

Various types of alterations, e.g., somatic alterations and germline mutations, can be detected by a method (e.g., a sequencing, alignment, or mutation calling method) described herein. In certain embodiments, a germline muta-tion is further identified by a method using the SGZ (so-matic-germline-zygosity) algorithm.

In clinical practice, matched normal controls are not commonly obtained. Without wishing to be bound by theory, it is believed that in some embodiments, although well-characterized genomic alterations do not require normal tissue for interpretation, at least some alterations will be unknown in whether they are germline or somatic, in the absence of a matched normal control. SGZ is a computa-tional method for predicting somatic versus germline origin and homozygous versus heterozygous or sub-clonal state of variants identified from next-generation sequencing of can-cer specimens.

The SGZ method does not require a matched normal control, allowing for broad application in a clinical setting. SGZ predicts the somatic vs. germline status of each altera-tion identified by modeling the alteration's allele frequency (AF), taking into account the tumor content, tumor ploidy, and the local copy number. Accuracy of the prediction depends on the depth of sequencing and copy number model fit, which can be achieved by sequencing to high depth, covering cancer-related genes and genome-wide single nucleotide polymorphisms (SNPs). Calls are made using a statistic based on read depth and local variability of SNP AF.

In some embodiments, the method further comprises characterizing a variant, e.g., a mutation, in a tissue (e.g., a tumor) or a sample, from a subject, e.g., a human, e.g., a cancer patient, comprising:

a) acquiring:

i) a sequence coverage input (SCI), which comprises, for each of a plurality of selected subject intervals, e.g., exons, a value for normalized sequence cover-age at the selected subject intervals;

ii) an SNP allele frequency input (SAFI), which com-prises, for each of a plurality of selected germline SNPs, a value for the allele frequency, in the tumor or sample;

iii) a variant allele frequency input (VAFI), which comprises the allele frequency for said variant, e.g., mutation, in the tumor or sample;

b) acquiring values, as a function of SCI and SAFI, for:

C, for each of a plurality of genomic segments, wherein C is a genomic segment total copy number;

M, for each of a plurality of genomic segments, wherein M is a genomic segment minor allele copy number; and p, wherein p is sample purity; and c) acquiring one or both of:

i) a value for variant type, e.g. mutation type, e.g., g, which is indicative of the variant, e.g., a mutation, being somatic, a subclonal somatic variant, germline, or not-distinguishable, and is a function of VAFI, p, C, and M;

ii) an indication of the zygosity of the variant, e.g., mutation, in the tumor or sample, as function of C and M.

In an embodiment, the analysis can be performed without the need for analyzing non-tumor tissue from the subject. In an embodiment, the analysis is performed without analyzing non-tumor tissue from the subject, e.g., non-tumor tissue from the same subject is not sequenced.

In an embodiment, the SCI comprises values that are a function, e.g., the log of the ratio, of the number of reads for a subject interval, e.g., from the sample, and the number or reads for a control, e.g., a process-matched control. In an embodiment, the SCI comprises values, e.g., log r values, for at least 10, 25, 50, 100, 150, 200, 250, 300, 350, 400, 450, 500, 1,000, 2,000, 3,000, 4,000, 5,000, 6,000, 7,000, 8,000, 9,000, or 10,000, subject intervals, e.g., exons. In an embodiment, the SCI comprises values, e.g., log r values, for at least 100 subject intervals, e.g., exons. In an embodiment, the SCI comprises values, e.g., log r values, for 1,000 to 10,000, 2,000 to 9,000, 3,000 to 8,000, 3,000 to 7,000, 3,000 to 6,000, or 4,000 to 5,000, subject intervals, e.g., exons. In an embodiment, the SCI comprises values, e.g., log r values, for subject intervals, e.g., exons, from at least 10, 25, 50, 100, 150, 200, 250, 300, 350, 400, 450, 500, 1,000, 2,000, 3,000, or 4,000, genes.

In an embodiment, at least one, a plurality, or substantially all of the values comprised in the SCI are corrected for correlation with GC content.

In an embodiment, a subject interval, e.g., an exon, from the sample has at least 10, 20, 30, 40, 50, 100, 150, 200, 250, 300, 350, 400, 450, 500, 600, 700, 800, 900, or 1,000 reads. In an embodiment, a plurality, e.g., at least 10, 25, 50, 100, 150, 200, 250, 300, 350, 400, 450, 500, 1,000, 2,000, 3,000, 4,000, 5,000, 6,000, 7,000, 8,000, 9,000, or 10,000, subject intervals, e.g., exons, from the sample has a number of reads. In an embodiment, the number of reads is at least 10, 20, 30, 40, 50, 100, 150, 200, 250, 300, 350, 400, 450, 500, 600, 700, 800, 900, or 1,000. In an embodiment, the plurality of germline SNPs comprise at least 10, 25, 50, 100, 150, 200, 250, 300, 350, 400, 450, 500, 1,000, 2,000, 3,000, 4,000, 5000, 6000, 7000, 8000, 9000, 10,000, or 15,000 germline SNPs.

In an embodiment, the plurality of germline SNPs comprises at least 100 germline SNPs. In an embodiment, the plurality of germline SNPs comprises 500 to 5,000, 1,000 to 4,000, or 2,000 to 3,000 germline SNPs. In an embodiment, the allele frequency is a minor allele frequency. In an embodiment, the allele frequency is an alternative allele, e.g., an allele other than a standard allele in a human genome reference database.

In an embodiment, the method comprises characterizing a plurality of variants, e.g., mutants, in the sample. In an embodiment, the method comprises characterizing at least 2, 3, 4, 5, 6, 7, 8 9, 10, 25, 50, 100, 150, 200, 250, 300, 350, 400, 450, or 500 variants, e.g., mutants. In an embodiment, the method comprises characterizing variants, e.g., mutants, in at least 2, 3, 4, 5, 6, 7, 8 9, 10, 25, 50, 100, 150, 200, 250, 300, 350, 400, 450, or 500 different genes.

In an embodiment, the method comprises acquiring a VAFI for at least 2, 3, 4, 5, 6, 7, 8 9, 10, 25, 50, 100, 150, 200, 250, 300, 350, 400, 450, or 500 variants, e.g., mutants. In an embodiment, the method comprises performing one, two or all, of steps a), b), and c) for at least 2, 3, 4, 5, 6, 7, 8 9, 10, 25, 50, 100, 150, 200, 250, 300, 350, 400, 450, or 500 variants, e.g., mutants. In an embodiment, values of C, M, and p are, have, or can be obtained by, fitting a genome-wide copy number model to one or both of the SCI and the SAFI. In an embodiment, values of C, M, and p fit a plurality of genome-wide copy number model inputs of the SCI and the SAFI. In an embodiment, a genomic segment comprises a plurality of subject intervals, e.g., exons, e.g., subject intervals which have been assigned a SCI value.

In an embodiment, a genomic segment comprises at least 10, 20, 30, 40, 50, 60, 70, 80, 90, 100, 125, 150, 175, 200, 225, 250, 275, 300, 400, or 500 subject intervals, e.g., exons. In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100, subject intervals, e.g., exons. In an embodiment, a genomic segment comprises between 100 and 10,000, 100 and 5,000, 100 and 4,000, 100 and 3,000, 100 and 2,000, or 100 and 1,000, subject intervals, e.g., exons. In an embodiment, a genomic segment comprises 10 to 1,000, 20 to 900, 30 to 700, 40 to 600, 50 to 500, 60 to 400, 70 to 300, 80 to 200, 80 to 150, or 80 to 120, 90 to 110, or about 100 genomic SNPs, which have been assigned a SAFI value. In an embodiment, a genomic segment comprises between 100 and 10,000, 100 and 5,000, 100 and 4,000, 100 and 3,000, 100 and 2,000, or 100 and 1,000, genomic SNPs which have been assigned a SAFI value.

In an embodiment, each of a plurality of genomic segments are characterized by having one or both of:

a measure of normalized sequence coverage, e.g., log r, that differ by no more than a preselected amount, e.g., the values for $\log_2 r$ for subject intervals, e.g., exons, within the boundaries of the genomic segment differ by no more than a reference value, or are substantially constant; and SNP allele frequencies for germline SNPs that differ by no more than a preselected amount, e.g., the values for germline SNP allele frequencies for subject intervals, e.g., exons, within the boundaries of the genomic segment differ by no more than a reference value, or are substantially constant.

In an embodiment, the number of subject intervals, e.g., exons, that are contained in, or are combined to form, a genomic segment is at least 2, 5, 10, 15, 20, 50, or 100 times the number of genomic segments. In an embodiment, the number of subject intervals, e.g., exons, is at least 3, 4, 5, 6, 7, 8, 9, 10, 11, 12, 13, 14, or 15 times the number of genomic segments.

In an embodiment, a boundary for a genomic segment is provided. In an embodiment, the method comprises assembling sequences for subject intervals, e.g., exons, into genetic segments.

In an embodiment, the method comprises assembling sequences for subject intervals, with a method described herein, e.g., a method comprising a circular binary segmentation (CBS), an HMM based method, a Wavelet based method, or a Cluster along Chromosomes method.

In an embodiment, fitting the genome-wide copy number model to the SCI comprises using the equation of:

$$logRatio_i = \log_2 \frac{pC_i + 2(1-p)}{p\psi + 2(1-p)},$$

where $\psi$ is tumor ploidy.

In an embodiment, $\psi=(\Sigma_i l_i C_i/\Sigma_i l_i$, let $l_i$ be the length of a genomic segment.

In an embodiment, fitting the genome-wide copy number model to the SAFI comprises using the equation of:

$$AF = \frac{pM + g(1-p)}{pC + 2(1-p)},$$

where AF is allele frequency.

In an embodiment, the fitting comprises using Gibbs sampling. In an embodiment, fitting comprises using e.g., Markov chain Monte Carlo (MCMC) algorithm, e.g., ASCAT (Allele-Specific Copy Number Analysis of Tumors), OncoSNP, or PICNIC (Predicting Integral Copy Numbers In Cancer). In an embodiment, fitting comprises using Metropolis-Hastings MCMC. In an embodiment, fitting comprises using a non-Bayesian approach, e.g., a frequentist approach, e.g., using least squares fitting.

In an embodiment, g is determined by determining the fit of values for VAFI, p, C, and M to a model for somatic/germline status. In an embodiment, the method comprises acquiring an indication of heterozygosity for said variant, e.g., mutation. In an embodiment, sample purity (p) is global purity, e.g., is the same for all genomic segments.

In an embodiment, the value of g is acquired by:

$$AF = \frac{pM + g(1-p)}{pC + 2(1-p)},$$

where AF is allele frequency.

In an embodiment, a value of g that is close to 0, e.g., does not differ significantly from 0, indicates the variant is a somatic variant. In an embodiment, a value of g that is 0, or close to 0, e.g., within a distance from 0, e.g., a value of g of less than 0.4, indicates the variant is a somatic variant. In an embodiment, a value of g that is close to 1, e.g., does not differ significantly from 1, indicates the variant is a germline variant. In an embodiment, a value of g that is 1, or close to 1, e.g., within a distance from 1, e.g., a value of g of more than 0.6, indicates the variant is a germline variant. In an embodiment, a value of g is less than 1 but more than 0, e.g., if it is less than 1 by an amount and more than 0 by an amount, e.g., if g is between 0.4 and 0.6, it indicates an indistinguishable result.

In an embodiment, a value of g that is significantly less than 0, is indicative of a subclonal somatic variant.

In an embodiment, the value of g is acquired by:

$$AF = \frac{pM' + g(1-p)}{pC + 2(1-p)},$$

where AF is allele frequency, and M'=C−M (e.g., when M is a non-minor allele frequency), e.g., the variant is a germline polymorphism if g=1 and the variant is a somatic mutation if g=0.

In an embodiment, the somatic/germline status is determined, e.g., when the sample purity is below about 40%, e.g., between about 10% and 30%, e.g., between about 10% and 20%, or between about 20% and 30%.

In an embodiment, when: a value of M equal to 0 not equal to C is indicative of absence of the variant, e.g., mutation, e.g., not existent in the tumor; a non-zero value of M equal to C is indicative of homozygosity of the variant, e.g., mutation, e.g., with loss of heterozygosity (LOH); a value of M equal to 0 equal to C indicates a homozygous deletion of the variant, e.g., mutation, e.g., not existent in the tumor; and a non-zero value of M not equal to C is indicative of heterozygosity of the variant, e.g., mutation.

In an embodiment, the method comprises acquiring an indication of zygosity for said variant, e.g., mutation. In an embodiment, the mutation status is determined as homozygous (e.g., LOH) if M=C≠0. In an embodiment, the mutation status is determined as homozygous deletion if M=C=0. In an embodiment, the mutation status is determined as heterozygous is 0<M<C. In an embodiment, the mutation is absent from the tumor if M=0 and C≠0. In an embodiment, the zygosity is determined, e.g., when the sample purity is greater than about 80%, e.g., between about 90% and 100%, e.g., between about 90% and 95%, or between about 95% and 100%.

In an embodiment, the control is a sample of euploid (e.g., diploid) tissue from a subject other than the subject from which the sample is from, or a sample of mixed euploid (e.g., diploid) tissues from one or more (e.g., at least 2, 3, 4, or 5) subjects other than the subject from which the sample is from. In an embodiment, the method comprises sequencing each of the selected subject intervals and each of the selected germline SNPs, e.g., by next generation sequencing (NGS). In an embodiment, the sequence coverage prior to normalization is at least about 10X, 20X, 30X, 50X, 100X, 250X, 500X, 750X, 800X, 900X, 1,000X, 1,500X, 2,000X, 2,500X, 3,000X, 3,500X, 4,000X, 4,500X, 5,000X, 5,500X, 6,000X, 6,500X, 7,000X, 7,500X, 8,000X, 8,500X, 9,000X, 9,500X, or 10,000X the depth of the sequencing.

In an embodiment, the subject has received an anti-cancer therapy. In an embodiment the subject has received an anti-cancer therapy and is resistant to the therapy or exhibits disease progression. In an embodiment the subject has received an anti-cancer therapy which is selected from: a therapeutic agent that has been approved by the FDA, EMA, or other regulatory agency; or a therapeutic agent that has been not been approved by the FDA, EMA, or other regulatory agency. In an embodiment the subject has received an anti-cancer therapy in the course of a clinical trial, e.g., a Phase I, Phase II, or Phase III clinical trial (or in an ex-US equivalent of such a trial). In an embodiment the variant is positively associated with the type of tumor present in the subject, e.g., with occurrence of, or resistance to treatment. In an embodiment the variant is not positively associated with the type of tumor present in the subject. In an embodiment the variant is positively associated with a tumor other than the type of tumor present in the subject. In an embodiment the variant is a variant that is not positively associated with the type of tumor present in the subject.

In an embodiment, the method can memorialize, e.g., in a database, e.g., a machine readable database, provide a report containing, or transmit, a descriptor for one or more of: the presence, absence, or frequency, of other mutations in the tumor, e.g., other mutations associated with the tumor type in the sample, other mutations not associated with the tumor type in the sample, or other mutations associated with a tumor other than the tumor type in the sample; the characterization of the variant; the allele or gene; or the tumor type, e.g., the name of the type of tumor, whether the tumor is primary or secondary; a subject characteristic; or therapeutic alternatives, recommendations, or choices.

In an embodiment, a descriptor relating to the characterization of the variant comprises a descriptor for zygosity or germline vs somatic status. In an embodiment, a descriptor relating to a subject characteristic comprises a descriptor for one or more of: the subject's identity; one or more of the subject's, age, gender, weight, or other similar characteristic, occupation; the subject's medical history, e.g., occurrence of the tumor or of other disorders; the subject's family medical history, e.g., relatives who share or do not share the variant; or the subject's prior treatment history, e.g., the treatment received, response to a previously administered anti-cancer therapy, e.g., disease resistance, responsiveness, or progression.

The SGZ algorithm is also described in Sun et al. *PLoS Comput Biol.* 2018; 14(2):e1005965; Sun et al. *Cancer Research* 2014; 74(19S):1893-1893; International Application Publication No. WO2014/183078, U.S. Pat. No. 9,792, 403, and U.S. Application Publication No. 2014/0336996, the contents of which are incorporated by reference in their entirety.

Tumor Mutational Burden

The methods and compositions described herein can be used to evaluate tumor mutational burden (TMB).

The terms "mutational burden," "mutation burden," "mutation load," and "mutational load" are used interchangeably herein. In the context of a tumor, a mutational load is also referred to herein as "tumor mutational burden," "tumor mutation burden," or "TMB." Without wishing to be bound by theory, it is believed that in some embodiments, TMB can be considered as a type of genomic signature, e.g., a continuous/complex biomarker.

As used herein, the term "mutation burden" or "mutational burden" refers to the level, e.g., number, of an alteration (e.g., one or more alterations, e.g., one or more somatic alterations) per a predefined unit (e.g., per megabase) in a set of genes (e.g., in the coding regions of the set of genes). Mutational burden can be measured, e.g., on a whole genome or exome basis, or on the basis of a subset of genome or exome. In certain embodiments, the mutational burden measured on the basis of a subset of genome or exome can be extrapolated to determine a whole genome or exome mutational burden.

In an embodiment, the method comprises:
a) providing a sequence, e.g., a nucleotide sequence, of a set of subject intervals (e.g., coding subject intervals) from the sample, wherein the set of subject intervals are from a set of genes; and
b) determining a value for the mutational burden, wherein the value is a function of the number of an alteration (e.g., one or more alterations), e.g., a somatic alteration (e.g., one or more somatic alterations), in the set of subject intervals.

In certain embodiments, the number of an alteration excludes a functional alteration in a subject interval. In other embodiments, the number of an alteration excludes a germline alteration in a subject interval. In certain embodiments, the number of an alteration excludes a functional alteration in a subject interval and a germline alteration in a subject interval.

In certain embodiments, the set of subject intervals comprises coding subject intervals. In other embodiments, the set of subject intervals comprises non-coding subject intervals. In certain embodiments, the set of subject intervals comprises coding subject intervals. In other embodiments, the set of subject intervals comprises one or more coding subject intervals and one or more non-coding subject intervals. In certain embodiments, about 5% or more, about 10% or more, about 20% or more, about 30% or more, about 40% or more, about 50% or more, about 60% or more, about 70% or more, about 80% or more, about 90% or more, or about 95% or more, of the subject intervals in the set of subject intervals are coding subject intervals. In other embodiments, about 90% or less, about 80% or less, about 70% or less, about 60% or less, about 50% or less, about 40% or less, about 30% or less, about 20% or less, about 10% or less, or about 5% or less, of the subject intervals in the set of subject intervals are non-coding subject intervals.

In other embodiments, the set of subject intervals does not comprise the entire genome or the entire exome. In other embodiments, the set of coding subject intervals does not comprise the entire exome.

In certain embodiments, the set of genes does not comprise the entire genome or the entire exome. In other embodiments, the set of genes comprises or consists of one or more genes set forth in Tables 1A-5A.

In certain embodiments, the value is expressed as a function of the set of genes. In certain embodiments, the value is expressed as a function of the coding regions of the set of genes. In other embodiments, the value is expressed as a function of the non-coding regions of the set of genes. In certain embodiments, the value is expressed as a function of the exons of the set of genes. In other embodiments, the value is expressed as a function of the introns of the set of genes.

In certain embodiments, the value is expressed as a function of the set of genes sequenced. In certain embodiments, the value is expressed as a function of the coding regions of the set of genes sequenced. In other embodiments, the value is expressed as a function of the non-coding regions of the set of genes sequenced. In certain embodiments, the value is expressed as a function of the exons of the set of genes sequenced. In other embodiments, the value is expressed as a function of the introns of the set of genes sequenced.

In certain embodiments, the value is expressed as a function of the number of an alteration (e.g., a somatic alteration) in a number of positions of the set of genes. In certain embodiments, the value is expressed as a function of the number of an alteration (e.g., a somatic alteration) in a number of positions of the coding regions of the set of genes. In other embodiments, the value is expressed as a function of the number of an alteration (e.g., a somatic alteration) in a number of positions of the non-coding regions of the set of genes. In certain embodiments, the value is expressed as a function of the number of an alteration (e.g., a somatic alteration) in a number of positions of the exons of the set of genes. In other embodiments, the value is expressed as a function of the number of an alteration (e.g., a somatic alteration) in a number of positions of the introns of the set of genes.

In certain embodiments, the value is expressed as a function of the number of an alteration (e.g., a somatic alteration) in a number of positions of the set of genes sequenced. In certain embodiments, the value is expressed as a function of the number of an alteration (e.g., a somatic alteration) in a number of positions of the coding regions of the set of genes sequenced. In other embodiments, the value is expressed as a function of the number of an alteration (e.g., a somatic alteration) in a number of positions of the non-coding regions of the set of genes sequenced. In certain embodiments, the value is expressed as a function of the number of an alteration (e.g., a somatic alteration) in a number of positions of the exons of the set of genes sequenced. In other embodiments, the value is expressed as a function of the number of an alteration (e.g., a somatic alteration) in a number of positions of the introns of the set of genes sequenced.

In certain embodiments, the value is expressed as a function of the number of an alteration (e.g., a somatic alteration) per a unit, e.g., as a function of the number of a somatic alteration per megabase.

In certain embodiments, the value is expressed as a function of the number of an alteration (e.g., a somatic alteration) per megabase in the set of genes. In certain embodiments, the value is expressed as a function of the number of an alteration (e.g., a somatic alteration) per megabase in the coding regions of the set of genes. In other embodiments, the value is expressed as a function of the number of an alteration (e.g., a somatic alteration) per megabase in the non-coding regions of the set of genes. In certain embodiments, the value is expressed as a function of the number of an alteration (e.g., a somatic alteration) per megabase in the exons of the set of genes. In other embodiments, the value is expressed as a function of the number of an alteration (e.g., somatic alteration) per megabase in the introns of the set of genes.

In certain embodiments, the value is expressed as a function of the number of an alteration (e.g., a somatic alteration) per megabase in the set of genes sequenced. In certain embodiments, the value is expressed as a function of the number of an alteration (e.g., a somatic alteration) per megabase in the coding regions of the set of genes sequenced. In other embodiments, the value is expressed as a function of the number of an alteration (e.g., a somatic alteration) per megabase in the non-coding regions of the set of genes sequenced. In certain embodiments, the value is expressed as a function of the number of an alteration (e.g., a somatic alteration) per megabase in the exons of the set of genes sequenced. In other embodiments, the value is expressed as a function of the number of an alteration (e.g., a somatic alteration) per megabase in the introns of the set of genes sequenced.

In certain embodiments, the mutational burden is extrapolated to a larger portion of the genome, e.g., to the exome or the entire genome, e.g., to obtain the total mutational burden. In other embodiments, the mutational burden is extrapolated to a larger portion of the exome, e.g., to the entire exome.

In certain embodiments, the sample is from a subject. In certain embodiments, the subject has a disorder, e.g., a cancer. In other embodiments, the subject is receiving, or has received, a therapy, e.g., an immunotherapy.

In certain embodiments, the mutational burden is expressed as a percentile, e.g., among the mutational burdens in samples from a reference population. In certain embodiments, the reference population includes patients having the same type of cancer as the subject. In other embodiments, the reference population includes patients who are receiving, or have received, the same type of therapy, as the subject.

In certain embodiments, the method comprises:

(i) acquiring a library comprising a plurality of tumor nucleic acid molecules from the sample;

(ii) contacting the library with a target capture reagent to provide selected tumor nucleic acid molecules, wherein said target capture reagent hybridizes with the tumor nucleic acid molecule, thereby providing a library catch;

(iii) acquiring a read for a subject interval comprising an alteration (e.g., a somatic alteration) from a tumor nucleic acid molecule from said library catch, e.g., by a next-generation sequencing method;

(iv) aligning said read by an alignment method;

(v) assigning a nucleotide value from said read for a nucleotide position;

(vi) selecting a set of subject intervals (e.g., coding subject intervals) from a set of the assigned nucleotide positions, wherein the set of subject intervals are from a set of genes; and (vii) determining a value for the mutational burden, wherein the value is a function of the number of an alteration (e.g., one or more alterations), e.g., a somatic alteration (e.g., one or more somatic alterations), in the set of subject intervals.

In certain embodiments, the number of an alteration (e.g., a somatic alteration) excludes a functional alteration in a subject interval. In other embodiments, the number of an alteration excludes a germline alteration in a subject interval. In certain embodiments, the number of an alteration (e.g., a somatic alteration) excludes a functional alteration in a subject interval and a germline alteration in a subject interval.

Other methods for evaluating tumor mutational burden are described in International Application Publication No. WO2017/151524, the content of which is incorporated by reference in its entirety.

Gene Selection

The selected genes or gene products (also referred to herein as the "target genes or gene products") can include subject intervals comprising intragenic regions or intergenic regions. For example, the subject intervals can include an exon or an intron, or a fragment thereof, typically an exon sequence or a fragment thereof. The subject interval can include a coding region or a non-coding region, e.g., a promoter, an enhancer, a 5' untranslated region (5' UTR), or a 3' untranslated region (3' UTR), or a fragment thereof. In other embodiments, the subject interval includes a cDNA or a fragment thereof. In other embodiments, the subject interval includes an SNP, e.g., as described herein.

In other embodiments, the subject intervals include substantially all exons in a genome, e.g., one or more of the subject intervals as described herein (e.g., exons from selected genes or gene products of interest (e.g., genes or gene products associated with a cancerous phenotype as described herein)). In one embodiment, the subject interval includes a somatic mutation, a germline mutation or both. In one embodiment, the subject interval includes an alteration, e.g., a point or a single mutation, a deletion mutation (e.g., an in-frame deletion, an intragenic deletion, a full gene deletion), an insertion mutation (e.g., intragenic insertion), an inversion mutation (e.g., an intra-chromosomal inversion), a linking mutation, a linked insertion mutation, an inverted duplication mutation, a tandem duplication (e.g., an intrachromosomal tandem duplication), a translocation (e.g., a chromosomal translocation, a non-reciprocal translocation), a rearrangement, a change in gene copy number, or a combination thereof. In certain embodiments, the subject interval constitutes less than 5%, 1%, 0.5%, 0.1%, 0.05%, 0.01%, 0.005%, or 0.001% of the coding region of the genome of the tumor cells in a sample. In other embodiments, the subject intervals are not involved in a disease, e.g., are not associated with a cancerous phenotype as described herein.

In one embodiment, the target gene or gene product is a biomarker. As used herein, a "biomarker" or "marker" is a gene, mRNA, or protein which can be altered, wherein said alteration is associated with cancer. The alteration can be in amount, structure, and/or activity in a cancer tissue or cancer cell, as compared to its amount, structure, and/or activity, in a normal or healthy tissue or cell (e.g., a control), and is associated with a disease state, such as cancer. For example, a marker associated with cancer, or predictive of responsiveness to anti-cancer therapeutics, can have an altered nucleotide sequence, amino acid sequence, chromosomal translocation, intra-chromosomal inversion, copy number, expression level, protein level, protein activity, epigenetic modification (e.g., methylation or acetylation status, or post-translational modification, in a cancer tissue or cancer cell as compared to a normal, healthy tissue or cell. Furthermore, a "marker" includes a molecule whose structure is altered, e.g., mutated (contains a mutation), e.g., differs from the wild-type sequence at the nucleotide or amino acid level, e.g., by substitution, deletion, or insertion, when present in a tissue or cell associated with a disease state, such as cancer.

In one embodiment, the target gene or gene product includes a single nucleotide polymorphism (SNP). In another embodiment, the gene or gene product has a small deletion, e.g., a small intragenic deletion (e.g., an in-frame or frame-shift deletion). In yet another embodiment, the target sequence results from the deletion of an entire gene. In still another embodiment, the target sequence has a small insertion, e.g., a small intragenic insertion. In one embodiment, the target sequence results from an inversion, e.g., an intrachromosomal inversion. In another embodiment, the target sequence results from an interchromosal transloca-tion. In yet another embodiment, the target sequence has a tandem duplication. In one embodiment, the target sequence has an undesirable feature (e.g., high GC content or repeat element). In another embodiment, the target sequence has a portion of nucleotide sequence that cannot itself be successfully targeted, e.g., because of its repetitive nature. In one embodiment, the target sequence results from alternative splicing. In another embodiment, the target sequence is chosen from a gene or gene product, or a fragment thereof according to Tables 1A-5A.

In an embodiment, the target gene or gene product, or a fragment thereof, is an antibody gene or gene product, an immunoglobulin superfamily receptor (e.g., B-cell receptor (BCR) or T-cell receptor (TCR)) gene or gene product, or a fragment thereof.

Human antibody molecules (and B cell receptors) are composed of heavy and light chains with both constant (C) and variable (V) regions that are encoded by genes on at least the following three loci.

1. Immunoglobulin heavy locus (IGH@) on chromosome 14, containing gene segments for the immunoglobulin heavy chain;
2. Immunoglobulin kappa (κ) locus (IGK@) on chromosome 2, containing gene segments for the immunoglobulin light chain;
3. Immunoglobulin lambda (λ) locus (IGL@) on chromosome 22, containing gene segments for the immunoglobulin light chain.

Each heavy chain and light chain gene contains multiple copies of three different types of gene segments for the variable regions of the antibody proteins. For example, the immunoglobulin heavy chain region can contain one of five different classes γ, δ, α, β and ε, 44 Variable (V) gene segments, 27 Diversity (D) gene segments, and 6 Joining (J) gene segments. The light chains can also possess numerous V and J gene segments, but do not have D gene segments. The lambda light chain has 7 possible C regions and the kappa light chain has 1.

Immunoglobulin heavy locus (IGH@) is a region on human chromosome 14 that contains genes for the heavy chains of human antibodies (or immunoglobulins). For example, the IGH locus includes IGHV (variable), IGHD (diversity), IGHJ (joining), and IGHC (constant) genes. Exemplary genes encoding the immunoglobulin heavy chains include, but are not limited to IGHV1-2, IGHV1-3, IGHV1-8, IGHV1-12, IGHV1-14, IGHV1-17, IGHV1-18, IGHV1-24, IGHV1-45, IGHV1-46, IGHV1-58, IGHV1-67, IGHV1-68, IGHV1-69, IGHV1-38-4, IGHV1-69-2, IGHV2-5, IGHV2-10, IGHV2-26, IGHV2-70, IGHV3-6, IGHV3-7, IGHV3-9, IGHV3-1, IGHV3-13, IGHV3-15, IGHV3-16, IGHV3-19, IGHV3-20, IGHV3-21, IGHV3-22, IGHV3-23, IGHV3-25, IGHV3-29, IGHV3-30, IGHV3-30-2, IGHV3-30-3, IGHV3-30-5, IGHV3-32, IGHV3-33, IGHV3-33-2, IGHV3-35, IGHV3-36, IGHV3-37, IGHV3-38, IGHV3-41, IGHV3-42, IGHV3-43, IGHV3-47, IGHV3-48, IGHV3-49, IGHV3-50, IGHV3-52, IGHV3-53, IGHV3-54, IGHV3-57, IGHV3-60, IGHV3-62, IGHV3-63, IGHV3-64, IGHV3-65, IGHV3-66, IGHV3-71, IGHV3-72, IGHV3-73, IGHV3-74, IGHV3-75, IGHV3-76, IGHV3-79, IGHV3-38-3, IGHV3-69-1, IGHV4-4, IGHV4-28, IGHV4-30-1, IGHV4-30-2, IGHV4-30-4, IGHV4-31, IGHV4-34, IGHV4-39, IGHV4-55, IGHV4-59, IGHV4-61, IGHV4-80, IGHV4-38-2, IGHV5-51, IGHV5-78, IGHV5-10-1, IGHV6-1, IGHV7-4-1, IGHV7-27, IGHV7-34-1, IGHV7-40, IGHV7-56, IGHV7-81, IGHVII-1-1, IGHVII-15-1, IGHVII-20-1, IGHVII-22-1, IGHVII-26-2, IGHVII-28-1, IGHVII-30-1, IGHVII-31-1, IGHVII-33-1, IGHVII-40-1, IGHVII-43-1, IGHVII-44-2, IGHVII-46-1, IGHVII-49-1, IGHVII-51-2, IGHVII-53-1, IGHVII-60-1, IGHVII-62-1, IGHVII-65-1, IGHVII-67-1, IGHVII-74-1, IGHVII-78-1, IGHVIII-2-1, IGHVIII-5-1, IGHVIII-5-2, IGHVIII-11-1, IGHVIII-13-1, IGHVII-16-1, IGHVIII-22-2, IGHVIII-25-1, IGHVIII-26-1, IGHVIII-38-1, IGHVIII-44, IGHVIII-47-1, IGHVIII-51-1, IGHVIII-67-2, IGHVIII-67-3, IGHVIII-67-4, IGHVIII-76-1, IGHVIII-82, IGHVIV-44-1, IGHD1-1, IGHD1-7, IGHD1-14, IGHD1-20, IGHD1-26, IGHD2-2, IGHD2-8, IGHD2-15, IGHD2-21, IGHD3-3, IGHD3-9, IGHD3-10, IGHD3-16, IGHD3-22, IGHD4-4, IGHD4-11, IGHD4-17, IGHD4-23, IGHD5-5, IGHD5-12, IGHD5-18, IGHD5-24, IGHD6-6, IGHD6-13, IGHD6-19, IGHD6-25, IGHD7-27, IGHJ1, IGHJ1P, IGHJ2, IGHJ2P, IGHJ3, IGHJ3P, IGHJ4, IGHJ5, IGHJ6, IGHA1, IGHA2, IGHG1, IGHG2, IGHG3, IGHG4, IGHGP, IGHD, IGHE, IGHEP1, IGHM, and IGHV1-69D.

Immunoglobulin kappa locus (IGK@) is a region on human chromosome 2 that contains genes for the kappa (κ) light chains of antibodies (or immunoglobulins). For example, the IGK locus includes IGKV (variable), IGKJ (joining), and IGKC (constant) genes. Exemplary genes encoding the immunoglobulin kappa light chains include, but are not limited to, IGKV-5, IGKV1-6, IGKV1-8, IGKV1-9, IGKV1-12, IGKV1-13, IGKV1-16, IGKV1-17, IGKV1-22, IGKV1-27, IGKV1-32, IGKV1-33, IGKV1-35, IGKV1-37, IGKV1-39, IGKV1D-8, IGKV1D-12, IGKV1D-13, IGKV1D-16 IGKV1D-17, IGKV1D-22, IGKV1D-27, IGKV1D-32, IGKV1D-33, IGKV1D-35, IGKV1D-37, IGKV1D-39, IGKV1D-42, IGKV1D-43, IGKV2-4, IGKV2-10, IGKV2-14, IGKV2-18, IGKV2-19, IGKV2-23, IGKV2-24, IGKV2-26, IGKV2-28, IGKV2-29, IGKV2-30, IGKV2-36, IGKV2-38, IGKV2-40, IGKV2D-10, IGKV2D-14, IGKV2D-18, IGKV2D-19, IGKV2D-23, IGKV2D-24, IGKV2D-26, IGKV2D-28, IGKV2D-29, IGKV2D-30, IGKV2D-36, IGKV2D-38, IGKV2D-40, IGKV3-7, IGKV3-11, IGKV3-15, IGKV3-20, IGKV3-25, IGKV3-31, IGKV3-34, IGKV3D-7, IGKV3D-1, IGKV3D-15, IGKV3D-20, IGKV3D-25, IGKV3D-31. IGKV3D-34, IGKV4-1, IGKV5-2, IGKV6-21, IGKV6D-21, IGKV6D-41, IGKV7-3, IGKJ1, IGKJ2, IGKJ3, IGKJ4, IGKJ5, and IGKC.

Immunoglobulin lambda locus (IGL@) is a region on human chromosome 22 that contains genes for the lambda light chains of antibody (or immunoglobulins). For example, the IGL locus includes IGLV (variable), IGU (joining), and IGLC (constant) genes. Exemplary genes encoding the immunoglobulin lambda light chains include, but are not limited to, IGLV1-36, IGLV1-40, IGLV1-41, IGLV1-44, IGLV1-47, IGLV1-50, IGLV1-51, IGLV1-62, IGLV2-5, IGLV2-8, IGLV2-11, IGLV2-14, IGLV2-18, IGLV2-23, IGLV2-28, IGLV2-33, IGLV2-34, IGLV3-1, IGLV3-2, IGLV3-4, IGLV3-6, IGLV3-7, IGLV3-9, IGLV3-10, IGLV3-12, IGLV3-13, IGLV3-15, IGLV3-16, IGLV3-17, IGLV3-19, IGLV3-21, IGLV3-22, IGLV3-24, IGLV3-25, IGLV3-26, IGLV3-27, IGLV3-29, IGLV3-30, IGLV3-31, IGLV3-32, IGLV4-3, IGLV4-60, IGLV4-69, IGLV5-37, IGLV5-39, IGLV5-45, IGLV5-48, IGLV5-52, IGLV6-57, IGLV7-35, IGLV7-43, IGLV7-46, IGLV8-61, IGLV9-49, IGLV10-54, IGLV10-67, IGLV11-55, IGLVI-20, IGLVI-38, IGLVI-42, IGLVI-56, IGLVI-63, IGLVI-68, IGLVI-70, IGLVIV-53, IGLVIV-59, IGLVIV-64, IGLVIV-65, IGLVIV-66-1, IGLVV-58, IGLVV-66, IGLVVI-22-1, IGLVVI-25-1, IGLVVII-41-1, IGLJI, IGL2, IGU3, IGL4, IGUS, IGL6, IGU7, IGLC1, IGLC2, IGLC3, IGLC4, IGLC5, IGLC6, and IGLC7.

The B-cell receptor (BCR) is composed of two parts: i) a membrane-bound immunoglobulin molecule of one isotype (e.g., IgD or IgM). With the exception of the presence of an integral membrane domain, these can be identical to their secreted forms and ii) a signal transduction moiety: a heterodimer called Ig-α/Ig-β (CD79), bound together by disulfide bridges. Each nucleic acid molecule of the dimer spans the plasma membrane and has a cytoplasmic tail bearing an immunoreceptor tyrosine-based activation motif (ITAM).

The T-cell receptor (TCR) is composed of two different protein chains (i.e., a heterodimer). In 95% of T cells, this consists of an alpha (α) and beta (β) chain, whereas in 5% of T cells this consists of gamma (γ) and delta (δ) chains. This ratio can change during ontogeny and in diseased states. The T cell receptor genes are similar to immunoglobulin genes in that they too contain multiple V, D and J gene segments in their beta and delta chains (and V and J gene segments in their alpha and gamma chains) that are rearranged during the development of the lymphocyte to provide each cell with a unique antigen receptor.

T-cell receptor alpha locus (TRA) is a region on human chromosome 14 that contains genes for the TCR alpha chains. For example, the TRA locus includes, e.g., TRAV (variable), TRAJ (joining), and TRAC (constant) genes. Exemplary genes encoding the T-cell receptor alpha chains include, but are not limited to, TRAV1-1, TRAV1-2, TRAV2, TRAV3, TRAV4, TRAV5, TRAV6, TRAV7, TRAV8-1, TRAV8-2, TRAV8-3, TRAV8-4, TRAV8-5, TRAV8-6, TRAV8-7, TRAV9-1, TRAV9-2, TRAV10, TRAV11, TRAV12-1, TRAV12-2, TRAV12-3, TRAV13-1, TRAV13-2, TRAV14DV4, TRAVIS, TRAV16, TRAV17, TRAV18, TRAV19, TRAV20, TRAV21, TRAV22, TRAV23DV6, TRAV24, TRAV25, TRAV26-1, TRAV26-2, TRAV27, TRAV28, TRAV29DV5, TRAV30, TRAV31, TRAV32, TRAV33, TRAV34, TRAV35, TRAV36DV7, TRAV37, TRAV38-1, TRAV38-2DV8, TRAV39, TRAV40, TRAV41, TRAJ1, TRAJ2, TRAJ3, TRAJ4, TRAJ5, TRAJ6, TRAJ7, TRAJ8, TRAJ9, TRAJ10, TRAJ11, TRAJ12, TRAJ13, TRAJ14, TRAJ15, TRAJ16, TRAJ17, TRAJ18, TRAJ19, TRAJ20, TRAJ21, TRAJ22, TRAJ23, TRAJ24, TRAJ25, TRAJ26, TRAJ27, TRAJ28, TRAJ29, TRAJ30, TRAJ31, TRAJ32, TRAJ33, TRAJ34, TRAJ35, TRAJ36, TRAJ37, TRAJ38, TRAJ39, TRAJ40, TRAJ41, TRAJ42, TRAJ43, TRAJ44, TRAJ45, TRAJ46, TRAJ47, TRAJ48, TRAJ49, TRAJ50, TRAJ51, TRAJ52, TRAJ53, TRAJ54, TRAJ55, TRAJ56, TRAJ57, TRAJ58, TRAJ59, TRAJ60, TRAJ61, and TRAC.

T-cell receptor beta locus (TRB) is a region on human chromosome 7 that contains genes for the TCR beta chains. For example, the TRB locus includes, e.g., TRBV (variable), TRBD (diversity), TRBJ (joining), and TRBC (constant) genes. Exemplary genes encoding the T-cell receptor beta chains include, but are not limited to, TRBV1, TRBV2, TRBV3-1, TRBV3-2, TRBV4-1, TRBV4-2, TRBV4-3, TRBV5-1, TRBV5-2, TRBV5-3, TRBV5-4, TRBV5-5, TRBV5-6, TRBV5-7, TRBV6-2, TRBV6-3, TRBV6-4, TRBV6-5, TRBV6-6, TRBV6-7, TRBV6-8, TRBV6-9, TRBV7-1, TRBV7-2, TRBV7-3, TRBV7-4, TRBV7-5, TRBV7-6, TRBV7-7, TRBV7-8, TRBV7-9, TRBV8-1, TRBV8-2, TRBV9, TRBV10-1, TRBV10-2, TRBV10-3, TRBV11-1, TRBV11-2, TRBV11-3, TRBV12-1, TRBV112-2, TRBV112-3, TRBV112-4, TRBV112-5, TRBV13, TRBV14, TRBV15, TRBV116, TRBV117, TRBV18, TRBV19, TRBV20-1, TRBV21-1, TRBV22-1, TRBV23-1, TRBV24-1, TRBV25-1, TRBV26, TRBV27, TRBV28, TRBV29-1, TRBV30, TRBVA, TRBVB, TRBV5-8, TRBV6-1, TRBD1, TRBD2, TRBJ1-1, TRBJ1-2, TRBJ1-3, TRBJ1-4, TRBJ1-5, TRBJ1-6, TRBJ2-1, TRBJ2-2, TRBJ2-2P, TRBJ2-3, TRBJ2-4, TRBJ2-5, TRBJ2-6, TRBJ2-7, TRBC1, and TRBC2.

T-cell receptor delta locus (TRD) is a region on human chromosome 14 that contains genes for the TCR delta chains. For example, the TRD locus includes, e.g., TRDV (variable), TRDJ (joining), and TRDC (constant) genes. Exemplary genes encoding the T-cell receptor delta chains include, but are not limited to, TRDV1, TRDV2, TRDV3, TRDD1, TRDD2, TRDD3, TRDJ1, TRDJ2, TRDJ3, TRDJ4, and TRDC.

T-cell receptor gamma locus (TRG) is a region on human chromosome 7 that contains genes for the TCR gamma chains. For example, the TRG locus includes, e.g., TRGV (variable), TRGJ (joining), and TRGC (constant) genes. Exemplary genes encoding the T-cell receptor gamma chains include, but are not limited to, TRGV1, TRGV2, TRGV3, TRGV4, TRGV5, TRGV5P, TRGV6, TRGV7, TRGV8, TRGV9, TRGV10, TRGV11, TRGVA, TRGVB, TRGJ1, TRGJ2, TRGJP, TRGJP1, TRGJP2, TRGC1, and TRGC2.

In one embodiment, the target gene or gene product, or a fragment thereof, is selected from any of the genes or gene products described in Tables 1A-5A.

TABLE 1A

Exemplary genes with complete exonic coverage
in an exemplary DNA-seq target capture reagent ABL1
ACTB
AKT1
AKT2
AKT3
ALK
AMER1 (FAM123B or WTX)

TABLE 1A-continued

Exemplary genes with complete exonic coverage
in an exemplary DNA-seq target capture reagent

| |
| --- |
| APC |
| APH1A |
| AR |
| ARAF |
| ARFRP1 |
| ARHGAP26 (GRAF) |
| ARID1A |
| ARID2 |
| ASMTL |
| ASXL1 |
| ATM |
| ATR |
| ATRX |
| AURKA |
| AURKB |
| AXIN1 |
| AXL |
| B2M |
| BAP1 |
| BARD1 |
| BCL10 |
| BCL11B |
| BCL2 |
| BCL2L2 |
| BCL6 |
| BCL7A |
| BCOR |
| BCORL1 |
| BIRC3 |
| BLM |
| BRAF |
| BRCA1 |
| BRCA2 |
| BRD4 |
| BRIP1 (BACH1) |
| BRSK1 |
| BTG2 |
| BTK |
| BTLA |
| c11or30 (EMSY) |
| CAD |
| CARD11 |
| CASP8 |
| CBFB |
| CBL |
| CCND1 |
| CCND2 |
| CCND3 |
| CCNE1 |
| CCT6B |
| CD22 |
| CD274 (PDL1) |
| CD36 |
| CD58 |
| CD70 |
| CD79A |
| CD79B |
| CDC73 |
| CDH1 |
| CDK12 |
| CDK4 |
| CDK6 |
| CDK8 |
| CDKN1B |
| CDKN2A |
| CDKN2B |
| CDKN2C |
| CEBPA |
| CHD2 |
| CHEK1 |
| CHEK2 |
| CIC |
| CIITA |
| CKS1B |
| CPS1 |
| CRBN |
| CREBBP |

TABLE 1A-continued

Exemplary genes with complete exonic coverage
in an exemplary DNA-seq target capture reagent

| |
| --- |
| CRKL |
| CRLF2 |
| CSF1R |
| CSF3R |
| CTCF |
| CTNNA1 |
| CTNNB1 |
| CUX1 |
| CXCR4 |
| DAXX |
| DDR2 |
| DDX3X |
| DNM2 |
| DNMT3A |
| DOT1L |
| DTX1 |
| DUSP2 |
| DUSP9 |
| EBF1 |
| ECT2L |
| EED |
| EGFR |
| ELP2 |
| EP300 |
| EPHA3 |
| EPHA5 |
| EPHA7 |
| EPHB1 |
| ERBB2 |
| ERBB3 |
| ERBB4 |
| ERG |
| ESR1 |
| ETS1 |
| ETV6 |
| EXOSC6 |
| EZH2 |
| FAF1 |
| FAM46C |
| FANCA |
| FANCC |
| FANCD2 |
| FANCE |
| FANCF |
| FANCG |
| FANCL |
| FAS (TNFRSF6) |
| FBXO11 |
| FBXO31 |
| FBXW7 |
| FGF10 |
| FGF14 |
| FGF19 |
| FGF23 |
| FGF3 |
| FGF4 |
| FGF6 |
| FGFR1 |
| FGFR2 |
| FGFR3 |
| FGFR4 |
| FHIT |
| FLCN |
| FLT1 |
| FLT3 |
| FLT4 |
| FLYWCH1 |
| FOXL2 |
| FOXO1 |
| FOXO3 |
| FOXP1 |
| FRS2 |
| GADD45B |
| GATA1 |
| GATA2 |
| GATA3 |
| GID4 (c17orf39) |

TABLE 1A-continued

Exemplary genes with complete exonic coverage
in an exemplary DNA-seq target capture reagent GNA11
GNA12
GNA13
GNAQ
GNAS
GPR124
GRIN2A
GSK3B
GTSE1
HDAC1
HDAC4
HDAC7
HGF
HIST1H1C
HIST1H1D
HIST1H1E
HIST1H2AC
HIST1H2AG
HIST1H2AL
HIST1H2AM
HIST1H2BC
HIST1H2BJ
HIST1H2BK
HIST1H2BO
HIST1H3B
HNF1A
HRAS
HSP90AA1
ICK
ID3
IDH1
IDH2
IGF1R
IKBKE
IKZF1
IKZF2
IKZF3
IL7R
INHBA
INPP4B
INPP5D (SHIP)
IRF1
IRF4
IRF8
IRS2
JAK1
JAK2
JAK3
JARID2
JUN
KAT6A (MYST3)
KDM2B
KDM4C
KDM5A
KDM5C
KDM6A
CALR
KDR
KEAP1
KIT
KLHL6
KMT2A (MLL)
)
KMT2C (MLL3)
KRAS
LEF1
LMO1
LRP1B
LRRK2
MAF
MAFB
MAGED1
MALT1
MAP2K1
MAP2K2
MAP2K4
MAP3K1

TABLE 1A-continued

Exemplary genes with complete exonic coverage
in an exemplary DNA-seq target capture reagent MAP3K13
MAP3K14
MAP3K6
MAP3K7
MAPK1
MCL1
MDM2
MDM4
MED12
MEF2B
MEF2C
MEN1
MET
MIB1
MITF
MKI67
MLH1
MPL
MRE11A
MSH2
MSH3
MSH6
MTOR
MUTYH
MYC
MYCL (MYCL1)
KMT2D (MLL2)
MYCN
MYD88
MYO18A
NCOR2
NCSTN
NF1
NF2
NFE2L2
NFKBIA
NKX2-1
NOD1
NOTCH1
NOTCH2
NPM1
NRAS
NT5C2
NTRK1
NTRK2
NTRK3
NUP93
NUP98
P2RY8
PAG1
PAK3
PALB2
PASK
PAX5
PBRM1
PC
PCBP1
PCLO
PDCD1
PDCD11
PDCD1LG2 (PDL2)
PDGFRA
PDGFRB
PDK1
PHF6
PIK3CA
PIK3CG
PIK3R1
PIK3R2
PIM1
PLCG2
PMS2
PNRC1
POTI
PPP2R1A
PRDM1
PRKAR1A

TABLE 1A-continued

Exemplary genes with complete exonic coverage
in an exemplary DNA-seq target capture reagent PRKDC
PRSS8
PTCH1
PTEN
PTPN11
PTPN2
PTPN6 (SHP-1)
PTPRO
RAD21
RAD50
RAD51
RAF1
RARA
RASGEF1A
RB1
REL
RELN
RET
RHOA
RICTOR
RNF43
ROS1
RPTOR
RUNX1
S1PR2
SDHA
SDHB
SDHC
SDHD
SERP2
SETBP1
SETD2
SF3B1
SGK1
SH2B3
SMAD2
SMAD4
SMARCA1
SMARCA4
SMARCB1
SMC1A
SMC3
SMO
SOCS1
SOCS2
SOCS3
SOX10
SOX2
SPEN
SPOP
SRC TABLE 1A-continued Exemplary genes with complete exonic coverage
in an exemplary DNA-seq target capture reagent SRSF2
STAG2
STAT3
STAT4
STAT5A
STAT5B
STAT6
STK11
SUFU
SUZ12
TAF1
TBL1XR1
TCF3
TCE1A
TET2
TGFBR2
TLL2
TMEM30A
TMSB4XP8 (TMSL3)
TNFAIP3
TNFRSF11A
TNFRSF14
TNFRSF17
TOP1
TP53
TP63
TRAF2
TRAF3
TRAF5
TSC1
TSC2
TSHR
TUSC3
TYK2
U2AF1
U2AF2
VHL
WDR90
WHSC1 (MMSET or NSD2)
WISP3
WT1
XBP1
XPO1
YY1AP1
ZMYM3
ZNF217
ZNF24 (ZSCAN3)
ZNF703
ZRSR2

TABLE 1B

| Select DNA rearrangements | | | | | | | | | |
|---|---|---|---|---|---|---|---|---|---|
| ALK | BCL2 | BCL6 | BCR | BRAF | CCND1 | CRLF2 | EGFR | EPOR | ETV1 |
| ETV4 | ETV5 | ETV6 | EWSR1 | FGFR2 | IGH | IGK | IGL | JAK1 | JAK2 |
| KMT2A(MLL) | MYC | NTRK1 | PDGFRA | PDGFRB | RAFI | RARA | RET | ROS1 | TMPRSS2 |
| TRG | | | | | | | | | |

TABLE 1C

| Select RNA gene fusions | | | | | | | | | |
|---|---|---|---|---|---|---|---|---|---|
| ABI1 | ABL1 | ABL2 | ACSL6 | AFF1 | AFF4 | ALK | ARHGAP26 (GRAF) | ARHGEF12 | ARID1A |
| ARNT | ASXL1 | ATF1 | ATG5 | ATIC | BCL10 | BCL11A | BCL11B | BCL2 | BCL3 |
| BCL6 | BCL7A | BCL9 | BCOR | BCR | BIRC3 | BRAF | BTG1 | CAMTA1 | CARS |
| CBFA2T3 | CBFB | CBL | CCND1 | CCND2 | CCND3 | CD274 (PD-L1) | CDK6 | CDX2 | CHIC2 |
| CHN1 | CIC | CIITA | CLP1 | CLTC | CLTCL1 | CNTRL (CEP110) | COL1A1 | CREB3L1 | CREB3L2 |

TABLE 1C-continued

| Select RNA gene fusions | | | | | | | | | |
|---|---|---|---|---|---|---|---|---|---|
| CREBBP | CRLF2 | CSF1 | CTNNB1 | DDIT3 | DDX10 | DDX6 | DEK | DUSP22 | EGFR |
| EIF4A2 | ELF4 | ELL | ELN | EML4 | EP300 | EPOR | EPS15 | ERBB2 | ERG |
| ETS1 | ETV1 | ETV4 | ETV5 | ETV6 | EWSR1 | FCGR2B | FCRL4 | FEV | FGFR1 |
| FGFR1OP | FGFR2 | FGFR3 | FLI1 | FNBP1 | FOXO1 | FOXO3 | FOXO4 | FOXP1 | FSTL3 |
| FUS | GAS7 | GLI1 | GMPS | GPHN | HERPUD1 | HEY1 | HIP1 | HIST1H41 | HLF |
| HMGA1 | HMGA2 | HOXA11 | HOXA13 | HOXA3 | HOXA9 | HOXC11 | HOXC13 | HOXD11 | HOXD13 |
| HSP90AA1 | HSP90AB1 | IGH | IGK | IGL | IKZF1 | IL21R | IL3 | IRF4 | ITK |
| JAK1 | JAK2 | JAK3 | JAZF1 | KAT6A (MYST3) | KDSR | KIF5B | KMT2A (MLL) | LASP1 | LCP1 |
| LMO1 | LMO2 | LPP | LYL1 | MAF | MAFB | MALT1 | MDS2 | MECOM | MKL1 |
| MLF1 | MLLT1 (ENL) | MLLT10 (AF10) | MLLT3 | MLLT4 (AF6) | MLLT6 | MN1 | MNX1 | MSI2 | MSN |
| MUC1 | MYB | MYC | MYH11 | MYH9 | NACA | NBEAP1 (BCL8) | NCOA2 | NDRG1 | NF1 |
| NF2 | NFKB2 | NIN | NOTCH1 | NPM1 | NR4A3 | NSD1 | NTRK1 | NTRK2 | NTRK3 |
| NUMA1 | NUP214 | NUP98 | NUTM2A | OMD | P2RY8 | PAFAH1B2 | PAX3 | PAX5 | PAX7 |
| PBX1 | PCM1 | PCSK7 | PDCD1LG2 (PD-L2) | PDE4DIP | PDGFB | PDGFRA | PDGFRB | PER1 | PHF1 |
| PICALM | PIM1 | PLAG1 | PML | POU2AF1 | PPP1CB | PRDM1 | PRDM16 | PRRX1 | PSIP1 |
| PTCH1 | PTK7 | RABEP1 | RAF1 | RALGDS | RAP1GDS1 | RARA | RBM15 | RET | RHOH |
| RNF213 | ROS1 | RPL22 | RPN1 | RUNX1 | RUNX1T1 (ETO) | RUNX2 | SEC31A | SEPT5 | SEPT6 |
| SEPT9 | SET | SH3GL1 | SLC1A2 | SNX29 (RUNDC2A) | SRSF3 | SS18 | SSX1 | SSX2 | SSX4 |
| STAT6 | STL | SYK | TAF15 | TAL1 | TAL2 | TBL1XR1 | TCF3(E2A) | TCL1A (TCL1) | TEC |
| TET1 | TFE3 | TFG | TFPT | TFRC | TLX1 | TLX3 | TMPRSS2 | TNFRSF11A | TOP1 |
| TP63 | TPM3 | TPM4 | TRIM24 | TRIP11 | TTL | TYK2 | USP6 | WHSC1 (MMSET) | or |
| NSD2 | WHSC1L1 | YPEL5 | ZBTB16 | ZMYM2 | ZNF384 | ZNF52 | | | |

TABLE 2A

| Exemplary genes with select introns covered in an exemplary DNA-seq target capture reagent | | | | | | | | | |
|---|---|---|---|---|---|---|---|---|---|
| ABL1 | ABL2 | ACVR1B | AKT1 | AKT2 | AKT3 | ALK | AMER1 (FAM123B) | APC | AR |
| ARAF | ARFRP1 | ARID1A | ARID1B | ARID2 | ASXL1 | ATM | ATR | ATRX | AURKA |
| AURKB | AXIN1 | AXL | BAP1 | BARD1 | BCL2 | BCL2L1 | BCL2L2 | BCL6 | BCOR |
| BCORL1 | BLM | BRAF | BRCA1 | BRCA2 | BRD4 | BRIP1 | BTG1 | BTK | C11orf30 (EMSY) |
| CARD11 | CBFB | CBL | CCND1 | CCND2 | CCND3 | CCNE1 | CD274 (PD-L1) | CD79A | CD79B |
| CDC73 | CDH1 | CDK12 | CDK4 | CDK6 | CDK8 | CDKN1A | CDKN1B | CDKN2A | CDKN2B |
| CDKN2C | CEBPA | CHD2 | CHD4 | CHEK1 | CHEK2 | CIC | CREBBP | CRKL | CRLF2 |
| CSF1R | CTCF | CTNNA1 | CTNNB1 | CUL3 | CYLD | DAXX | DDR2 | DICER1 | DNMT3A |
| DOT1L | EGFR | EP300 | EPHA3 | EPHA5 | EPHA7 | EPHB1 | ERBB2 | ERBB3 | ERBB4 |
| ERG | ERRFI1 | ESR1 | EZH2 | FAM46C | FANCA | FANCC | FANCD2 | FANCE | FANCF |
| FANCG | FANCL | FAS | FAT1 | FBXW7 | FGF10 | FGF14 | FGF19 | FGF23 | FGF3 |
| FGF4 | FGF6 | FGFR1 | FGFR2 | FGFR3 | FGFR4 | FH | FLCN | FLT1 | FLT3 |
| FLT4 | FOXL2 | FOXP1 | FRS2 | FUBP1 | GABRA6 | GATA1 | GATA2 | GATA3 | GATA4 |
| GATA6 | GID4 (C17orf39) | GLI1 | GNA11 | GNA13 | GNAQ | GNAS | GPR124 | GRIN2A | GRM3 |
| GSK3B | H3F3A | HGF | HNF1A | HRAS | HSD3B1 | HSP90AA1 | IDH1 | IDH2 | IGF1R |
| IGF2 | IKBKE | IKZF1 | IL7R | INHBA | INPP4B | IRF2 | IRF4 | IRS2 | JAK1 |
| JAK2 | JAK3 | JUN | KAT6A (MYST3) | KDM5A | KDM5C | KDM6A | KDR | KEAP1 | KEL |
| KIT | KLHL6 | KMT2A (MLL) | KMT2C (MLL3) | KMT2D (MLL2) | KRAS | LMO1 | LRP1B | LYN | LZTR1 |
| MAGI2 | MAP2K1 (MEK1) | MAP2K2 (MEK2) | MAP2K4 | MAP3K1 | MCL1 | MDM2 | MDM4 | MED12 | MEF2B |
| MEN1 | MET | MITF | MLH1 | MPL | MRE11A | MSH2 | MSH6 | MTOR | MUTYH |
| MYC | MYCL (MYCL1) | MYCN | MYD88 | NF1 | NF2 | NFE2L2 | NFKBIA | NKX2-1 | NOTCH1 |
| NOTCH2 | NOTCH3 | NPM1 | NRAS | NSD1 | NTRK1 | NTRK2 | NTRK3 | NUP93 | PAK3 |
| PALB2 | PARK2 | PAX5 | PBRM1 | PDCD1LG2 (PD-L2) | PDGFRA | PDGFRB | PDK1 | PIK3C2B | PIK3CA |
| PIK3CB | PIK3CG | PIK3R1 | PIK3R2 | PLCG2 | PMS2 | POLD1 | POLE | PPP2R1A | PRDM1 |
| PREX2 | PRKAR1A | PRKCI | PRKDC | PRSS8 | PTCH1 | PTEN | PTPN11 | QKI | RAC1 |
| RAD50 | RAD51 | RAF1 | RANBP2 | RARA | RB1 | RBM10 | RET | RICTOR | RNF43 |
| ROS1 | RPTOR | RUNX1 | RUNX1T1 | SDHA | SDHB | SDHC | SDHD | SETD2 | SF3B1 |
| SLIT2 | SMAD2 | SMAD3 | SMAD4 | SMARCA4 | SMARCB1 | SMO | SNCAIP | SOCS1 | SOX10 |
| SOX2 | SOX9 | SPEN | SPOP | SPTA1 | SRC | STAG2 | STAT3 | STAT4 | STK11 |
| SUFU | SYK | TAF1 | TBX3 | TERC | TERT (Promoter only) | | TET2 | TGFBR2 | TNFAIP3 |

TABLE 2A-continued

| Exemplary genes with select introns covered in an exemplary DNA-seq target capture reagent | | | | | | | | | |
|---|---|---|---|---|---|---|---|---|---|
| TNFRSF14 | TOP1 | TOP2A | TP53 | TSC1 | TSC2 | TSHR | U2AF1 | VEGFA | VHL |
| WISP3 | WT1 | XPO1 | ZBTB2 | ZNF217 | ZNF703 | | | | |

TABLE 2B

| Select rearrangements | | | | | | | | | |
|---|---|---|---|---|---|---|---|---|---|
| ALK | BCL2 | BCR | BRAF | BRCA1 | BRCA2 | BRD4 | EGFR | ETV1 | ETV4 |
| ETV5 | ETV6 | FGFR1 | FGFR2 | FGFR3 | KIT | MSH2 | MYB | MYC | NOTCH2 |
| NTRK1 | NTRK2 | PDGFRA | RAF1 | RARA | RET | ROS1 | TMPRSS2 | | |

TABLE 3A

| Exemplary genes targeted in an exemplary RNA-seq target capture reagent | | | |
|---|---|---|---|
| BRCA1 | CRKL | MDM2 | SMO |
| BRCA2 | EGFR | MET | TP53 |
| CCND1 | ERBB2 | MYC | VEGFA |
| CD274 (PD-L1) | ERRFI1 | MYCN | |
| CDH1 | FGFR1 | NF1 | |
| CDK4 | FGFR2 | PDCD1LG2 (PD-L2) | |
| CDK6 | FOXL2 | PTEN | |
| CDKN2A | KRAS | PTPN11 | |

TABLE 3B

| Select Exons | | | | | | | | | |
|---|---|---|---|---|---|---|---|---|---|
| ABL1 | AKT1 | ALK | ARAF | BRAF | BTK | CTNNB1 | DDR2 | ESR1 | EZH2 |
| FGFR3 | FLT3 | GNA11 | GNAQ | GNAS | HRAS | IDH1 | IDH2 | JAK2 | JAK3 |
| KIT | MAP2K1 (MEK1) | MAP2K2 (MEK2) | MPL | MTOR | MYD88 | NPM1 | NRAS | PDGFRA | PDGFRB |
| PIK3CA | RAF1 | RET | TERT | | | | | | |

TABLE 3C

| Select rearrangements | | |
|---|---|---|
| ALK | FGFR3 | RET |
| EGFR | PDGFRA | ROS1 |

TABLE 3D

| Exemplary genes with exonic coverage in an exemplary DNA-seq target capture reagent | | | | | | | | | |
|---|---|---|---|---|---|---|---|---|---|
| ABL1 | AKT1 | ALK | ARAF | BRAF | BTK | CTNNB1 | DDR2 | ESR1 | EZH2 |
| Exons 4-9 | Exon 3 | Exons 20-29 | Exons 4, 5, 7, 11, 13, 15, 16 | Exons 11-18 | Exons 12, 15 | Exon 3 | Exons 5, 17, 18 | Exons 4-8 | Exons 4, 16, 18 |
| FGFR3 | FLT3 | GNA11 | GNAQ | GNAS | HRAS | IDH1 | IDH2 | JAK2 | JAK3 |
| Exons 7, 9, 14 | Exons 14, 15, 20 | Exons 4, 5 | Exons 4, 5 | Exons 1, 8 | Exons 2, 3 | Exon 4 | Exon 4 | Exon 14 | Exons 5, 11-13, 15, 16 |
| KIT | MAP2K1 (MEK1) | MAP2K2 (MEK2) | MPL | MTOR | MYD88 | NPM1 | NRAS | PDGFRA | PDGFRB |
| Exons 8, 9, 11-13, 17 | Exons 2, 3 | Exons 2-4, 6, 7 | Exon 10 | Exons 19, 30, 39, 40, 43-45, 47, 48, 53, 56 | Exon 4 | Exons 4-6, 8, 10 | Exons 2, 3 | Exons 12, 18 | Exons 12-21, 23 |
| PIK3CA | RAF1 | RET | ROS1 | TERT | | | | | |
| Exons 2, 3, 5-8, 10, 14, 19, 21 | Exons 3-7, 10, 14, 15, 17 | Exons 11, 13-16 | Exons 36-38, 40 | (promoter only) | | | | | |

TABLE 3E

| Exemplary genes with complete coding sequence coverage | | | | | | | | | |
|---|---|---|---|---|---|---|---|---|---|
| APC | AR | ATM | BRCA1 | BRCA2 | CCND1 | CD274 (PD-1) | CDH1 | CDK4 | CDK6 |
| CDK12 | CDKN2A | CHEK2 | CRKL | EGFR | ERBB2 | ERRF11 | FGFR1 | FGFR2 | FOXL2 |
| KRAS | MDM2 | MET | MYC | MYCN | NF1 | PALB2 | PDCD1LG2 (PD-L2) | PTEN | PTPN11 |
| RB1 | SMO | STK11 | TP53 | VEGFA | | | | | |

TABLE 4A

| Additional exemplary genes with complete exonic coverage in an exemplary DNA-seq target capture reagent | | | | | | | | | |
|---|---|---|---|---|---|---|---|---|---|
| ABL1 | ACVR1B | AKT1 | AKT2 | AKT3 | ALK | ALOX12B | AMER1 (FAM123B) | APC | AR |
| ARAF | ARFRP1 | ARID1A | ASXL1 | ATM | ATR | ATRX | AURKA | AURKB | AXIN1 |
| AXL | BAP1 | BARD1 | BCL2 | BCL2L1 | BCL2L2 | BCL6 | BCOR | BCORL1 | BRAF |
| BRCA1 | BRCA2 | BRD4 | BRIP1 | BTG1 | BTG2 | BTK | C11orf30 (EMSY) | CALR | CARD11 |
| CASP8 | CBFB | CBL | CCND1 | CCND2 | CCND3 | CCNE1 | CD22 | CD274 (PD-L1) | CD70 |
| CD79A | CD79B | CDC73 | CDH1 | CDK12 | CDK4 | CDK6 | CDK8 | CDKN1A | CDKN1B |
| CDKN2A | CDKN2B | CDKN2C | CEBPA | CHEK1 | CHEK2 | CIC | CREBBP | CRKL | CSF1R |
| CSF3R | CTCF | CTNNA1 | CTNNB1 | CUL3 | CUL4A | CXCR4 | CYP17A1 | DAXX | DDR1 |
| DDR2 | DIS3 | DNMT3A | DOT1L | EED | EGFR | EP300 | EPHA3 | EPHB1 | EPHB4 |
| ERBB2 | ERBB3 | ERBB4 | ERCC4 | ERG | ERRFI1 | ESR1 | EZH2 | FAM46C | FANCA |
| FANCC | FANCG | FANCL | FAS | FBXW7 | FGF10 | FGF12 | FGF14 | FGF19 | FGF23 |
| FGF3 | FGF4 | FGF6 | FGFR1 | FGFR2 | FGFR3 | FGFR4 | FH | FLCN | FLT1 |
| FLT3 | FOXL2 | FUBP1 | GABRA6 | GATA3 | GATA4 | GATA6 | GID4 (C17orf39) | GNA11 | GNA13 |
| GNAQ | GNAS | GRM3 | GSK3B | H3F3A | HDAC1 | HGF | HNF1A | HRAS | HSD3B1 |
| ID3 | IDH1 | IDH2 | IGF1R | IKBKE | IKZF1 | INPP4B | IRF2 | IRF4 | IRS2 |
| JAK1 | JAK2 | JAK3 | JUN | KDM5A | KDM5C | KDM6A | KDR | KEAP1 | KEL |
| KIT | KLHL6 | KMT2A (MLL) | KMT2D (MLL2) | KRAS | LTK | LYN | MAF | MAP2K1 (MEK1) | MAP2K2 (MEK2) |
| MAP2K4 | MAP3K1 | MAP3K13 | MAPK1 | MCL1 | MDM2 | MDM4 | MED12 | MEF2B | MEN1 |
| MERTK | MET | MITF | MKNK1 | MLH1 | MPL | MRE11A | MSH2 | MSH3 | MSH6 |
| MST1R | MTAP | MTOR | MUTYH | MYC | MYCL (MYCL1) | MYCN | MYD88 | NBN | NF1 |
| NF2 | NFE2L2 | NFKBIA | NKX2-1 | NOTCH1 | NOTCH2 | NOTCH3 | NPM1 | NRAS | NT5C2 |
| NTRK1 | NTRK2 | NTRK3 | P2RY8 | PALB2 | PARK2 | PARP1 | PARP2 | PARP3 | PAX5 |
| PBRM1 | PDCD1 (PD-1) | PDCD1LG2 (PD-L2) | PDGFRA | PDGFRB | PDK1 | PIK3C2B | PIK3C2G | PIK3CA | PIK3CB |
| PIK3R1 | PIM1 | PMS2 | POLD1 | POLE | PPARG | PPP2R1A | PPP2R2A | PRDM1 | PRKAR1A |
| PRKCI | PTCH1 | PTEN | PTPN11 | PTPRO | QKI | RAC1 | RAD21 | RAD51 | RAD51B |
| RAD51C | RAD51D | RAD52 | RAD54L | RAF1 | RARA | RB1 | RBM10 | REL | RET |
| RICTOR | RNF43 | ROS1 | RPTOR | SDHA | SDHB | SDHC | SDHD | SETD2 | SF3B1 |
| SGK1 | SMAD2 | SMAD4 | SMARCA4 | SMARCB1 | SMO | SNCAIP | SOCS1 | SOX2 | SOX9 |
| SPEN | SPOP | SRC | STAG2 | STAT3 | STK11 | SUFU | SYK | TBX3 | TEK |
| TET2 | TGFBR2 | TIPARP | TNFAIP3 | TNFRSF14 | TP53 | TSC1 | TSC2 | TYRO3 | U2AF1 |
| VEGFA | VHL | WHSC1 (MMSET) | WHSC1L1 | WT1 | XPO1 | XRCC2 | ZNF217 | ZNF703 | |

TABLE 4B

| Select rearrangements | | | | | | | | | |
|---|---|---|---|---|---|---|---|---|---|
| ALK | BCL2 | BCR | BRAF | BRCA1 | BRCA2 | CD74 | EGFR | ETV4 | ETV5 |
| ETV6 | EWSR1 | EZR | FGFR1 | FGFR2 | FGFR3 | KIT | KMT2A (MLL) | MSH2 | MYB |
| MYC | NOTCH2 | NTRK1 | NTRK2 | NUTM1 | PDGFRA | RAF1 | RARA | RET | ROS1 |
| RSPO2 | SDC4 | SLC34A2 | TERC | TERT (promoter only) | TMPRSS2 | | | | |

TABLE 5A

| Exemplary genes with complete or select exonic coverage | | | | | | | | | |
|---|---|---|---|---|---|---|---|---|---|
| AKT1 | ALK | APC | AR | ARAF | ARID1A | ATM | BRAF | BRCA1 | BRCA2 |
| CCND1 | CCND2 | CCNE1 | CDH1 | CDK4 | CDK6 | CDKN2A | CTNNB1 | DDR2 | EGFR |
| ERBB2 (HER2) | ESR1 | EZH2 | FBXW7 | FGFR1 | FGFR2 | FGFR3 | GATA3 | GNA11 | GNAQ |
| GNAS | HNF1A | HRAS | IDH1 | IDH2 | JAK2 | JAK3 | KIT | KRAS | MAP2K1 (MEK1) |
| MAP2K2 (MEK2) | MAPK1 (ERK2) | MAPK3 (ERK1) | MET | MLH1 | MPL | MTOR | MYC | NF1 | NFE2L2 |
| NOTCH1 | NPM1 | NRAS | NTRK1 | NTRK3 | PDGFRA | PIK3CA | PTEN | PTPN11 | RAF1 |
| RB1 | RET | RHEB | RHOA | RIT1 | ROS1 | SMAD4 | SMO | STK11 | TERT |
| TP53 | SC1 | VHL | TSC1 | | | | | | |

Additional exemplary genes are described, e.g., in Tables 1-11 of International Application Publication No. WO2012/092426, the content of which is incorporated by reference in its entirety.

Applications of the foregoing methods include, but are not limited to, using a library of oligonucleotides containing all known sequence variants (or a subset thereof) of a particular gene or genes for sequencing in medical specimens.

OTHER EMBODIMENTS

Alternatively, or in combination with the methods described herein, in some embodiments, the method further comprises one or more (e.g., 2, 3, 4, 5, 6, 7, or all) of (a)-(h):

(a) providing nucleic acid molecules (e.g., cfDNA) from a sample (e.g., a blood sample), e.g., using a plurality of target capture reagents described herein;

(b) attaching adapters comprising barcodes that comprises a plurality of different barcode sequences to the nucleic acid molecules, thereby generating tagged parent nucleic acid molecules;

(c) amplifying the tagged parent nucleic acid molecules to produce amplified tagged progeny nucleic acid molecules;

(d) sequencing the amplified tagged progeny nucleic acid molecules to produce a plurality of sequence reads from each of the tagged parent nucleic acid molecules, wherein each sequence read of the plurality of sequence reads comprises a barcode sequence and a sequence derived from a nucleic acid molecule;

(e) mapping sequence reads of the plurality of sequence reads to one or more reference sequences;

(f) grouping the sequence reads mapped in e) into families based at least on barcode sequences of the sequence reads, each of the families comprising sequence reads comprising the same barcode sequence, whereby each of the families comprises sequence reads amplified from the same tagged parent nucleic acid molecule;

(g) at each of a plurality of subject intervals in the one or more reference sequences, collapsing sequence reads in each family to yield a mutation call for each family at the subject interval; or (h) detecting, at one or more subject intervals, one or more genomic aberrations, e.g., an indel, copy number variation, transversion, translocation, inversion, deletion, aneuploidy, partial aneuploidy, polyploidy, chromosomal instability, chromosomal structure alteration, gene fusion, chromosome fusion, gene truncation, gene amplification, gene duplication, chromosomal lesion, DNA lesion, abnormal change in nucleic acid chemical modification, abnormal change in epigenetic pattern, abnormal change in nucleic acid methylation, or a combination thereof.

Alternatively, or in combination with the methods described herein, in some embodiments, the method further comprises one or more (e.g., 2, 3, 4, 5, 6, 7, 8, or all) of (a)-(i), e.g., to quantify a genomic alteration (e.g., a single nucleotide variant):

(a) providing nucleic acid molecules (e.g., cfDNA) from a sample (e.g., a blood sample), e.g., using a plurality of target capture reagents described herein;

(b) attaching adapters comprising barcodes that comprises distinct barcode sequences to said nucleic acid molecules to generate tagged parent nucleic acid molecules;

(c) amplifying the tagged parent nucleic acid molecules to produce amplified tagged progeny nucleic acid molecules;

(d) sequencing the amplified tagged progeny nucleic acid molecules to produce a plurality of sequence reads from each parent nucleic acid molecules, wherein each sequence read comprises a barcode sequence and a sequence derived from the nucleic acid molecules;

(e) grouping the plurality of sequence reads produced from each tagged parent nucleic acid molecule into families based on (i) the barcode sequence and (ii) one or more of: sequence information at a beginning of the sequence derived from the nuclei acid, sequence information at an end of the sequence derived from the nucleic acid, or length of the sequence read, wherein each family comprises sequence reads of tagged progeny nucleic acid molecules amplified from a unique nucleic acid molecule among the tagged parent nucleic acid molecules;

(f) comparing the sequence reads grouped within each family to each other to determine consensus sequences for each family, wherein each of the consensus sequences corresponds to a unique nucleic acid molecule among the tagged parent nucleic acid molecules;

(g) providing one or more reference sequences comprising one or more subject intervals;

(h) identifying consensus sequences that map to a given subject interval of said one or more subject intervals; or (i) calculating a number of consensus sequences that map to the given subject interval that comprises a genomic alteration, thereby quantifying the genomic alteration in the sample.

Alternatively, or in combination with the methods described herein, in some embodiments, the method further comprises one or more (e.g., 2, 3, 4, 5, 6, 7, or all) of (a)-(h):

(a) providing nucleic acid molecules (e.g., cfDNA) from a sample (e.g., a blood sample), e.g., using a plurality of target capture reagents described herein;

(b) converting the plurality of nucleic acid molecules into a plurality of tagged parent nucleic acid molecules, wherein each of the tagged parent nucleic acid molecules comprises (i) a sequence from a nucleic acid molecule of the plurality of nucleic acid molecules, and (ii) an identifier sequence comprising one or more barcodes;

(c) amplifying the plurality of tagged parent nucleic acid molecules to produce a corresponding plurality of amplified progeny nucleic acid molecules;

(d) sequencing the plurality of amplified progeny nucleic acid molecules to produce a set of sequence reads;

(e) mapping sequence reads of the set of sequence reads to one or more reference sequences;

(f) grouping the sequence reads into families, each of the families comprising sequence reads comprising the same identifier sequence and having the same start and stop positions, wherein each of the families comprises sequence reads amplified from the same tagged parent nucleic acid molecule;

(g) at each subject interval of a plurality of subject intervals in the one or more reference sequences, collapsing sequence reads in each family to yield a mutation call for each family at the subject interval; or (h) determining a frequency of one or more mutations called at the subject interval from among the families.

Alternatively, or in combination with the methods described herein, in some embodiments, the method further comprises one or more (e.g., 2, 3, 4, 5, or all) of (a)-(f), e.g., to detect copy number variation:

(a) providing nucleic acid molecules (e.g., cfDNA) from a sample (e.g., a blood sample), e.g., using a plurality of target capture reagents described herein;

(b) sequencing the nucleic acid molecules, wherein each of the nucleic acid molecules generates a plurality of sequence reads;

(c) filtering out reads that fail to meet a set accuracy, quality score, or mapping score threshold;

(d) mapping the plurality of sequence reads to a reference sequence;

(e) quantifying mapped reads or unique sequence reads in a plurality of regions of the reference sequence; and (f) determining copy number variation in one or more of the plurality of predefined regions by: i) normalizing a number of reads in the plurality of regions to each other, or a number of unique sequence reads in the plurality of regions to each other; and/or ii) processing a number of reads in the plurality of regions or a number of unique sequence reads in the plurality of regions with numbers obtained from a control sample.

Alternatively, or in combination with the methods described herein, in some embodiments, the method further comprises one or more (e.g., 2, 3, 4, 5, 6, 7, or all) of (a)-(h), e.g., to detect copy number variation:

(a) providing nucleic acid molecules (e.g., cfDNA) from a sample (e.g., a blood sample), e.g., using a plurality of target capture reagents described herein;

(b) sequencing the nucleic acid molecules, wherein each of the nucleic acid molecules generates a plurality of sequence reads;

(c) filtering out reads that fail to meet a set accuracy, quality score, or mapping score threshold;

(d) mapping sequence reads derived from the sequencing onto a reference sequence;

(e) determining unique sequence reads corresponding to the nucleic acid molecules from among the sequence reads;

(f) identifying a subset of mapped unique sequence reads that include a variant as compared to the reference sequence at each mappable base position;

(g) for each mappable base position, calculating a ratio of (a) a number of mapped unique sequence reads that include a variant as compared to the reference sequence, to (b) a number of total unique sequence reads for each mappable base position; and (h) processing the ratio with a similarly derived number from a reference sample.

Alternatively, or in combination with the methods described herein, in some embodiments, the method further comprises one or more (e.g., 2, 3, 4, 5, 6, 7, or all) of (a)-(h):

(a) tagging double-stranded DNA molecules (e.g., cfDNA) in a sample (e.g., a blood sample) from a subject with a set of duplex tags, wherein the set of duplex tags comprises a plurality of different molecular barcodes, wherein each duplex tag of the set of duplex tags differently tags complementary strands of a double-stranded DNA molecule of the double-stranded DNA molecules in the sample to provide tagged strands, and wherein the tagging is performed with at least a 10X excess of duplex tags as compared to the double-stranded DNA molecules, which excess of duplex tags is sufficient to tag at least 20% of the double-stranded DNA molecules in the sample from the subject;

(b) for each genetic locus in a set of one or more genetic loci in a reference genome, selectively enriching the tagged strands for a subset of the tagged strands that maps to the genetic locus, to provide enriched tagged strands, e.g., using a plurality of target capture reagents described herein;

(c) sequencing at least a portion of the enriched tagged strands to generate a plurality of raw sequence reads from the sample from the subject;

(d) grouping the plurality of raw sequence reads into a plurality of families, each family comprising raw sequence reads generated from a same parent polynucleotide, which grouping is based on (i) molecular barcodes associated with the parent polynucleotides and (ii) information from beginning and/or end portions of the raw sequences of the parent polynucleotides;

(e) collapsing the plurality of raw sequence reads grouped into the plurality of families into a plurality of consensus sequence reads, each consensus sequence read of the plurality of consensus sequence reads (i) comprising a plurality of consensus bases for each genetic locus in the set of one or more genetic loci and (ii) being representative of single strands of the double-stranded DNA molecules;

(f) for each genetic locus in the set of one or more genetic loci, calculating a first quantitative measure of the enriched tagged strands that map to the genetic locus for which complementary strands are detected in the plurality of consensus sequence reads;

(g) for each genetic locus in the set of one or more genetic loci, calculating a second quantitative measure of the enriched tagged strands that map to the genetic locus for which only one strand among complementary strands is detected in the plurality of consensus sequence reads; or (h) for each genetic locus in the set of one or more genetic loci, calculating a third quantitative measure of the enriched tagged strands that map to the genetic locus for which neither complementary strand is detected in the plurality of consensus sequence reads, wherein the third quantitative measure is calculated based at least in part on the first and second quantitative measures, thereby detecting the double-stranded DNA molecules in the sample from the subject.

Alternatively, or in combination with the methods described herein, in some embodiments, the method further comprises one or both of (a)-(b), e.g., for enriching for multiple genomic regions:

(a) bringing a predetermined amount of nucleic acid from a sample in contact with a plurality of target capture reagents described herein comprising:

(i) a first plurality of target capture reagents that selectively hybridizes to a first set of genomic regions of the nucleic acid from the sample, which first plurality of target capture reagents is provided at a first concentration that is less than a saturation point of the first plurality of target capture reagents, and (ii) a second plurality of target capture reagents that selectively hybridizes to a second set of genomic regions of the nucleic acid from the sample, which second plurality of target capture reagents is provided at a second concentration that is at or above a saturation point of the second plurality of target capture reagents; and (b) enriching the nucleic acid from the sample for the first set of genomic regions and the second set of genomic regions, thereby producing an enriched nucleic acid.

Alternatively, or in combination with the methods described herein, in some embodiments, the method further comprises one or more (e.g., 2, 3, 4, or all) of (a)-(e):

(a) providing a plurality of target capture reagent mixtures, wherein each of the plurality of target capture reagent mixtures comprises a first plurality of target capture reagents that selectively hybridizes to a first set of genomic regions and a second plurality target capture reagents that selectively hybridizes to a second set of genomic regions, wherein the first plurality of target capture reagents is at different concentrations across the plurality of target capture reagent mixtures and the second plurality of target capture reagents is at the same concentration across the plurality of target capture reagent mixtures;

(b) contacting each of the plurality of target capture reagent mixtures with a sample (e.g., a blood sample) to capture nucleic acids from the sample with the first plurality of target capture reagents and the second plurality of target capture reagents, wherein the second plurality of target capture reagents in each target capture reagent mixture is provided at a first concentration that is at or above a saturation point of the second plurality of target capture reagents, wherein nucleic acids from the sample are captured by the first plurality of target capture reagents and the second plurality of target capture reagents;

(c) sequencing a portion of the nucleic acids captured with each target capture reagent mixture to produce sets of sequence reads within an allocated number of sequence reads;

(d) determining the read depth of sequence reads for the first plurality of target capture reagents and the second plurality of target capture reagents for each target capture reagent mixture; or (e) identifying at least one target capture reagent mixture that provides read depths for the second set of genomic regions;

wherein the read depths for the second set of genomic regions provides a sensitivity of detecting of a genetic variant of at least 0.0001% minor allele frequency (MAF).

Alternatively, or in combination with the methods described herein, in some embodiments, the method further comprises one or more (e.g., 2 or all) of (a)-(c):

(a) non-uniquely tagging a population of extracellular polynucleotides obtained from a bodily sample from a subject to produce a population of non-uniquely tagged extracellular polynucleotides;

(b) sequencing the population of non-uniquely tagged extracellular polynucleotides to produce a base call at a mappable position in the non-uniquely tagged extracellular polynucleotides; and (c) for the base call at the mappable position, measuring a frequency of unique molecules containing the base call in relation to the total number of unique molecules having a base call;

wherein a frequency of unique molecules containing the base call at the mappable position that is above a set measure of deviation from a plurality of reference sequences indicates a rare mutation at the mappable position.

Other embodiments are described in U.S. Pat. Nos. U.S. Pat. Nos. 9,598,731, 9,834,822, 9,840,743, 9,902,992, 9,920,366, 9,850,523, and 10,041,127 the contents of each of which are hereby incorporated by reference in their entity.

In embodiments of a method described herein a step or parameter in the method is used to modify a downstream step or parameter in the method.

In an embodiment, a characteristic of the sample is used to modify a downstream step or parameter in one or more or all of: isolation of nucleic acid from said sample; library construction; design or selection of target capture reagents (e.g., baits); hybridization conditions; sequencing; read mapping; selection of a mutation calling method; mutation calling; or mutation annotation.

In an embodiment, a characteristic of an isolated tumor, or control, nucleic acid is used to modify a downstream step or parameter in one or more or all of: isolation of nucleic acid from said sample; library construction; design or selection of target capture reagents (e.g., baits); hybridization conditions; sequencing; read mapping; selection of a mutation calling method; mutation calling; or mutation annotation.

In an embodiment, a characteristic of a library is used to modify a downstream step or parameter in one or more or all of: re-isolation of nucleic acid from said sample; subsequent library construction; design or selection of target capture reagents (e.g., baits); hybridization conditions; sequencing; read mapping; selection of a mutation calling method; mutation calling; or mutation annotation.

In an embodiment, a characteristic of a library catch is used to modify a downstream step or parameter in one or more or all of: re-isolation of nucleic acid from said sample; subsequent library construction; design or selection of target capture reagents (e.g., baits); hybridization conditions; sequencing; read mapping; selection of a mutation calling method; mutation calling; or mutation annotation.

In an embodiment, a characteristic of the sequencing method is used to modify a downstream step or parameter in one or more or all of: re-isolation of nucleic acid from said sample; subsequent library construction; design or selection of target capture reagents (e.g., baits); subsequent determination of hybridization conditions subsequent sequencing; read mapping; selection of a mutation calling method; mutation calling; or mutation annotation.

In an embodiment, characteristic of the collection of mapped reads is used to modify a downstream step or parameter in one or more or all of: re-isolation of nucleic acid from said sample; subsequent library construction; design or selection of target capture reagents (e.g., baits); subsequent determination of hybridization conditions subsequent sequencing; subsequent read mapping; selection of a mutation calling method; mutation calling; or mutation annotation.

In an embodiment, the method comprises acquiring a value for a sample characteristic, e.g., acquiring a value: for the proportion of tumor cells in said sample; for the cellularity of said sample; or from an image of the sample. In embodiments, the method includes, responsive to said acquired value for a sample characteristic, selecting a parameter for: isolation of nucleic acid from a sample, library construction; design or selection of target capture reagents (e.g., baits); target capture reagent (e.g., bait)/ library nucleic acid molecule hybridization; sequencing; or mutation calling.

In an embodiment, the method further comprising acquiring a value for the amount of tumor tissue present in said sample, comparing said acquired value with a reference criterion, and if said reference criterion is met, accepting said sample, e.g., accepting said sample if said sample contains greater than 30%, 40% or 50% tumor cells. In an embodiment, a method further comprises acquiring a sub-sample enriched for tumor cells, e.g., by macrodissecting tumor tissue from said sample, from a sample that fails to meet the reference criterion.

In an embodiment, the method further comprising acquiring a value for the amount of tumor nucleic acids (e.g., DNA) present in said sample, comparing said acquired value with a reference criterion, and if said reference criterion is met, accepting said sample. In an embodiment, the method further comprises acquiring a sub-sample enriched for tumor nucleic acids, e.g., by macrodissecting tumor tissue from said sample, from a sample that fails to meet the reference criterion.

In an embodiment, a method further comprises providing an association of a tumor type, a gene, and a genetic alteration (a TGA) for a subject. In an embodiment, a method further comprises providing a database having a plurality of elements, wherein each element comprises a TGA.

In an embodiment, a method further comprises characterizing a TGA of a subject comprising: determining if said TGA is present in a database, e.g., a database of validated TGAs; associating information for the TGA from the database with said TGA (annotating) from said subject; and optionally, determining if a second or subsequent TGA for said subject is present in said database and if so associating information for the second or subsequent TGA from the database with said second TGA present in said patient. In an embodiment, the method further comprises memorializing the presence or absence of a TGA, and optionally an associated annotation, of a subject to form a report. In an embodiment, a method further comprises transmitting said report to a recipient party.

In an embodiment, a method further comprises characterizing a TGA of a subject comprising: determining if said TGA is present in a database, e.g., a database of validated TGAs; or determining if a TGA not in said database has a known clinically relevant gene or alteration and if so providing an entry for said TGA in said database. In an embodiment, the method further comprises memorializing the presence or absence of a mutation found in the DNA of the sample from a subject to form a report.

The present disclosure may be defined, e.g., in any of the following numbered embodiments.

1. A plurality of target capture reagents, comprising first target capture reagents (R1s) and second target capture reagents (R2s), wherein:

R1s comprise R1s that comprise a functional first member of a binding pair, and optionally, R1s that lack a functional first member of the binding pair; and R2s comprise R2s that comprise a functional first member of the binding pair and R2s that lack a functional first member of the binding pair;

wherein the first member of the binding pair is capable of binding to a second member of the binding pair disposed on substrate, and wherein the proportion of R1s that comprises a functional first member of the binding pair is greater than the proportion of R2s that comprise a functional first member of the binding pair.

2. The plurality of target capture reagents of embodiment 1, wherein the proportion of R1s that comprise a functional first member of the binding pair is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the proportion of R2s that comprise a functional first member of the binding pair.

3. The plurality of target capture reagents of embodiment 1 or 2, wherein each of the R1s is capable of forming a first fragment/first target capture reagent (F1/R1) hybrid, and each of the R2s is capable of forming a second fragment/second target capture reagent (F2/R2) hybrid, and wherein F1, F2, or both, comprises a subject interval from a gene described in Tables 1A-5A.

4. The plurality of target capture reagents of embodiment 3, wherein:

F1 comprises a high sequencing depth event; and

F2 comprises a low sequencing depth event, e.g., the level of which is associated with determination of one or more biomarkers, e.g., tumor mutational burden (TMB), or microsatellite instability (MSI).

5. The plurality of target capture reagents of any of the preceding embodiments, further comprising third target capture reagents (R3s), wherein R3s comprise R3s that comprise a functional first member of the binding pair and R3s that lack a functional first member of the binding pair;

wherein the first member of the binding pair is capable of binding to a second member of the binding pair disposed on substrate, and wherein the proportion of R2s that comprises a functional first member of the binding pair is greater than the proportion of R3s that comprise a functional first member of the binding pair.

6. The plurality of target capture reagents of any of the preceding embodiments, wherein each of the R3s is capable of forming a third fragment/first target capture reagent (F3/R3) hybrid, and wherein F3 comprises a subject interval from a gene described in Tables 1A-5A.

7. A method of analyzing a sample, comprising:

contacting a plurality of first fragment/first target capture reagent (F1/R1) hybrids with substrate to form F1/R1 hybrid/substrate complexes; and contacting a plurality of second fragment/second target capture reagent (F2/R2) hybrids with substrate to form F2/R2 hybrid/substrate complexes, wherein the proportion of F1/R1 hybrids which bind to substrate is greater than the proportion of F2/R2 hybrids which bind to substrate, thereby analyzing the sample.

8. The method of embodiment 7, wherein:

F1 comprises a high sequencing depth event; and

F2 comprises a low sequencing depth event, e.g., the level of which is associated with determination of one or more biomarkers, e.g., tumor mutational burden (TMB), or microsatellite instability (MSI).

9. The method of embodiment 7 or 8, wherein a portion of the R1s and a portion of the R2s comprise a functional first member of a binding pair, and wherein the first member of the binding pair is capable of binding to a second member of the binding pair disposed on substrate.

10. The method of any of embodiments 7-9, wherein a portion of the R1s, a portion of the R2s, or both, lack a functional first member of a binding pair, e.g., an altered or blocked first member that is not capable of binding, or has reduced binding affinity, to a second member of the binding pair disposed on substrate.

11. The method of any of embodiments 7-10, wherein:

the R1s comprise R1s that comprise a functional first member of a binding pair and R1s that lack a functional first member of the binding pair; and the R2s comprise R2s that comprise a functional first member of a binding pair and R2s that lack a functional first member of the binding pair.

12. The method of any of embodiments 7-11, wherein the proportion of R is that comprise a functional first member of the binding pair is greater than the proportion of R2s that comprise a functional first member of the binding pair.

13. The method of embodiment 11, wherein the proportion of R1s that comprise a functional first member of the binding pair is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the proportion of R2s that comprise a functional first member of the binding pair.

14. The method of any of embodiments 7-13, wherein the proportion of R1s that comprise a functional first member of the binding pair and the proportion of R2s that comprise a functional first member of the binding pair are such that, upon formation of the F1/R1 hybrid/substrate complexes and the F2/R2 hybrid/substrate complexes, the number of F1s in the F1/R1 hybrid/substrate complexes and the number of F2s in the F2/R2 hybrid/substrate complexes have one or both of the following relationships:

(i) the number of F1s is greater than, or is substantially the same as, the number of F2s; and/or (ii) the number of F1s comprising an alteration in a first subject interval is greater than, or is substantially the same as, the number of F2s comprising an alteration in a second subject interval.

15. The method of embodiment 14, wherein the number of F1s is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F2s.

16. The method of embodiment 14 or 15, wherein the number of F1s comprising an alteration in a first subject interval is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F2s comprising an alteration in a second subject interval.

17. The method of any of embodiments 14-16, wherein the first subject interval, the second subject interval, or both, is from a gene described in Tables 1A-5A.

18. The method of any of embodiments 14-17, wherein the alteration in the first subject interval is present at a mutant allele frequency of equal to or greater than about 0.1% (e.g., equal to or greater than about 0.2%, 0.3%, 0.4%, 0.5%, 0.6%, 0.7%, 0.8%, or 0.9%, e.g., about 0.1% to 0.9%, 0.2% to 0.8%, 0.3% to 0.7%, or 0.4% to 0.6%) in the sample.

19. The method of any of embodiments 14-18, wherein the alteration in the second subject interval is present at a mutant allele frequency of equal to or greater than about 1% (e.g., equal to or greater than about 2%, 3%, 4%, 5%, 6%, 7%, 8%, or 9%, e.g., about 1% to 9%, 2% to 8%, 3% to 7%, or 4% to 6%) in the sample.

20. The method of any of embodiments 7-19, wherein F1, F2, or both, comprises a subject interval from a gene described in Tables 1A-5A.

21. The method of embodiment 20, wherein the subject interval in F1 is sequenced to a first depth, and the subject interval in F2 is sequenced to a second depth, wherein the first depth is at least 1, 2, 3, 4, 5, 6, 7, 8, 9, or 10-fold greater than the second depth.

22. The method of any of embodiments 14-21, wherein F1 comprises a subject interval from a gene described in Tables 1A-5A, and wherein the subject interval comprises an alteration, e.g., a somatic alteration, e.g., a functional alteration in cancer.

23. The method of embodiment 17, wherein the subject interval is sequenced to at least about 5,000X depth.

24. The method of any of embodiments 7-23, wherein F2 comprises a subject interval from a gene described in Tables 1A-5A, and wherein the subject interval comprises an alteration, e.g., a somatic alteration, wherein the determination of the alteration is used for evaluating one or more genomic signatures, e.g., continuous/complex biomarkers.

25. The method of embodiment 24, wherein the subject interval is sequenced to at least about 800X but less than about 5,000X., e.g., for evaluating one or more genomic signatures, e.g., continuous/complex biomarkers.

26. The method of any of embodiments 7-25, further contacting a plurality of third fragment/third target capture reagent (F3/R3) hybrids with substrate to form F3/R3 hybrid/substrate complexes.

27. The method of embodiment 25 or 26, wherein R3s comprise R3s that comprise a functional first member of the binding pair and R3s that lack a functional first member of the binding pair.

28. The method of any of embodiments 26-27, wherein the proportion of R2s that comprise a functional first member of the binding pair is greater than the proportion of R3s that comprise a functional first member of the binding pair.

29. The method of any of embodiments 26-28, wherein the proportion of R2s that comprise a functional first member of the binding pair is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the proportion of R3s that comprise a functional first member of the binding pair.

30. The method of any of embodiments 26-29, wherein the proportion of R2s that comprise a functional first member of the binding pair and the proportion of R3s that comprise a functional first member of the binding pair are such that, upon formation of the F2/R2 hybrid/substrate complexes and the F3/R3 hybrid/substrate complexes, the number of F2s in the F2/R2 hybrid/substrate complexes and the number of F3s in the F3/R3 hybrid/substrate complexes have one or both of the following relationships:

(i) the number of F2s is greater than the number of F3s; and/or (ii) the number of F2s comprising an alteration in a second subject interval is greater than the number of F3s comprising an alteration in a third subject interval.

31. The method of embodiment 30, wherein the number of F2s is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F3s.

32. The method of embodiment 30 or 31, wherein the number of F2s comprising an alteration in a second subject interval is at least 0.5, 1, 2, 3, 4, 5, 6, 7, 8, 9, 10, 20, 30, 40, 50, 60, 70, 80, 90, 100, 200, 300, 400, 500, 600, 700, 800, 900, or 1,000-fold, greater than the number of F3s comprising an alteration in a third subject interval.

33. The method of any of embodiments 30-32, wherein the second subject interval, the third subject interval, or both, is from a gene described in Tables 1A-5A.

34. The method of any of embodiments 26-33, wherein one, two or all of F1, F2, or F3 comprises a subject interval from a gene described in Tables 1A-5A.

35. The method of embodiment 34, wherein the subject interval in F2 is sequenced to a second depth, and the subject interval in F3 is sequenced to a third depth, wherein the second depth is at least 1, 2, 3, 4, 5, 6, 7, 8, 9, or 10-fold greater than the third depth.

36. The method of any of embodiments 26-35, wherein F3 comprises a subject interval from a gene described in Tables 1A-5A, and wherein the subject interval comprises a germline alteration, e.g., a germline SNP.

37. The method of embodiment 36, wherein the subject interval is sequenced to at least about 100X depth but less than about 800X.

38. The method of any of embodiments 7-37, further comprising providing the sample from a subject.

39. The method of any of embodiments 7-38, wherein the sample comprises DNA, e.g., genomic DNA, e.g., cell-free DNA (cfDNA) or circulating tumor DNA (ctDNA).

40. The method of any of embodiments 7-39, wherein the sample comprises RNA, e.g., mRNA.

41. The method of embodiment 40, further comprising providing cDNA from RNA.

42. The method of any embodiments 7-41, further comprising obtaining, e.g., isolating, nucleic acids from the sample.

43. The method of any of embodiments 7-42, further comprising fragmenting nucleic acids in the sample to provide F1 and F2.

44. The method of any of embodiments 7-43, further comprising amplifying F1 to provide a plurality of F1s, and amplifying F2 to provide a plurality of F2s.

45. The method of any of embodiments 7-44, further comprising attaching adapter sequences to F1 and F2 to provide adapterized F1 (AF1) and adapterized F2 (AF2).

46. The method of any of embodiments 7-45, further comprising amplifying AF1 to provide a plurality of AF1s, and amplifying AF2 to provide a plurality of AF2s.

47. The method of any of embodiments 7-46, further comprising contacting a plurality of F1s to R1 to provide a plurality of F1/R1 hybrids, and contacting a plurality of F2s to R2 to provide a plurality of F2/R2 hybrids.

48. The method of any of embodiments 7-47, further comprising contacting a plurality of AF1s to R1 to provide a plurality of AF1/R1 hybrids, and contacting a plurality of AF2s to R2 to provide a plurality of AF2/R2 hybrids.

49. The method of any of embodiments 7-48, wherein:
contacting a plurality of F1/R1 hybrids with substrate to form F1/R1 hybrid/substrate complexes comprises contacting a plurality of AF1/R1 hybrids with substrate to form AF1/R1 hybrid/substrate complexes; and
contacting a plurality of F2/R2 hybrids with substrate to form F2/R2 hybrid/substrate complexes comprises contacting a plurality of AF2/R2 hybrids with substrate to form AF2/R2 hybrid/substrate complexes.

50. The method of any of embodiments 47-49, wherein the contacting occurs in solution.

51. The method of any of embodiments 47-49, wherein the contacting occurs on a solid surface.

52. The method of any of embodiments 8-51, wherein the first member of the binding pair comprises a biotin moiety, and wherein the second member of the binding pair comprises a streptavidin or avidin (or a modified version, e.g., NeutrAvidin or CaptAvidin) moiety.

53. The method of any of embodiments 8-51, wherein the first member of the binding pair comprises a digoxigenin moiety, and wherein the second member of the binding pair comprises an anti-digoxigenin antibody moiety.

54. The method of any of embodiments 8-51, wherein the first member of the binding pair comprises an FITC moiety, and wherein the second member of the binding pair comprises an anti-FITC antibody moiety.

55. The method of any of embodiments 8-51, wherein the first member of the binding pair in R1 is coupled to a moiety (e.g., a nucleotide sequence) in R1 that captures (e.g., hybridizes to) F1 via a linker, and wherein the first member of the binding pair in R2 is coupled to a moiety (e.g., a nucleotide sequence) in R2 that captures (e.g., hybridizes to) F2 via a linker,
optionally, wherein the linker is a cleavable linker.

56. The method of any of embodiments 7-55, further comprising sequencing F1 from the plurality of F1/R1 hybrid/substrate complexes, and sequencing F2 from the plurality of F2/R2 hybrid/substrate complexes.

57. The method of embodiment 56, wherein F1 is sequenced to a greater depth than F2, e.g., at least 1, 2, 3, 4, 5, 6, 7, 8, 9, or 10-fold greater.

58. A method of analyzing a sample, comprising:

a) providing a plurality of first fragment/first target capture reagent (F1/R1) hybrids and a plurality of second fragment/second target capture reagent (F2/R2) hybrids, wherein the proportion of R1s that comprise a functional first member of the binding pair is greater than the proportion of R2s that comprise a functional first member of the binding pair, and wherein the first member of the binding pair is capable of binding to a second member of the binding pair disposed on substrate;

b) contacting the plurality of F1/R1 hybrids with substrate to form F1/R1 hybrid/substrate complexes, and contacting the plurality of F2/R2 hybrids with substrate to form F2/R2 hybrid/substrate complexes, wherein the proportion of F1/R1 hybrids which bind to the substrate is greater than the proportion of F2/R2 hybrids which bind to the substrate; and c) sequencing F1 from the plurality of F1/R1 hybrid/substrate complexes, and sequencing F2 from the plurality of F2/R2 hybrid/substrate complexes, wherein F1 is sequenced to a greater depth than F2, thereby analyzing the sample.

59. The method of embodiment 58, wherein:

F1 comprises a high sequencing depth event; and

F2 comprises a low sequencing depth event, e.g., the level of which is associated with determination of one or more biomarkers, e.g., tumor mutational burden (TMB), or microsatellite instability (MSI).

60. A method of analyzing a sample, comprising:

1) providing a sample, e.g., a sample comprising genomic DNA, e.g., cell-free DNA (cfDNA) or circulating tumor DNA (ctDNA), from a subject;

2) obtaining, e.g., isolating, nucleic acids from the sample;

3) fragmenting the nucleic acids to provide a plurality of fragments (Fs);

4) attaching adapter sequences to the plurality of fragments (Fs) to provide a plurality of adapterized fragments (AFs);

5) amplifying a first AF (AF1) to provide a plurality of AF1, and amplifying a second AF (AF2) to provide a plurality of AF2;

6) contacting a plurality of AF1 with first target capture reagents (R1s), each comprising a nucleotide sequence that hybridizes to AF1, to provide a plurality of AF1/R1 hybrids, and contacting a plurality of AF2 with second target capture reagents (R2s), each comprising a nucleotide sequence that hybridizes to AF2, to provide a plurality of AF2/R2 hybrids, wherein a portion of the R1s and a portion of the R2s comprise a functional first member of a binding pair, and wherein the first member of the binding pair is capable of binding to a second member of the binding pair disposed on substrate, and wherein a portion of the R1s, a portion of the R2s, or both, lack a functional first member of a binding pair;

7) contacting the plurality of AF1/R1 hybrids with substrate to form AF1/R1 hybrid/substrate complexes, and contacting the plurality of AF2/R2 hybrids with substrate to form AF2/R2 hybrid/substrate complexes, wherein the proportion of AF1/R1 hybrids which bind to the substrate is greater than the proportion of AF2/R2 hybrids which bind to the substrate; and 8) sequencing AF1 from the plurality of AF1/R1 hybrid/substrate complexes, and sequencing AF2 from the plurality of AF2/R2 hybrid/substrate complexes, optionally, wherein AF1 is sequenced to a greater depth than AF2, e.g., at least 1, 2, 3, 4, 5, 6, 7, 8, 9, or 10-fold greater;

thereby analyzing the sample.

61. The method of embodiment 60, wherein:

AF1 comprises a high sequencing depth event; and

AF2 comprises a low sequencing depth event, e.g., the level of which is associated with determination of one or more biomarkers, e.g., tumor mutational burden (TMB), or microsatellite instability (MSI).

62. The method of any of embodiments 7-61, further comprising acquiring a library comprising a plurality of nucleic acid molecules from the sample.

63. The method of embodiment 62, further comprising contacting the library with target capture reagents to provide selected nucleic acid molecules, wherein said target capture reagents hybridize with the nucleic acid molecule, thereby providing a library catch.

64. The method of embodiment 63, further comprising acquiring a read for a subject interval comprising an alteration (e.g., a somatic alteration) from a nucleic acid molecule from said library or library catch, thereby acquiring a read for the subject interval, e.g., by a next-generation sequencing method.

65. The method of embodiment 64, comprising acquiring reads for subject intervals in a plurality of genes.

66. The method of embodiment 65, wherein the plurality of genes comprises genes in mutant form, e.g., the mutant genes are associated with an effect on cell division, growth or survival, or are associated with cancer.

67. The method of embodiment 65 or 66, wherein the plurality of genes comprises at least about 50 or more, about 100 or more, about 150 or more, about 200 or more, about 250 or more, about 300 or more, about 350 or more, about 400 or more, about 450 or more, about 500 or more genes, or about 1,000 or more genes, or all genes for whole exon sequencing (WES).

68. The method of any of embodiments 64-67, wherein the plurality of genes comprises at least about 50 or more, about 100 or more, about 150 or more, about 200 or more, about 250 or more, about 300 or more, or all of the genes described in Tables 1A-5A.

69. The method of any of embodiments 64-68, wherein acquiring reads for subject intervals comprises sequencing subject intervals from at least about 50 or more, about 100 or more, about 150 or more, about 200 or more, about 250 or more, about 300 or more, or all of the genes described in Tables 1A-5A.

70. The method of any of embodiments 64-69, wherein subject intervals are sequenced to greater than about 100X, greater than about 250X, greater than about 500X, greater than about 800X, greater than about 1,000X, greater than about 2,000X, greater than about 3,000X, greater than about 4,000X, or greater than about 5,000X, average depth.

71. The method of any of embodiments 64-70, wherein subject intervals are sequenced to greater than about 100X, greater than about 250X, greater than about 500X, greater than about 800X, greater than about 1,000X, greater than about 2,000X, greater than about 3,000X, greater than about 4,000X, or greater than about 5,000X, average depth, at greater than about 95%, greater than about 97%, or greater than about 99%, of the genes (e.g., exons) sequenced.

72. The method of any of embodiments 64-71, further comprising aligning said read by an alignment method.

73. The method of embodiment 72, further comprising assigning a nucleotide value from said read for a nucleotide position.

74. The method of any of embodiments 7-73, further comprising evaluating one or more genomic signatures, e.g., continuous/complex biomarkers in the sample.

75. The method of embodiment 74, wherein the sample is a blood sample.

76. The method of any of embodiments 7-75, further comprising characterizing an alteration in the sample as a somatic or germline alteration.

77. The method of any of embodiments 7-76, further comprising determining the zygosity of an alteration in the sample.

78. The method of any of embodiments 7-77, further comprising classifying the sample or a subject from which the sample was obtained responsive to the analysis of the sample.

79. The method of any of embodiments 7-78, further comprising providing a report, e.g., an electronic, web-based, or paper report, to the subject from which the sample is obtained or to another person or entity, a caregiver, a physician, an oncologist, a hospital, clinic, third-party payor, insurance company or government office.

EXAMPLES

This invention is further illustrated by the following examples which should not be construed as limiting. The contents of all references, figures, sequence listing, patents and published patent applications cited throughout this application are hereby incorporated by reference.

Example 1: Detection of Alterations in Cell-Free DNA

Introduction

The cell free DNA (cfDNA) assay described in this Example is a next generation sequencing based assay for detection of, e.g., substitutions, insertion and deletion alterations (indels) in, e.g., about or more than 60 genes, select copy number alterations (CNAs) and select gene rearrangements using circulating-free DNA (cfDNA) isolated from plasma derived from the anti-coagulated peripheral whole blood of patients with cancer. Due to the low amount of circulating tumor DNA (ctDNA) fraction of cell-free DNA, target capture content is restricted to achieve a narrow high sequencing depth of the target region for high sensitivity and specificity. The cfDNA assay described in this Example can also be used for genomic signatures through the use of a larger gene panel (>300 genes) to achieve wide moderate coverage across the target capture region. In most cases the narrow target capture region is restricted to 0.1-0.3 Mb in aggregate target size to achieve high sensitivity and specificity at a reasonable sequencing cost while a genomic signature requires a minimal aggregate target capture region of 0.8-1.0 Mb. Currently, the addition of the genomic signature analysis to the standard cfDNA assay utilizes parallel workflows, each starting from two blood collection tubes and requiring twice the sequencing data generation of the single assay.

The study described in this Example was designed with the goal of optimizing the current cfDNA assay workflow in order to combine relevant genomic alteration calling at high sensitivity and specificity with the detection of the genomic signature and only require a total of two tubes of blood per patient being tested. The experiments outlined were designed to evaluate several options for a combined assay that could achieve both narrow high sequencing depth and wide moderate sequencing depth within the sequencing data target of <200M read pairs. Workflow optimizations for the combined assays were evaluated to assess the feasibility of utilizing each option to satisfy the requirements of the cfDNA assay.

The study described in this Example evaluated several options for achieving the combined assay design requirements. The first option was to evaluate a dual (parallel) hybrid capture ("HC") approach from the same library construction ("LC") material, which included development work to increase the amount of LC post PCR output material that can be created to reach a minimum sufficient amount to support dual hybrid capture reactions without significantly decreasing the complexity of the library by over amplification, among other considerations (the activities related to such first option, as set forth more full below, collectively, "Path 1"). A second option was to evaluate utilizing the genomic signature target capture reagent at a wide high sequencing depth to call both genomic alterations and genomic signatures, evaluating optimizing the sequence loading density to retain performance of genomic alteration and genomic signature calling (the activities related to such second option, as set forth more fully below, collectively "Path 2").

A third option was to evaluate a complex target capture reagent strategy that uses a combination of 5'biotinylated probes and unmodified probes (sometimes referred to as anti-target capture reagents or blocking target capture reagents) to modulate target sequencing depth on a specific, per-target basis. For example, a biotinylated probe (e.g., a 5'biotinylated probe) is a target capture reagent that comprises a functional first member of a binding pair (e.g., as described herein). As another example, an unmodified probe (e.g., anti-target capture reagent, blocking probe, probe that is not biotinylated) is a target capture reagent that lacks a functional first member of a binding pair (e.g., as described herein). This strategy would allow narrow high sequencing depth of specified targets and wide moderate sequencing depth across the rest of the target region for the genomic signature. The experiments were designed to evaluate the ability of a single hybridization reaction where the amount of target pulled from the genome library and subsequently sequenced can be predetermined by the ratio of the modified and unmodified probes. This allows the use of a single HC reaction as outlined in Path 2 but to also have the ability to have low, high, and intermediate target sequencing depths that were achieved in Path 1 (the activities related to such third option, as set forth more fully below, collectively "Path 2B").

Results:

Path 1

Dual Hybrid Capture from a Single Library Construction

The library construction protocol optimizations led to higher efficiency and uniformity of LC output as demonstrated in the process qualification where 192 DNA samples representing a range of LC inputs of 20 ng to 100 ng were run across three separate LC plates, captured with an equal representation of target capture reagents for the narrow high sequencing depth (NHSD, 0.3 Mb) and a target capture reagent for the wide moderate sequencing depth (WMSD, 2 Mb). Prior development work has validated that the automated cfDNA Assay Library construction protocols installed on the automated liquid handling workstations met or exceeded the expected clinical performance through the evaluation of QC criteria of exemplar samples run through the process. Library construction yields of 100% samples in the low input (220-50 ng) and high input (>50-100 ng) all achieved >2 µg LC yield, 100% samples captured with NHSD target capture reagents had 5000X median unique sequencing depth and 100% samples captured with the WMSD target capture reagents had 2800X median unique sequencing depth. The protocol optimization achieved the required result of providing enough LC output for parallel hybrid capture reactions. Post deployment showed equivalent LC yield distributions for all input concentrations. In contrast, the protocol prior to optimization illustrated that in LC yield scaling with LC inputs it would be challenging to have two hybrid capture reactions for the wide range of LC inputs used in the cfDNA assay.

Enzymatically fragmented normal human DNA underwent cfDNA Assay library construction and six replicates were each split into two HC reactions. One HC reaction was performed with the NHSD target capture reagent, the other was performed with the WMSD target capture reagent. The samples were loaded onto a HiSeq 4000 flow cell for a target 100M read pairs per sample. As outlined in Table 6, each sample with over 150M read pairs achieved the target raw, unique, and redundant sequencing depth specification for both the NHSD and WMSD target captures, proving that the dual HC from a single LC path achieved the coverage goal.

Variant Level Performance Evaluation of 1LC>2HC

To further evaluate the dual HC from a single LC at variant level concordance, 43 exemplar samples underwent NHSD target capture for short nucleotide variants, insertions/deletions, gene rearrangements, and WMSD target capture for genomic signatures.

1. ALK intron 19 rearrangement (N=5)
2. EGFR exon 19 deletion (N=5)
3. EGFR L858R (N=5)
4. RET rearrangement (N=5)
5. Genomic signatures 0.88 to 27.2 mut/mb (N=23)

The experimental results at the variant level for dual HC from a single library show that the Path 1 achieved feasibility. The target coverage profiles were achieved for both target capture reagent sets and variant level concordance achieved.

Path 2

Single Hybrid Capture from a Single Library Construction

Enzymatically fragmented normal human DNA underwent cfDNA Assay library construction and six replicates underwent a single HC reactions performed with the WMSD target capture reagent set. This experiment was used to determine if wide high sequencing depth (WHSD) could be achieved by sequencing the 200M read budget from the parallel assays with a single target capture. The samples were loaded onto a HiSeq 4000 flow cell for a target <200M read pairs per sample. As outlined in Table 7, each sample achieved the target raw, unique, and redundant sequencing depth specification only for the WMSD target captures but not for the NHSD target captures, showing that the dual HC from a single LC path did not achieve the goal at the 200M read pairs per sample budget. The redundant coverage for the NHSD target regions was not high enough to achieve the required data for the combined assay performance requirements. It is estimated that one would need ~700M reads to achieve sufficient redundant sequencing depth for the cfDNA Assay (~700M=~30,000x/~7500x*-170M) which is well above the requirement to not sequence more than 200M read pairs per sample. No further data was collected for this path.

TABLE 6

Coverage results from dual HC from a single library (n = 6 replicates).

| Total Read Pairs | NHSD Raw sequencing depth | NHSD Unique sequencing depth | NHSD Redundant sequencing depth | WMSD Raw sequencing depth | WMSD Unique sequencing depth | WMSD Redundant sequencing depth |
|---|---|---|---|---|---|---|
| 95M | 14894 | 6034 | 3417 | 1991 | 1370 | 419 |
| 93M | 15606 | 6318 | 3455 | 1833 | 1272 | 382 |
| 168M | 26560 | 8978 | 5734 | 3200 | 2246 | 671 |
| 182M | 28498 | 7717 | 5060 | 3675 | 2301 | 843 |
| 186M | 28351 | 9320 | 6116 | 3464 | 2309 | 757 |
| 173M | 28304 | 5789 | 4104 | 3473 | 1877 | 831 |

NHSD = narrow high sequencing depth,
WMSD = wide moderate sequencing depth

TABLE 7

| | | NHSD Raw sequencing depth | NHSD Unique sequencing depth | NHSD Redundant sequencing depth | WMSD Raw sequencing depth | WMSD Unique sequencing depth | WMSD Redundant sequencing depth |
|---|---|---|---|---|---|---|---|
| Specimen | Total Read Pairs | | | | | | |
| A | 170M | 7492 | 3876 | 1852 | 6103 | 1370 | 1481 |
| B | 164M | 7340 | 3857 | 1690 | 5728 | 1272 | 1326 |
| C | 85M | 3539 | 2463 | 754 | 2917 | 2246 | 587 |
| D | 96M | 4100 | 2514 | 943 | 3291 | 2301 | 732 |
| E | 173M | 6937 | 4076 | 1663 | 5754 | 2309 | 1348 |
| F | 170M | 7421 | 3090 | 1668 | 5827 | 1877 | 1359 |

Sequencing depth results from single HC from a single library (n = 6 replicates).

NHSD = narrow high sequencing depth,
WMSD = wide moderate sequencing depth

Path 2B

Complex Target Capture Reagent Strategy for Coverage Modulation

Experiment 1: Addition of Blocking Target Capture Reagents for APC and ATM Titrated into the NHSD Target Capture Reagent As a first proof of concept evaluation of the ability of unmodified target capture reagents to impact the capture performance of specific targets, excess unmodified target capture reagents of two genes, APC and ATM, were added in a titration of 1X-2X of the biotinylated target capture reagent into the NHSD target capture reagent. Table 8 and FIG. 1 show the results of this experiment, indicating that the coverage of specific targets could be lowered with the addition of the unmodified blocker or anti-target capture reagents, but that the effect of putting excess blocker into excess target capture reagent was not as pronounced as it could be if the total target capture reagent amount was kept constant and the ratio of blocker to target capture reagent was adjusted.

TABLE 8

Addition of unmodified APC and ATM target capture reagents lowered the target coverage

| Sample | Un-modified target capture reagent | Median Exon sequencing depth (All Exons) | Median sequencing depth (APC and ATM exons) | Un-modified to Modified target capture reagent mix Ratio | Redundant sequencing depth |
|---|---|---|---|---|---|
| NHSD | 0 | 4,721 | 4,752 | 100.7% | 1481 |
| NHSD (APC/ATM-) | 1.0× | 3,788 | 3,216 | 84.9% | 1326 |
| NHSD (APC/ATM-) | 1.4× | 3,684 | 3,059 | 83.0% | 587 |
| NHSD (APC/ATM-) | 1.6× | 4,432 | 3,546 | 80.0% | 732 |
| NHSD (APC/ATM-) | 1.8× | 3,362 | 2,497 | 74.3% | 1348 |
| NHSD (APC/ATM-) | 2.0× | 2,231 | 1,732 | 77.6% | 1359 |

Figure 2:
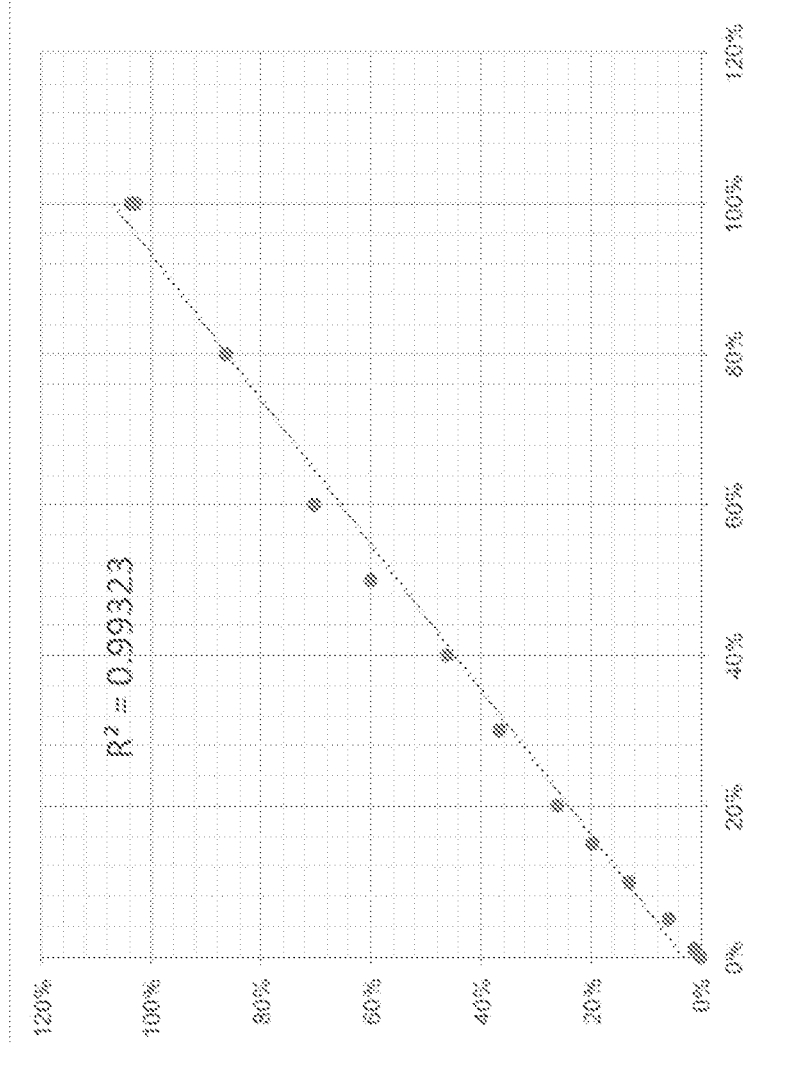
FIG. 2 is a graph depicting the observed versus expected median coverage of the APC target region compared to all other NHC target regions.

Experiment 2: Addition of Blocking Target Capture Reagents for APC and ATM Titrated into NHSD Target Capture Reagent In experiment 2, the total target capture reagent amount of 0.032 pM in the final pool was kept constant and the ratio of the biotinylated to non-biotinylated target capture reagent was titrated to illustrate the anti-target capture reagent strategy for the single gene target APC. The target capture reagents for the gene APC (164 target capture reagents) was a full gene subpool added to the NHSD target capture reagent, which allowed the creation of a target capture reagent set backbone that had the NHSD target capture reagent without the target reagents for the APC gene. A range of 100% biotinylated APC to 99% non-biotinylated to 1% biotinylated APC was evaluated to show a wide range of observed versus expected sequencing depth as shown in FIG. 2 and Table 9. The NHSD target capture reagent that has 100% biotinylated APC was compared to 100% APC to show that the addition of APC back into the target capture reagent did not have an adverse effect on APC sequencing depth. By keeping the target capture reagent amount constant, there was a predictable sequencing depth suppression response showing that the anti-target capture reagent method was successful and that a larger scale test could be the next experiment.

TABLE 9

Observed versus expected median coverage of APC/median sequencing depth of all targets

| Expected | Observed |
|---|---|
| 100% | 104% |
| 100% | 103% |
| 80% | 86% |
| 60% | 70% |
| 50% | 60% |
| 40% | 46% |
| 30% | 37% |
| 20% | 26% |
| 15% | 20% |
| 10% | 13% |
| 5% | 6% |
| 1% | 1% |
| 0% | 0% |

Experiment 3: Addition of Blocking Target Capture Reagents for Targets Other than the NHSD Targets The goal of experiment 3 was to continue with the complex target capture reagents strategy to obtain high depth on the NHSD region and target lower depth on the non-NHSD (also referred to as WMSD targets herein) region, to have narrow high sequencing depth (NHSD) and wide moderate sequencing depth (WMSD) obtained by a single hybrid capture reaction.

A target capture reagent set was formulated as a full prototype by utilizing three subpools of target capture reagents. NHSD target capture reagent (3780 target capture reagents, 0.3 Mb) was combined with unmodified target capture reagents (total targets minus the NHSD targets, no biotin, 22563 target capture reagents, 1.7 Mb) at the NHSD/ non-NHSD target ratio (14% NHSD: 86% non-NHSD). This mixture was then titrated into the full target capture set (2.0 Mb, 26343) to alter the ratio of the non-NHSD region with and without biotin. A titration series of (NHSD-biotin/no-biotin):non-NHSD biotin was done at 100, 50, 30, 20, 10, 5, 1, 0% to first determine the ratio of target capture reagents required to achieve the target sequencing depth profiles of each component.

Figure 3:
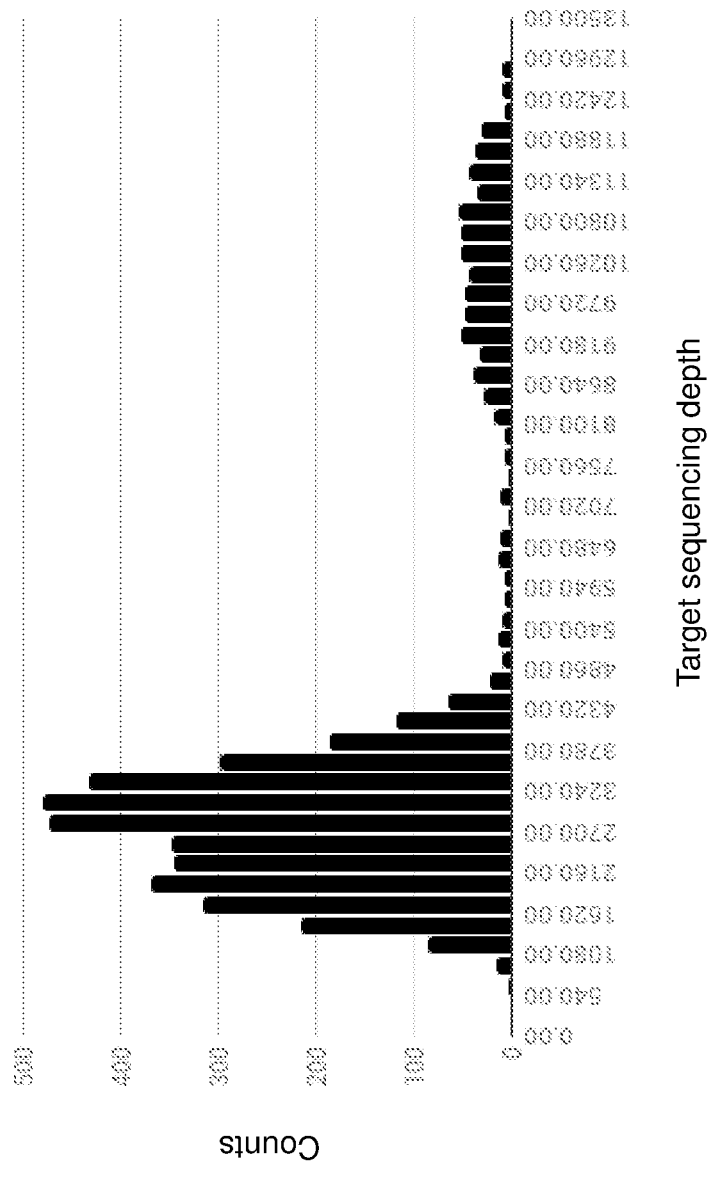
FIG. 3 is a histogram showing the average consensus target coverage illustrating the separation of narrow high coverage (NHC) targets from the blocked reduced coverage non-NHC targets. The y-axis depicts counts and the x-axis depicts target sequencing depth.

Results of the titration, shown in Tables 10 and 11, indicate the ability to reduce the non-NHSD and maintain the required NHSD. The 10% formulation (90% no-biotin to 10% biotin) was chosen as the formulation to use on exemplar samples. The sequencing depth results for the titration are shown in Tables 10 and 11. FIG. 3 shows the results of Experiment 3 for the 10% formulation, in the form of a histogram. As shown in FIG. 3, the NHSD (narrow high sequencing depth) targets segregate into a separate cluster on the right of the graph, from the non-NHSD targets which form a distinct group on the left of the graph. The NHSD targets have a higher sequencing depth compared to the non-NHSD targets (also referred to as WMSD targets herein). This experiment was also performed with clinical samples and similar results were obtained.

TABLE 10

Results for the narrow high sequencing depth (NHSD) region in the anti-target capture reagent titration

| % non-NHSD anti-target capture reagent[1] | Sampled Read Pairs | Raw sequencing depth | Unique sequencing depth | Redundant sequencing depth | Median Redundancy |
|---|---|---|---|---|---|
| 0 | 67M | 14008 | 5572 | 2953 | 2.55 |
| 1 | 63M | 12790 | 3571 | 2281 | 3.75 |
| 5 | 67M | 11710 | 5735 | 2633 | 2.11 |
| 10 | 62M | 9805 | 5686 | 2307 | 1.75 |
| 20 | 66M | 8268 | 4898 | 1912 | 1.7 |
| 30 | 67M | 6954 | 4570 | 1527 | 1.52 |
| 50 | 68M | 5204 | 3655 | 1073 | 1.42 |
| 100 | 69M | 2855 | 2131 | 525 | 1.34 |

[1]% Non-NHSD anti-target capture reagent refers to % WMSD anti-target capture reagent

TABLE 11

Results for the wide moderate sequencing depth (WMSD) target region in the anti-target capture reagent titration

| % non-NHSD anti-target capture reagent[1] | Sampled Read Pairs | Raw sequencing depth | Unique sequencing depth | Redundant sequencing depth | Median Redundancy |
|---|---|---|---|---|---|
| 0 | 67M | 380 | 340 | 36 | 1.12 |
| 1 | 63M | 369 | 314 | 46 | 1.18 |
| 5 | 67M | 610 | 546 | 57 | 1.12 |
| 10 | 62M | 831 | 745 | 76 | 1.11 |
| 20 | 66M | 1190 | 1040 | 131 | 1.14 |
| 30 | 67M | 1452 | 1268 | 160 | 1.14 |
| 50 | 68M | 1818 | 1535 | 235 | 1.18 |
| 100 | 69M | 2199 | 1721 | 367 | 1.28 |

[1]% Non-NHSD anti-target capture reagent refers to % WMSD anti-target capture reagent Summary In this Example, the results for three different paths for the combination of genomic alteration calling at high sensitivity and specificity with genomic signature calling in a single assay are described and summarized. This analysis demonstrated that (a) parallel hybrid capture after a single library construction achieves sequencing depth specifications and maintains variant level concordance for specific genomic signatures, and single nucleotide variants (SNVs), indels, and rearrangements, (b) 200M read pairs is not enough sequencing to achieve the wide high sequencing depth required of high sensitivity and specificity, and (c) preliminary data utilizing the anti-target capture reagent approach suggests the anti-target capture reagent strategy can be used to achieve the required high narrow sequencing depth on defined targets and wide moderate sequencing depth on the specific genomic signature regions, allowing a single hybrid capture reaction to achieve the goals of a combined assay that achieves the performance specifications within a feasible sequencing depth.

Additional examples relevant to the methods and systems described herein are described, e.g., in International Patent Application Publication Nos. WO 2012/092426 and WO 2016/090273, the contents of the aforesaid publications and examples are incorporated by reference in its entirety.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

Also incorporated by reference in their entirety are any polynucleotide and polypeptide sequences which reference an accession number correlating to an entry in a public database, such as those maintained by The Institute for Genomic Research (TIGR) on the world wide web at tigr.org and/or the National Center for Biotechnology Information (NCBI) on the world wide web at ncbi.nlm.nih.gov.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A plurality of target capture reagents, comprising first target capture reagents (R1s), wherein each R1 comprises an oligonucleotide comprising a first nucleic acid sequence that hybridizes to a first target nucleic acid sequence, wherein the oligonucleotides of the R1s are the same, and second target capture reagents (R2s), wherein each R2 comprises an oligonucleotide comprising a second nucleic acid sequence that hybridizes to a second target nucleic acid sequence, wherein the oligonucleotides of the R2s are the same, wherein:

a first portion of the R1s comprises a first member of a binding pair;

a second portion of the R1s lacks the first member of the binding pair;

a first portion of the R2s comprises the first member of the binding pair; and a second portion of the R2s lacks the first member of the binding pair;

wherein the first member of the binding pair binds a second member of the binding pair disposed on a substrate, and wherein the proportion of R1s that comprises the first member of the binding pair is greater than the proportion of R2s that comprise the first member of the binding pair.

2. The plurality of target capture reagents of claim 1, wherein the proportion of R1s that comprise the first member of the binding pair is at least 2-fold greater than the proportion of R2s that comprise the first member of the binding pair.

3. The plurality of target capture reagents of claim 1, wherein each of the R1s forms a first fragment/first target capture reagent (F1/R1) hybrid, and F1 comprises a sequence associated with a phenotype, treatment outcome, diagnosis, or prognosis.

4. The plurality of target capture reagents of claim 1, further comprising third target capture reagents (R3s), wherein each R3 comprises an oligonucleotide comprising a third nucleic acid sequence that hybridizes to a third target nucleic acid sequence, wherein the oligonucleotides of the R3s are the same, wherein:

a first portion of the R3s comprises the first member of the binding pair;

a second portion of the R3s lacks the first member of the binding pair; and the proportion of R2s that comprises the first member of the binding pair is greater than the proportion of R3s that comprise the first member of the binding pair.

5. The plurality of target capture reagents of claim 1, wherein the proportion of R1s that comprise the first member of the binding pair is at least 0.5-fold greater than the proportion of R2s that comprise the first member of the binding pair.

6. The plurality of target capture reagents of claim 1, wherein:

the first member of the binding pair comprises biotin; and the second member of the binding pair comprises streptavidin or avidin, or a modified version thereof.

7. The plurality of target capture reagents of claim 1, wherein:

the first member of the binding pair comprises a digoxigenin moiety; and the second member of the binding pair comprises an anti-digoxigenin antibody.

8. The plurality of target capture reagents of claim 1, wherein:

the first member of the binding pair comprises a FITC moiety; and the second member of the binding pair comprises an anti-FITC antibody.

9. The plurality of target capture reagents of claim 1, wherein:

the first target sequence is associated with a phenotype, treatment outcome, diagnosis or prognosis; and the second target sequence is associated with a determination of tumor mutational burden, microsatellite instability, or both.

10. A composition comprising the plurality of target capture reagents of claim 1, and a library comprising a plurality of nucleic acid molecules obtained from a sample.

11. The composition of claim 10, wherein the nucleic acid molecules are attached to adapter sequences for sequencing the nucleic acid molecules.

12. The composition of claim 10, wherein the sample comprises genomic DNA, cell-free DNA (cfDNA), circulating tumor DNA (ctDNA), or RNA.

13. The composition of claim 10, wherein the sample comprises cfDNA.

14. The composition of claim 10, wherein the sample is a blood sample or a plasma sample.

15. The composition of claim 10, wherein the sample is a solid tissue sample.

16. The composition of claim 10, wherein the sample is a formalin-fixed paraffin embedded (FFPE) sample.

17. The composition of claim 10, wherein the composition is a solution.

18. The composition of claim 10, further comprising the substrate on which the second member of the binding pair is disposed, and wherein the first binding pair is bound to the second binding pair.

19. The plurality of target capture reagents of claim 1, wherein the first target sequence comprises a somatic alteration.

20. The plurality of target capture reagents of claim 19, wherein the somatic alteration is associated with an effect on cell division, growth, or survival.

21. The plurality of target capture reagents of claim 19, wherein the second target sequence comprises a germline alteration.

22. The plurality of target capture reagents of claim 1, wherein the second target sequence comprises a germline alteration.

23. The plurality of target capture reagents of claim 1, wherein the first target sequence is associated with responsiveness or non-responsiveness to a therapeutic modality.

\* \* \* \* \*